United States Patent
Williams et al.

(10) Patent No.: US 12,161,714 B2
(45) Date of Patent: Dec. 10, 2024

(54) USE OF ENDOGENOUS VIRAL VACCINE IN CHIMERIC ANTIGEN RECEPTOR T CELL THERAPY

(71) Applicant: CITY OF HOPE, Duarte, CA (US)

(72) Inventors: John C. Williams, Monrovia, CA (US); Christine Brown, Pasadena, CA (US); Don J. Diamond, Glendora, CA (US); Xiuli Wang, Temple City, CA (US); Stephen J. Forman, Pasadena, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 18/346,677

(22) Filed: Jul. 3, 2023

(65) Prior Publication Data

US 2024/0207393 A1    Jun. 27, 2024

Related U.S. Application Data

(60) Continuation of application No. 17/465,728, filed on Sep. 2, 2021, now Pat. No. 11,690,908, which is a division of application No. 16/342,426, filed as application No. PCT/US2017/057466 on Oct. 19, 2017, now Pat. No. 11,116,834.

(60) Provisional application No. 62/410,383, filed on Oct. 19, 2016.

(51) Int. Cl.
| | |
|---|---|
| *A61K 35/17* | (2015.01) |
| *A61K 38/00* | (2006.01) |
| *A61K 39/00* | (2006.01) |
| *A61K 39/12* | (2006.01) |
| *A61K 39/245* | (2006.01) |
| *A61K 48/00* | (2006.01) |
| *A61P 35/00* | (2006.01) |
| *C07K 14/03* | (2006.01) |
| *C07K 14/725* | (2006.01) |
| *C07K 16/18* | (2006.01) |

(52) U.S. Cl.
CPC ............ *A61K 39/245* (2013.01); *A61K 35/17* (2013.01); *A61P 35/00* (2018.01); *C07K 14/03* (2013.01); *C07K 14/7051* (2013.01); *C07K 16/18* (2013.01); *A61K 38/00* (2013.01); *A61K 2039/5158* (2013.01)

(58) Field of Classification Search
CPC .............. A61K 35/17; A61K 39/4611; A61K 39/4631; A61K 2239/13; A61K 2239/28
See application file for complete search history.

(56) References Cited

U.S. PATENT DOCUMENTS

| | | | |
|---|---|---|---|
| 7,163,685 B2 | 1/2007 | Diamond et al. | |
| 8,580,276 B2 | 11/2013 | Diamond et al. | |
| 9,669,108 B2 | 6/2017 | Williams | |
| 9,675,689 B2 | 6/2017 | Diamond et al. | |
| 11,116,834 B2 | 9/2021 | Williams et al. | |
| 11,690,908 B2 | 7/2023 | Williams et al. | |
| 2012/0301400 A1 | 11/2012 | Williams et al. | |
| 2014/0065181 A1 | 3/2014 | Diamond et al. | |
| 2017/0246292 A1 | 8/2017 | Diamond et al. | |

FOREIGN PATENT DOCUMENTS

| | | |
|---|---|---|
| WO | WO-2012/048332 A2 | 4/2012 |
| WO | WO-2012/048332 A3 | 4/2012 |
| WO | WO-2013/055404 A1 | 4/2013 |
| WO | WO-2015/105522 A1 | 7/2015 |
| WO | WO-2016/054603 A2 | 4/2016 |
| WO | WO-2016/054603 A3 | 4/2016 |
| WO | WO-2016/154628 A1 | 9/2016 |
| WO | WO-2016/161018 A1 | 10/2016 |
| WO | WO-2016/187158 A1 | 11/2016 |

OTHER PUBLICATIONS

Brown, C.E. et al. (Apr. 15, 2012, e-published Mar. 8, 2012). "Stem-like tumor-initiating cells isolated from IL13Rα2 expressing gliomas are targeted and killed by IL 13-zetakine-redirected T Cells," *Clin Cancer Res* 18(8):2199-2209.

Byrne, H. et al. (Nov. 2013, e-published Oct. 2, 2013). "A tale of two specificities: bispecific antibodies for therapeutic and diagnostic applications," *Trends Biotechnol* 31(11):621-632.

International Search Report mailed on Jan. 16, 2018, for PCT Application No. PCT/US2017/057466, filed Oct. 19, 2017, 3 pages.

Jakob, C.G. et al. (May-Jun. 2013, e-published Apr. 2, 2013). "Structure reveals function of the dual variable domain immunoglobulin (DVD-Ig™) molecule," *MAbs* 5(3):358-363.

Jensen, M.C. et al. (Jan. 2014). "Design and implementation of adoptive therapy with chimeric antigen receptor-modified T cells," *Immunol Rev* 257(1):127-144.

Mardiros, A. et al. (Oct. 31, 2013, e-published Sep. 12, 2013). "T cells expressing CD123-specific chimeric antigen receptors exhibit specific cytolytic effector functions and antitumor effects against human acute myeloid leukemia," *Blood* 122(18):3138-3148.

(Continued)

*Primary Examiner* — Barry A Chestnut
(74) *Attorney, Agent, or Firm* — Mintz Levin Cohn Ferris Glovsky and Popeo PC

(57) ABSTRACT

Provided herein are, inter alia, methods and compositions including T cells expressing (i) a recombinant CAR protein which includes a peptide binding site and is capable of specifically binding cancer-specific antigens and (ii) a T cell receptor specific for a viral antigen (e.g., a CMV pp65 protein). The engineered T cells provided herein may be used in combination with a viral vaccine (e.g. cytomegalovirus (CMV) Triplex Vaccine) to treat a variety of cancers. The methods described herein also permit in vivo expansion of CMV-specific CAR T cells, instead of or in addition to ex vivo expansion, avoiding excessive T cell exhaustion that results in some cases from ex vivo manufacturing.

6 Claims, 25 Drawing Sheets
Specification includes a Sequence Listing.

(56) References Cited

OTHER PUBLICATIONS

Wang, X. et al. (Jul. 2015, e-published Apr. 2, 2015). "CMVpp65 Vaccine Enhances the Antitumor Efficacy of Adoptively Transferred CD19-Redirected CMV-Specific T Cells," *Clin Cancer Res* 21(13):2993-3002.

Wang, X. et al. (Jun. 16, 2016, e-published Apr. 26, 2016). "Phase 1 studies of central memory-derived CD19 CAR T-cell therapy following autologous HSCT in patients with B-cell NHL," *Blood* 127(24):2980-2990.

Written Opinion mailed on Jan. 16, 2018, for PCT Application No. PCT/US2017/057466, filed Oct. 19, 2017, 6 pages.

Wu, C.Y. et al. (Oct. 16, 2015, e-published Sep. 24, 2015). "Remote control of therapeutic T cells through a small molecule-gated chimeric receptor," *Science* 350(6258):aab4077.

* p < 0.05

| Healthy Donor | IFN+ Cells Prior to capture | IFNγ+ Cells Post capture | IFNγ+ CD8 | IFN+ CD4 | %yield from PBMC |
|---|---|---|---|---|---|
| Donor 1 | 1.8% | 71% | 40% | 31% | 0.2 |
| Donor 1 | 3.7% | 61% | 33% | 28% | 0.3 |
| Donor 1 | 3.2% | 76% | 40% | 36% | 0.2 |
| Donor 2 | 4.8% | 81% | 36% | 45% | 0.4 |
| Donor 3 | 5.6% | 70% | 21% | 49% | 0.1 |
| Mean±SEM | 3.8±0.7% | 71.8±3.3% | 34.5±3.5% | 37.0±4.0% | 0.24±0.05% |

FIG. 14D

USE OF ENDOGENOUS VIRAL VACCINE IN CHIMERIC ANTIGEN RECEPTOR T CELL THERAPY

CROSS-REFERENCES TO RELATED APPLICATIONS

This application is a continuation of and claims priority to U.S. application Ser. No. 17/465,728, filed on Sep. 2, 2021, which issued as U.S. Pat. No. 11,690,908 and is a divisional of and claims priority to U.S. application Ser. No. 16/342,426, filed on Apr. 16, 2019, which issued as U.S. Pat. No. 11,116,834 and which is a national stage application of and claims priority to International Application No. PCT/US2017/057466, filed on Oct. 19, 2017, which claims priority to U.S. Provisional Application No. 62/410,383, filed Oct. 19, 2016, the disclosure of each is incorporated herein in their-entirety and for all purposes.

REFERENCE TO A "SEQUENCE LISTING," A TABLE, OR A COMPUTER PROGRAM LISTING APPENDIX SUBMITTED ON A COMPACT DISK

The Sequence Listing written in file 048440-632C01US_Sequence Listing.xml, created on Nov. 9, 2023, 220,265 bytes, machine format IBM-PC, MS-Windows operating system, is hereby incorporated by reference in its entirety for all purposes.

BACKGROUND OF THE INVENTION

Cancer is the second leading cause of death in the United States, killing more people than the next five causes combined including chronic respiratory disease, Alzheimer's disease and diabetes. While extraordinary strides have been made in the detection, prevention and treatment of cancer, there remains an urgent need, especially in advanced cases, to produce therapies that not only halt tumor progression but effectively eliminate all tumor cells. One approach is adoptive T cell immunotherapy (5-7). This method requires the harvesting of the patient's T cells, engineering of these cells with a chimeric antigen receptor (CAR) that recognizes a tumor antigen, and subsequent re-introduction of the modified cells to the patient. The re-programmed T cells then directly target antigen-expressing tumor cells, bypassing the requirement for MHC peptide, and elicit a powerful but localized immune response. This method of treatment (8) has produced some positive results in early clinical trials for a handful, but not for all patients. There is a need in the art to better understand CAR T cell therapy's success and failure. For example, there is a need in the art for the ability to characterize the density of the CARs on the transformed cells, to track administered CAR T cells at any point during therapy and correlate this distribution to therapeutic outcomes, to rapidly functionalize CAR T cells, monitoring the number, location and viability of the transplanted CAR T cells in situ and to selectively eliminate CAR T cells if necessary. Meaningful correlations would aid clinicians in determining the best treatment options and give researchers important clues to modify and improve this therapeutic approach. Over 70,000 new cases of non-Hodgkin lymphoma (NHL) are diagnosed each year in the United States with about 20,000 deaths due to NHL each year, representing the 5th leading cause of cancer deaths. The majority of these patients have widespread disease at the time of diagnosis and over two-thirds will suffer a recurrence after remission induction with cytotoxic chemotherapy and rituximab. Efforts to improve the survival of patients with recurrent lymphoma have focused mainly on the use of autologous hematopoietic cell transplant (HCT), which is curative in approximately half of good-risk patients, but confers a less than 15% 5-year event-free survival in patients with poor prognostic features. Allogeneic HCT provides a tumor-free stem cell graft, cells that have not been damaged by prior chemotherapy and the opportunity for graft-versus-lymphoma (GVL) effect, and has been increasingly applied in patients with relapsed NHL. Although relapse rates are improved over autologous HCT, allogeneic HCT is associated with both significant risks of transplant-related complications and also disease recurrence. Thus, there is an important need for the development of new therapies that can consolidate the tumor cytoreduction achieved with autologous or allogeneic HCT by eradicating the limited number of tumor cells surviving after autologous myeloablative and reduced intensity allogeneic conditioning. A Phase I clinical trial using ex vivo-expanded autologous central memory-enriched T cells (TCM) transduced with lentivirus expressing CD19-specific CAR has demonstrated the data safety and feasibility of CD19 CAR T cell therapy after HCT Wang et al., *Blood* 127:2980, 2016). Provided herein are compositions and methods addressing these and other needs in the art

BRIEF SUMMARY OF THE INVENTION

In an aspect is provided a method for treating a disease in a subject in need thereof, the method including: (i) administering to a subject a therapeutically effective amount of a composition including a population of human T cells expressing a T cell receptor specific for a cytomegalovirus (CMV) antigen and a recombinant chimeric antigen receptor (CAR) protein, wherein the recombinant CAR protein includes: (A) an antibody region including a central cavity formed by a heavy chain variable (VH) region, a light chain variable (VL) region, a heavy chain constant region (CH) and a light chain constant region (CL), wherein the central cavity forms a peptide binding site including framework region amino acid residues; and (B) a transmembrane domain; and (ii) administering to the subject a therapeutically effective amount of a viral vector, wherein the viral vector encodes (a) a CMV pp65 protein and (b) a fusion protein including exon 4 of CMV protein IE1 (e4) and exon 5 of CMV protein IE2 (e5); and wherein the viral vector is administered either prior to or subsequent to administering the composition including a population of human T cells to the subject, thereby treating the subject.

In an aspect is provided a method for forming a population of human T cells expressing a recombinant CAR protein and a T cell receptor specific for a CMV antigen, the method including: (1) administering a viral vector encoding: (a) a CMV pp65 protein and (b) a fusion protein including exon 4 of CMV protein IE1 (e4) and exon 5 of CMV protein IE2 (e5) to a CMV-seronegative human donor; (2) obtaining PBMCs from the human donor; (3) contacting the PBMCs with at least one CMV antigen; (3) allowing the contacted cells to produce a population of cells enriched for stimulated cells specific for CMV; (4) transducing at least a portion of the enriched population of cells with a vector expressing a recombinant CAR protein, thereby forming a population of human T cells expressing a T cell receptor specific for a CMV antigen and a recombinant CAR protein.

In an aspect is provided a method for forming a population of human T cells expressing a recombinant CAR protein and a T cell receptor specific for a CMV antigen, the method including: (1) administering a viral vector encoding: (a) a CMV pp65 protein and (b) a fusion protein including exon 4 of CMV protein IE1 (e4) and exon 5 of CMV protein IE2 (e5) to a CMV-seropositive human donor; (2) obtaining PBMCs from the CMV-seropositive human donor; (3) contacting the PBMCs with at least one CMV antigen; (4) allowing the contacted cells to produce a population of cells enriched for stimulated cells specific for CMV; (5) transducing at least a portion of the enriched population of cells with a vector expressing a recombinant CAR protein, thereby forming a population of human T cells expressing a T cell receptor specific for a CMV antigen and a recombinant CAR protein.

In an aspect is provided a method for treating a disease in a subject in need thereof including: (i) administering to a subject a therapeutically effective amount of a composition including a population of human T cells expressing a T cell receptor specific for a viral antigen and a recombinant chimeric antigen receptor (CAR) protein, wherein the recombinant CAR protein includes: (A) an antibody region including a central cavity formed by a heavy chain variable (VH) region, a light chain variable (VL) region, a heavy chain constant region (CH) and a light chain constant region (CL), wherein the central cavity forms a peptide binding site including framework region amino acid residues; and (B) a transmembrane domain; and (ii) administering to the subject the viral antigen either prior to or subsequent to administering the composition including a population of human T cells to the subject.

In an aspect is provided a cell including a T cell receptor specific for a cytomegalovirus (CMV) antigen and a recombinant CAR protein, wherein the recombinant CAR protein includes: (A) an antibody region including a central cavity formed by a heavy chain variable (VH) region, a light chain variable (VL) region, a heavy chain constant region (CH) and a light chain constant region (CL), wherein the central cavity forms a peptide binding site including framework region amino acid residues; and (B) a transmembrane domain.

In an aspect is provided a cell including a T cell receptor specific for a viral antigen and a recombinant CAR protein, wherein the recombinant CAR protein includes: (A) an antibody region including a central cavity formed by a heavy chain variable (VH) region, a light chain variable (VL) region, a heavy chain constant region (CH) and a light chain constant region (CL), wherein the central cavity forms a peptide binding site including framework region amino acid residues; and (B) a transmembrane domain.

BRIEF DESCRIPTION OF THE DRAWINGS

FIG. 1A: Schematic representation of chimeric antigen receptors. To specifically target tumors, full mAbs or Fab fragments that recognize tumor associated antigens are directly fused to the transmembrane domain and zeta chain. In addition, the meditope binding site can be grafted onto the mAB/Fabs, providing an additional means of adding functionality to CAR T cells. FIG. 1B. Since two chains have to be expressed (e.g., the light and heavy chains of the mAb plus the transmembrane and intracellular signaling segments), there are two different possibility to express the different chains. Specifically, the light chain followed by the heavy chain or the heavy chain followed by the light chain.

FIG. 2A. Diagram of the lentiviral CAR cassette for expressing the HER2-specific CAR, including the 2A ribosomal skip sequence and truncated CD19 (CD19t) which serves as an inert immunogenic marker of cell transduction. FIG. 2B. Tcm lentivirally transduced to express HER2R:28ζ display stable cell surface expression of both the CAR and CD19 proteins.

FIG. 3A. Flow cytometry analysis evaluating HER2 surface expression in a panel of breast tumor lines, and the HER2-negative U87 glioblastoma cell line. FIG. 3B. 4-hour chromium release assay evaluating killing by HER2-28z CAR T cells demonstrates that both high and low-expressing HER2+ tumor lines are killed.

FIG. 4A: Crystal structure. 5-Diphenyl-meditope and protein L are bound to trastuzumab memAb. Extracellular domain of HER2 defining the antigen binding site, was superimposed using pdb 1n8z. Note: protein L and the meditope are distinct and distant from the antigen binding site. FIG. 4B FACS. SKBR3 cells were treated with labeled trastuzumab (parental; memAb) and either sequentially or pre-mixed with labeled meditope-protein L (MPL6). Only the trastuzumab memAb shifts the meditope-Protein L, indicating that antigen binding does not preclude meditope binding. FIG. 4C Fluorescence microscopy. GFP fused to meditope-Protein L (MPL6-GFP) colocalizes with trastuzumab memAb using SKBR3 cells (top row) but not with parental trastuzumab (bottom row). This indicates a bulky biologics does not impair antigen binding. FIG. 4D Super resolution microscopy. Individual HER2 receptors can be visualized and quantified using paGFP fused to meditope-Protein L (MPL6-GFP) and trastuzumab memAb. Left panel shows entire cell. Right panel shows individual receptors.

FIG. 8A: Target Cell Expression of CEA. FIG. 8B: 4-hour Chromium Release Assay. muT84.66 derived CEA-scFv-CAR T cells recognize and kill CEA+ target cells in a 4-hour chromium release assay. By comparison the humanized M5A derived CEA-scFv-CAR T cells do not kill CEA+ Target cells.

BSA-PBS. The cells were then labeled on ice for 1 h with: PE-anti-CD19 or isotype control, biotinylated anti-Fcγ followed by streptavidin-PE, or double-labeled with Pacific Blue-soluble HER2 and Alexa Fluor 488-meditope Fc (MFC). At the end of the incubations, the cells were washed once and resuspended in 800 μl of wash buffer. Sytox blue was added to the unlabeled cells for viability and membrane permeability assessments. Cells were gated with forward and side scatter only. Sytox Blue and Pacific Blue have considerable overlap in their spectra, thus the Sytox Blue signal of the unlabeled samples have "leaked" into the Pacific Blue channel. It has been noted that when CHO—S cells express membrane-bound proteins, their membrane becomes more permeable to Sytox Blue dye as shown with the group of cells in yellow oval. Both meCAR- and HER2CAR-transfected cells are CD19, CH3 and sHER2 positive, but only the meCAR is also positive for MFC binding.

Figure 11A:
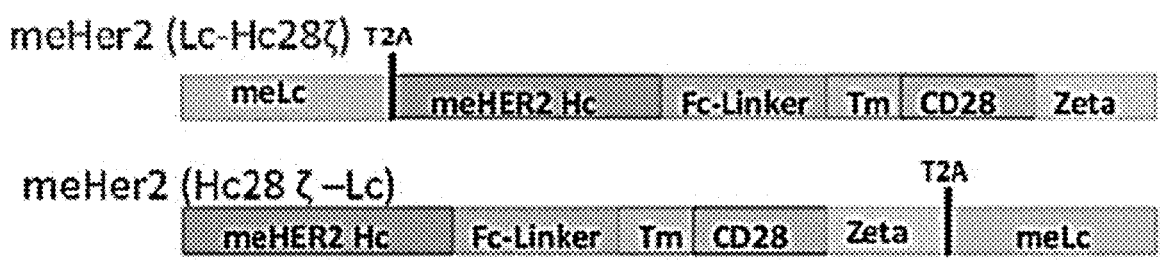
Figure 11B:
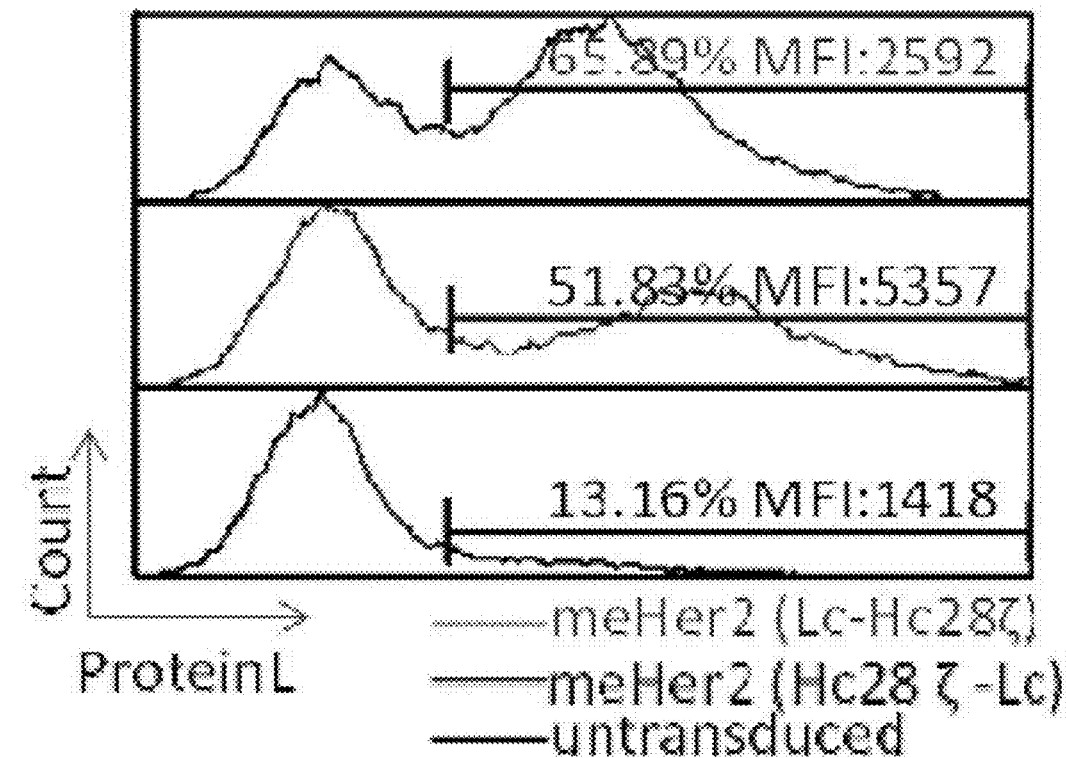
Figure 11B:
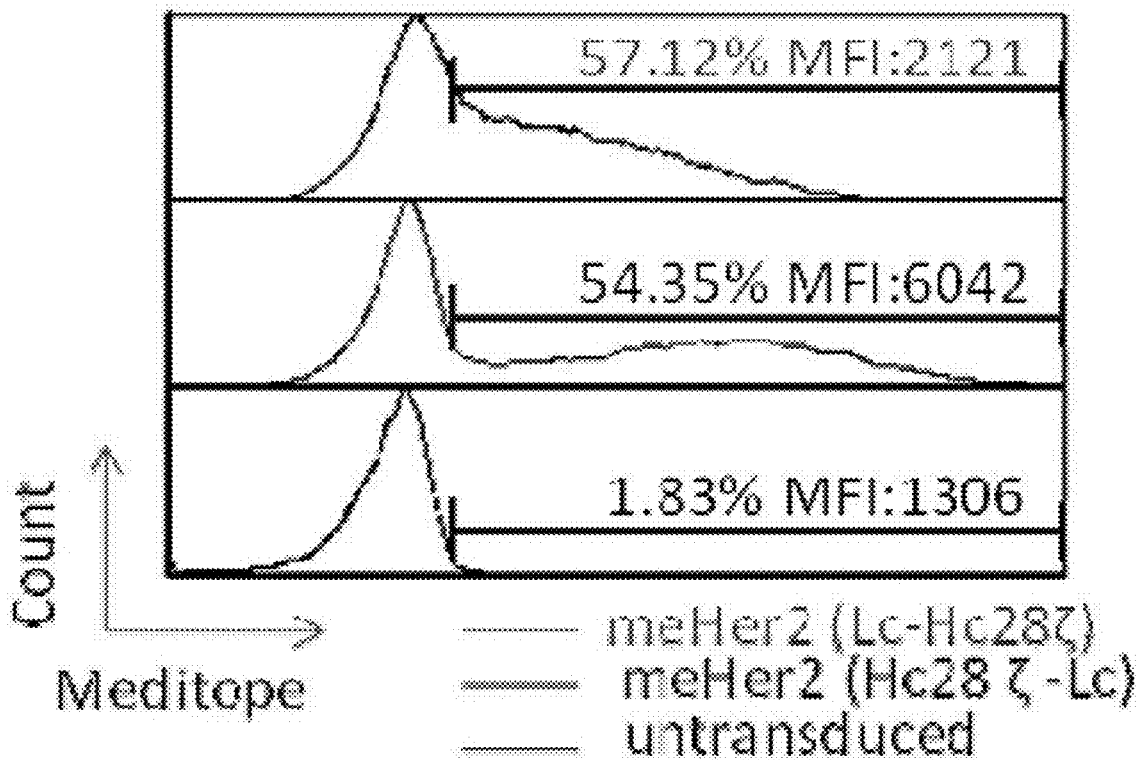
Figure 11C:
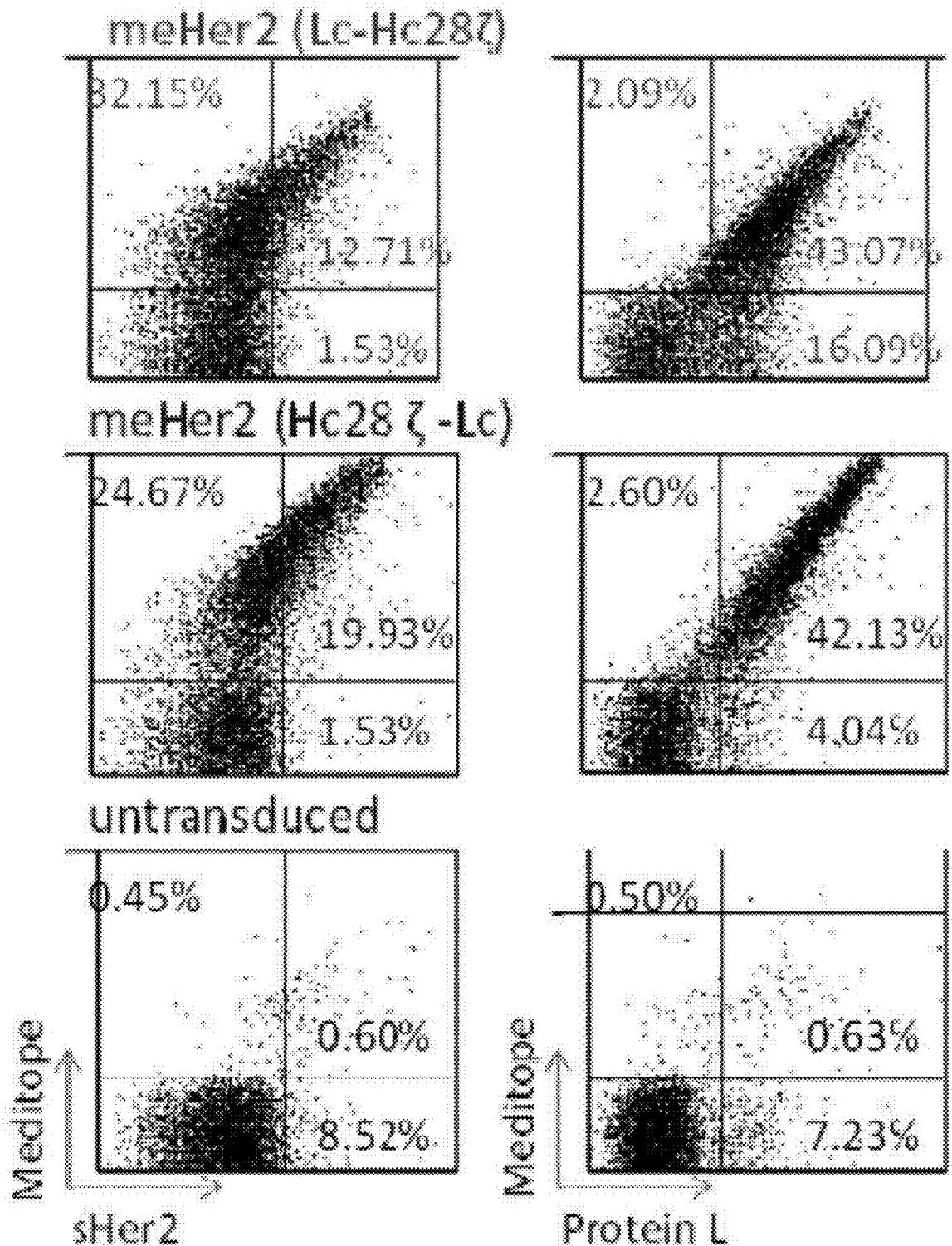

FIGS. 11A-11C. Expression of meditope-enabled Fab-CARs in primary human T cells. FIG. 11A: Schematic of meditope (me)-enabled trastuzumab Fab-CAR cassette (me-HER2), with the T2A ribosomal skip sequence separating the antibody light chain (meLc) and the heavy chain fused to the IgG4-CH3-Fc linker, CD28 transmembrane domain (Tm) and the CD28 and CD3ζ cytoplasmic signaling domains (Hc28ζ). Expression is driven by the EF1α promoter and was tested in two orientations: Lc-Hc28ζ and Hc28ζ-Lc. FIG. 11B: Primary human T cells were lentivirally transduced and expression of the meHER2-CARs was evaluated by flow cytometry. Protein L staining, which binds the Fab light chain, confirms cell surface expression of both CAR orientations, with higher expression levels (MFI) observed for the Hc28 ζ-Lc (MFI 5357) vs Lc-Hc28 ζ (MFI 2592) orientation. Meditope-AF647 staining confirms the functional formation of the CAR meditope pocket, with greater binding to the Hc28 ζ-Lc (MFI 6042) vs Lc-Hc28ζ (MFI 2121) orientation. FIG. 11C: meHER2-CAR T cells pre-bound to meditope peptide retain the ability to bind protein L and soluble HER2-antigen, suggesting that meditope binding does not alter antigen binding properties and structural components of the Fab.

Figure 12A:
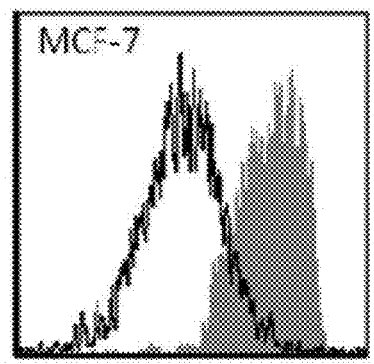
Figure 12A:
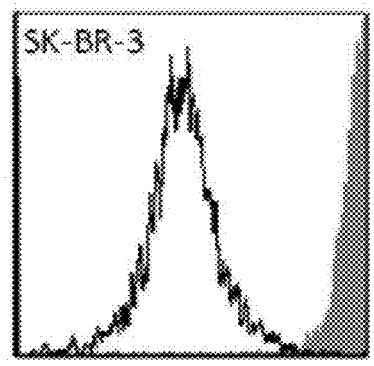
Figure 12B:
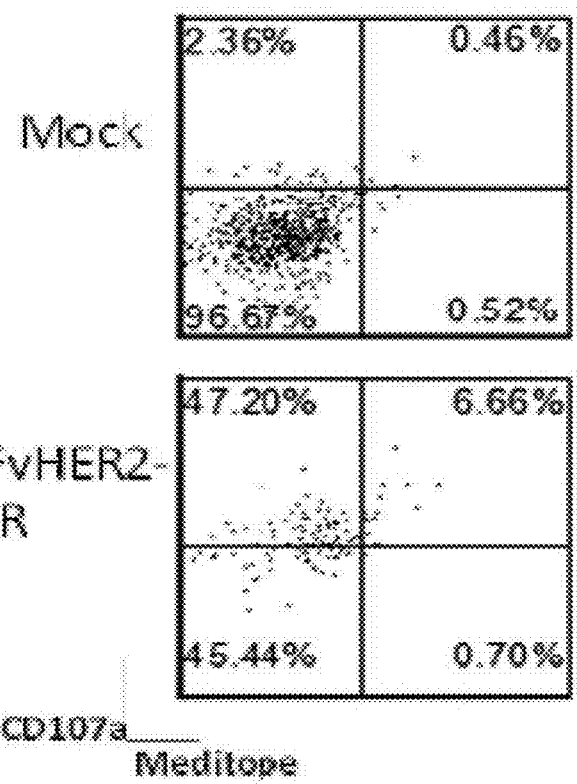
Figure 12C:
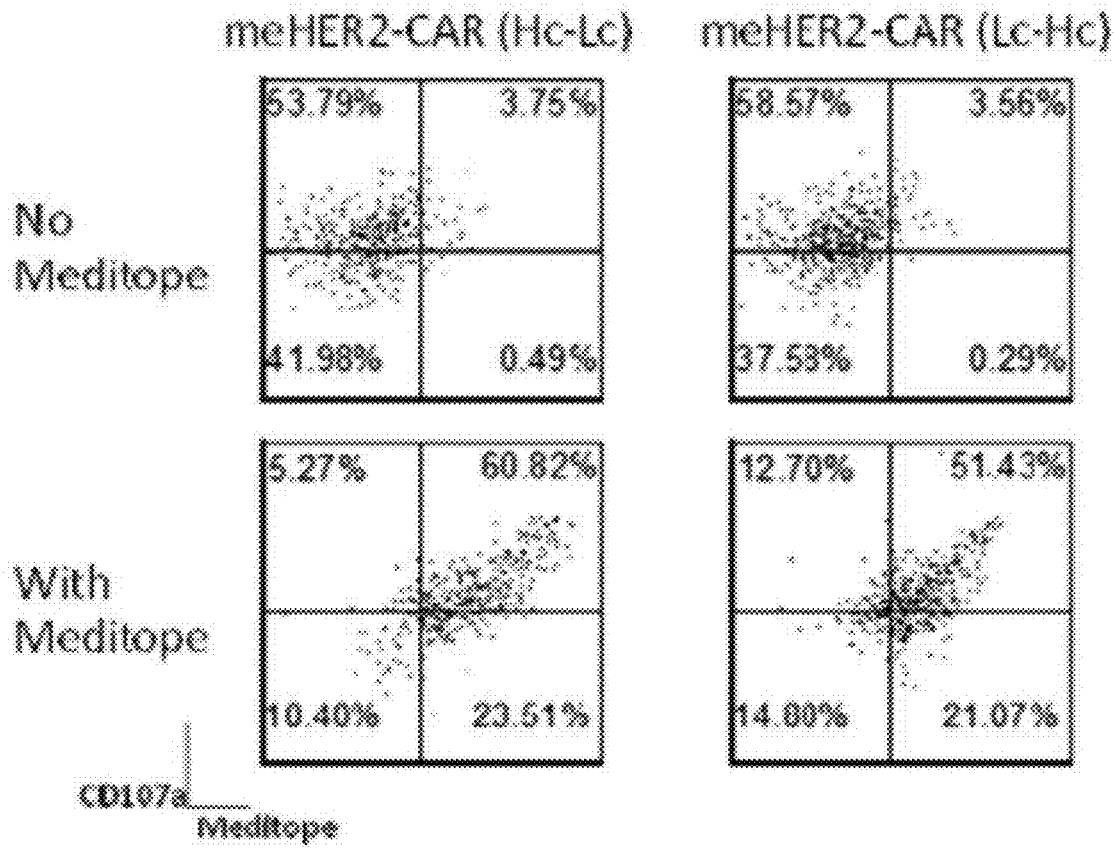
Figure 12D:
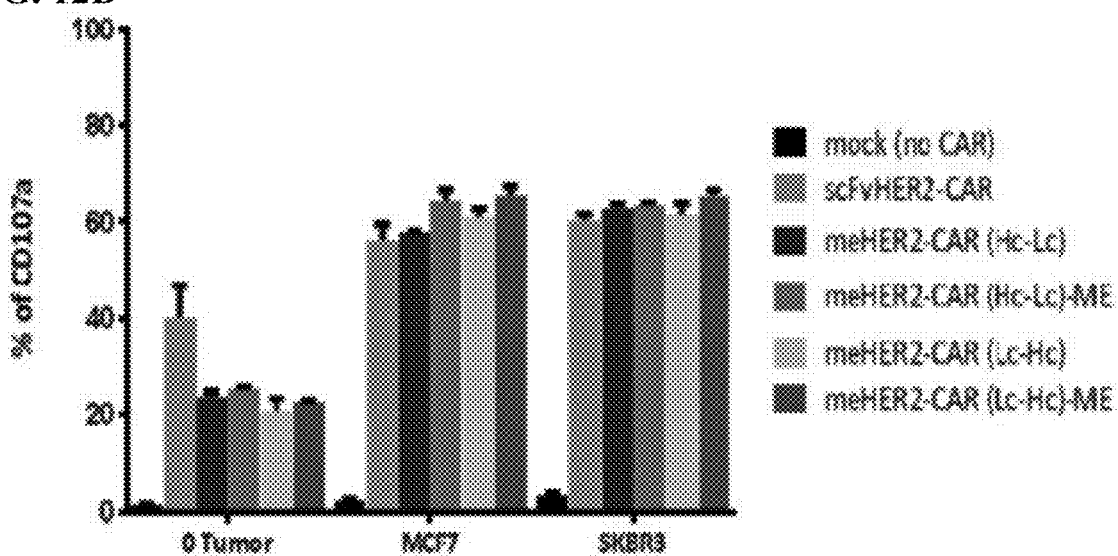

FIGS. 12A-12D. Meditope-enabled HER2-CAR (me-HER2) T cells degranulate at comparable levels to scFvHER2-CAR T cells in response to HER2+ targets and meditope peptide does not negatively impact T cell degranulation. FIG. 12A: HER2+ breast cancer lines MCF-7 and SK-BR-3 were assessed for cell surface expression of HER2 by flow cytometry (Biolegend; Cat #324413). MCF-7 expresses relatively low levels of HER2 as compared to SK-BR-3 which over-expresses HER2. FIGS. 12B-12D CD107a degranulation assay. HD187.2 T cells were engineered to express either meHER2(Hc-Lc):28ζ CAR, meHER2 (Lc-Hc):28ζ CAR, scFvHER2:28ζ CAR or no CAR (mock). Versions of the meHER2:28ζ-CAR differ only in the orientation of the heavy chain (Hc) and light chain (Lc), see FIG. 11A. FIG. 12B: Representative FACs showing CD107a degranulation for mock T cells (negative control) and scFvHER2-CAR T cells (positive control) following co-culture at a 1:1 effector to MCF-7 ratio (based on CAR expression) for 5 hours. CD107a degranulation (BD Pharmingen™; Cat #555800), gated on CAR+ CD8+ cells, was detected by flow cytometry (Miltenyi Biotec; MACSQuant) and analyzed using FCS Express (De Novo Software). FIG. 12C: meHER2(Hc-Lc):28ζ and meHER2 (Lc-Hc):28ζ T cells were incubated with and without meditope-AF647 (ME; 200 nM) and degranulation to MCF-7 targets was evaluated as described in FIG. 12B. FIG. 12D: Bar graph depicting comparable degranulation of all meHER2 and scFvHER2-CAR T cell lines to either MCF-7 or SK-BR-3. meHER2-CAR T cells incubated with and without meditope peptide show comparable activation as assessed by CD107a degranulation. Plotted are average and standard deviation of three wells per condition. Cells were gated on the CD8 CAR population.

Figure 13A:
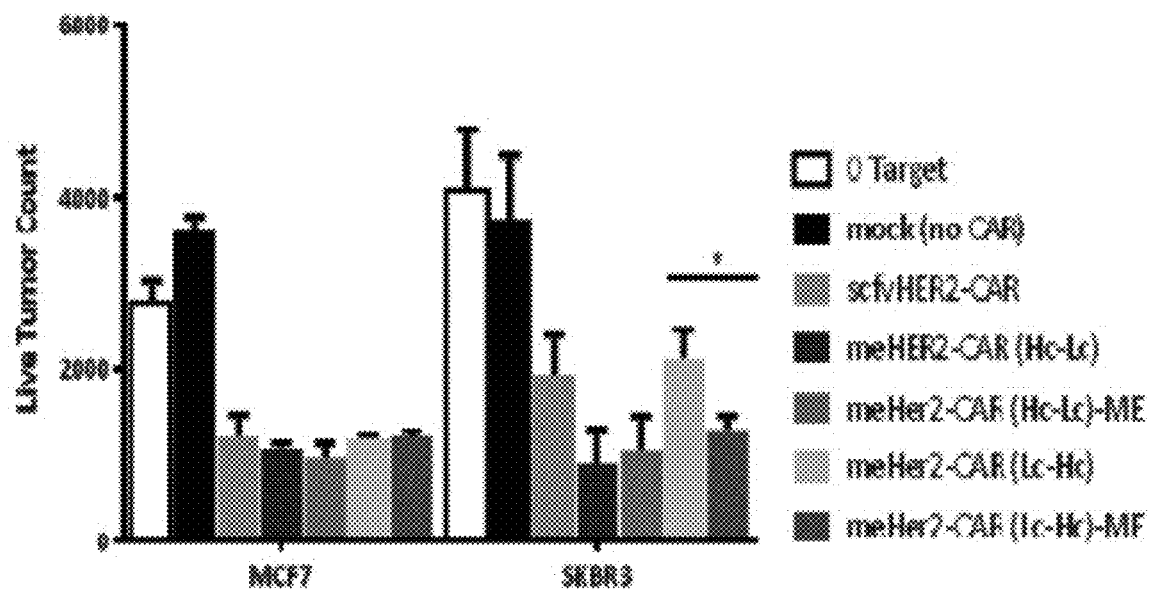
Figure 13B:
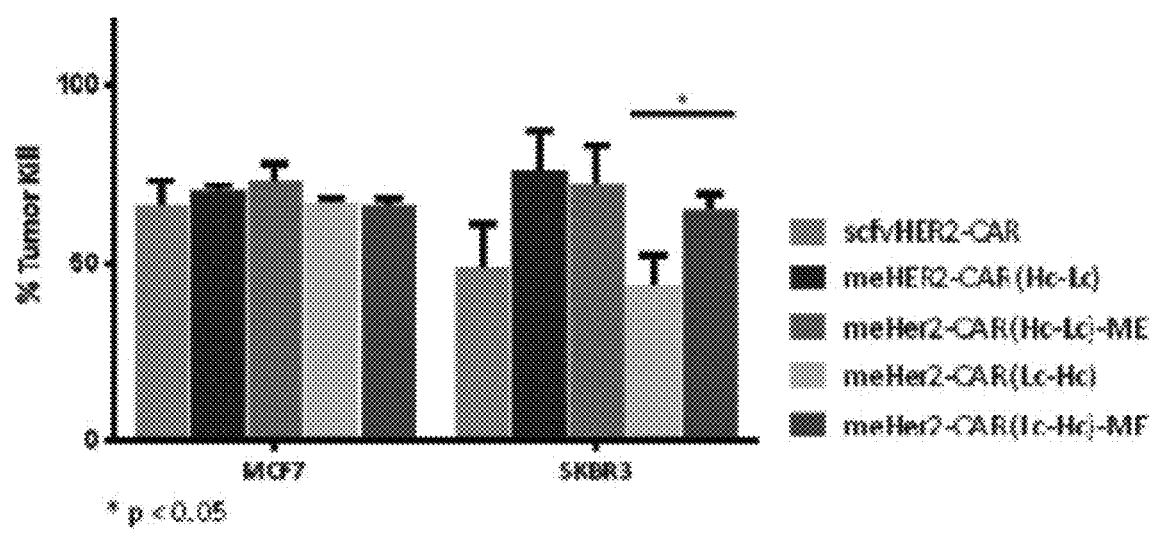

FIGS. 13A-13B. Meditope-enabled HER2-CARs (me-HER2) and scFvHER2 CAR-engineered T cells kill HER2+ targets at comparable efficiency and meditope peptide does not negatively impact T cell killing. Long term killing assay to compare killing potency of meHER2 and scFvHER2-CAR T cells. HD187.2 T cells were engineered to express either meHER2(Hc-Lc):28ζ CAR, meHER2(Lc-Hc):28ζ CAR, scFvHER2:28ζ CAR or no CAR (mock). Versions of the meHER2:28ζ-CAR differ only in the orientation of the heavy chain (Hc) and light chain (Lc), see FIG. 11A. HER2-CAR T cells lines, or mock control were co-cultured with HER2 breast cancer lines, MCF-7 and SKBR3, for 48-hours at a 1:4 effector to target ratio (based on CAR expression). Killing was assessed by quantifying the number of live tumor cells remaining after co-incubation. A viability stain, DAPI (Molecular Probes™; Cat #D21490) and a human leukocyte antigen, CD45 (BD Biosciences; Cat #347464), were used to exclude the dead cells and T cells from the live tumor count. meCAR-T cells were incubated with and without meditope-AF647 (200 nM) prior to co-culture to evaluate the impact of meditope peptide on meHER2 redirected killing potential. FIG. 13A; Bar graph depicts the average live tumor count (DAPI-CD45−) of three replicate wells per combination. FIG. 13B: Bar graph represents the percent tumor killed per condition when normalized to mock.

Figure 14A:
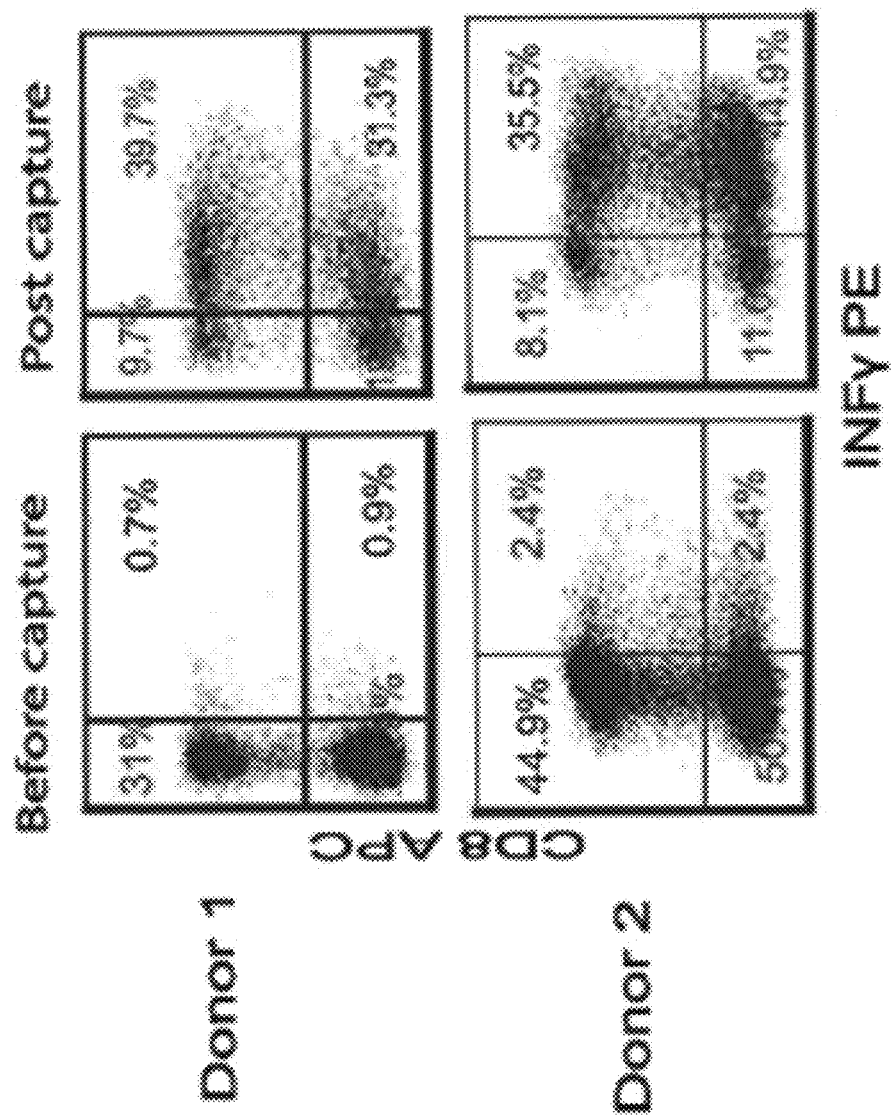
Figure 14B:
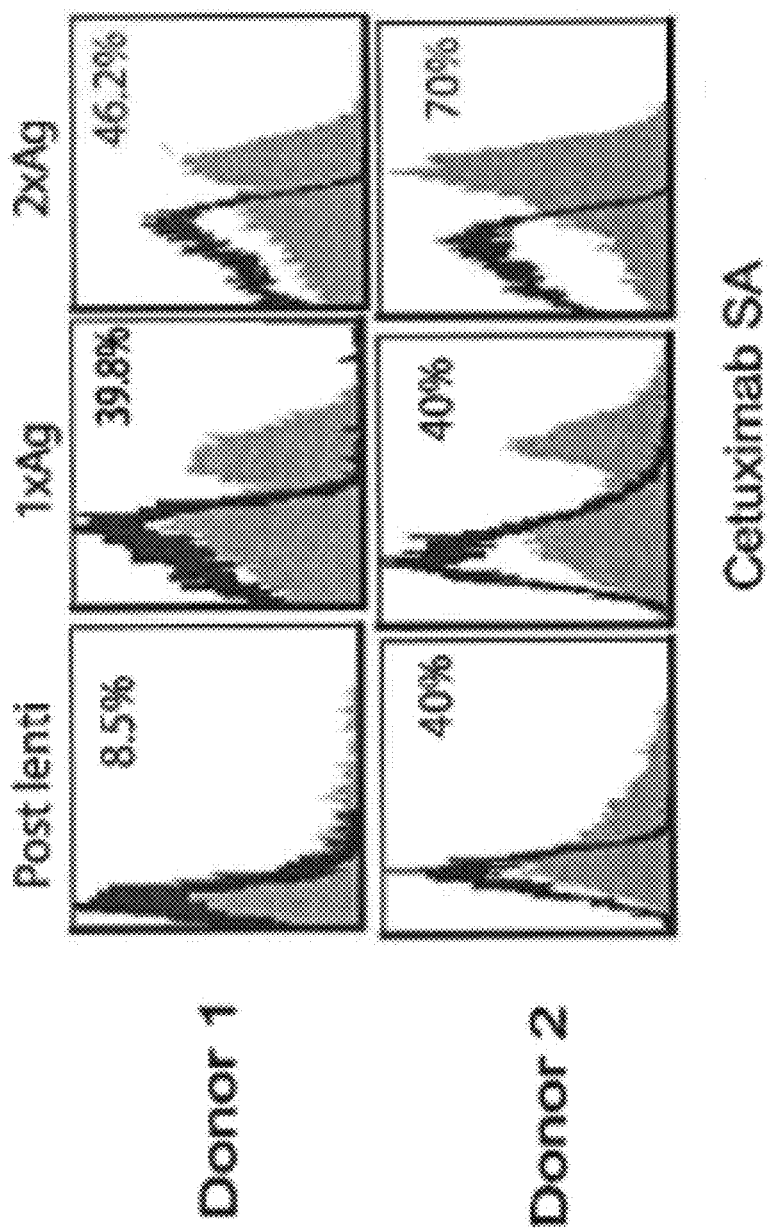
Figure 14C:
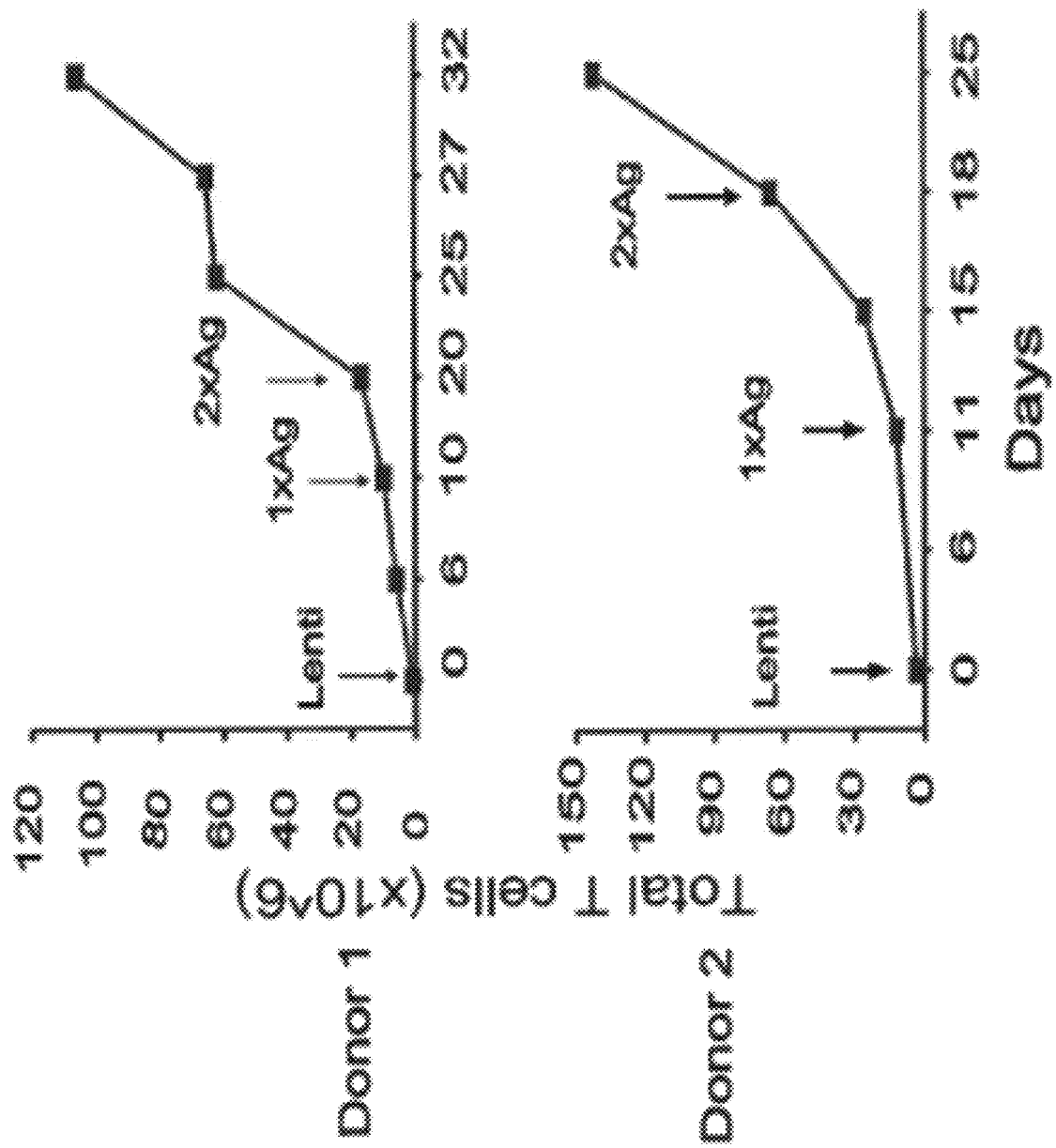

FIGS. 14A-14D depict the development of clinically feasible platform for derivation of CMV/CAR T cells and the schematic structure of a lentiviral vector expressing a CD19 CAR. FIG. 14A: CMV-specific T cells from CMV immune HLA A2 donors were selected using IFNγ capture after overnight stimulation with cGMP grade CMVpp65 protein. After selection, the cells were stained with antibodies specific to IFNγ, CD4, and CD8. The frequency of each population is presented after exclusion of dead cells with DAPI. FIG. 14B: The selected cells were transduced with the second generation CD19CAR with a double mutation in the spacer, 24 hours after the IFNγ capture. 7-10 days later, the transduced cells were stimulated with irradiated CD19 expressing NIH3T3 cells at 10:1 ratio (3T3:T cells) and the stimulation was repeated 7 days post the first stimulation. CAR expression was defined by cetuximab-biotin and streptavidin (SA) APC-Cy7 staining. Percentages of CAR+ cells are indicated in each histogram (filled gray), and based on subtraction of that stained with SA-APC-Cy7 alone (black line). FIG. 14C: Growth of total cell number was determined by Guava Viacount at different time points. FIG. 14D: Schematic diagram of 10039 nt lentiviral vector encoding a CD19 CAR. Within the 3183 nucleotide long CD19R: CD28:z(CO)-T2A-EGFRt construct, the CD19-specific scFv, IgG4 Fc spacer, the CD28 transmembrane and cytoplasmic signaling domains, three-glycine linker, and CD3z cytoplasmic signaling domains of the CD19R:CD28:z(CO) CAR containing the 2 point mutations, L235E and N297Q, in the CH2 portion of the IgG4 spacer (CD19R(EQ)), as well as the T2A ribosome skip and truncated EGFR sequences are indicated. The human GM-CSF receptor alpha signal sequences that drive surface translocation of the CD19R: CD28:z(CO) CAR and EGFRt are also indicated.

Figure 15A:
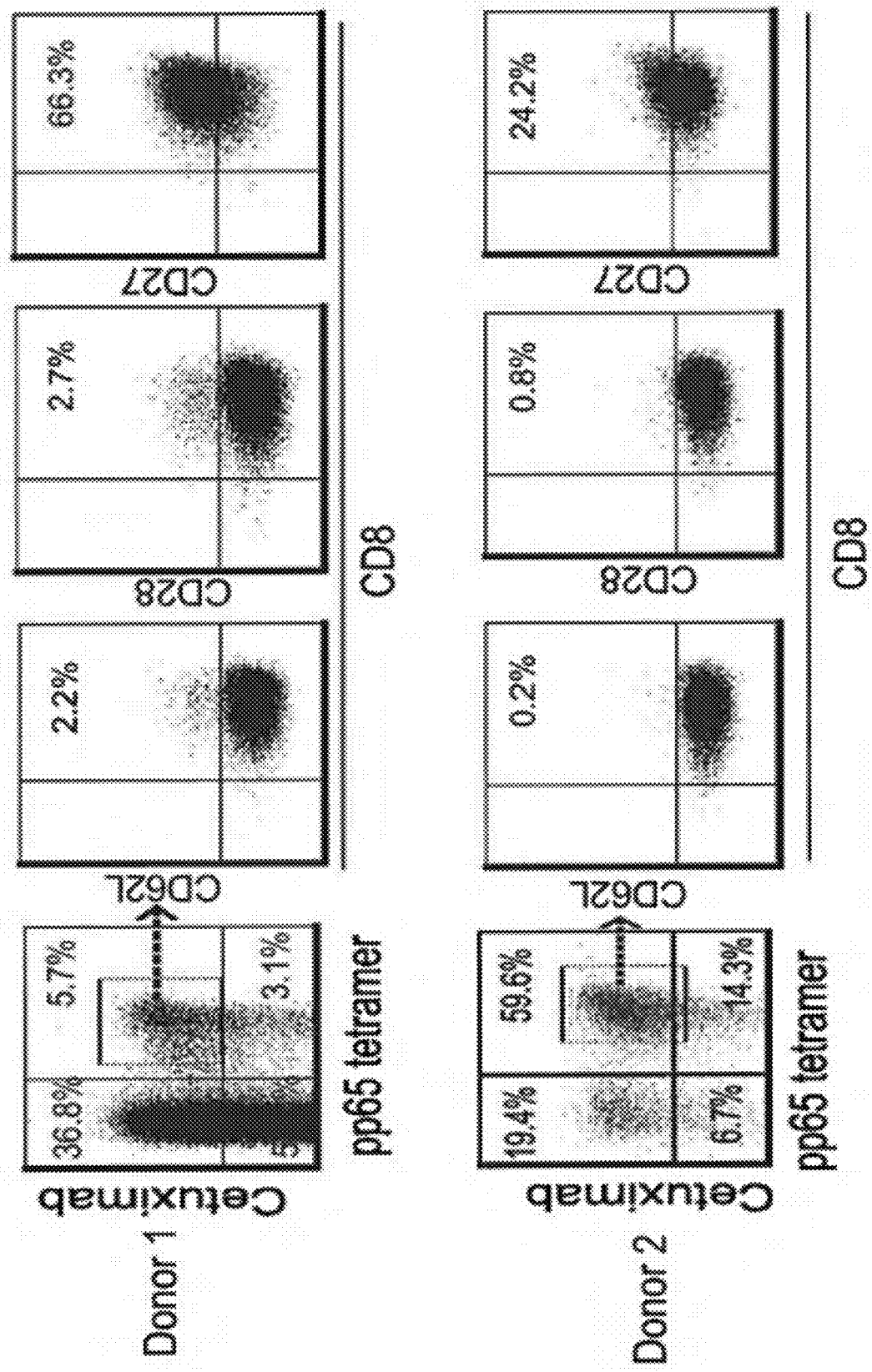
Figure 15B:
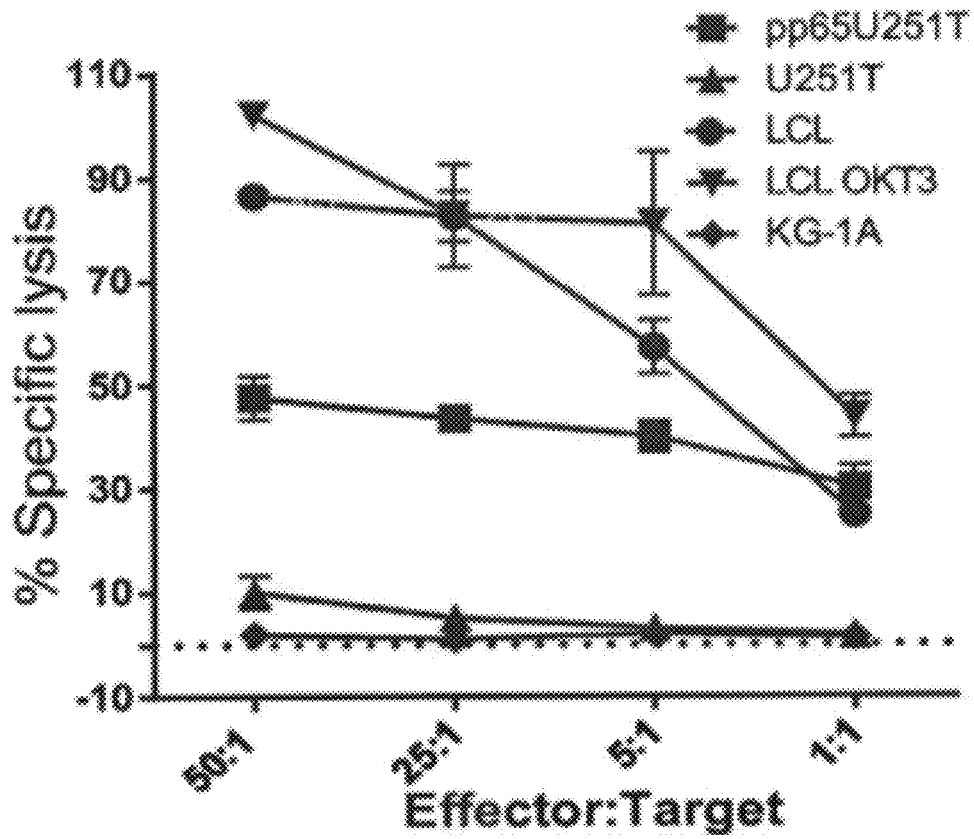
Figure 15C:
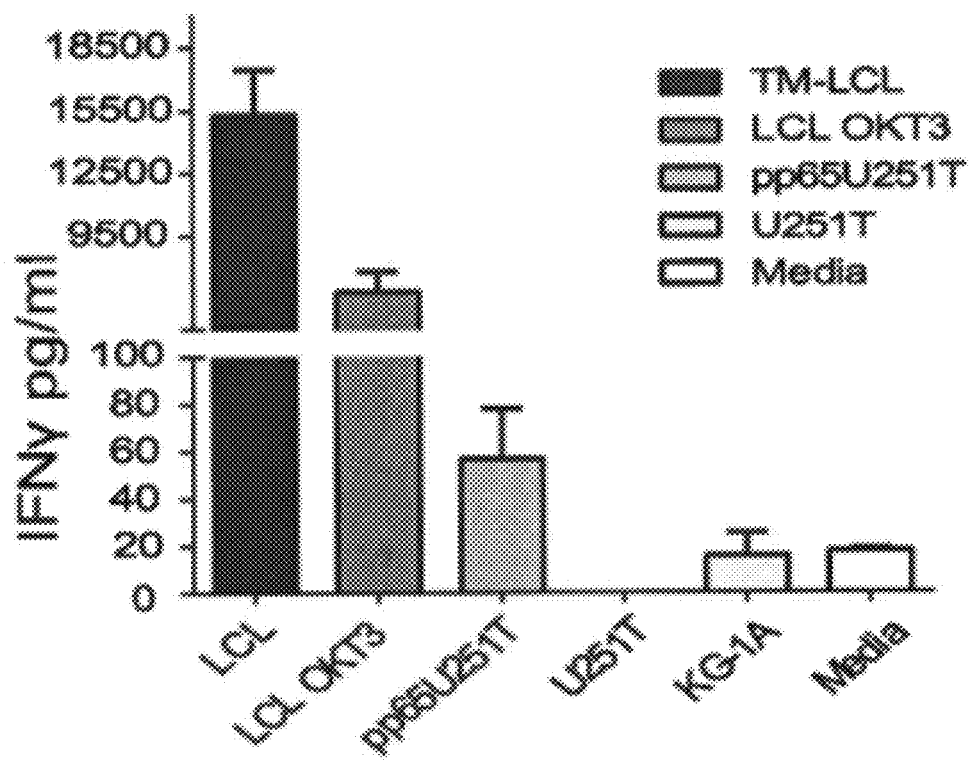
Figure 15D:
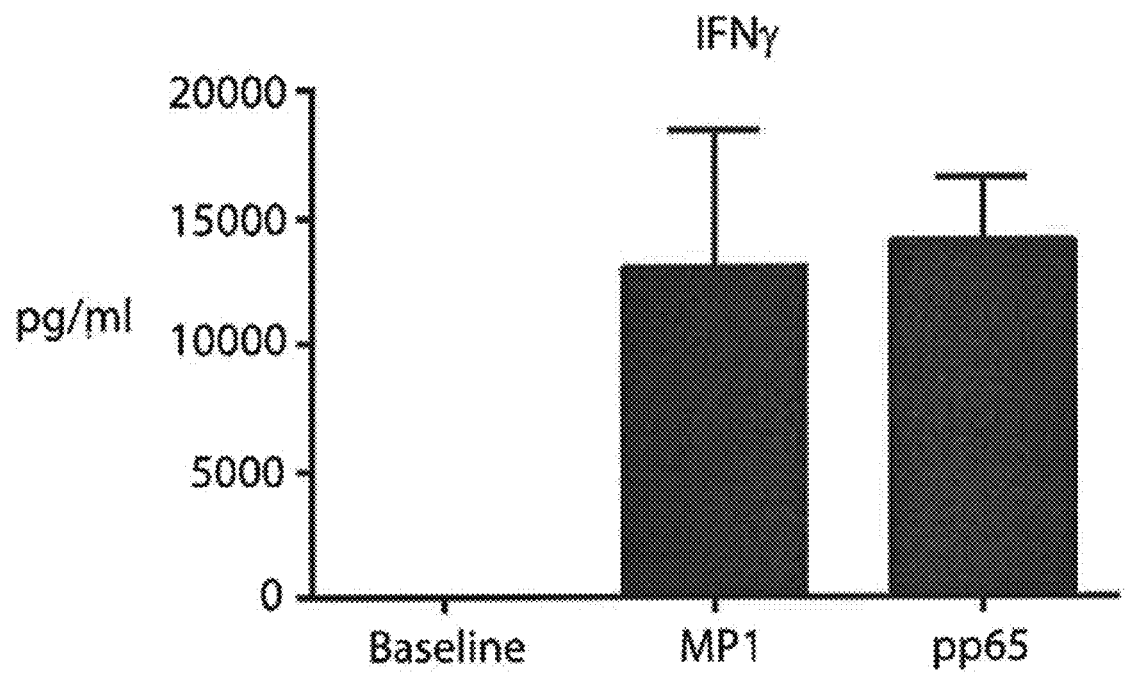
Figure 15D:
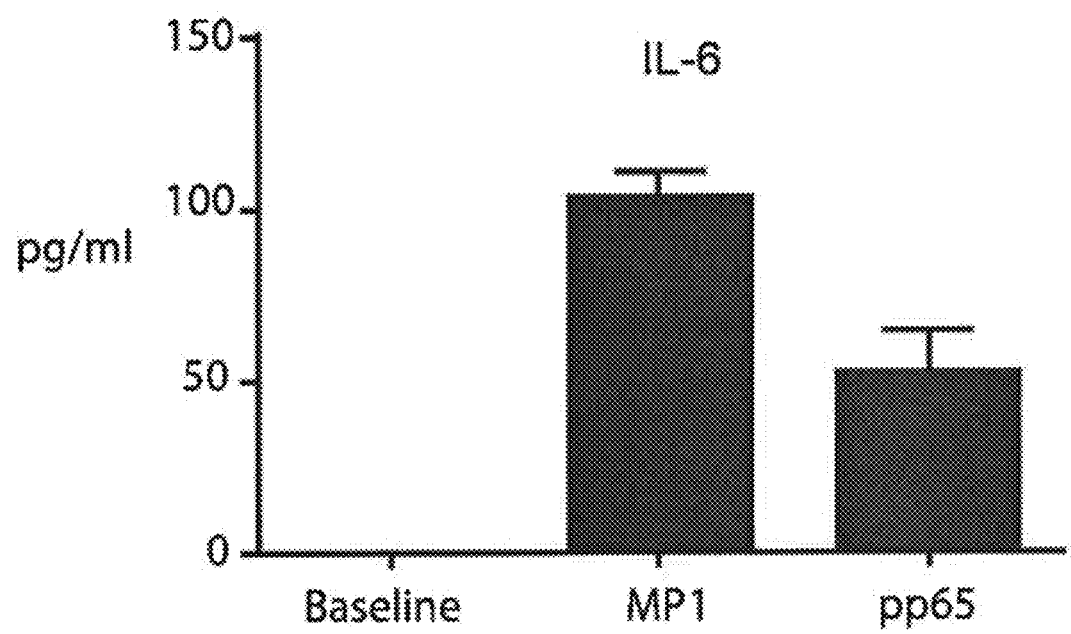

FIGS. 15A-15D. FIGS. 15A-15C depict the results of studies demonstrating that CMV/CAR T cells exhibit specific effector function after engagement with CD19+ and CMVpp65+ tumors. FIG. 15A: 7 days after the second CD19 Ag stimulation, T cells were stained with HLA A2 restricted pp65 tetramer, cetuximab-biotin, anti-CD8 and antibodies specific to central memory T cell surface markers. Percent positive cells are indicated after dead cell exclusion with DAPI, gating based on pp65 tetramer and cetuximab double-positivity, and isotype-matched stained samples. FIG. 15B: Four-hour $^{51}$Cr release assays were performed using the CMV/CAR T cells and indicated $^{51}$Cr-labeled target cells at different effector:target (E:T) ratios. OKT3-expressing LCLs were used as positive controls, KG1A and U251T as negative controls. CD19+ LCL and engineered pp65U251T cells were used as target for CD19 and CMV-specific T cells, respectively. Data from a representative donor is presented. FIG. 15C: CMV/CAR T cells ($10^5$) were activated overnight with $10^5$ LCL-OKT3, LCL, or KG1a in 96-well tissue culture plates and $10^5$ U251T and engineered pp65 expressing U251T cells (pp65U251T) in 24-well tissue culture plates. Supernatants were collected after overnight co-incubation of CMV/CAR T cells and stimulators. Cytokine levels with indicated stimulators (means±SEM of triplicate wells) were determined using cytometric bead array. FIG. 15D depicts the results of studies examining cytokine levels in the serum of CMV/CAR T cell treated tumor bearing mice. NSG mice were injected i.v. on day 0 with $2.5\times10^6$ GFPffluc+ LCL cells. Three days after tumor inoculation, recipient mice were administered i.v. with 2×106 CMV/CAR cells that underwent 2 rounds of CD19 stimulation. Vaccine was given by i.v. injection of peptide (pp65 or MP1) pulsed autologous T cells on day 14. Thirteen days post vaccine, serum of recipient mice was collected and levels of human cytokines were determined by cytometric bead array. Cytokine levels in the serum of untreated mice was used as baseline. Mean and SEMs from triplicates are presented.

DETAILED DESCRIPTION OF THE INVENTION

Definitions

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable non-cyclic straight or branched chain, or combinations thereof, including at least one carbon atom and at least one heteroatom (e.g. O, N, P, Si or S) and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—

S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S(O$_2$)—R', where R' is a substituted or unsubstituted alkyl group as defined above. R' may have a specified number of carbons (e.g., "C$_1$-C$_4$ alkylsulfonyl").

Each of the above terms (e.g., "alkyl," "heteroalkyl,", "cycloalkyl", "heterocycloalkyl", "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R")=NR''', —S(O)R', —S(O)$_2$R', —S(O)$_2$N(R)('R"—NRSO$_2$R'), —CN, and —NO$_2$ in a number ranging from zero to (2m'+1), where m' is the total number of carbon atoms in such radical. R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', NR"C(O)$_2$R', NRC(NR'R")=NR''', S(O)R', —S(O)$_2$R', —S(O)$_2$N(R')(R", —NRSO$_2$R'), —CN, —NO$_2$, —R', —N$_3$, —CH(Ph)$_2$, fluoro(C$_1$-C$_4$)alkoxy, and fluoro (C$_1$-C$_4$)alkyl, in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R'''' groups when more than one of these groups is present.

Where a moiety is substituted with an R substituent, the group may be referred to as "R-substituted." Where a moiety is R-substituted, the moiety is substituted with at least one R substituent and each R substituent is optionally different. For example, where a moiety herein is $R^{1A}$-substituted or unsubstituted alkyl, a plurality of $R^{1A}$ substituents may be attached to the alkyl moiety wherein each $R^{1A}$ substituent is optionally different. Where an R-substituted moiety is substituted with a plurality R substituents, each of the R-substituents may be differentiated herein using a prime symbol (') such as R', R", etc. For example, where a moiety is $R^{3A}$-substituted or unsubstituted alkyl, and the moiety is substituted with a plurality of $R^{3A}$ substituents, the plurality of $R^{3A}$ substituents may be differentiated as $R^{3A'}$, $R^{3A''}$, $R^{3A'''}$, etc. In some embodiments, the plurality of R substituents is 3. In some embodiments, the plurality of R substituents is 2.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where variables s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

As used herein, the term "conjugate" refers to the association between atoms or molecules. The association can be direct or indirect. For example, a conjugate between a nucleic acid and a protein can be direct, e.g., by covalent bond, or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive moieties or functional groups used for conjugate chemistries (including "click chemistries" as known in the art) herein include, for example:

(a) carboxyl groups and various derivatives thereof including, but not limited to, N-hydroxysuccinimide esters, N-hydroxybenzotriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold;

(h) amine or sulfhydryl groups, which can be, for example, acylated, alkylated or oxidized;

(i) alkenes, which can undergo, for example, cycloadditions, acylation, Michael addition, etc.;

(j) epoxides, which can react with, for example, amines and hydroxyl compounds;

(k) phosphoramidites and other standard functional groups useful in nucleic acid synthesis;

(l) metal silicon oxide bonding;

(m) metal bonding to reactive phosphorus groups (e.g. phosphines) to form, for example, phosphate diester bonds; and (n) sulfones, for example, vinyl sulfone.

Chemical synthesis of compositions by joining small modular units using conjugate ("click") chemistry is well known in the art and described, for example, in H. C. Kolb, M. G. Finn and K. B. Sharpless ((2001). "Click Chemistry: Diverse Chemical Function from a Few Good Reactions". Angewandte Chemie International Edition 40 (11): 2004-2021); R. A. Evans ((2007). "The Rise of Azide-Alkyne 1,3-Dipolar 'Click' Cycloaddition and its Application to Polymer Science and Surface Modification". Australian Journal of Chemistry 60 (6): 384-395; W. C. Guida et al. Med. Res. Rev. p 3 1996; Spiteri, Christian and Moses, John E. ((2010). "Copper-Catalyzed Azide-Alkyne Cycloaddition: Regioselective Synthesis of 1,4,5-Trisubstituted 1,2,3-Triazoles". Angewandte Chemie International Edition 49 (1): 31-33); Hoyle, Charles E. and Bowman, Christopher N. ((2010). "Thiol-Ene Click Chemistry". Angewandte Chemie International Edition 49 (9): 1540-1573); Blackman, Melissa L. and Royzen, Maksim and Fox, Joseph M. ((2008). "Tetrazine Ligation: Fast Bioconjugation Based on Inverse-Electron-Demand Diels-Alder Reactivity". Journal of the American Chemical Society 130 (41): 13518-13519); Devaraj, Neal K. and Weissleder, Ralph and Hilderbrand, Scott A. ((2008). "Tetrazine Based Cycloadditions: Application to Pretargeted Live Cell Labeling". Bioconjugate Chemistry 19 (12): 2297-2299); Stöckmann, Henning; Neves, Andre; Stairs, Shaun; Brindle, Kevin; Leeper, Finian ((2011). "Exploring isonitrile-based click chemistry for ligation with biomolecules". Organic & Biomolecular Chemistry), all of which are hereby incorporated by reference in their entirety and for all purposes.

The reactive functional groups can be chosen such that they do not participate in, or interfere with, the chemical stability of the proteins or nucleic acids described herein. By way of example, the nucleic acids can include a vinyl sulfone or other reactive moiety (e.g., maleimide). Optionally, the nucleic acids can include a reactive moiety having the formula —S—S—R. R can be, for example, a protecting group. Optionally, R is hexanol. As used herein, the term hexanol includes compounds with the formula $C_6H_{13}OH$ and includes, 1-hexanol, 2-hexanol, 3-hexanol, 2-methyl-1-pentanol, 3-methyl-1-pentanol, 4-methyl-1-pentanol, 2-methyl-2-pentanol, 3-methyl-2-pentanol, 4-methyl-2-pentanol, 2-methyl-3-pentanol, 3-methyl-3-pentanol, 2,2-dimethyl-1-butanol, 2,3-dimethyl-1-butanol, 3,3-dimethyl-1-butanol, 2,3-dimethyl-2-butanol, 3,3-dimethyl-2-butanol, and 2-ethyl-1-butanol. Optionally, R is 1-hexanol.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "cell" as used herein, refers to a cell carrying out metabolic or other functions sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

The term "peptidyl" and "peptidyl moiety" refers to a monovalent peptide.

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

A "labeled protein or polypeptide" is one that is bound, either covalently, through a linker or a chemical bond, or noncovalently, through ionic, van der Waals, electrostatic, or hydrogen bonds to a label such that the presence of the labeled protein or polypeptide may be detected by detecting the presence of the label bound to the labeled protein or polypeptide. Alternatively, methods using high affinity interactions may achieve the same results where one of a pair of binding partners binds to the other, e.g., biotin, streptavidin.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An amino acid modification refers to an amino acid substitution, insertion, and/or deletion in a protein or peptide sequence. An "amino acid substitution" or "substitution" refers to replacement of an amino acid at a particular position in a parent peptide or protein sequence with another amino acid. A substitution can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. The following are examples of various groupings of amino acids: 1) Amino acids with nonpolar R groups: Alanine, Valine, Leucine, Isoleucine, Proline, Phenylalanine, Tryptophan, Methionine; 2) Amino acids with uncharged polar R groups: Glycine, Serine, Threonine, Cysteine, Tyrosine, Asparagine, Glutamine; 3) Amino acids with charged polar R groups (negatively charged at pH 6.0): Aspartic acid, Glutamic acid; 4) Basic amino acids (positively charged at pH 6.0): Lysine, Arginine, Histidine (at pH 6.0). Another grouping may be those amino acids with phenyl groups: Phenylalanine, Tryptophan, and Tyrosine.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that may be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence. An amino acid residue in a protein "corresponds" to a given residue when it occupies the same essential structural position within the protein as the given residue. For example, a selected residue in a selected antibody (or Fab domain) corresponds to light chain threonine at Kabat position 40, when the selected residue occupies the same essential spatial or other structural relationship as a light chain threonine at Kabat position 40. In some embodiments, where a selected protein is aligned for maximum homology with the light chain of an antibody (or Fab domain), the position in the aligned selected protein aligning with threonine 40 is said to correspond to threonine 40. Instead of a primary sequence alignment, a three dimensional structural alignment can also be used, e.g., where the structure of the selected protein is aligned for maximum correspondence with the light chain threonine at Kabat position 40, and the overall structures compared. In this case, an amino acid that occupies the same essential position as threonine 40 in the structural model is said to correspond to the threonine 40 residue.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids sequences encode any given amino acid residue. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers to nucleic acids that have the same basic chemical structure as a naturally occurring nucleic acid. Such analogues have modified sugars and/or modified ring substituents, but retain the same basic chemical structure as the naturally occurring nucleic acid. A nucleic acid mimetic refers to chemical compounds that have a structure that is different the general chemical structure of a nucleic acid, but that functions in a manner similar to a naturally occurring nucleic acid. Examples of such analogues include, without limitation, phosphorothiolates, phosphoramidates, methyl phosphonates, chiral-methyl phosphonates, 2-O-methyl ribonucleotides, and peptide-nucleic acids (PNAs).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length. The present invention includes polypeptides that are substantially identical to any of SEQ ID NOs: 1-35.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross-reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al., 1989 *Molecular Cloning: A Laboratory Manual*, 18.1-18.88.

Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell. Expression of a transfected gene can further be accomplished by transposon-mediated insertion into to the host genome. During transposon-mediated insertion, the gene is positioned in a predictable manner between two transposon linker sequences that allow insertion into the host genome as well as subsequent excision. Stable expression of a transfected gene can further be accomplished by infecting a cell with a lentiviral vector, which after infection forms part of (integrates into) the cellular genome thereby resulting in stable expression of the gene.

The terms "plasmid", "vector" or "expression vector" refer to a nucleic acid molecule that encodes for genes and/or regulatory elements necessary for the expression of genes. Expression of a gene from a plasmid can occur in cis or in trans. If a gene is expressed in cis, the gene and the regulatory elements are encoded by the same plasmid. Expression in trans refers to the instance where the gene and the regulatory elements are encoded by separate plasmids.

The terms "transfection", "transduction", "transfecting" or "transducing" can be used interchangeably and are defined as a process of introducing a nucleic acid molecule or a protein to a cell. Nucleic acids are introduced to a cell using non-viral or viral-based methods. The nucleic acid molecules may be gene sequences encoding complete proteins or functional portions thereof. Non-viral methods of transfection include any appropriate transfection method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. In some embodiments, the nucleic acid molecules are introduced into a cell using electroporation following standard procedures well known in the art. For viral-based methods of transfection any useful viral vector may be used in the methods described herein. Examples for viral vectors include, but are not limited to retroviral, adenoviral, lentiviral and adeno-associated viral vectors. In some embodiments, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) *Gene Therapy* 8:1-4 and Prochiantz (2007) *Nat. Methods* 4:119-20.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody plays a significant role in determining the specificity and affinity of binding. In some embodiments, antibodies or fragments of antibodies may be derived from different organisms, including humans, mice, rats, hamsters, camels, etc. Antibodies of the invention may include antibodies that have been modified or mutated at one or more amino acid positions to improve or modulate a desired function of the antibody (e.g. glycosylation, expression, antigen recognition, effector functions, antigen binding, specificity, etc.).

Antibodies are large, complex molecules (molecular weight of ~150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions come together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-dimensional space to form the actual antibody binding site which docks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) or light chain variable region and variable heavy chain (VH) or heavy chain variable region refer to these light and heavy chain regions, respectively. The terms variable light chain (VL) and light chain variable region as referred to herein may be used interchangeably. The terms variable heavy chain (VH) and heavy chain variable region as referred to herein may be used interchangeably. The Fc (i.e. fragment crystallizable region) is the "base" or "tail" of an immunoglobulin and is typically composed of two heavy chains that contribute two or three constant domains depending on the class of the antibody. By binding to specific proteins the Fc region ensures that each antibody generates an appropriate immune response for a given antigen. The Fc region also binds to various cell receptors, such as Fc receptors, and other immune molecules, such as complement proteins.

The term "antigen" as provided herein refers to molecules capable of binding to the antibody region provided herein, wherein the binding site is not the peptide binding site.

Antibodies exist, for example, as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially the antigen binding portion with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

A single-chain variable fragment (scFv) is typically a fusion protein of the variable regions of the heavy (VH) and light chains (VL) of immunoglobulins, connected with a short linker peptide of 10 to about 25 amino acids. The linker may usually be rich in glycine for flexibility, as well as serine or threonine for solubility. The linker can either connect the N-terminus of the VH with the C-terminus of the VL, or vice versa.

The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 30% but preferably 50%, 75%, 90% or even 99% as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

For preparation of suitable antibodies of the invention and for use according to the invention, e.g., recombinant, monoclonal, or polyclonal antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633, 425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676, 980, WO 91/00360; WO 92/200373; and EP 03089).

Methods for humanizing or primatizing non-human antibodies are well known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) Nature 321:522; and Verhoyen et al. (1988) Science 239:1534). Humanized antibodies are further described in, e.g., Winter and Milstein (1991) Nature 349:293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immunol., 44:65-92 (1988), Verhoeyen et al., Science 239:1534-1536 (1988) and Presta, Curr. Op. Struct. Biol. 2:593-596 (1992), Padlan, Molec. Immun., 28:489-498 (1991); Padlan, Molec. Immun., 31(3): 169-217 (1994)), by substituting rodent CDRs or CDR sequences for the corresponding sequences of a human antibody. Accordingly, such humanized antibodies are chimeric antibodies (U.S. Pat. No. 4,816, 567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

A "therapeutic antibody" as provided herein refers to any antibody or functional fragment thereof that is used to treat cancer, autoimmune diseases, transplant rejection, cardiovascular disease or other diseases or conditions such as those described herein. Non-limiting examples of therapeutic antibodies include murine antibodies, murinized or humanized chimera antibodies or human antibodies including, but not limited to, Erbitux (cetuximab), ReoPro (abciximab), Simulect (basiliximab), Remicade (infliximab); Orthoclone OKT3 (muromonab-CD3); Rituxan (rituximab), Bexxar (tositumomab) Humira (adalimumab), Campath (alemtuzumab), Simulect (basiliximab), Avastin (bevacizumab), Cimzia (certolizumab pegol), Zenapax (daclizumab), Soliris (eculizumab), Raptiva (efalizumab), Mylotarg (gemtuzumab), Zevalin (ibritumomab tiuxetan), Tysabri (natalizumab), Xolair (omalizumab), Synagis (palivizumab), Vectibix (panitumumab), Lucentis (ranibizumab), and Herceptin (trastuzumab).

Techniques for conjugating therapeutic agents to antibodies are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery ($2^{nd}$ Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)). As used herein, the term "antibody-drug conjugate" or "ADC" refers to a therapeutic agent conjugated or otherwise covalently bound to an antibody. A "therapeutic agent" as referred to herein, is a composition useful in treating or preventing a disease such as cancer.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions typically requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity). protein).

A "ligand" refers to an agent, e.g., a polypeptide or other molecule, capable of binding to a receptor.

The term "recombinant" when used with reference, for example, to a cell, a nucleic acid, a protein, or a vector, indicates that the cell, nucleic acid, protein or vector has been modified by or is the result of laboratory methods. Thus, for example, recombinant proteins include proteins produced by laboratory methods. Recombinant proteins can include amino acid residues not found within the native (non-recombinant) form of the protein or can be include amino acid residues that have been modified, e.g., labeled.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, an antigen binding domain as described herein and a compound provided herein (e.g., a compound including a peptidyl moiety, meditope). In embodiments contacting includes, for example, allowing a compound described herein to interact with a steric hindering chemical molecule.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

"Patient" or "subject in need thereof" refers to a living organism suffering from or prone to a disease or condition that can be treated by administration of a composition or pharmaceutical composition as provided herein. Non-limiting examples include humans, other mammals, bovines, rats, mice, dogs, monkeys, goat, sheep, cows, deer, and other non-mammalian animals. In some embodiments, a patient is human.

The terms "disease" or "condition" refer to a state of being or health status of a patient or subject capable of being treated with a compound, pharmaceutical composition, or method provided herein. In embodiments, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma).

The terms "treating", or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease. In embodiments, "treating" refers to treatment of cancer.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "therapeutically effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

"Anti-cancer agent" is used in accordance with its plain ordinary meaning and refers to a composition (e.g. compound, drug, antagonist, inhibitor, modulator) having anti-neoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer.

The term "associated" or "associated with" in the context of a substance or substance activity or function associated with a disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma)) means that the disease (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma) is caused by (in whole or in part), or a symptom of the disease is caused by (in whole or in part) the substance or substance activity or function.

"Chemotherapeutic" or "chemotherapeutic agent" is used in accordance with its plain ordinary meaning and refers to a chemical composition or compound having antineoplastic properties or the ability to inhibit the growth or proliferation of cells.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by using a method as described herein), results in reduction of the disease or one or more disease symptoms.

DESCRIPTION

The methods and compositions provided herein relate, inter alia, to T cells expressing (i) a recombinant CAR protein which includes a peptide binding site and is capable of specifically binding cancer-specific antigens and (ii) a T cell receptor specific for a viral antigen (e.g., a CMV pp65 protein). The engineered T cells provided herein may be used in combination with a viral vaccine (e.g. cytomegalovirus (CMV) Triplex Vaccine) provided herein to treat a variety of cancers. The methods provided herein include administering the engineered T cells which recognize a cancer antigen (e.g., CD19, HER2) in addition to a viral (e.g., CMV) antigen to a patient. Subsequent to administration of the engineered T cells, a viral vaccine (e.g., CMV Triplex Vaccine) is administered to the patient. The vaccine can promote proliferation of the engineered T cells and enhance their anti-cancer activity. Thus, the methods can improve T cell resistance and provide a means by which to re-stimulate CAR T cells after relapse. In addition, the methods can provide more reliable engraftment and persistence in a low target-antigen setting (e.g., post-myeloablative HCT) with re-expansion of CAR T cells by viral (e.g. CMV) vaccine administration. The methods described herein also permit in vivo expansion of CMV-specific CAR T cells, instead of or in addition to ex vivo expansion, avoiding excessive T cell exhaustion that results in some cases from ex vivo manufacturing.

In an aspect is provided a method for treating a disease in a subject in need thereof, the method including: (i) administering to a subject a therapeutically effective amount of a composition including a population of human T cells expressing a T cell receptor specific for a cytomegalovirus (CMV) antigen and a recombinant chimeric antigen receptor (CAR) protein, wherein the recombinant CAR protein includes: (A) an antibody region including a central cavity formed by a heavy chain variable (VH) region, a light chain variable (VL) region, a heavy chain constant region (CH) and a light chain constant region (CL), wherein the central cavity forms a peptide binding site including framework region amino acid residues; and (B) a transmembrane domain; and (ii) administering to the subject a therapeutically effective amount of a viral vector, wherein the viral vector encodes (a) a CMV pp65 protein and (b) a fusion protein including exon 4 of CMV protein IE1 (e4) and exon 5 of CMV protein IE2 (e5); and wherein the viral vector is administered either prior to or subsequent to administering the composition including a population of human T cells to the subject, thereby treating the subject.

In embodiments, the antibody region is an antibody fragment. In embodiments, the antibody region includes an Fc domain. In embodiments, the antibody region is a humanized antibody region.

In embodiments, the recombinant CAR protein further includes an intracellular T-cell signaling domain. In embodiments, the intracellular T-cell signaling domain is a CD3ζ intracellular T-cell signaling domain.

In embodiments, the recombinant CAR protein further includes an intracellular co-stimulatory signaling domain. In embodiments, the intracellular co-stimulatory signaling domain is a CD28 intracellular co-stimulatory signaling domain, a 4-1BB intracellular co-stimulatory signaling domain, an ICOS intracellular co-stimulatory signaling domain, or an OX-40 intracellular co-stimulatory signaling domain. In embodiments, the intracellular co-stimulatory signaling domain is a CD28 intracellular co-stimulatory signaling domain. In embodiments, the intracellular co-stimulatory signaling domain is a 4-1BB intracellular co-stimulatory signaling domain. In embodiments, the intracellular co-stimulatory signaling domain is an ICOS intracellular co-stimulatory signaling domain. In embodiments, the intracellular co-stimulatory signaling domain is an OX-40 intracellular co-stimulatory signaling domain.

In embodiments, the recombinant CAR protein further includes a spacer region. In embodiments, the spacer region is between the transmembrane domain and the antibody region.

In embodiments, the recombinant CAR protein further includes a linker domain. In embodiments, the linker domain is between the transmembrane domain and the intracellular T-cell signaling domain. In embodiments, the linker domain is between the intracellular T-cell signaling domain and the intracellular co-stimulatory signaling domain. In embodiments, the linker domain includes the sequence GGCGG or GGG.

In embodiments, the recombinant CAR protein is an anti-CD19 protein, anti-CD20 protein, anti-CD22 protein, anti-CD30 protein, anti-CD33 protein, anti-CD44v6/7/8 protein, anti-CD123 protein, anti-CEA protein, anti-EGP-2 protein, anti-EGP-40 protein, anti-erb-B2 protein, anti-erb-B2,3,4 protein, anti-FBP protein, anti-fetal acetylcholine receptor protein, anti-GD2 protein, anti-GD3 protein, anti-Her2/neu protein, anti-IL-13R-a2 protein, anti-KDR protein, anti k-light chain protein, anti-LeY protein, anti-L1 cell adhesion molecule protein, anti-MAGE-A1 protein, anti-mesothelin protein, anti-murine CMV infected cell protein, anti-MUC2 protein, anti-NKGD2 protein, anti, oncofetal antigen protein, anti-PCSA protein, anti-PSMA protein, anti-TAA (targeted by mAb IfE) protein, anti-EGFR protein, anti-TAG-72 protein or anti-VEGF-72 protein.

In embodiments, the recombinant CAR protein is an anti-CD19 protein. In embodiments, the recombinant CAR protein is an anti-CD20 protein. In embodiments, the recombinant CAR protein is an anti-CD22 protein. In embodiments, the recombinant CAR protein is an anti-CD30 protein. In embodiments, the recombinant CAR protein is an anti-CD33 protein. In embodiments, the recombinant CAR protein is an anti-CD44v6/7/8 protein. In embodiments, the recombinant CAR protein is an anti-CD123 protein. In embodiments, the recombinant CAR protein is an anti-CEA protein. In embodiments, the recombinant CAR protein is an anti-EGP-2 protein. In embodiments, the recombinant CAR protein is an anti-EGP-40 protein. In embodiments, the recombinant CAR protein is an anti-erb-B2 protein. In embodiments, the recombinant CAR protein is an anti-erb-B2,3,4 protein. In embodiments, the recombinant CAR protein is an anti-FBP protein. In embodiments, the recombinant CAR protein is an anti-fetal acetylcholine receptor protein. In embodiments, the recombinant CAR protein is an anti-GD2 protein. In embodiments, the recombinant CAR protein is an anti-GD3 protein. In embodiments, the recombinant CAR protein is an anti-Her2/neu protein. In embodiments, the recombinant CAR protein is an anti-IL-13R-a2 protein. In embodiments, the recombinant CAR protein is an anti-KDR protein. In embodiments, the recombinant CAR protein is an anti k-light chain protein. In embodiments, the recombinant CAR protein is an anti-LeY protein. In embodiments, the recombinant CAR protein is an anti-L1 cell adhesion molecule protein. In embodiments, the recombinant CAR protein is an anti-MAGE-A1 protein, anti-mesothelin protein. In embodiments, the recombinant CAR protein is an anti-murine CMV infected cell protein. In embodiments, the recombinant CAR protein is an anti-MUC2 protein. In embodiments, the recombinant CAR protein is an anti-NKGD2 protein. In embodiments, the recombinant CAR protein is an anti-oncofetal antigen protein. In embodiments, the recombinant CAR protein is an anti-PCSA protein. In embodiments, the recombinant CAR protein is an anti-PSMA protein. In embodiments, the recombinant CAR protein is an anti-TAA (targeted by mAb IfE) protein. In embodiments, the recombinant CAR protein is an anti-EGFR protein. In embodiments, the recombinant CAR protein is an anti-TAG-72 protein. In embodiments, the recombinant CAR protein is an anti-VEGF-72 protein.

In embodiments, the step of administering a therapeutically effective amount of a viral vector to the subject includes administering recombinant MVA virus.

In embodiments, expression of (a) a CMV pp65 protein and (b) the fusion protein including exon 4 of CMV protein IE1 (e4) and exon 5 of CMV protein IE2 (e5) is under the control of mH5 promoter.

In embodiments, the subject is immunocompromised. In embodiments, the subject receives immunosuppressive therapy. In embodiments, the subject is immunocompetent.

In embodiments, the subject is CMV-seronegative prior to treatment.

In embodiments, the subject received hematopoietic stem cells (HSCs) from a CMV-seropositive or a CMV-seronegative donor prior to administering the therapeutically effective amount of the composition including a population of human T cells expressing a T cell receptor specific for a CMV antigen and a recombinant CAR protein. In embodiments, the subject received hematopoietic stem cells (HSCs) from a CMV-seropositive donor prior to administering the therapeutically effective amount of the composition including a population of human T cells expressing a T cell receptor specific for a CMV antigen and a recombinant CAR protein. In embodiments, the subject received hematopoietic stem cells (HSCs) from a CMV-seronegative donor prior to administering the therapeutically effective amount of the composition including a population of human T cells expressing a T cell receptor specific for a CMV antigen and a recombinant CAR protein.

In embodiments, the viral vector is administered to the hematopoietic stem cell donor prior to harvesting the stem cells.

In embodiments, the recombinant CAR protein is capable of binding CD19. In embodiments, the recombinant CAR protein is capable of binding HER2.

In embodiments, the HSCs are autologous HSCs. In embodiments, the HSCs are allogenic HSCs.

In embodiments, the subject is suffering from cancer. In embodiments, the subject is suffering from non-Hodgkin's Lymphoma. In embodiments, the subject is suffering from a solid tumor cancer or a hematologic malignancy. In embodiments, the subject is suffering from a solid tumor cancer. In embodiments, the subject is suffering from a hematologic malignancy.

In embodiments, the subject is suffering from ovarian cancer, renal cell carcinoma, a B-cell malignancy, leukemia, lymphoma, breast cancer, colorectal cancer, prostate cancer, neuroblastoma, melanoma, medulloblastoma, lung cancer, osteosarcoma, glioblastoma or glioma. In embodiments, the subject is suffering from ovarian cancer. In embodiments, the subject is suffering from renal cell carcinoma. In embodiments, the subject is suffering from a B-cell malignancy. In embodiments, the subject is suffering from leukemia. In embodiments, the subject is suffering from lymphoma. In embodiments, the subject is suffering from breast cancer. In embodiments, the subject is suffering from colorectal cancer. In embodiments, the subject is suffering from prostate cancer. In embodiments, the subject is suffering from neuroblastoma. In embodiments, the subject is suffering from melanoma. In embodiments, the subject is suffering from medulloblastoma. In embodiments, the subject is suffering from lung cancer. In embodiments, the subject is suffering from osteosarcoma. In embodiments, the subject is suffering from glioblastoma. In embodiments, the subject is suffering from glioma.

In embodiments, administration of the viral vector occurs at least 5 days after treatment with the composition including a population of human T cells. In embodiments, the viral vector is administered to the subject prior to and subsequent to the administration of the composition including a population of human T cells.

In embodiments, the viral vector is administered to the subject only prior to the administration of the composition including a population of human T cells. In embodiments, the viral vector is administered to the subject only subsequent to the administration of the composition including a population of human T cells.

In embodiments, the viral vector is administered to the subject or the hematopoietic stem cell transplant donor at least twice subsequent to the administration of the composition comprising a population of human T cells. In embodiments, the viral vector is administered to the subject or the hematopoietic stem cell transplant donor at least three times subsequent to the administration of the composition comprising a population of human T cells. In embodiments, the viral vector is administered to the subject or the hematopoietic stem cell transplant donor at least four times subsequent to the administration of the composition comprising a population of human T cells. In embodiments, the viral vector is administered to the subject or the hematopoietic stem cell transplant donor at least five times subsequent to the administration of the composition comprising a population of human T cells. In embodiments, the viral vector is administered to the subject or the hematopoietic stem cell transplant donor at least six times subsequent to the administration of the composition comprising a population of human T cells. In embodiments, the viral vector is administered to the subject or the hematopoietic stem cell transplant donor at least seven times subsequent to the administration of the composition comprising a population of human T cells. In embodiments, the viral vector is administered to the subject or the hematopoietic stem cell transplant donor at least eighth times subsequent to the administration of the composition comprising a population of human T cells. In embodiments, the viral vector is administered to the subject or the hematopoietic stem cell transplant donor at least nine times subsequent to the administration of the composition comprising a population of human T cells. In embodiments, the viral vector is administered to the subject or the hematopoietic stem cell transplant donor at least ten times subsequent to the administration of the composition comprising a population of human T cells.

In embodiments, the viral vector is administered to the subject at least four times. In embodiments, the viral vector is administered to the subject at least five times. In embodiments, the viral vector is administered to the subject at least six times. In embodiments, the viral vector is administered to the subject at least seven times. In embodiments, the viral vector is administered to the subject at least eight times. In embodiments, the viral vector is administered to the subject at least nine times. In embodiments, the viral vector is administered to the subject at least ten times.

In embodiments, the population of human T cells expressing a T cell receptor specific for a CMV antigen and a recombinant CAR protein is formed by: (1) isolating PBMCs or a T cell subpopulation from a CMV-seropositive human donor; (2) contacting the PBMCs or the T cell subpopulation with at least one CMV antigen; (3) allowing the contacted cells to produce a population of cells enriched for stimulated cells specific for CMV; (4) transducing at least a portion of the enriched population of cells with a vector expressing a recombinant CAR protein, thereby forming a population of human T cells expressing a T cell receptor specific for a CMV antigen and a recombinant CAR protein.

In embodiments, the step of allowing the contacted cells to produce a population of cells enriched for stimulated cells specific for CMV includes allowing the stimulated cells to produce a population of cells enriched for cells expressing an activation marker.

In embodiments, the population of human T cells expressing a T cell receptor specific for a CMV antigen and a recombinant CAR protein is formed by: (1) administering a viral vector encoding: (a) a CMV pp65 protein and (b) a fusion protein including exon 4 of CMV protein IE1 (e4) and exon 5 of CMV protein IE2 (e5) to a human donor to convert a CMV-seronegative human donor to a CMV-seropositive human donor containing T cells responsive to CMV antigens pp65, IE1 and IE2; (2) obtaining PBMCs from the CMV-seropositive human donor; (3) contacting the PBMCs with at least one CMV antigen; (4) allowing the contacted cells to produce a population of cells enriched for stimulated cells specific for CMV; (5) transducing at least a portion of the enriched population of cells with a vector expressing a recombinant CAR protein, thereby forming a population of T cell expressing a T cell receptor specific for a CMV antigen and a recombinant CAR protein.

In embodiments, the population of human T cells expressing a T cell receptor specific for a CMV antigen and a recombinant CAR protein is formed by: (1) administering a viral vector encoding: (a) a CMV pp65 protein and (b) a fusion protein including exon 4 of CMV protein IE1 (e4) and exon 5 of CMV protein IE2 (e5) to a CMV-seropositive human donor; (2) allowing PBMCs from the CMV-seropositive human donor; (3) contacting the PBMCs with at least one CMV antigen; (4) allowing the contacted cells to produce a population of cells enriched for stimulated cells specific for CMV; (5) transducing at least a portion of the enriched population of cells with a vector expressing a recombinant CAR protein, thereby providing a population of human T cells expressing a T cell receptor specific for a CMV antigen and a recombinant CAR protein.

In an aspect is provided a method for forming a population of human T cells expressing a recombinant CAR protein and a T cell receptor specific for a CMV antigen, the method including: (1) administering a viral vector encoding: (a) a CMV pp65 protein and (b) a fusion protein including exon 4 of CMV protein IE1 (e4) and exon 5 of CMV protein IE2 (e5) to a CMV-seronegative human donor; (2) obtaining PBMCs from the human donor; (3) contacting the PBMCs with at least one CMV antigen; (3) allowing the contacted cells to produce a population of cells enriched for stimulated cells specific for CMV; (4) transducing at least a portion of the enriched population of cells with a vector expressing a recombinant CAR protein, thereby forming a population of human T cells expressing a T cell receptor specific for a CMV antigen and a recombinant CAR protein.

In a aspect is provided a method for forming a population of human T cells expressing a recombinant CAR protein and a T cell receptor specific for a CMV antigen, the method including: (1) administering a viral vector encoding: (a) a CMV pp65 protein and (b) a fusion protein comprising exon 4 of CMV protein IE1 (e4) and exon 5 of CMV protein IE2 (e5) to a CMV-seropositive human donor; (2) obtaining PBMCs from the CMV-seropositive human donor; (3) contacting the PBMCs with at least one CMV antigen; (4) allowing the contacted cells to produce a population of cells enriched for stimulated cells specific for CMV; (5) transducing at least a portion of the enriched population of cells with a vector expressing a recombinant CAR protein, thereby forming a population of human T cells expressing a T cell receptor specific for a CMV antigen and a recombinant CAR protein.

In embodiments, the method further includes expanding the population of human T cells expressing a recombinant CAR protein and a T cell receptor specific for a CMV antigen.

In embodiments, the activation marker is IFN-γ, CD137 or CD107. In embodiments, the activation marker is IFN-γ. In embodiments, the activation marker is CD137. In embodiments, the activation marker is CD107.

In embodiments, the CMV antigen is a pp65 protein or an antigenic portion thereof. In embodiments, the CMV antigen includes two or more different antigenic pp65 proteins. In embodiments, the CMV antigen includes three or more different antigenic pp65 proteins. In embodiments, the CMV antigen includes four or more different antigenic pp65 proteins. In embodiments, the CMV antigen includes five or more different antigenic pp65 proteins. In embodiments, the CMV antigen includes six or more different antigenic pp65 proteins. In embodiments, the CMV antigen includes seven or more different antigenic pp65 proteins. In embodiments, the CMV antigen includes eight or more different antigenic pp65 proteins. In embodiments, the CMV antigen includes nine or more different antigenic pp65 proteins. In embodiments, the CMV antigen includes ten or more different antigenic pp65 proteins.

In embodiments, the enriched population of cells is at least 40% IFN-γ positive, at least 20% CD8 positive, and at least 20% CD4 positive.

In embodiments, the enriched population of cells is cultured for fewer than 10 days prior to the step of transducing the enriched population of cells with a vector encoding a recombinant CAR protein. In embodiments, the enriched population of cells is cultured for fewer than 9 days prior to the step of transducing the enriched population of cells with a vector encoding a recombinant CAR protein. In embodiments, the enriched population of cells is cultured for fewer than 8 days prior to the step of transducing the enriched population of cells with a vector encoding a recombinant CAR protein. In embodiments, the enriched population of cells is cultured for fewer than 7 days prior to the step of transducing the enriched population of cells with a vector encoding a recombinant CAR protein. In embodiments, the enriched population of cells is cultured for fewer than 6 days prior to the step of transducing the enriched population of cells with a vector encoding a recombinant CAR protein. In embodiments, the enriched population of cells is cultured for fewer than 5 days prior to the step of transducing the enriched population of cells with a vector encoding a recombinant CAR protein. In embodiments, the enriched population of cells is cultured for fewer than 4 days prior to the step of transducing the enriched population of cells with a vector encoding a recombinant CAR protein. In embodiments, the enriched population of cells is cultured for fewer than 3 days prior to the step of transducing the enriched population of cells with a vector encoding a recombinant CAR protein. In embodiments, the enriched population of cells is cultured for fewer than 2 days prior to the step of transducing the enriched population of cells with a vector encoding a recombinant CAR protein. In embodiments, the enriched population of cells is cultured for fewer than 1 day prior to the step of transducing the enriched population of cells with a vector encoding a recombinant CAR protein.

In embodiments, the method further includes expanding the CMV specific T cells expressing a recombinant CAR protein by exposing the T cells to an antigen that binds to the recombinant CAR protein.

In embodiments, the step of expanding the CMV-specific T cells expressing a recombinant CAR protein includes exposing the cells to T cells expressing the antigen that binds the recombinant CAR protein.

In embodiments, the expansion takes place in the presence of at least one exogenously added interleukin. In embodiments, the expansion takes place in the presence of at least 2 exogenously added interleukins. In embodiments, the expansion takes place in the presence of at least 3 exogenously added interleukins. In embodiments, the expansion takes place in the presence of at least 4 exogenously added interleukins. In embodiments, the expansion takes place in the presence of at least 5 exogenously added interleukins. In embodiments, the expansion takes place in the presence of at least 6 exogenously added interleukins. In embodiments, the expansion takes place in the presence of at least 7 exogenously added interleukins. In embodiments, the expansion takes place in the presence of at least 8 exogenously added interleukins. In embodiments, the expansion takes place in the presence of at least 9 exogenously added interleukins. In embodiments, the expansion takes place in the presence of at least 10 exogenously added interleukins.

In embodiments, the population of human T cells is autologous to the subject. In embodiments, the population of human T cells is allogeneic to the subject.

In embodiments, the method reduces the risk of CMV infection. In embodiments, the method reduces CMV viremia and/or disease. In embodiments, the method reduces CMV viremia. In embodiments, the method reduces CMV disease.

In embodiments, the subject was CMV-immune prior to treatment and the method reduces the risk of CMV infection. In embodiments, the subject was CMV-immune prior to treatment and the method reduces the risk of CMV infection.

In an aspect is provided a method for treating a disease in a subject in need thereof including: (i) administering to a subject a therapeutically effective amount of a composition including a population of human T cells expressing a T cell receptor specific for a viral antigen and a recombinant chimeric antigen receptor (CAR) protein, wherein the recombinant CAR protein includes: (A) an antibody region including a central cavity formed by a heavy chain variable (VH) region, a light chain variable (VL) region, a heavy chain constant region (CH) and a light chain constant region (CL), wherein the central cavity forms a peptide binding site including framework region amino acid residues; and (B) a transmembrane domain; and (ii) administering to the subject the viral antigen either prior to or subsequent to administering the composition including a population of human T cells to the subject.

In embodiments, the viral antigen is an endogenous viral antigen.

In an aspect is provided a cell including a T cell receptor specific for a cytomegalovirus (CMV) antigen and a recombinant CAR protein, wherein the recombinant CAR protein includes: (A) an antibody region including a central cavity formed by a heavy chain variable (VH) region, a light chain variable (VL) region, a heavy chain constant region (CH) and a light chain constant region (CL), wherein the central cavity forms a peptide binding site including framework region amino acid residues; and (B) a transmembrane domain.

In an aspect is provided a cell including a T cell receptor specific for a viral antigen and a recombinant CAR protein, wherein the recombinant CAR protein includes: (A) an antibody region including a central cavity formed by a heavy chain variable (VH) region, a light chain variable (VL) region, a heavy chain constant region (CH) and a light chain constant region (CL), wherein the central cavity forms a peptide binding site including framework region amino acid residues; and (B) a transmembrane domain.

Provided herein is a method for treating a patient including providing a composition including a population of T cells expressing both a T cell receptor specific for a cytomegalovirus (CMV) antigen and a recombinant CAR protein. The recombinant CAR protein includes: (A) an antibody region comprising a central cavity formed by a heavy chain variable (VH) region, a light chain variable (VL) region, a heavy chain constant region (CH) and a light chain constant region (CL), wherein said central cavity forms a peptide binding site comprising framework region amino acid residues; and (B) a transmembrane domain. The method includes administering the composition to the patient; and administering to the patient a viral vector encoding: (i) CMV pp65 and (ii) a fusion protein comprising exon 4 of CMV protein IE1 (e4) and exon 5 of CMV protein IE2 (e5) either prior to or subsequent to administering the composition including a population of T cells to the patient.

In embodiments, the antibody region is an antibody fragment.

In embodiments, the antibody region comprises an Fc domain.

In embodiments, the antibody region is a humanized antibody region.

In embodiments, the recombinant CAR protein further includes an intracellular T-cell signaling domain.

In embodiments, the intracellular T-cell signaling domain is a CD3ζ intracellular T-cell signaling domain.

In embodiments, the recombinant CAR protein further includes an intracellular co-stimulatory signaling domain.

In embodiments, the intracellular co-stimulatory signaling domain is a CD28 intracellular co-stimulatory signaling domain, a 4-1BB intracellular co-stimulatory signaling domain, a ICOS intracellular co-stimulatory signaling domain, or an OX-40 intracellular co-stimulatory signaling domain.

In embodiments, the recombinant CAR protein further includes a spacer region.

In embodiments, the spacer region is between said transmembrane domain and the antibody region.

In embodiments, the recombinant CAR protein further includes a linker domain.

In embodiments, the linker domain is between said transmembrane domain and the intracellular T-cell signaling domain.

In embodiments, the linker domain is between the intracellular T-cell signaling domain and the intracellular co-stimulatory signaling domain.

In embodiments, the linker domain includes the sequence GGCGG or GGG.

In embodiments, the recombinant CAR protein is an anti-CD19 protein, anti-CD20 protein, anti-CD22 protein, anti-CD30 protein, anti-CD33 protein, anti-CD44v6/7/8 protein, anti-CD123 protein, anti-CEA protein, anti-EGP-2 protein, anti-EGP-40 protein, anti-erb-B2 protein, anti-erb-B2,3,4 protein, anti-FBP protein, anti-fetal acetylcholine receptor protein, anti-GD2 protein, anti-GD3 protein, anti-Her2/neu protein, anti-IL-13R-a2 protein, anti-KDR protein, anti k-light chain protein, anti-LeY protein, anti-L1 cell adhesion molecule protein, anti-MAGE-A1 protein, anti-mesothelin protein, anti-murine CMV infected cell protein, anti-MUC2 protein, anti-NKGD2 protein, anti, oncofetal antigen protein, anti-PCSA protein, anti-PSMA protein, anti-TAA (targeted by mAb IfE) protein, anti-EGFR protein, anti-TAG-72 protein or anti-VEGF-72 protein.

In embodiments, the step of administering a viral vector to the patient includes administering recombinant MVA virus.

In embodiments, the expression of (i) CMV pp65 and (ii) the fusion protein includes exon 4 of CMV protein IE1 (e4) and exon 5 of CMV protein IE2 (e5) is under the control of mH5 promoter.

In embodiments, the step of providing a population of T cells expressing a T cell receptor specific for a CMV antigen and a recombinant CAR protein includes: (i.i) providing PBMC or a T cell subpopulation from a CMV-seropositive human donor; (ii.i) exposing the PBMC or the T cell subpopulation to at least one CMV antigen; (iii.i) treating the exposed cells to produce a population of cells enriched for stimulated cells specific for CMV; and (iv.i) transducing at least a portion of the enriched population of cells with a vector expressing a recombinant CAR protein.

In embodiments, the step of treating the exposed cells to produce a population of cells enriched for stimulated cells specific for CMV includes treating the stimulated cells to produce a population of cells enriched for cells expressing an activation marker.

In embodiments, the step of providing a population of T cell expressing a T cell receptor specific for a CMV antigen and a recombinant CAR protein includes: (a) administering a viral vector encoding: (i) CMV pp65 and (ii) a fusion protein including exon 4 of CMV protein IE1 (e4) and exon 5 of CMV protein IE2 (e5) to a human donor to convert a CMV-seronegative human donor to one containing T cells responsive to CMV antigens pp65, IE1 and IE2; (b) obtaining PBMC from the CMV-seropositive human donor; (c) exposing the PBMC to at least one CMV antigen; (d) treating the exposed cells to produce a population of cells enriched for stimulated cells specific for CMV; (e) transducing at least a portion of the enriched population of cells with a vector expressing a recombinant CAR protein, thereby providing a population of T cell expressing a recombinant CAR protein and a T cell receptor specific for a CMV antigen.

In embodiments, the step of providing a population of T cell expressing a T cell receptor specific for a CMV antigen and a recombinant CAR protein includes: (a) administering a viral vector encoding: (i) CMV pp65 and (ii) a fusion protein comprising exon 4 of CMV protein IE1 (e4) and exon 5 of CMV protein IE2 (e5) to a CMV-seropositive human donor; (b) obtaining PBMC from the CMV-seropositive human donor; (b) exposing the PBMC to at least one CMV antigen; (c) treating the exposed cells to produce a population of cells enriched for stimulated cells specific for CMV; (d) transducing at least a portion of the enriched population of cells with a vector expressing a recombinant CAR protein, thereby providing a population of T cell expressing a recombinant CAR protein and a T cell receptor specific for a CMV antigen.

Also provided herein is a method for preparing T cells expressing a recombinant CAR protein and a T cell receptor specific for a CMV antigen. The method includes: (a) administering a viral vector encoding: (i) CMV pp65 and (ii) a fusion protein comprising exon 4 of CMV protein IE1 (e4) and exon 5 of CMV protein IE2 (e5) to a CMV-seropositive human donor; (b) obtaining PBMC from the CMV-seropositive human donor; (b) exposing the PBMC to at least one CMV antigen; (c) treating the exposed cells to produce a population of cells enriched for stimulated cells specific for CMV; (d) transducing at least a portion of the enriched population of cells with a vector expressing a recombinant CAR protein, thereby providing a population of T cell expressing a recombinant CAR protein and a T cell receptor specific for a CMV antigen.

Also provided herein is a method for preparing T cells expressing a recombinant CAR protein and a T cell receptor specific for a CMV antigen. The method includes: a) administering a viral vector encoding: (i) CMV pp65 and (ii) a fusion protein comprising exon 4 of CMV protein IE1 (e4) and exon 5 of CMV protein IE2 (e5) to a CMV-seropositive human donor; (b) obtaining PBMC from the CMV-seropositive human donor; (b) exposing the PBMC to at least one CMV antigen; (c) treating the exposed cells to produce a population of cells enriched for stimulated cells specific for CMV; (d) transducing at least a portion of the enriched population of cells with a vector expressing a recombinant CAR protein, thereby providing a population of T cell expressing a recombinant CAR protein and a T cell receptor specific for a CMV antigen.

Also provided herein is a method for treating a patient. The method includes: (a) providing a composition comprising a population of T cells expressing both a T cell receptor specific for a viral antigen and a recombinant CAR protein. The recombinant CAR protein includes: (A) an antibody region comprising a central cavity formed by a heavy chain variable (VH) region, a light chain variable (VL) region, a heavy chain constant region (CH) and a light chain constant region (CL), wherein said central cavity forms a peptide binding site comprising framework region amino acid residues; and (B) a transmembrane domain. The method includes administering the composition to the patient; and administering to the patient said viral antigen either prior to or subsequent to administering the composition comprising a population of T cells to the patient.

In embodiments, the viral antigen is an endogenous viral antigen.

Also provided herein is a cell including a T cell receptor specific for a cytomegalovirus (CMV) antigen and a recombinant CAR protein. The recombinant CAR protein includes: (A) an antibody region comprising a central cavity formed by a heavy chain variable (VH) region, a light chain variable (VL) region, a heavy chain constant region (CH) and a light chain constant region (CL), wherein said central cavity forms a peptide binding site comprising framework region amino acid residues; and (B) a transmembrane domain.

Also provided herein is a cell including a T cell receptor specific for a viral antigen and a recombinant CAR protein. The recombinant CAR protein includes: (A) an antibody region comprising a central cavity formed by a heavy chain variable (VH) region, a light chain variable (VL) region, a heavy chain constant region (CH) and a light chain constant region (CL), wherein said central cavity forms a peptide binding site includes a framework region amino acid residues; and (B) a transmembrane domain.

In one aspect, an isolated nucleic acid is provided. The nucleic acid encodes a protein including (i) an antibody region including a central cavity formed by a heavy chain variable (VH) region, a light chain variable (VL) region, a heavy chain constant region (CH) and a light chain constant region (CL), wherein the central cavity forms a peptide binding site including framework region amino acid residues; and (ii) a transmembrane domain.

In one aspect, an isolated nucleic acid is provided. The nucleic acid encodes a protein including (i) an antibody region including a central cavity formed by a heavy chain variable (VH) region and a light chain variable (VL) region, wherein the central cavity forms a peptide binding site including framework region amino acid residues; and (ii) a transmembrane domain.

In another aspect, an isolated nucleic acid is provided. The isolated nucleic acid encodes a protein including a first portion including an antibody heavy chain variable domain and a second portion including an antibody light chain variable domain and an antibody light chain constant domain, wherein the first portion further includes a transmembrane domain.

In another aspect, an expression vector including a nucleic acid provided herein including embodiments thereof is provided.

In another aspect, a T lymphocyte including the expression vector provided herein including embodiments thereof is provided.

In another aspect, a mammalian cell including the expression vector provided herein including embodiments thereof is provided.

In another aspect, a recombinant protein is provided. The recombinant protein includes (i) an antibody region including a central cavity formed by a heavy chain variable (VH) region and a light chain variable (VL) region, wherein the central cavity forms a peptide binding site including framework region amino acid residues; and (ii) a transmembrane domain.

In another aspect, a recombinant protein is provided. The recombinant protein includes a first portion including an antibody heavy chain variable domain and a second portion including an antibody light chain variable domain and an antibody light chain constant domain, wherein the first portion further includes a transmembrane domain, and wherein the antibody heavy chain variable domain, the antibody light chain variable domain and the antibody light chain constant domain together form an antibody region.

In another aspect, a mammalian cell including the recombinant protein provided herein including embodiments thereof is provided, wherein the transmembrane domain is within the cell membrane of the mammalian cell.

In another aspect, a T lymphocyte including the recombinant protein provided herein including embodiments thereof is provided, wherein the transmembrane domain is within the cell membrane of the T lymphocyte.

In another aspect, a method of treating cancer is provided. The method includes administering to a subject in need thereof an effective amount of a mammalian cell provided herein including embodiments thereof, wherein the antibody region is an anti-cancer antibody region.

In another aspect, a method of treating cancer is provided. The method includes administering to a subject in need thereof an effective amount of the T-lymphocyte provided herein including embodiments thereof, wherein the antibody region is an anti-cancer antibody region.

In another aspect, a method of reprogramming a T lymphocyte is provided. The method includes contacting a T lymphocyte with the expression vector provided herein including embodiments thereof.

In another aspect, a method of detecting a cancer is provided. The method includes (i) administering to a cancer patient an effective amount of a T lymphocyte including the recombinant protein provided herein including embodiments thereof and a compound including a peptidyl moiety capable of binding to the peptide binding site, wherein the compound further includes a detectable label, and wherein the antibody region is an anti-cancer antibody region. The method includes (ii) allowing the compound to bind to the peptide binding site thereby forming a recombinant protein-compound complex. And (iii) the recombinant protein-compound complex is detected within the cancer patient thereby detecting the cancer.

Recombinant Nucleic Acids Encoding Recombinant Car Protein

Provided herein are compositions which exhibit novel diagnostic capabilities and allow to rapidly add functionality to adoptive immunotherapy. The recombinant proteins (i.e. recombinant CAR proteins) provided herein are useful, inter alia, for a broad variety of therapeutic and diagnostic purposes. For example, the recombinant proteins provided herein including embodiments thereof may be used as non-invasive means to characterize chimeric antigen receptor (CAR) T cells before and/or during treatment of diseases (e.g., cancer). By adding functionality to the CAR immunoreceptors a population of patients with antigen-positive tumors can be efficiently treated and monitored irrespective of their HLA genotype. Adoptive immunotherapy using T lymphocytes that express these functionally improved tumor-specific CARs can be a powerful therapeutic strategy for the treatment of cancer and other diseases (e.g., infectious diseases (e.g., HIV infection)). Further, using the recombinant proteins provided herein including embodiments thereof allow for testing and improvement of the functionality and safety of CAR T cells.

In another aspect, an isolated nucleic acid is provided. The nucleic acid encodes a recombinant CAR protein including (i) an antibody region including a central cavity formed by a heavy chain variable (VH) region and a light chain variable (VL) region, wherein the central cavity forms a peptide binding site including framework region amino acid residues; and (ii) a transmembrane domain.

An "antibody region" as provided herein refers to a monovalent or multivalent protein moiety that forms part of the protein (i.e. recombinant CAR protein) provided herein including embodiments thereof. A person of ordinary skill in the art would therefore immediately recognize that the antibody region is a protein moiety capable of binding an antigen (epitope). Thus, the antibody region provided herein may include a domain of an antibody or fragment (e.g., Fab) thereof. In embodiments, the antibody region is a protein conjugate. A "protein conjugate" a provided herein refers to a construct consisting of more than one polypeptide, wherein the polypeptides are bound together covalently or non-covalently. In embodiments, the protein conjugate includes a Fab moiety (a monovalent Fab) covalently attached to an scFv moiety (a monovalent scFv). In embodiments, the protein conjugate includes a plurality of (at least two) Fab moieties. In embodiments, the polypeptides of a protein conjugate are encoded by one nucleic acid molecule. In embodiments, the polypeptides of a protein conjugate are encoded by different nucleic acid molecules. In embodiments, the polypeptides are connected through a linker. In embodiments, the polypeptides are connected through a chemical linker.

In embodiments, the antibody region includes a plurality of variable light chain domains and a plurality of variable heavy chain domains. A "variable light chain domain" as provided herein refers to a polypeptide included in (forming part of) a light chain variable (VL) region. In embodiments, the variable light chain region is a light chain variable (VL) domain. A "variable heavy chain domain" as provided herein refers to a polypeptide included in (forming part of) a heavy chain variable (VH) region. In embodiments, the variable heavy chain region is a heavy chain variable (VH) domain. In embodiments, each of said plurality of variable light chain domains and plurality of variable heavy chain domains is chemically different. Where the plurality of variable light chain domains and plurality of variable heavy chain domains is chemically different, each of the variable light chain domains and the variable heavy chain domains bind a different antigen (epitope). The antigens bound by chemically different variable light chain domains and different variable heavy chain domains may form part of the same protein or a different protein. In embodiments, the antigen forms part of a cancer cell. In embodiments, the antibody region includes a first variable light chain domain and a first variable heavy chain domain and a second variable light chain domain and a second variable heavy chain domain. The first variable heavy chain domain and the first variable light chain domain form a first paratope binding a first epitope and the second variable heavy chain domain and the second variable light chain domain form a second paratope binding to a second epitope, wherein the first and the second paratope are independently different. The term "paratope" refers to the antigen binding site of an antibody or fragment thereof.

In embodiments, the antibody region includes a first variable light chain domain and a first variable heavy chain domain, a second variable light chain domain and a second variable heavy chain domain, a third variable light chain domain and a third variable heavy chain domain, and a forth variable light chain domain and a forth variable heavy chain domain. The first variable heavy chain domain and the first variable light chain domain form a first paratope binding a first epitope, the second variable heavy chain domain and the second variable light chain domain form a second paratope binding to a second epitope, the third variable heavy chain domain and the third variable light chain domain form a third paratope binding a third epitope, the forth variable heavy chain domain and the forth variable light chain domain form a forth paratope binding to a second epitope, wherein the first, the second, the third and the forth paratope are independently different.

In embodiments, the first, the second, the third and the forth paratope are connected through a chemical linker. In embodiments, the chemical linker is a covalent linker, a non-covalent linker, a peptide linker (a linker including a peptide moiety), a cleavable peptide linker, a substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene or any combination thereof. Thus, a chemical linker as provided herein may include a plurality of chemical moieties, wherein each of the plurality of moieties is chemically different. In embodiments, the linker is a peptide linker. In embodiments, the peptide linker has a length of about 5- to about 15 amino acid residues.

In embodiments, the antibody region is a bispecific antibody. In embodiments, the antibody region is a tetravalent antibody. In embodiments, the antibody region is a tetravalent IgG. In embodiments, the antibody region is a dual-variable domain immunoglobulin as described in Jakob C G et al. (MAbs. 2013 May 1; 5(3): 358-363) and Byrne H et al. (Cell Volume 31, Issue 11, p 621-632, November 2013), which are hereby incorporated by reference in their entirety and for all purposes.

In embodiments, the antibody region includes SEQ ID NO:31 and SEQ ID NO:32. In embodiments, the antibody region includes SEQ ID NO:33 and SEQ ID NO:34. In embodiments, the antibody region includes SEQ ID NO:35 and SEQ ID NO:36. In embodiments, the antibody region includes SEQ ID NO:37 and SEQ ID NO:38. In embodiments, the antibody region includes SEQ ID NO:39 and SEQ ID NO:40. In embodiments, the antibody region includes SEQ ID NO:41 and SEQ ID NO:42. In embodiments, the antibody region includes SEQ ID NO:43 and SEQ ID NO:44. In embodiments, the antibody region includes SEQ ID NO:45 and SEQ ID NO:46. In embodiments, the antibody region includes SEQ ID NO:47 and SEQ ID NO:48. In embodiments, the antibody region includes SEQ ID NO:49 and SEQ ID NO:50. In embodiments, the antibody region includes SEQ ID NO:51 and SEQ ID NO:52. In embodiments, the antibody region includes SEQ ID NO:53 and SEQ ID NO:54. In embodiments, the antibody region includes SEQ ID NO:55 and SEQ ID NO:56. In embodiments, the antibody region includes SEQ ID NO:57 and SEQ ID NO:58. In embodiments, the antibody region includes SEQ ID NO:59 and SEQ ID NO:60. In embodiments, the antibody region includes SEQ ID NO:61 and SEQ ID NO:62. In embodiments, the antibody region includes SEQ ID NO:63 and SEQ ID NO:64. In embodiments, the antibody region includes SEQ ID NO:65 and SEQ ID NO:66. In embodiments, the antibody region includes SEQ ID NO:67 and SEQ ID NO:68. In embodiments, the antibody region includes SEQ ID NO:69 and SEQ ID NO:70. In embodiments, the antibody region includes SEQ ID NO:71 and SEQ ID NO:72. In embodiments, the antibody region includes SEQ ID NO:73 and SEQ ID NO:74. In embodiments, the antibody region includes SEQ ID NO:75 and SEQ ID NO:76. In embodiments, the antibody region includes SEQ ID NO:77 and SEQ ID NO:78. In embodiments, the antibody region includes SEQ ID NO:79 and SEQ ID NO:80. In embodiments, the antibody region includes SEQ ID NO:81 and SEQ ID NO:82. In embodiments, the antibody region includes SEQ ID NO:87 and SEQ ID NO:88. In embodiments, the antibody region includes SEQ ID NO:89 and SEQ ID NO:90. In embodiments, the antibody region includes SEQ ID NO:91 and SEQ ID NO:92. In embodiments, the antibody region includes SEQ ID NO:93 and SEQ ID NO:94. In embodiments, the antibody region includes SEQ ID NO:95 and SEQ ID NO:96.

The "heavy chain variable (VH) region" as provided herein is a polypeptide which includes the variable domain of a heavy chain of an antibody or a fragment thereof. Likewise, the "light chain variable (VL) region" as provided herein is a polypeptide including the variable domain of a light chain of an antibody or a fragment thereof. In embodiments, the heavy chain variable (VH) region is the variable region of the heavy chain of an antibody. In embodiments, the heavy chain variable (VH) region is the variable region of the heavy chain of an antibody fragment. In embodiments, the heavy chain variable (VH) region is the variable region of the heavy chain of a Fab. In embodiments, the light chain variable (VL) region is the variable region of the light chain of an antibody. In embodiments, the light chain variable (VL) region is the variable region of the light chain of an antibody fragment. In embodiments, the light chain variable (VL) region is the variable region of the light chain of a Fab.

In embodiments, the antibody region further includes a heavy chain constant region (CH) and a light chain constant region (CL). In embodiments, the heavy chain constant region (CH) is the constant region of the heavy chain of an antibody or fragment thereof. In embodiments, the light chain constant region (CL) is the constant region of the light chain of an antibody or fragment thereof. In embodiments, the heavy chain constant region (CH) is the constant region of a Fab. In embodiments, the light chain constant region (CL) is the constant region of the light chain of a Fab. In embodiments, the heavy chain constant region (CH) is the constant region of a F(ab)'2 dimer. In embodiments, the light chain constant region (CL) is the constant region of the light chain of a F(ab)'2 dimer. In embodiments, the antibody region includes an Fc domain. In embodiments, the antibody region is a humanized antibody region. In embodiments, the antibody region is a humanized mouse antibody region. In embodiments, the antibody region does not include an scFV antibody region. Where the antibody region does not include a scFv antibody region, the antibody region does not include a fusion protein of the variable regions of the heavy (VH) and light chains (VL) of immunoglobulins, connected with a short linker peptide.

The "central cavity" with respect to the three-dimensional structure of a Fab, refers to the internal cavity of the Fab lined by portions of the heavy and light chain variable and constant regions and including amino acids lining a hole within the cavity. In embodiments, the central cavity including the hole has a structure, e.g., as depicted in, or similar to, FIG. 4A. In embodiments, where the antibody region includes a Fab, the central cavity thus is lined by residues of the VH, VL, CH1, and CL regions. The central cavity does not include the antigen binding site. Thus, in embodiments the compound that binds to the central cavity does not impact (e.g. measurably impact) the binding of the antibody region to the epitope. In other words, in embodiments, occupancy of this site does not affect antigen binding. In embodiments, the central cavity is lined by amino acid residues capable of interacting with a compound including a peptidyl moiety (e.g. a meditope) provided herein including embodiments thereof (e.g., a peptide of formula (I) or (II)). The amino acids residues capable of interacting with the compound including a peptidyl moiety (e.g. a meditope) may from part of the peptide binding site (also referred to herein as a meditope binding site). The peptide binding site may be engineered into any appropriate antibody thereby forming an antibody or antibody region with the peptide binding site (also referred to herein as a meditope enabled antibody or meditope enabled antibody region).

In embodiments, the amino acid residues lining the central cavity include a residue at a position corresponding to Kabat position 83, a residue at a position corresponding to Kabat position 30 or a residue at a position corresponding to Kabat position 52. In embodiments, the amino acid residues lining the central cavity include a residue at a position corresponding to Kabat position 40, a residue at a position corresponding to Kabat position 41, a residue at a position corresponding to Kabat position 30, a residue at a position corresponding to Kabat position 52, a residue at a position corresponding to Kabat position 83, or a residue at a position corresponding to Kabat position 85. In embodiments, the amino acid residues lining the central cavity include a residue at a position corresponding to Kabat position 40. In embodiments, the amino acid residues lining the central cavity include a residue at a position corresponding to Kabat position 41. In embodiments, the amino acid residues lining the central cavity include a residue at a position corresponding to Kabat position 30. In embodiments, the amino acid residues lining the central cavity include a residue at a position corresponding to Kabat position 52. In embodiments, the amino acid residues lining the central cavity include a residue at a position corresponding to Kabat 83. In embodiments, the amino acid residues lining the central cavity include a residue at a position corresponding to Kabat position 85.

In embodiments, the amino acid residues lining the central cavity include a residue at a position corresponding to Kabat position 30. In embodiments, the residue at a position corresponding to Kabat position 30 is a negatively charged amino acid residue. In embodiments, the residue at a position corresponding to Kabat position 30 is aspartic acid. In embodiments, the amino acid residues lining the central cavity include a residue at a position corresponding to Kabat position 52. In embodiments, the residue at a position corresponding to Kabat position 52 is a negatively charged amino acid residue. In embodiments, the residue at a position corresponding to Kabat position 52 is aspartic acid. In embodiments, the amino acid residues lining the central cavity include a residue at a position corresponding to Kabat position 83. In embodiments, the residue at a position corresponding to Kabat position 83 is a negatively charged amino acid residue. In embodiments, the residue at a position corresponding to Kabat position 83 is glutamic acid. In embodiments, the residue at a position corresponding to Kabat position 83 is isoleucine. In embodiments, the amino acid residues lining the central cavity include a residue at a position corresponding to Kabat position 85.

In embodiments, the central cavity is lined by (formed by) a light chain residue at a position corresponding to Kabat position Gln38, Thr40, Gln41, Gly42, Ser43, Asp 52, Asp85, Ile83, Tyr87, Lys103, Val163, Thr164, or Glu165. A "light chain residue" as provided herein refers to a residue forming part of a light chain of an antibody or antibody fragment. In embodiments, the central cavity is lined (e.g., formed) by a light chain residue at a position corresponding to Kabat position Gln38. In embodiments, the central cavity is lined (e.g., formed) by a light chain residue at a position corresponding to Kabat position Thr40 In embodiments, the central cavity is lined (e.g., formed) by a light chain residue at a position corresponding to Kabat position Gln41. In embodiments, the central cavity is lined (e.g., formed) by a light chain residue at a position corresponding to Kabat position Gly42. In embodiments, the central cavity is lined (e.g., formed) by a light chain residue at a position corresponding to Kabat position to Ser43. In embodiments, the central cavity is lined (e.g., formed) by a light chain residue at a position corresponding to Kabat position Asp85. In embodiments, the central cavity is lined (e.g., formed) by a light chain residue at a position corresponding to Kabat position Tyr87. In embodiments, the central cavity is lined (e.g., formed) by a light chain residue at a position corresponding to Kabat position Lys103. In embodiments, the central cavity is lined (e.g., formed) by a light chain residue at a position corresponding to Kabat position Val163. In embodiments, the central cavity is lined (e.g., formed) by a light chain residue at a position corresponding to Kabat position Thr164 In embodiments, the central cavity is lined (e.g., formed) by a light chain residue at a position corresponding to Kabat position Glu165.

In embodiments, the central cavity is lined by (formed by) a heavy chain residue at a position corresponding to Kabat position Asp 30, Gln39, Pro40, Thr91, Ala92, Ile93, Tyr95, Gln112, Leu115, Glu155, Pro156, Pro174, Ala175, or Tyr183. A "heavy chain residue" as provided herein refers to a residue forming part of a heavy chain of an antibody or antibody fragment. In embodiments, the central cavity is lined (e.g., formed) by a heavy chain residue at a position corresponding to Kabat position Gln39. In embodiments, the central cavity is lined (e.g., formed) by a heavy chain residue at a position corresponding to Kabat position. In embodiments, the central cavity is lined (e.g., formed) by a heavy chain residue at a position corresponding to Kabat position Pro40. In embodiments, the central cavity is lined (e.g., formed) by a heavy chain residue at a position corresponding to Kabat position Thr91. In embodiments, the central cavity is lined (e.g., formed) by a heavy chain residue at a position corresponding to Kabat position Ala92. In embodiments, the central cavity is lined (e.g., formed) by a heavy chain residue at a position corresponding to Kabat position Ile93. In embodiments, the central cavity is lined (e.g., formed) by a heavy chain residue at a position corresponding to Kabat position Tyr95. In embodiments, the central cavity is lined (e.g., formed) by a heavy chain residue at a position corresponding to Kabat position Gln112. In embodiments, the central cavity is lined (e.g., formed) by a heavy chain residue at a position corresponding to Kabat position Leu115. In embodiments, the central cavity is lined (e.g., formed) by a heavy chain residue at a position corresponding to Kabat position Glu155. In embodiments, the central cavity is lined (e.g., formed) by a heavy chain residue at a position corresponding to Kabat position Pro156. In embodiments, the central cavity is lined (e.g., formed) by a heavy chain residue at a position corresponding to Kabat position Pro174. In embodiments, the central cavity is lined (e.g., formed) by a heavy chain residue at a position corresponding to Kabat position Ala175. In embodiments, the central cavity is lined (e.g., formed) by a heavy chain residue at a position corresponding to Kabat position Tyr183.

The central cavity provided herein includes a peptide binding site (also referred to herein as a meditope binding site) including framework region amino acid (FR) residues. In embodiments, the peptide binding site does not include CDR residues of the heavy chain or the light chain. In embodiments, the peptide binding site includes FR residues of the heavy chain or the light chain. In embodiments, the peptide binding site includes FR residues of the heavy chain and the light chain. In embodiments, the peptide binding site includes a residue at a position corresponding to Kabat position 83, a residue at a position corresponding to Kabat position 30 or a residue at a position corresponding to Kabat position 52. In embodiments, the peptide binding site includes a residue at a position corresponding to Kabat position 40, a residue at a position corresponding to Kabat position 41, a residue at a position corresponding to Kabat position 30, a residue at a position corresponding to Kabat position 52, a residue at a position corresponding to Kabat position 83, or a residue at a position corresponding to Kabat position 85. In embodiments, the peptide binding site includes a residue at a position corresponding to Kabat position 40. In embodiments, the peptide binding site includes a residue at a position corresponding to Kabat position 41. In embodiments, the peptide binding site includes a residue at a position corresponding to Kabat position 30. In embodiments, the peptide binding site includes a residue at a position corresponding to Kabat position 52. In embodiments, the peptide binding site includes a residue at a position corresponding to Kabat position 83. In embodiments, the peptide binding site includes a residue at a position corresponding to Kabat position 85. In embodiments, residues forming a peptide binding site are described in published US application US20120301400 A1, which is hereby incorporate by reference in its entirety and for all purposes.

In embodiments, the central cavity is lined by amino acid residues capable of binding a compound including a peptidyl moiety. Thus, in embodiments, the peptide binding site provided herein is capable of binding a compound including a peptidyl moiety. In embodiments, the peptide binding site is capable of binding the peptidyl moiety. In embodiments, the peptide binding site provided herein is bound to a compound including a peptidyl moiety. In embodiments, the peptide binding site is bound to the peptidyl moiety. In embodiments, the peptidyl moiety is a moiety as described in published US application US20120301400 A1 and Avery et al. 2015 (Scientific Reports 5:7817) which are hereby incorporated by reference in their entirety and for all purposes.

In embodiments, the compound that binds to the peptide binding site is a peptide or includes a peptidyl moiety. In embodiments, the compound is a substituted peptide. In embodiments, the peptide is between 5 and 16 amino acids in length. In embodiments, the compound includes a substituted peptidyl moiety. In embodiments, the peptidyl moiety is between 5 and 16 amino acids in length. The peptide or peptidyl moiety provided herein may also be referred to as a "meditope." In embodiments, the peptide or peptidyl moiety has the formula:

$$X1-X2-X3-X4-X5-X6-X7-X8-X9-X10-X11-X12 \qquad (I).$$

Where the sequence of Formula (I) is a peptidyl moiety, a person having ordinary skill in the art will immediately understand that the peptidyl moiety is attached to the remainder of the compound at one or more attachments points. In formula (I), X1 is Cys, Gly, β-alanine, 2,3-diaminopropionic acid, β-azidoalanine, or null; X2 is Gln or null; X3 is Phe, Tyr, β-β'-diphenyl-Ala, His, Asp, 2-bromo-L-phenylalanine, 3-bromo-L-phenylalanine, 4-bromo-L-phenylalanine, Asn, Gln, a modified Phe, a hydratable carbonyl-containing residue or a boronic acid-containing residue; X4 is Asp or Asn; X5 is Leu; β-β'-diphenyl-Ala, Phe, a non-natural analog of phenylalanine, tryptophan, tyrosine, a hydratable carbonyl-containing residue or a boronic acid-containing residue; X6 is Ser or Cys; X7 is Thr, Ser or Cys; X8 is Arg, a modified (substituted) Arg, a hydratable carbonyl or a boronic acid-containing residue; X9 is Arg or Ala; X10 is Leu, Gln, Glu, β-β'-diphenyl-Ala, Phe, a non-natural analog of phenylalanine, tryptophan, tyrosine, a hydratable carbonyl-containing residue or a boronic acid-containing residue; X11 is Lys; and X12 is Cys, Gly, 7-aminoheptanoic acid, β-alanine, diaminopropionic acid, propargylglycine, isoaspartic acid or null; wherein the modified Phe is a Phe with one or more halogen incorporated into the phenyl ring and wherein the modified Arg has a structure of the formula:

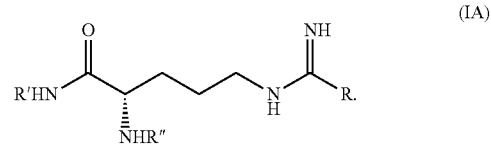

(IA)

In formula (IA), R, R' and R" are independently substituted or unsubstituted alkyl, substituted or unsubstituted aryl, substituted or unsubstituted heteroaryl, or NHR'" and R'" is substituted or unsubstituted alkyl, substituted or unsubstituted aryl, substituted or unsubstituted heteroaryl. In embodiments, R'" is unsubstituted alkyl, unsubstituted aryl or unsubstituted heteroaryl.

In embodiments, the peptide is a cyclic peptide. In embodiments, the peptidyl moiety is a cyclic peptidyl moiety. In embodiments, the peptide or peptidyl moiety includes a disulfide bridge, a thioether bridge, a lactam linkage, cycloaddition. In embodiments, the cyclic portion of the cyclic peptide or cyclic peptidyl moiety is formed through binding between X1 and X12, X1 and X11, X3 and X11, X4 and X11, or X2 and X12. In embodiments, the non-natural amino acid is β-β'-diphenyl-Ala, branched alkyl, substituted or unsubstituted aryl or substituted or unsubstituted heteroaryl. In embodiments, each of the one or more halogen is an ortho-, meta-, or para-bromo phenyl substituent.

In embodiments, the peptide or peptidyl moiety has the formula:

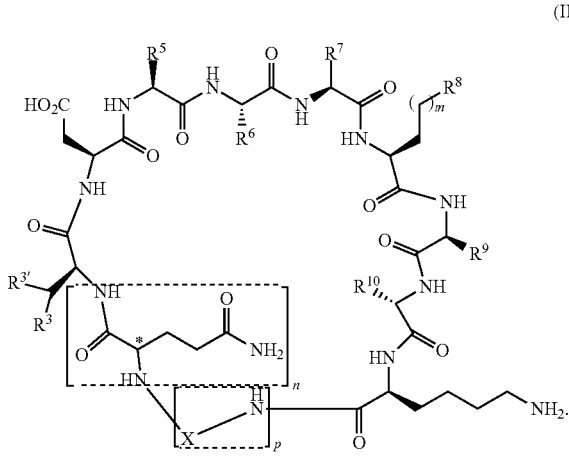

(II)

In formula (II), $R^3$ is hydrogen, $R^{3A}$-substituted or unsubstituted aryl, wherein $R^{3A}$ is hydrogen, halogen or $C_{1-4}$ unsubstituted alkyl. $R^{3'}$ is hydrogen, $R^{3A'}$-substituted or unsubstituted aryl, wherein $R^{3A'}$ is hydrogen, halogen or $C_{1-4}$ unsubstituted alkyl. $R^5$ is $R^{5A}$-substituted or unsubstituted $C_{1-8}$ (e.g., $C_{1-4}$) alkyl. $R^{5A}$ is oxo, acetal, ketal, $-B(OH)_2$, boronic ester, phosphonate ester, ortho ester, $-CO_2C_{1-4}$ alkyl, $-CH=CH-CHO$, $-CH=CH-C(O)R^{5A'}$, $-CH=CH-CO_2R^{5A'}$, $-CO_2H$, $-CONH_2$, or $R^{5A''}$-substituted or unsubstituted aryl, $R^{5A''}$-substituted or unsubstituted heteroaryl (e.g., naphthyl, imidazole, indole), wherein $R^{5A'}$ is substituted or unsubstituted $C_{1-4}$ alkyl and $R^{5A''}$ is $-OH$, fluoro, chloro, bromo or iodo. $R^6$ is $-L^{6'}OH$ or $-L^{6'}SH$, wherein $L^{6'}$ is substituted or unsubstituted $C_{1-4}$ alkylene. $R^7$ is $-L^{7'}OH$ or $-L^{7'}SH$, wherein $L^{4'}$ is substituted or unsubstituted $C_{1-4}$ alkyl. The symbol m is 0, 1, 2, 3, 4, or 5.

In formula (II), $R^8$ is $-OH$, $-NR^aR^b$, $-N(R^c)C(O)R^e$, or $-N(R^c)C(=NR^d)R^e$. $R^a$ is H. $R^b$ is H or $C_{1-8}$ alkyl optionally substituted with one or more substituents selected from the group consisting of oxo, acetal, and ketal, $-B(OH)_2$, $-SH$, boronic ester, phosphonate ester, ortho ester, $-CH=CH-CHO$, $-CH=CH-C(O)C_{1-4}$ alkyl, $-CH=CH-CO_2C_{1-4}$ alkyl, $-CO_2H$, or $-CO_2C_{1-4}$ alkyl group. $R^c$ is H, $C_{1-8}$ alkyl, $C_{3-8}$ cycloalkyl, branched alkyl, or aryl. Rd is H or a $C_{1-8}$ alkyl, $C_{2-8}$ alkenyl, $C_{2-8}$ alkynyl, $C_{3-8}$ cycloalkyl, branched alkyl, or aryl group, each optionally substituted with one or more substituents selected from the group consisting of $-N_3$, $-NH_2$, $-OH$, $-SH$, halogen, oxo, acetal, ketal, $-B(OH)_2$, boronic ester, phosphonate ester, ortho ester, $-CH=CH-CHO$, $-CH=CH-C(O)C_{1-4}$alkyl, $-CH=CH-CO_2C_{1-4}$alkyl, $-CO_2H$, and $-CO_2C_{1-4}$ alkyl group. $R^e$ is H, $-NHR^d$; or a $C_{1-12}$ alkyl, $C_{3-8}$ cycloalkyl, $C_{2-12}$ alkenyl, $C_{2-8}$ alkynyl, or aryl group, each optionally substituted with one or more substituents selected from the group consisting of $-N_3$, $-NH_2$, $-OH$, $-SH$, oxo, $C_{2-4}$ acetal, $C_{2-4}$ ketal, $-B(OH)_2$, boronic ester, phosphonate ester, ortho ester, $-CH=CH-CHO$, $-CH=CH-C(O)C_{1-4}$ alkyl, $-CH=CH-CO_2C_{1-4}$ alkyl, and $-CO_2C_{1-4}$ alkyl group.

In formula (II), $R^9$ is substituted or unsubstituted $C_{1-4}$ alkyl. $R^{10}$ is $R^{10A}$-substituted or unsubstituted $C_{1-8}$ alkyl, wherein $R^{10A}$ is oxo, acetal, ketal, $-B(OH)_2$, boronic ester, phosphonate ester, ortho ester, $-CH=CH-CHO$, $-CH=CH-C(O)C_{1-4}$ alkyl, $-CH=CH-CO_2C_{1-4}$ alkyl, $-CO_2C_{1-4}$ alkyl, $-CO_2H$, $-CONH_2$, $R^{10B}$-substituted or unsubstituted phenyl, $R^{10B}$-substituted or unsubstituted naphthyl, $R^{10B}$-substituted or unsubstituted imidazolyl, or $R^{10B}$-substituted or unsubstituted indolyl, wherein $R^{10B}$ is $-OH$ or halogen. The symbol n is 0 or 1. The symbol p is 0 or 1.

In formula (II), X is RX-substituted or unsubstituted $C_{1-8}$ alkylene, $R^x$-substituted or unsubstituted $C_{2-8}$ alkenylene, $R^x$ is oxo, $-C(O)$, $-NH_2$, $-NHC(O)$ or $-NHC(O)RY$, wherein one carbon of the alkenylene is optionally replaced with $-C(O)NH$, a 5-membered heteroarylene, or $-S-S$, and $R^y$ is $-C_{1-4}$ alkyl, $-CH(R^z)C(O)$ or $-CH(R^z)CO_2H$, wherein $R^z$ is $-H$ or $R^{z'}$-substituted or unsubstituted $-C_{1-4}$ alkyl, wherein $R^{z'}$ is $-OH$, $-SH$, or $-NH_2$. Formula (I) or (II) includes all appropriate pharmaceutically acceptable salts. More information regarding the concepts of peptide binding sites (meditope binding sites) and peptides (meditopes) can be found in international application serial no. PCT/US2011/055656, PCT/US2015/053880, PCT/US2012/032938 and US application serial no. U.S. Ser. No. 14/453,586, which are hereby incorporated in their entirety and for all purposes.

The compounds provided herein may include a therapeutic agent, a diagnostic agent or a detectable agent (also referred to herein as a detectable agent) attached to the peptidyl moiety. In embodiments, the compound is conjugated to a therapeutic agent, a diagnostic agent, or a detectable agent. In embodiments, the peptidyl moiety (e.g., the peptide of formula (I) or (II)) is conjugated to a therapeutic agent, a diagnostic agent or a detectable agent. In embodiments, the antibody region is conjugated to a therapeutic agent, a diagnostic agent, or a detectable agent.

The therapeutic agent, diagnostic agent or detectable agent may be attached through a chemical linker to the compound (e.g. to the peptidyl moiety) and/or the antibody region provided herein including embodiments thereof. In embodiments, the chemical linker is a covalent linker, a non-covalent linker, a peptide linker (a linker including a peptide moiety), a cleavable peptide linker, a substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene or any combination thereof.

A chemical linker as provided herein may include a plurality of chemical moieties, wherein each of the plurality of moieties is chemically different. In embodiments, the therapeutic agent, diagnostic agent or detectable agent is attached to the compound through a non-covalent or covalent linker. In embodiments, the therapeutic agent, diagnostic agent or detectable agent is attached to the peptidyl moiety through a non-covalent or covalent linker. In embodiments, the therapeutic agent, diagnostic agent or detectable agent is attached to the antibody region through a non-covalent or covalent linker. Typically, the linker may be a covalent linker as described herein and formed through conjugate (e.g. "click") chemistry. The linker may further be a cleavable peptide linker as described herein. Where the therapeutic, diagnostic or detectable agent forms part (e.g., through covalent attachment) of the compound, the peptidyl moiety and/or the antibody region provided herein, including embodiments thereof, the therapeutic, diagnostic or detectable agent may be referred to as a "therapeutic moiety", "diagnostic moiety", or "detectable moiety", respectively. In embodiments, the peptide moiety (meditope) contains a reactive amine functionality (e.g., Lys1 1), which is used for conjugation of the meditope (peptidyl moiety), e.g., to a scaffold or linker or to a functional moiety, such as a diagnostic, e.g., imaging, agent or therapeutic moiety as described herein. In embodiments, thiol functionalities are introduced in any suitable position on the meditope (peptidyl moiety) and are selectively modified using reagents containing imagining agents, other proteins and peptides, metal chelators, siRNAs, nanoparticles, and cytotoxic drugs. Coupling of therapeutic or diagnostic moieties to the peptidyl moiety provided herein can be performed using peptide chemistry methodology well known in the art and described, for example in WO 2013055404 A1, which is hereby incorporated by reference for all purposes and its entirety.

Therapeutic moieties as provided herein may include, without limitation, peptides, proteins, nucleic acids, nucleic acid analogs, small molecules, antibodies, enzymes, prodrugs, cytotoxic agents (e.g. toxins) including, but not limited to ricin, doxorubicin, daunorubicin, taxol, ethidium bromide, mitomycin, etoposide, tenoposide, vincristine, vinblastine, colchicine, dihydroxy anthracin dione, actinomycin D, diptheria toxin, *Pseudomonas* exotoxin (PE) A, PE40, abrin, and glucocorticoid. In embodiments, the therapeutic moiety is an anti-cancer agent or chemotherapeutic agent as described herein. In embodiments, the therapeutic moiety is a nucleic acid moiety, a peptide moiety or a small molecule drug moiety. In embodiments, the therapeutic moiety is a nucleic acid moiety. In embodiments, the therapeutic moiety is an antibody moiety. In embodiments, the therapeutic moiety is a peptide moiety. In embodiments, the therapeutic moiety is a small molecule drug moiety. In embodiments, the therapeutic moiety is a nuclease. In embodiments, the therapeutic moiety is an immunostimulator. In embodiments, the therapeutic moiety is a toxin. In embodiments, the therapeutic moiety is a nuclease.

The compound, peptidyl moiety or antibody region provided herein may include an imaging or detectable moiety. In embodiments, the detectable moiety is connected to the compound through a covalent linker. In embodiments, the detectable moiety is connected to the antibody region through a covalent linker. In embodiments, detectable moiety is connected to peptidyl moiety through a covalent linker. An "imaging or detectable moiety" as provided herein is a monovalent compound detectable by spectroscopic, photochemical, biochemical, immunochemical, chemical, or other physical means. In embodiments, the imaging moiety is covalently attached to the compound. In embodiments, the imaging moiety is covalently attached to the antibody region. In embodiments, the imaging moiety is covalently attached to the peptidyl moiety. Exemplary imaging moieties include without limitation 32P, radionuclides, positron-emitting isotopes, fluorescent dyes, fluorophores, antibodies, bioluminescent molecules, chemiluminescent molecules, photoactive molecules, metals, electron-dense reagents, enzymes (e.g., as commonly used in an ELISA), magnetic contrast agents, quantum dots, nanoparticles, biotin, digoxigenin, haptens and proteins or other entities which can be made detectable, e.g., by incorporating a radiolabel into a peptide or antibody specifically reactive with a target peptide. Any method known in the art for conjugating an antibody to the moiety may be employed, e.g., using methods described in Hermanson, Bioconjugate Techniques 1996, Academic Press, Inc., San Diego. Exemplary fluorophores include fluorescein, rhodamine, GFP, coumarin, FITC, AlExa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese. In embodiments, the imaging moiety is a bioluminescent molecule. In embodiments, the imaging moiety is a photoactive molecule. In embodiments, the imaging moiety is a metal. In embodiments, the imaging moiety is a nanoparticle.

A wide variety of CAR have been described in the scientific literature. In general CARs include an extracellular antigen-binding domain (often a scFv derived from variable heavy and light chains of an antibody), a spacer domain, a transmembrane domain and an intracellular signaling domain. The intracellular signaling domain usually includes the endodomain of a T cell co-stimulatory molecule (e.g., CD28, 4-1BB or OX-40) and the intracellular domain of CD3ζ.

A "transmembrane domain" as provided herein refers to a polypeptide forming part of a biological membrane. The transmembrane domain provided herein is capable of spanning a biological membrane (e.g., a cellular membrane) from one side of the membrane through to the other side of the membrane. In embodiments, the transmembrane domain spans from the intracellular side to the extracellular side of a cellular membrane. Transmembrane domains may include non-polar, hydrophobic residues, which anchor the proteins provided herein including embodiments thereof in a biological membrane (e.g., cellular membrane of a T cell). Any transmembrane domain capable of anchoring the proteins provided herein including embodiments thereof are contemplated. In embodiments, the transmembrane domain is L-selectin. The term "L-selectin" as provided herein includes any of the recombinant or naturally-occurring forms of the L-selectin protein, also known as CD62L, or variants or homologs thereof that maintain L-selectin activity (e.g. within at least 50%, 80%, 90%, 95%, 96%, 97%, 98%, 99% or 100% activity compared to L-selectin). In embodiments, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring L-selectin polypeptide. In embodiments, L-selectin is the protein as identified by the NCBI sequence reference GI:262206315, homolog or functional fragment thereof. Non-limiting examples of transmembrane domains include the transmembrane domains of CD8, CD4 or CD3-zeta.

In embodiments, the transmembrane domain is a CD28 transmembrane domain.

The term "CD28 transmembrane domain" as provided herein includes any of the recombinant or naturally-occurring forms of the transmembrane domain of CD28, or variants or homologs thereof that maintain CD28 transmembrane domain activity (e.g. within at least 50%, 80%, 90%, 95%, 96%, 97%, 98%, 99% or 100% activity compared to the CD28 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD28 transmembrane domain polypeptide. In embodiments, the CD28 transmembrane domain is the protein as identified by SEQ ID NO:22, SEQ ID NO:2, homolog or functional fragment thereof. In embodiments, CD28 is the protein as identified by the NCBI sequence reference GI:340545506, homolog or functional fragment thereof.

In embodiments, the transmembrane domain is the protein identified by SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, homolog or functional fragment thereof.

A variety of transmembrane domains can be used the methods provided herein. Table 1 and Table 3 include examples of suitable transmembrane domains. Where a spacer region is present, the transmembrane domain is located carboxy terminal to the spacer region.

In embodiments, the recombinant CAR protein provided herein includes an intracellular T-cell signaling domain. In embodiments, the intracellular T-cell signaling domain is a CD3ζ intracellular T-cell signaling domain. An "intracellular T-cell signaling domain" as provided herein includes amino acid sequences capable of providing primary signaling in response to binding of an antigen to the antibody region provided herein including embodiments thereof. In embodiments, the signaling of the intracellular T-cell signaling domain results in activation of the T cell expressing the same. In embodiments, the signaling of the intracellular T-cell signaling domain results in proliferation (cell division) of the T cell expressing the same. In embodiments, the signaling of the intracellular T-cell signaling domain results expression by said T cell of proteins known in the art to characteristic of activated T cell (e.g., CTLA-4, PD-1, CD28, CD69). In embodiments, the intracellular T-cell signaling domain includes the signaling domain of the zeta chain of the human CD3 complex. In embodiments, the intracellular T-cell signaling domain is a CD3ζ intracellular T-cell signaling domain. In embodiments, the intracellular T-cell signaling domain is SEQ ID NO:11.

In embodiments, the recombinant CAR protein provided herein includes an intracellular co-stimulatory signaling domain. An "intracellular co-stimulatory signaling domain" as provided herein includes amino acid sequences capable of providing co-stimulatory signaling in response to binding of an antigen to the antibody region provided herein including embodiments thereof. In embodiments, the signaling of the co-stimulatory signaling domain results in production of cytokines and proliferation of the T cell expressing the same. In embodiments, the intracellular co-stimulatory signaling domain is a CD28 intracellular co-stimulatory signaling domain, a 4-1BB intracellular co-stimulatory signaling domain, a ICOS intracellular co-stimulatory signaling domain, or an OX-40 intracellular co-stimulatory signaling domain. In embodiments, the intracellular co-stimulatory signaling domain includes a CD28 intracellular co-stimulatory signaling domain, a 4-1BB intracellular co-stimulatory signaling domain, a ICOS intracellular co-stimulatory signaling domain, an OX-40 intracellular co-stimulatory signaling domain or any combination thereof. Exemplary intracellular co-stimulatory signaling domains including sequences and accession numbers are listed in Table 2. In embodiments, the intracellular co-stimulatory signaling domain includes the protein identified by SEQ ID NO: 12, SEQ ID NO: 13, SEQ ID NO: 14, SEQ ID NO: 15 or SEQ ID NO:16. In embodiments, the intracellular co-stimulatory signaling domain is SEQ ID NO:12, SEQ ID NO:13, SEQ ID NO:14, SEQ ID NO: 15 or SEQ ID NO:16.

In embodiments, the recombinant CAR protein provided herein includes a linker domain. In embodiments, the linker domain is between the transmembrane domain and the intracellular T-cell signaling domain. In embodiments, the linker domain is between the intracellular T-cell signaling domain and the intracellular co-stimulatory signaling domain. In embodiments, the linker domain includes the sequence GGCGG or GGG.

In embodiments, the recombinant CAR protein provided herein includes a spacer region. In embodiments, the spacer region is between the transmembrane domain and the antibody region. A "spacer region" as provided herein is a polypeptide connecting the antibody region with the transmembrane domain. In embodiments, the spacer region connects the heavy chain constant region with the transmembrane domain. In embodiments, the binding affinity of the antibody region to an antigen is increased compared to the absence of the spacer region. In embodiments, the steric hindrance between an antibody region and an antigen is decreased in the presence of the spacer region.

In embodiments, the spacer region includes an Fc region. Examples of spacer regions contemplated for the compositions and methods provided herein include without limitation, immunoglobulin molecules or fragments thereof (e.g., IgG1, IgG2, IgG3, IgG4) and immunoglobulin molecules or fragments thereof (e.g., IgG1, IgG2, IgG3, IgG4) including mutations affecting Fc receptor binding. In embodiments, the spacer region is a fragment of an IgG (e.g., IgG4), wherein said fragment includes a deletion of the CH2 domain. The spacer region may be a peptide linker. In embodiments, the spacer region is a serine-glycine linker. In embodiments, the spacer region has the sequence GGSG. In embodiments, the spacer region has the sequence GSGSGSGS. In embodiments, the spacer region is at least 4 amino acids in length. In embodiments, the spacer region is about 4 amino acids in length. In embodiments, the spacer region is between 4 and 250 amino acids in length. The spacer region may include residues capable of extending the half-life in vivo (e.g., plasma) of the proteins provided herein. In embodiments, the spacer region is 10 amino acids in length. In embodiments, the spacer region is 229 amino acids in length. In embodiments, the spacer region is GGGSSGGGSG. The spacer region may be "pasylated." The term "pasylated" or "pasylation" is used in its customary sense and refers to an amino acid sequences, which due to their high content in proline, alanine and serine form highly soluble biological polymers. Thus, in embodiments, the spacer region includes about 200 proline, alanine and serine residues combined. In embodiments, the spacer region includes from about 10 to about 200 proline, alanine and serine residues combined. In embodiments, the spacer region includes hydrophilic residues. In embodiments, the recombinant CAR protein does not include a spacer region. In embodiments, the nucleic acid does not include a spacer sequence encoding a spacer region. In embodiments, the nucleic acid does not include a spacer sequence encoding a spacer region as described in WO 2015105522 A1.

The CAR described herein can include a spacer region located between the cancer antigen targeting domain (e.g., a CD19 ScFv, e.g., the scFv portion can include the CD19 targeted scFv sequence of a CD19-targeted CAR such as that described in Wang et al. 2016 *Blood* 127:2980-2990) and the transmembrane domain. A variety of different spacer regions can be used. Some of them include at least portion of a human Fc region, for example a hinge portion of a human Fc region or a CH3 domain or variants thereof. Table 4 below provides various spacers that can be used in the CARs described herein.

Some spacer regions include all or part of an immunoglobulin (e.g., IgG1, IgG2, IgG3, IgG4) hinge region, i.e., the sequence that falls between the CH1 and CH2 domains of an immunoglobulin, e.g., an IgG4 Fc hinge or a CD8 hinge. Some spacer regions include an immunoglobulin CH3 domain or both a CH3 domain and a CH2 domain. The immunoglobulin derived sequences can include one ore more amino acid modifications, for example, 1, 2, 3, 4 or 5 substitutions, e.g., substitutions that reduce off-target binding.

The spacer region can also comprise a IgG4 hinge region having the sequence ESKYGPPCPSCP (SEQ ID NO:102) or ESKYGPPCPPCP (SEQ ID NO:101).

The spacer region can also comprise the sequence ESKYGPPCPPCP (SEQ ID NO:101) followed by the linker sequence GGGSSGGGSG (SEQ ID NO:100) followed by IgG4 CH3 sequence GQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK (SEQ ID NO:110). Thus, the entire spacer region can comprise the sequence: ESKYGPPCPPCPGGGSSGGGSGGQPREPQVYTLPPSQEEMTKNQVSLTCLVKGFY PSDIAVEWESNGQPENNYKTTPPVLDSDGSFFLYSRLTVDKSRWQEGNVFSCSVMHEALHNHYTQKSLSLSLGK (SEQ ID NO:107). In some cases, the spacer has 1, 2, 3, 4 or 5 single amino acid changes (e.g., conservative changes) compared to those shown in Table 4. In some cases, the IgG4 Fc hinge/linker region that is mutated at two positions (L235E; N297Q) in a manner that reduces binding by Fc receptors (FcRs).

In embodiments, the nucleic acid encoding the recombinant CAR protein includes (i) a heavy chain sequence encoding a heavy chain domain of the protein, the heavy chain domain includes a variable heavy chain domain and the transmembrane domain; and (ii) a light chain sequence encoding a light chain domain of the protein, the light chain domain includes a variable light chain domain, wherein the variable heavy chain domain and the variable light chain domain together form at least a portion of the antibody region.

In embodiments, the isolated nucleic acid encoding the recombinant CAR protein encodes from the 5' end to 3' end: a light chain sequence, a heavy chain sequence, a transmembrane sequence and an intracellular co-stimulatory signaling sequence. In embodiments, the isolated nucleic acid encodes from the 5' end to 3' end: a heavy chain sequence, a transmembrane sequence, an intracellular co-stimulatory signaling sequence and a light chain sequence. In embodiments, the isolated nucleic acid encoding the recombinant CAR protein encodes from the 5' end to 3' end: a light chain sequence, a self-cleaving peptidyl linker sequence, a heavy chain sequence, a spacer sequence, a transmembrane sequence, an intracellular co-stimulatory signaling sequence and an intracellular T-cell signaling sequence. In embodiments, the isolated nucleic acid encoding the recombinant CAR protein encodes from the 5' end to 3' end: a heavy chain sequence, a spacer sequence, a transmembrane sequence, an intracellular co-stimulatory signaling sequence, an intracellular T-cell signaling sequence, a self-cleaving peptidyl linker sequence and a light chain sequence.

A "light chain sequence" as provided herein refers to the nucleic acid sequence encoding for a light chain domain provided herein. A light chain domain provided herein may include a light chain variable (VL) region and/or a light chain constant region (CL). A "heavy chain sequence" as provided herein refers to the nucleic acid sequence encoding for a heavy chain domain provided herein. A heavy chain domain provided herein may include heavy chain variable (VH) region and/or a heavy chain constant region (CH). A "transmembrane sequence" as provided herein refers to the nucleic acid sequence encoding for a transmembrane domain provided herein. An "intracellular T-cell signaling sequence" as provided herein refers to the nucleic acid sequence encoding for a intracellular T-cell signaling domain provided herein. An "intracellular co-stimulatory signaling sequence" (also referred to herein as a costimulatory domain) as provided herein refers to the nucleic acid sequence encoding for a intracellular co-stimulatory signaling domain provided herein.

The costimulatory domain can be any domain that is suitable for use with a CD3ζ signaling domain. In some cases, the costimulatory domain is a CD28 costimulatory domain that includes a sequence that is at least 90%, at least 95%, at least 98% identical to or identical to:

```
RSKRSRGGHSDYMNMTPRRPGPTRKHYQPYAPPRDFAAYRS.
(SEQ ID NO: 121; LL to GG amino acid change
double underlined).
```

In some cases, the CD28 co-signaling domain has 1, 2, 3, 4 of 5 amino acid changes (preferably conservative and preferably not in the underlined GG sequence) compared to SEQ ID NO:121. In some cases the co-signaling domain is a 4-1BB co-signaling domain that includes a sequence that is at least 90%, at least 95%, at least 98% identical to or identical to:

```
                                    (SEQ ID NO: 122)
KRGRKKLLYIFKQPFMRPVQTTQEEDGCSCRFPEEEEGGCEL.
```

In some cases, the 4-1BB co-signaling domain has 1, 2, 3, 4 of 5 amino acid changes (preferably conservative) compared to SEQ ID NO:122.

The costimulatory domain(s) are located between the transmembrane domain and the CD3ζ signaling domain. Table 5 includes examples of suitable costimulatory domains together with the sequence of the CD3ζ signaling domain.

In various embodiments: the costimulatory domain is selected from the group consisting of: a costimulatory domain depicted in Table 5 or a variant thereof having 1-5 (e.g., 1 or 2) amino acid modifications, a CD28 costimulatory domain or a variant thereof having 1-5 (e.g., 1 or 2) amino acid modifications, a 4-1BB costimulatory domain or a variant thereof having 1-5 (e.g., 1 or 2) amino acid modifications and an OX40 costimulatory domain or a variant thereof having 1-5 (e.g., 1 or 2) amino acid modifications. In certain embodiments, a 4-1BB costimulatory domain or a variant thereof having 1-5 (e.g., 1 or 2) amino acid modifications in present. In some embodiments there are two costimulatory domains, for example a CD28 costimulatory domain or a variant thereof having 1-5 (e.g., 1 or 2) amino acid modifications (e.g., substitutions) and a 4-1BB co-stimulatory domain or a variant thereof having 1-5 (e.g., 1 or 2) amino acid modifications (e.g., substitutions). In various embodiments the 1-5 (e.g., 1 or 2) amino acid modification are substitutions. The costimulatory domain is amino terminal to the CD3ζ signaling domain and in some cases a short linker consisting of 2-10, e.g., 3 amino acids (e.g., GGG) is positioned between the costimulatory domain and the CD3ζ signaling domain.

CD3ζ Signaling Domain

The CD3ζ Signaling domain can be any domain that is suitable for use with a CD3ζ signaling domain. In some cases, the CD3ζ signaling domain includes a sequence that is at least 90%, at least 95%, at least 98% identical to or identical to:

(SEQ ID NO: 119)
RVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATK

DTYDALHMQALPPR.

In some cases, the CD3ζ signaling has 1, 2, 3, 4 of 5 amino acid changes (preferably conservative) compared to SEQ ID NO:119.

Truncated EGFR

The CD3ζ signaling domain can be followed by a ribosomal skip sequence (e.g., LEGGGEGRGSLLTCGD-VEENPGPR; SEQ ID NO:124) and a truncated EGFR having a sequence that is at least 90%, at least 95%, at least 98% identical to or identical to:

(SEQ ID NO: 125)
LVTSLLLCELPHPAFLLIPRKVCNGIGIGEFKDSLSINATNIKHFKNCT

SISGDLHILPVAFRGDSFTHTPPLDPQELDILKTVKEITGFLLIQAWPE

NRTDLHAFENLEIIRGRTKQHGQFSLAVVSLNITSLGLRSLKEISDGDV

IISGNKNLCYANTINWKKLFGTSGQKTKIISNRGENSCKATGQVCHALC

SPEGCWGPEPRDCVSCRNVSRGRECVDKCNLLEGEPREFVENSECIQCH

PECLPQAMNITCTGRGPDNCIQCAHYIDGPHCVKTCPAGVMGENNTLVW

KYADAGHVCHLCHPNCTYGCTGPGLEGCPTNGPKIPSIATGMVGALLLL

LVVALGIGLFM.

In some cases, the truncated EGFR has 1, 2, 3, 4 of 5 amino acid changes (preferably conservative) compared to SEQ ID NO:125.

In embodiments, the isolated nucleic acid encoding the recombinant CAR protein includes a self-cleaving peptidyl sequence encoding a self-cleaving peptidyl domain between the heavy chain sequence and the light chain sequence. In embodiments, the self-cleaving peptidyl linker sequence is a T2A sequence. In embodiments, the self-cleaving peptidyl linker sequence is a T2A sequence or a 2A sequence. In embodiments, the self-cleaving peptidyl linker sequence is a foot-and-mouth disease virus sequence. In embodiments, the self-cleaving peptidyl linker sequence is PVKQLLNFDLLKLAGDVESNPGP (SEQ ID NO:83). In embodiments, the self-cleaving peptidyl linker sequence is an equine rhinitis A virus sequence. In embodiments, the self-cleaving peptidyl linker sequence is QCTNYALLKLAGDVESNPGP (SEQ ID NO:84). In embodiments, the self-cleaving peptidyl linker sequence is a porcine teschovirus 1 sequence. In embodiments, the self-cleaving peptidyl linker sequence is ATNFSLLKQAGD-VEENPGP (SEQ ID NO:85). In embodiments, the self-cleaving peptidyl linker sequence is Thosea asigna virus sequence. In embodiments, the self-cleaving peptidyl linker sequence is EGRGSLLTCGDVESNPGP (SEQ ID NO:86). In embodiments, the light chain sequence is 3' to the heavy chain sequence. In embodiments, the light chain sequence is 5' to the heavy chain sequence.

In embodiments, the antibody region is a cetuximab meditope enabled domain, trastuzumab meditope enabled domain, pertuzumab meditope enabled domain, M5A meditope enabled domain or rituximab meditope enabled domain. In embodiments, the antibody region is a humanized cetuximab meditope enabled domain. In embodiments, the antibody region is a humanized rituximab meditope enabled domain.

In another aspect, an isolated nucleic acid is provided. The isolated nucleic acid encodes a recombinant CAR protein including a first portion including an antibody heavy chain variable domain and a second portion including an antibody light chain variable domain and an antibody light chain constant domain, wherein the first portion further includes a transmembrane domain. In embodiments, the recombinant CAR protein is the protein identified by SEQ ID NO:17. In embodiments, the recombinant CAR protein is the protein identified by SEQ ID NO:28.

In embodiments, the recombinant CAR protein includes from the N-terminus to the C-terminus: a signaling peptide of SEQ ID NO: 18, a heavy chain domain of SEQ ID NO:19, a hinge region of SEQ ID NO:20, a spacer region of SEQ ID NO:21, a transmembrane domain of SEQ ID NO:22, an intracellular co-stimulatory signaling domain of SEQ ID NO:23, a linker domain of SEQ ID NO:24, an intracellular T-cell signaling domain of SEQ ID NO:25, a first self-cleaving peptidyl linker domain of SEQ ID NO:26, a marker peptide of SEQ ID NO:29, a second self-cleaving peptidyl linker domain of SEQ ID NO:30, a signaling peptide of SEQ ID NO: 18 and a light chain domain of SEQ ID NO:27. In embodiments, the recombinant CAR protein includes from the N-terminus to the C-terminus: a signaling peptide of SEQ ID NO: 18, a heavy chain domain of SEQ ID NO: 19, a hinge region of SEQ ID NO:20, a spacer region of SEQ ID NO:21, a transmembrane domain of SEQ ID NO:22, an intracellular co-stimulatory signaling domain of SEQ ID NO:23, a linker domain of SEQ ID NO:24, an intracellular T-cell signaling domain of SEQ ID NO:25, a first self-cleaving peptidyl linker domain of SEQ ID NO:26, a marker peptide of SEQ ID NO:29, a second self-cleaving peptidyl linker domain of SEQ ID NO:30, a signaling peptide of SEQ ID NO:18 or a light chain domain of SEQ ID NO:27. In embodiments, the recombinant CAR protein includes from the N-terminus to the C-terminus: a signaling peptide of SEQ ID NO: 18, a heavy chain domain of SEQ ID NO: 19, a hinge region of SEQ ID NO:20, a spacer region of SEQ ID NO:21, a transmembrane domain of SEQ ID NO:22, an intracellular co-stimulatory signaling domain of SEQ ID NO:23, a linker domain of SEQ ID NO:24, an intracellular T-cell signaling domain of SEQ ID NO:25, a self-cleaving peptidyl linker domain of SEQ ID NO:26, a signaling peptide of SEQ ID NO: 18 and a light chain domain of SEQ ID NO:27. In embodiments, the recombinant CAR protein includes from the N-terminus to the C-terminus: a signaling peptide of SEQ ID NO: 18, a heavy chain domain of SEQ ID NO: 19, a hinge region of SEQ ID NO:20, a spacer region of SEQ ID NO:21, a transmembrane domain of SEQ ID NO:22, an intracellular co-stimulatory signaling domain of SEQ ID NO:23, a linker domain of SEQ ID NO:24, an intracellular T-cell signaling domain of SEQ ID NO:25, a self-cleaving peptidyl linker domain of SEQ ID NO:26, a signaling peptide of SEQ ID NO: 18 or a light chain domain of SEQ ID NO:27.

The term "signaling peptide" as referred to herein is used according to its ordinary meaning in the art and refers to a peptide having a length of about 5-30 amino acids. A signaling peptide is present at the N-terminus of newly synthesized proteins that form part of the secretory pathway. Proteins of the secretory pathway include, but are not limited to proteins that reside either inside certain organelles (the endoplasmic reticulum, Golgi or endosomes), are secreted from the cell, or are inserted into a cellular membrane. In embodiments, the signaling peptide forms part of the transmembrane domain of a protein.

The term "heavy chain domain" as referred to herein is used according to its ordinary meaning in the art and refers to a polypeptide including a heavy chain variable (VH) region and a heavy chain constant region (CH). The term "light chain domain" as referred to herein is used according to its ordinary meaning in the art and refers to a polypeptide including a light chain variable (VL) region and a light chain constant region (CL).

In embodiments, the protein includes from the N-terminus to the C-terminus: a signaling peptide of SEQ ID NO:126, a light chain domain of SEQ ID NO:127, a self-cleaving peptidyl linker domain of SEQ ID NO: 128, a heavy chain domain of SEQ ID NO:129, a hinge region of SEQ ID NO: 130, a first spacer region of SEQ ID NO:131, a second spacer region of SEQ ID NO: 132, a transmembrane domain of SEQ ID NO:133, an intracellular co-stimulatory signaling domain of SEQ ID NO: 134, a linker domain of SEQ ID NO:135, and an intracellular T-cell signaling domain of SEQ ID NO:136. In embodiments, the protein includes from the N-terminus to the C-terminus: a signaling peptide of SEQ ID NO: 126, a light chain domain of SEQ ID NO: 127, a self-cleaving peptidyl linker domain of SEQ ID NO: 128, a heavy chain domain of SEQ ID NO:129, a hinge region of SEQ ID NO: 130, a first spacer region of SEQ ID NO:131, a second spacer region of SEQ ID NO: 132, a transmembrane domain of SEQ ID NO:133, an intracellular co-stimulatory signaling domain of SEQ ID NO: 134, a linker domain of SEQ ID NO:135, or an intracellular T-cell signaling domain of SEQ ID NO:136.

In embodiments, the recombinant CAR protein includes from the N-terminus to the C-terminus: a signaling peptide of SEQ ID NO: 137, a heavy chain domain of SEQ ID NO:138, a hinge region of SEQ ID NO: 138, a first spacer region of SEQ ID NO:140, a second spacer region of SEQ ID NO: 141, a transmembrane domain of SEQ ID NO:142, an intracellular co-stimulatory signaling domain of SEQ ID NO:143, a linker domain of SEQ ID NO: 144, and an intracellular T-cell signaling domain of SEQ ID NO: 145, a self-cleaving peptidyl linker domain of SEQ ID NO: 146, and a light chain domain of SEQ ID NO:147. In embodiments, the recombinant CAR protein includes from the N-terminus to the C-terminus: a signaling peptide of SEQ ID NO: 137, a heavy chain domain of SEQ ID NO: 138, a hinge region of SEQ ID NO: 139, a first spacer region of SEQ ID NO: 140, a second spacer region of SEQ ID NO: 141, a transmembrane domain of SEQ ID NO:142, an intracellular co-stimulatory signaling domain of SEQ ID NO:143, a linker domain of SEQ ID NO: 144, and an intracellular T-cell signaling domain of SEQ ID NO: 145, a self-cleaving peptidyl linker domain of SEQ ID NO:146, or a light chain domain of SEQ ID NO:147.

In embodiments, the first portion further includes an intracellular T-cell signaling domain. In embodiments, the intracellular T-cell signaling domain is SEQ ID NO:11. In embodiments, the intracellular T-cell signaling domain is a CD3ζ intracellular T-cell signaling domain. In embodiments, the first portion includes an intracellular co-stimulatory signaling domain. In embodiments, the intracellular co-stimulatory signaling domain is a CD28 intracellular co-stimulatory signaling domain, a 4-1BB intracellular co-stimulatory signaling domain, a ICOS intracellular co-stimulatory signaling domain, or an OX-40 intracellular co-stimulatory signaling domain. In embodiments, the intracellular co-stimulatory signaling domain is SEQ ID NO:12, SEQ ID NO:13, SEQ ID NO:14, SEQ ID NO: 15 or SEQ ID NO: 16.

In embodiments, the first portion includes a linker domain. In embodiments, the linker domain is between the transmembrane domain and the intracellular T-cell signaling domain. In embodiments, the linker domain is between the intracellular T-cell signaling domain and the intracellular co-stimulatory signaling domain. In embodiments, the linker domain comprises the sequence GGCGG or GGG.

In embodiments, the first portion includes a CD3ζ intracellular T-cell signaling domain and intracellular co-stimulatory signaling domain. In embodiments, the first portion includes from the amino terminus to the carboxy terminus: the heavy chain variable domain, a heavy chain constant domain, the transmembrane domain, the CD3ζ intracellular T-cell signaling domain and an intracellular co-stimulatory signaling domain.

In embodiments, the isolated nucleic acid encoding the recombinant CAR molecule provided herein includes a spacer region positioned between the heavy chain variable domain and the transmembrane domain. In embodiments, the spacer region includes a hinge region. In embodiments, the hinge region is a CD8 hinge region. In embodiments, the hinge region is a CD28 hinge region. A "spacer region" as provided herein is a polypeptide connecting the antibody heavy chain variable domain with the transmembrane domain. Where the first portion of the recombinant CAR protein provided herein including embodiments thereof, includes a heavy chain constant domain, the heavy chain constant domain connects the heavy chain variable domain with the spacer region and the spacer region connects the heavy chain constant domain with the transmembrane domain. Thus in embodiments, the spacer region connects the heavy chain variable domain with the transmembrane domain. In embodiments, the spacer region connects the heavy chain constant domain with the transmembrane domain.

In embodiments, the antibody heavy chain variable domain and the antibody light chain variable domain are humanized. In embodiments, the first portion includes a heavy chain constant domain. In embodiments, the isolated nucleic acid includes a self-cleaving peptidyl sequence between the first portion and the second portion. In embodiments, the self-cleaving peptidyl encoding sequence is a T2A encoding sequence or a 2A encoding sequence. In embodiments, the self-cleaving peptidyl encoding sequence is a T2A encoding sequence or 2A encoding sequence. In embodiments, the nucleic acid sequence encoding the second portion is 3' to the nucleic acid sequence encoding the first portion.

In embodiments, the recombinant CAR protein or antibody region provided herein including embodiments thereof competes for antigen binding with, specifically binds to the same antigen or epitope as, and/or contains one, more, or all CDRs (or CDRs comprising at least at or about 75, 80, 85, 90, 91, 92, 93, 94, 95, 96, 97, 98, or 99% identity to the CDRs), e.g., including a heavy chain CDR 1, 2, and/or 3 and/or a light chain CDR1, 2, and/or 3, of one or more known antibodies, including any commercially available antibody, such as abagovomab, abciximab, adalimumab, adecatumumab, alemtuzumab, altumomab, altumomab pentetate, anatumomab, anatumomab mafenatox, arcitumomab, atlizumab, basiliximab, bectumomab, ectumomab, belimumab, benralizumab, bevacizumab, brentuximab, canakinumab, capromab, capromab pendetide, catumaxomab, certolizumab, clivatuzumab tetraxetan, daclizumab, denosumab, eculizumab, edrecolomab, efalizumab, etaracizumab, ertumaxomab, fanolesomab, Fbta05, fontolizumab, gemtuzumab, girentuximab, golimumab, ibritumomab, igovomab, infliximab, ipilimumab, labetuzumab, mepolizumab, muromonab, muromonab-CD3, natalizumab, necitumumab, nimotuzumab, ofatumumab, omalizumab, oregovomab, palivizumab, panitumumab, ranibizumab, rituximab, satumomab, sulesomab, ibritumomab, ibritumomab tiuxetan, tocilizumab, tositumomab, trastuzumab, Trbs07, ustekinumab, visilizumab, votumumab, zalutumumab, and/or brodalumab; and/or anrukinzumab, bapineuzumab, dalotuzumab, demcizumab, ganitumab, inotuzumab, mavrilimumab, moxetumomab pasudotox, rilotumumab, sifalimumab, tanezumab, tralokinumab, tremelimumab, urelumab, the antibody produced by the hybridoma 10B5 (see Edelson & Unanue, Curr Opin Immunol, 2000 August; 12(4):425-31), B6H12.2 (abcam) or other anti-CD47 antibody (see Chao et al., Cell, 142, 699-713, Sep. 3, 2010).

In embodiments, the recombinant CAR protein or antibody region specifically binds to an antigen selected from the group consisting of: CA-125, glycoprotein (GP) IIb/IIIa receptor, TNF-alpha, CD52, TAG-72, Carcinoembryonic antigen (CEA), interleukin-6 receptor (IL-6R), IL-2, interleukin-2 receptor α-chain (CD25), CD22, B-cell activating factor, interleukin-5 receptor (CD125), VEGF, VEGF-A, CD30, IL-1beta, prostate specific membrane antigen (PSMA), CD3, EpCAM, EGF receptor (EGFR), MUC1, human interleukin-2 receptor, Tac, RANK ligand, a complement protein, e.g., C5, EpCAM, CD11a, e.g., human CD11a, an integrin, e.g., alpha-v beta-3 integrin, vitronectin receptor alpha v beta 3 integrin, HER2, neu, CD3, CD15, CD20 (small and/or large loops), Interferon gamma, CD33, CA-IX, TNF alpha, CTLA-4, carcinoembryonic antigen, IL-5, CD3 epsilon, CAM, Alpha-4-integrin, IgE, e.g., IgE Fc region, an RSV antigen, e.g., F protein of respiratory syncytial virus (RSV), TAG-72, NCA-90 (granulocyte cell antigen), IL-6, GD2, GD3, IL-12, IL-23, IL-17, CTAA16.88, IL13, interleukin-1 beta, beta-amyloid, IGF-1 receptor (IGF-1R), delta-like ligand 4 (DLL4), alpha subunit of granulocyte macrophage colony stimulating factor receptor, hepatocyte growth factor, IFN-alpha, nerve growth factor, IL-13, CD326, Programmed cell death 1 ligand 1 (PD-L1, a.k.a. CD274, B7-H1), CD47, and CD137.

In embodiments, the recombinant CAR protein or antibody region is an anti-CD19 protein, anti-CD20 protein, anti-CD22 protein, anti-CD30 protein, anti-CD33 protein, anti-CD44v6/7/8 protein, anti-CD123 protein, anti-CEA protein, anti-EGP-2 protein, anti-EGP-40 protein, anti-erb-B2 protein, anti-erb-B2,3,4 protein, anti-FBP protein, anti-fetal acetylcholine receptor protein, anti-GD2 protein, anti-GD3 protein, anti-Her2/neu protein, anti-IL-13R-a2 protein, anti-KDR protein, anti k-light chain protein, anti-LeY protein, anti-L1 cell adhesion molecule protein, anti-MAGE-A1 protein, anti-mesothelin protein, anti-murine CMV infected cell protein, anti-MUC2 protein, anti-NKGD2 protein, anti, oncofetal antigen protein, anti-PCSA protein, anti-PSMA protein, anti-TAA (targeted by mAb IfE) protein, anti-EGFR protein, anti-TAG-72 protein or anti-VEGF-72 protein.

In embodiments, the recombinant CAR protein or antibody region has a light chain sequence including P8, V9 or I9, I10 or L10, Q38, R39, T40, N41 G42, S43, P44, R45, D82, I83, A84, D85, Y86, Y87, G99, A100, G101, T102, K103, L104, E105, R142, S162, V163, T164, E165, Q166, D167, S168, and/or Y173, according to Kabat numbering, and/or has a heavy chain having Q6, P9, R38, Q39, S40, P41, G42, K43, G44, L45, S84, D86, T87, A88, I89, Y90, Y91, W103, G104, Q105, G106, T107, L108, V111, T110, Y147, E150, P151, V152, T173, F174, P175, A176, V177, Y185, S186, and/or L187, according to Kabat numbering.

Also provided are complexes including an antibody region or protein bound to one or more compounds including a peptidyl moiety as provided herein. The antibody region or protein may be any of the antibodies described herein including fragments thereof. The one or more compounds including a peptidyl moiety as provided herein may include any one or more of the compounds described herein, such as those described in this section, including monovalent and multivalent compounds, and labeled compounds.

In another aspect, an expression vector including a nucleic acid provided herein (encoding the recombinant CAR protein and/or the T cell receptor specific for a viral antigen) including embodiments thereof is provided. In embodiments, the expression vector is a viral vector. In embodiments, the virus is a lentivirus or onco-retrovirus. In embodiments, the virus is a lentivirus or onco-retrovirus.

In another aspect, a mammalian cell including the expression vector encoding the recombinant CAR protein and/or the T cell receptor specific for a viral antigen provided herein including embodiments thereof is provided. In embodiments, the mammalian cell is a natural killer (Nk) cell. In embodiments, the mammalian cell is an induced pluripotent stem cell. In embodiments, the mammalian cell is a hematopoietic stem cell. In embodiments, the mammalian cell includes a recombinant CAR protein wherein the recombinant CAR protein includes a first polypeptide and a second polypeptide, the first polypeptide including a heavy chain variable domain, a heavy chain constant domain, a transmembrane domain, a CD3ζ signaling domain and a co-stimulatory T-cell signaling domain, the second polypeptide including a light chain variable domain and a light chain constant domain.

In another aspect, a T lymphocyte including the expression vector provided herein including embodiments thereof is provided. In embodiments, the T lymphocyte includes a recombinant CAR protein wherein the recombinant CAR protein includes a first polypeptide and a second polypeptide, the first polypeptide including a heavy chain variable domain, a heavy chain constant domain, a transmembrane domain, a CD3ζ signaling domain and a co-stimulatory T-cell signaling domain, the second polypeptide including a light chain variable domain and a light chain constant domain.

Recombinant CAR Proteins

The T cells provided herein express a T cell receptor specific for a viral antigen (e.g., CMV antigen) and a recombinant CAR protein which exhibits novel diagnostic capabilities and allows to rapidly add functionality to adoptive immunotherapy. The recombinant proteins (i.e. recombinant CAR proteins) provided herein are useful, inter alia, for a broad variety of therapeutic and diagnostic purposes. For example, the recombinant proteins provided herein including embodiments thereof may be used as non-invasive means to characterize chimeric antigen receptor (CAR) T cells before and/or during treatment of diseases (e.g., cancer). By adding functionality to the CAR immunoreceptors a population of patients with antigen-positive tumors can be efficiently treated and monitored irrespective of their HLA genotype. Adoptive immunotherapy using T lymphocytes that express these functionally improved tumor-specific CARs can be a powerful therapeutic strategy for the treatment of cancer and other diseases (e.g., infectious diseases (e.g., HIV infection)). Further, using the recombinant proteins provided herein including embodiments thereof allow for testing and improvement of the functionality and safety of CAR T cells.

In another aspect, a recombinant CAR protein is provided. The recombinant CAR protein includes (i) an antibody region including a central cavity formed by a heavy chain variable (VH) region and a light chain variable (VL) region, wherein the central cavity forms a peptide binding site including framework region amino acid residues; and (ii) a transmembrane domain. In embodiments, the antibody region further includes a heavy chain constant region (CH) and a light chain constant region (CL). In embodiments, the antibody region includes an Fc domain. In embodiments, the antibody region is a humanized antibody region (e.g. a humanized mouse antibody region). In embodiments, the antibody region does not include a scFv antibody region.

In embodiments, the recombinant CAR protein further includes an intracellular T-cell signaling domain as described herein. In embodiments, the intracellular T-cell signaling domain is a CD3ζ intracellular T-cell signaling domain. In embodiments, the recombinant CAR protein further includes an intracellular co-stimulatory signaling domain. In embodiments, the intracellular co-stimulatory signaling domain is a CD28 intracellular co-stimulatory signaling domain, a 4-1BB intracellular co-stimulatory signaling domain, a ICOS intracellular co-stimulatory signaling domain, or an OX-40 intracellular co-stimulatory signaling domain.

In embodiments, the recombinant CAR protein further includes a spacer region. In embodiments, the spacer region is between the transmembrane domain and the antibody region.

In embodiments, the recombinant CAR protein further includes a linker domain. In embodiments, the linker domain is between the transmembrane domain and the intracellular T-cell signaling domain. In embodiments, the linker domain is between the intracellular T-cell signaling domain and the intracellular co-stimulatory signaling domain. In embodiments, the linker domain includes the sequence GGCGG or GGG. In embodiments, the antibody region is a cetuximab meditope enabled domain, trastuzumab meditope enabled domain, pertuzumab meditope enabled domain, M5A meditope enabled domain or rituximab meditope enabled domain. In embodiments, a compound including an peptidyl moiety is bound to the peptide binding site. In embodiments, the compound is a multivalent meditope. A "multivalent meditope" as provided herein is a peptidyl moiety as described herein. Thus, a multivalent meditope is capable of binding the peptide binding site provided herein including embodiments thereof. In embodiments, the multivalent meditope binds to the FR lining the peptide binding site. In embodiments, the multivalent meditope is bound to therapeutic or diagnostic moiety through a chemical linker. In embodiments, the multivalent meditope has the structure of formula (I) or (II). The proteins and compounds may be any of the protein or compounds described herein including embodiments thereof.

In another aspect, a recombinant CAR protein is provided. The recombinant CAR protein includes a first portion including an antibody heavy chain variable domain and a second portion including an antibody light chain variable domain and an antibody light chain constant domain, wherein the first portion further includes a transmembrane domain, and wherein the antibody heavy chain variable domain, the antibody light chain variable domain and the antibody light chain constant domain together form an antibody region.

In another aspect, a mammalian cell including the T Cell receptor specific for a viral antigen and a recombinant CAR protein provided herein including embodiments thereof is provided, wherein the transmembrane domain is within the cell membrane of the mammalian cell. In embodiments, the mammalian cell is a natural killer (Nk) cell. In embodiments, the mammalian cell is an induced pluripotent stem cell. In embodiments, the mammalian cell is a hematopoietic stem cell.

In another aspect, a T lymphocyte including T Cell receptor specific for a viral antigen and the recombinant CAR protein provided herein including embodiments thereof is provided, wherein the transmembrane domain is within the cell membrane of the T lymphocyte.

CMV Triplex Vaccine Compositions and Uses

Described herein is the use of a viral vaccine (e.g. cytomegalovirus (CMV) Triplex Vaccine) in combination with engineered T cells that both recognize a viral antigen (e.g. CMV antigen) and express a recombinant CAR protein able to target an antigen expressed, for example, on normal B cells as well as on cancerous cells (CMV/meCAR T cells) to treat a variety of cancers. The term "CAR T cell" or "CAR T cells" as provided herein refers to a T cell expressing a recombinant CAR protein as described herein. The methods entail administering CMV/CAR T cells which recognize a tumor antigen (e.g., CD19) in addition to a CMV antigen to a patient. Subsequent to administration of the CMV/CAR T cells, a CMV Triplex Vaccine is administered to the patient. The vaccine can promote proliferation of the CMV/CAR T cells and enhance their anti-tumor activity. Thus, the methods can improve T cell resistance and provide a means by which to re-stimulate CAR T cells after relapse. In addition, the methods can provide more reliable engraftment and persistence in a low target-antigen setting (e.g., post-myeloablative HCT) with re-expansion of CAR T cells by CMV vaccine administration. The methods described herein also permit in vivo expansion of CMV-specific CAR T cells, instead of or in addition to ex vivo expansion, avoiding excessive T cell exhaustion that results in some cases from ex vivo manufacturing.

The CMV/CAR T cells can be prepared by a method comprising: (a) providing PBMC from a cytomegalovirus (CMV)-seropositive human donor; (b) exposing the PBMC to at least one CMV antigen (e.g., pp65 or a mixture of IE1/IE2 overlapping peptides); (c) treating the exposed cells to produce a population of cells enriched for stimulated cells specific for CMV (e.g., treating them to create a population of cells that is enriched for stimulated cells specific for CMV relative to the untreated population of cells); (d) transducing at least a portion of the enriched population of cells with a vector (e.g., a lentiviral vector) expressing a CAR, thereby preparing T cells specific for CMV and expressing a CAR. In some cases, a CMV vaccine, for example, the CMV Triplex Vaccine, can be administered to the donor prior to harvest of the PBMC in order to increase the frequency of CMV-seropositive T cells.

The CMV Triplex Vaccine is a recombinant MVA expressing a fusion protein of two CMV antigens, IE1-exon4 and IE2-exon5 and CMV antigen pp65. The sequence encoding the fusion protein is inserted in the MVA deletion-II locus and the sequence encoding the CMV pp65 antigen is inserted into the MVA deletion-III locus. The CMV Triplex Vaccine is described in greater detail in U.S. Pat. No. 8,580,276, hereby incorporated by reference.

The methods described herein include: a method for treating a patient comprising: (a) providing a composition comprising a population of T cells expressing both a chimeric antigen receptor (CAR) and a T cell receptor specific for a cytomegalovirus (CMV) antigen; (b) administering the composition to the patient; and (c) administering to the patient a viral vector encoding: (i) CMV pp65 and (ii) a fusion protein comprising exon 4 of CMV protein IE1 (e4) and exon 5 of CMV protein IE2 (e5) either prior to or subsequent to administering the composition comprising a population of T cells to the patient.

Described herein is a method for treating a patient comprising: (a) providing a composition comprising a population of T cells expressing both a chimeric antigen receptor (CAR) and a T cell receptor specific for a cytomegalovirus (CMV) antigen; (b) administering the composition to the patient; and (c) administering to the patient a viral vector encoding: (i) CMV pp65 and (ii) a fusion protein comprising exon 4 of CMV protein IE1 (e4) and exon 5 of CMV protein IE2 (e5) either prior to or subsequent to administering the composition comprising a population of T cells to the patient.

In various embodiments: the step of administering a viral vector to the patient comprises administering recombinant MVA virus; expression of (i) CMV pp65 and (ii) the fusion protein comprising exon 4 of CMV protein IE1 (e4) and exon 5 of CMV protein IE2 (e5) is under the control of mH5 promoter; the patient is immunocompromised; the patient is immunocompetent; the patient is CMV-seronegative prior to treatment; the patient is CMV-seropositive prior to treatment; the patient received hematopoietic stem cells (HSC) from a CMV-seropositive or CMV-seronegative donor prior to administering the comprising a population of T cells expressing both a chimeric antigen receptor (CAR) and a T cell receptor specific for a cytomegalovirus (CMV) antigen; and the CAR is targeted to CD19; administration of the viral vector occurs at least 5 days after treatment with the composition comprising a population of T cells; the viral vector is administered to the patient both prior to and subsequent to the administration of the composition comprising a population of T cells; the viral vector is administered to the hematopoietic stem cell donor prior to harvesting the stem cells; the viral vector is administered to the patient only prior to the administration of the composition comprising a population of T cells; the viral vector is administered to the patient only subsequent to the administration of the composition comprising a population of T cells; the viral vector is administered to the patient at least four times; the patient is suffering from non-Hodgkin's Lymphoma.

The CAR is selective can be selective for any antigen, for example: CD19, CS1, CD123, 5T4, 8H9, αvβ6 integrin, alphafetoprotein (AFP), B7-H6, CA-125 carbonic anhydrase 9 (CA9), CD19, CD20, CD22, CD30, CD33, CD38, CD44, CD44v6, CD44v7/8, CD52, CD123, CD171, carcinoembryonic antigen (CEA), EGFrvIII, epithelial glycoprotein-2 (EGP-2), epithelial glycoprotein-40 (EGP-40), ErbB1/EGFR, ErbB2/HER2/neu/EGFR2, ErbB3, ErbB4, epithelial tumor antigen (ETA), FBP, fetal acetylcholine receptor (AchR), folate receptor-α, G250/CAIX, ganglioside 2 (GD2), ganglioside 3 (GD3), HLA-A1, HLA-A2, high molecular weight melanoma-associated antigen (HMW-MAA), IL-13 receptor a2, KDR, k-light chain, Lewis Y (LeY), L1 cell adhesion molecule, melanoma-associated antigen (MAGE-A1), mesothelin, Murine CMV infected cella, mucin-1 (MUC1), mucin-16 (MUC16), natural killer group 2 member D (NKG2D) ligands, nerve cell adhesion molecule (NCAM), NY-ESO-1, Oncofetal antigen (h5T4), prostate stem cell antigen (PSCA), prostate-specific membrane antigen (PSMA), receptor-tyrosine kinase-like orphan receptor 1 (ROR1), TAA targeted by mAb IgE, tumor-associated glycoprotein-72 (TAG-72), tyrosinase, and vascular endothelial growth factor (VEGF) receptors.

In certain embodiments: the CAR is selective for an antigen selected from: CD19, CD123, CS1, BCMA, CD44v6, CD33, CD22, IL-13a2, PSA, HER-2, EGFRv3, CEA, and C7R; the CAR comprises: a scFv selective for the selected non-CMV antigen; a hinge/linker region; a transmembrane domain; a co-signaling domain; and CD3ζ signaling domain; the co-signaling domain is selected from a CD28 co-signaling domain and a 4-IBB co-signaling domain; transmembrane domain is selected from a CD28 transmembrane domain and a CD4 transmembrane domain.

In various embodiments of the treatment method: the population of human T cells is autologous to the patient; the population of human T cells is allogeneic to the patient; the method reduces the risk of CMV infection; the method reduces CMV viremia and/or disease; the patient was CMV-immune prior to treatment and the method reduces the risk of CMV infection; the patient was not CMV-immune prior to treatment and the method reduces CMV viremia or disease.

In some embodiments, the step of providing a population of T cells expressing a CAR and a T cell receptor specific for a CMV antigen comprises: (a) providing PBMC or a T cell subpopulation from a CMV-seropositive human donor; (b) exposing the PBMC or the T cell subpopulation to at least one CMV antigen; (c) treating the exposed cells to produce a population of cells enriched for stimulated cells specific for CMV; (d) transducing at least a portion of the enriched population of cells with a vector expressing a CAR. In some embodiments, the step of treating the exposed cells to produce a population of cells enriched for stimulated cells specific for CMV comprises treating the stimulated cells to produce a population of cells enriched for cells expressing an activation marker.

In some embodiments, the step of providing a population of T cell expressing a CAR and a T cell receptor specific for a CMV antigen comprises: (a) administering a viral vector encoding: (i) CMV pp65 and (ii) a fusion protein comprising exon 4 of CMV protein IE1 (e4) and exon 5 of CMV protein IE2 (e5) to a human donor to convert a CMV-seronegative human donor to one containing T cells responsive to CMV antigens pp65, IE1 and IE2; (b) obtaining PBMC from the CMV-seropositive human donor; (c) exposing the PBMC to at least one CMV antigen; (d) treating the exposed cells to produce a population of cells enriched for stimulated cells specific for CMV; (e) transducing at least a portion of the enriched population of cells with a vector expressing a CAR, thereby providing a population of T cell expressing a CAR and a T cell receptor specific for a CMV antigen.

In some embodiments, the step of providing a population of T cell expressing a CAR and a T cell receptor specific for a CMV antigen comprises: (a) administering a viral vector encoding: (i) CMV pp65 and (ii) a fusion protein comprising exon 4 of CMV protein IE1 (e4) and exon 5 of CMV protein IE2 (e5) to a CMV-seropositive human donor; (b) obtaining PBMC from the CMV-seropositive human donor; (b) exposing the PBMC to at least one CMV antigen; (c) treating the exposed cells to produce a population of cells enriched for stimulated cells specific for CMV; (d) transducing at least a portion of the enriched population of cells with a vector expressing a CAR, thereby providing a population of T cell expressing a CAR and a T cell receptor specific for a CMV antigen.

In the case of patients who have received HSC transplant, in some embodiments, the viral vector is administered to the patient or the hematopoietic stem cell transplant donor at least twice subsequent to the administration of the composition comprising a population of T cells, the hematopoietic stem cells were autologous to the patient; and the hematopoietic stem cells were allogenic to the patient.

Also described is a method for preparing T cells expressing a CAR and a T cell receptor specific for a CMV antigen, the method comprising: (a)) administering a viral vector encoding: (i) CMV pp65 and (ii) a fusion protein comprising exon 4 of CMV protein IE1 (e4) and exon 5 of CMV protein IE2 (e5) to a CMV-seropositive human donor; (b) obtaining PBMC from the CMV-seropositive human donor; (b) exposing the PBMC to at least one CMV antigen; (c) treating the exposed cells to produce a population of cells enriched for stimulated cells specific for CMV; (d) transducing at least a portion of the enriched population of cells with a vector expressing a CAR, thereby providing a population of T cell expressing a CAR and a T cell receptor specific for a CMV antigen.

Also described is a method for preparing T cells expressing a CAR and a T cell receptor specific for a CMV antigen, the method comprising: a)) administering a viral vector encoding: (i) CMV pp65 and (ii) a fusion protein comprising exon 4 of CMV protein IE1 (e4) and exon 5 of CMV protein IE2 (e5) to a CMV-seropositive human donor; (b) obtaining PBMC from the CMV-seropositive human donor; (b) exposing the PBMC to at least one CMV antigen; (c) treating the exposed cells to produce a population of cells enriched for stimulated cells specific for CMV; (d) transducing at least a portion of the enriched population of cells with a vector expressing a CAR, thereby providing a population of T cell expressing a CAR and a T cell receptor specific for a CMV antigen.

In various embodiments of the of the methods for producing T cells, the method further comprises expanding the population of T cell expressing a CAR and a T cell receptor specific for a CMV antigen.

In various embodiments of the of the methods for producing T cells: the activation marker is IFN-γ or other activation marker such as CD137, CD107 or other cytokines; the CMV antigen is pp65 protein or an antigenic portion thereof; the CMV antigen comprises two or more different antigenic CMV pp65 peptides; the step of transducing the enriched population of cells does not comprise CD3 stimulation; the step of transducing the enriched population of cells does not comprise CD28 stimulation; the step of transducing the enriched population of cells does not comprise CD28 stimulation or CD3 stimulation; the step of transducing the enriched population of cells does not comprise exposing the cells to an anti-CD28 antibody or an anti-CD3 antibody; the enriched population of cells is at least 40% IFN-γ positive, at least 20% CD8 positive, and at least 20% CD4 positive; the enriched population of cells are cultured for fewer than 10 days prior to the step of transducing the enriched population of cells with a vector encoding a CAR; the method further comprises expanding the CMV specific T cells expressing a CAR cells by exposing them to an antigen that binds to the CAR; the step of expanding the CMV-specific T cells expressing a CAR comprises exposing the cells to T cells expressing the antigen that binds the CAR; and the expansion takes place is the presence of at least one exogenously added interleukin.

In some cases, the method includes a step of preparing T cells specific for cytomegalovirus (CMV) and expressing a chimeric antigen receptor (CAR), the method comprising: (a) providing T cells (e.g., PBMC) from a cytomegalovirus CMV seropositive human donor; (b) exposing the PBMC to at least one CMV antigen; (c) treating the exposed cells to produce a population of cells enriched for stimulated cells specific for CMV; (d) transducing at least a portion of the enriched population of cells with a vector expressing a CAR, thereby preparing T cells specific for CMV and expressing a CAR. In various cases: the step of treating the exposed cells (e.g., using a selection step) to produce a population of cells enriched for stimulated cells specific for CMV comprises treating the stimulated cells to produce a population of cells enriched for cells expressing an activation marker (e.g., IFN-γ of IL-13); the PBMC are cultured for less than 5 days (less than 4, 3, 2, 1 days) prior to exposure to the CMV antigen; the cells are exposed to the CMV antigen for fewer than 3 days (fewer than 48 hrs, 36 hrs, 24 hrs) the CMV antigen is pp65 protein or an antigenic portion thereof; the CMV antigen comprises two or more different antigenic CMV pp65 peptides; the step of transducing the enriched population of cells does not comprise CD3 stimulation; the step of transducing the enriched population of cells does not comprise CD28 stimulation; the step of transducing the enriched population of cells does not comprise CD3 stimulation or CD28 stimulation; the enriched population of cells is at least 40% (e.g., 50%, 60%, 70%) IFN-γ positive, at least 20% (e.g., 25%, 30%, 35%) CD8 positive, and at least 20% (e.g., 25%, 30%, 35%) CD4 positive; the enriched population of cells are cultured for fewer than 10 (fewer than 9, 8, 7, 5, 3, 2) days prior to the step of transducing the enriched population of cells with a vector encoding a CAR. In some cases, the T cells are from a CMV positive donor and are exposed to a CMV antigen such as CMV pp65 or a mixture of CMV protein peptides (for example 10-20 amino acid peptides that are fragments of pp65) in the presence of IL-2 to create a population of stimulated cells. In some cases, the population of stimulated cells is treated to prepare a population of cells that express IFN-γ. In some cases, the CMV/CAR T cells do not recognize an antigen from a second virus. For example, they do not recognize an Epstein-Barr virus antigen or an influenza virus antigen or an Adenovirus antigen.

In some cases, the method further comprises expanding the CMV specific T cells expressing a CAR (CMV/CAR T cells) by exposing them an antigen that binds to the CAR.

In some cases, the CMV/CAR T cells are not expanded ex vivo by exposure to an antigen that binds the CAR, by a CMV antigen or by exposure to exogenously added cytokines.

In some cases, the step of expanding the CMV-specific T cells expressing a CAR comprises exposing the cells to T cells expressing the antigen that bind the CAR (e.g., the expansion takes place is the presence of at least one exogenously added interleukin (e.g., one or both of IL-1 and IL-15) and a T cell expressing the antigen recognized by the CAR.

In various cases, the CAR is selective for an antigen selected from: CD19, CS1, CD123, 5T4, 8H9, αvβ6 integrin, alphafetoprotein (AFP), B7-H6, CA-125 carbonic anhydrase 9 (CA9), CD19, CD20, CD22, CD30, CD33, CD38, CD44, CD44v6, CD44v7/8, CD52, CD123, CD171, carcinoembryonic antigen (CEA), EGFrvIII, epithelial glycoprotein-2 (EGP-2), epithelial glycoprotein-40 (EGP-40), ErbB1/EGFR, ErbB2/HER2/neu/EGFR2, ErbB3, ErbB4, epithelial tumor antigen (ETA), FBP, fetal acetylcholine receptor (AchR), folate receptor-α, G250/CAIX, ganglioside 2 (GD2), ganglioside 3 (GD3), HLA-A1, HLA-A2, high molecular weight melanoma-associated antigen (HMW-MAA), IL-13 receptor α2, KDR, k-light chain, Lewis Y (LeY), L1 cell adhesion molecule, melanoma-associated antigen (MAGE-A1), mesothelin, Murine CMV infected cella, mucin-1 (MUC1), mucin-16 (MUC16), natural killer group 2 member D (NKG2D) ligands, nerve cell adhesion molecule (NCAM), NY-ESO-1, Oncofetal antigen (h5T4), prostate stem cell antigen (PSCA), prostate-specific membrane antigen (PSMA), receptor-tyrosine kinase-like orphan receptor 1 (ROR1), TAA targeted by mAb IgE, tumor-associated glycoprotein-72 (TAG-72), tyrosinase, and vascular endothelial growth factor (VEGF) receptors.

In some cases, the CAR is selective for an antigen selected from: CD19, CD123, CS1, BCMA, CD44v6, CD33, CD22, IL-13α2, PSA, HER2, EGFRv3, CEA, and C7R.

In some cases, the CAR comprises: a scFv selective for the selected non-CMV antigen; a hinge/linker region; a transmembrane domain; a co-signaling domain; and CD3ζ signaling domain; the chimeric antigen receptor further comprises a spacer sequence located between the co-signaling domain and the CD3ζ signaling domain; the co-signaling domain is selected from a CD28 co-signaling domain and a 4-IBB co-signaling domain; the transmembrane domain is selected from a CD28 transmembrane domain and a CD4 transmembrane domain; the vector expressing the CAR expresses a truncated human EGFR from the same transcript encoding the CAR, wherein the truncated human EGFR lacks a EGF ligand binding domain and lacks a cytoplasmic signaling domain; the spacer sequence comprises or consists of 3-10 consecutive Gly; the hinge/linker region comprises at least 10 amino acids of an IgG constant region or hinge region; the IgG is IgG4; the hinge/linger region comprises an IgG4 CD3 domain; the hinge/linger region comprises an IgG4 Fc domain or a variant thereof; the hinge/linker region comprises or consists of 4-12 amino acids; and hinge/linker region is selected from the group consisting of: the sequence ESKYGPPCPPCPGGGSSGGGSG and the sequence GGGSSGGGSG.

In some cases, the CMV/CAR T cell population is a population in which at least 20% of the cells in the population are CD4+, in which at least 20% of the cells in the population are CD8+, or in which at least 60% of the cells in the population are IFNγ+.

In various cases: the T cells are specific for CMV pp65; and the CAR binds an antigen selected from: CD19, CD123, CS1, BCMA, CD44v6, CD33, CD22, IL-13a2, PSA, HER2, EGFRv3, CEA, and C7R.

Also described is a method of treating a patient suffering from cancer comprising administering a composition comprising CMV/CAR T cells followed by administration of CMV Triplex Vaccine. In various cases: the population of human T cells are autologous to the patient; the population of human T cells are allogenic to the patient; the population of human T cells are autologous to the patient; the method further comprises administering to the patient at least two or at least three doses of a CMV Triplex Vaccine.

Described below are T cells specific for CMV and CD19. These CMV/CAR T cells were generated using a rapid and efficient method for generating and selecting CMV-specific T cells. The method, which employs IFNγ capture of CMV-specific T cells, consistently and efficiently enriched CMV-specific T cells while preserving the broad spectrum of CMV repertoires. Moreover, the cells remained amenable to gene modification after a brief CMVpp65 stimulation, avoiding the need for CD3/CD28 bead activation prior to transduction. This is significant because CD3/CD28 activation can cause activation-induced cell death (AICD) of CMV-specific T cells. Engineering the bulk IFNγ-captured T cells with a CD19CAR lentivirus followed by stimulation with CD19 antigen resulted in 50 to 70% of the CAR T cells responding to pp65 stimulation, representing the subset of functional CMV/CAR T cells. The CMV/CAR T cells exhibited specific cytolytic activity and secreted IFNγ, as well as proliferating vigorously after engagement of endogenous CMVpp65 T cell receptors or engineered CD19 CARs. Upon transfer into tumor bearing mice, the CMV/CAR T cells mediated cytokine released syndrome (CRS), which has been found to correlate with anti-tumor efficacy in the clinic.

While the CMV/CAR T cells described herein express a CAR targeted to CD19, the same methods can be used to generate CMV CAR T cells targeted to any desired antigen.

Efficient in vivo activation of virus-specific T cells through the TCR demands that viral antigens are processed and presented in a human leukocyte antigen (HLA)-dependent manner. This can be achieved by administering CMV Triplex Vaccine to the patient subsequent to administration of the CMV/CAR T cells.

The antitumor activity of CMV/CAR T cells can be enhanced as a consequence of proliferation following CMV peptide vaccination. This suggests that the cell dose of CMV/CAR T cells could be significantly decreased as compared to conventional CAR T cells, due to their potential to proliferate in vivo in response to vaccine, avoiding prolonged culture times and the risk of terminal differentiation.

In some cases, such as in the CMV/CAR T cells targeted to CD19 described herein, the CMV/CAR T cells also express a truncated EGFR (EGFRt). Cells expressing EGFRt can be killed by administration of an antibody, such a cetuximab, targeted to EGFR. This permits control and reduction of potential on/off-target toxicity.

The administration of CMV Triplex Vaccine subsequent to treatment with CMV/CD19 CAR T cells can augment the antitumor activity of adoptively transferred CMV/CD19 CAR T cells in several scenarios: 1) to salvage patients not achieving complete remission or relapsing after CAR T cell therapy, 2) vaccine boost when CD19 CAR T cells are failing to persist regardless of tumor responses at that time, 3) planned vaccination on days post-administration CD19 CAR T cells. There is also potential benefit of using the CMV/CAR T cells pre-emptively post-allogeneic HCT, both to eliminate minimal residual disease (MRD) and control CMV, potentially preventing reactivation of virus or undergoing expansion in response to latent CMV reactivation.

Moreover, administration of CMV Triplex Vaccine has the potential to profoundly impact the general field of adoptive T cell therapy, since by transducing a variety of tumor-directed CARs into CMV-specific T cells, it is possible to tailor this strategy to a wide range of malignancies and tumor targets.

Triplex Vaccine

CMV Triplex Vaccine is a recombinant MVA that expresses three CMV antigens, i.e., at least a portion or Immediate-Early Gene-1 (IE1), at least a portion of Immediate-Early Gene-2 (IE2) and at least a portion of pp65. The IE1 antigen and the IE2 antigen can be expressed a fusion protein, for example, a protein encoded by the nucleotide sequence of SEQ ID NO:99. Expression of the CMV antigens can be under the control of a modified H5 (mH5) promoter. A CMV Triplex Vaccine is fully described in U.S. Pat. No. 8,580,276 and in Wang et al. (*Vaccine* 28:1547, 2010)

The CMV Triplex Vaccine can express CMV pp65 and a CMV IE fusion protein (IEfusion). The IEfusion can include an antigenic portion of IE1 (e.g., Exon 4) and an antigenic portion of 1E2 (e.g., Exon 5), wherein the antigenic portions elicit an immune response when expressed by a vaccine. In one aspect, the IEfusion is has the sequence encoded by SEQ ID NO:99 or another nucleotide sequence that encodes the same amino acid sequence as SEQ ID NO:99.

As explained in U.S. Pat. No. 8,580,276, the CMV Triplex Vaccine includes three of the best recognized antigens in the CD8 subset: pp65, IE1, and IE2. There is no region of homology greater than 5 amino acids between the major exons of both proteins. Individually, both antigens are recognized broadly by almost 70% of the general population (Sylwester et al. 2005). The divergent sequence of both IE1/e4 and IE2/e5 used here predicts an entirely different subset of HLA binding peptides using publicly available Class I and II motif algorithms (Peters and Sette 2007). Human subjects that were evaluated for recognition of both IE1 and IE2 antigens were found in many instances to recognize one or the other but not both. Among the research subjects analyzed, 24% recognized IE2 with or without pp65 to the exclusion of IE1. This result strongly suggests that the recognition elements for both antigens are unique, and by including both of them in the vaccine, the breadth of individuals with disparate HLA types that will recognize and develop an immune response to the vaccine is extended. The fusion of major exons from both antigens achieves the dual goal of reducing the number of separate inserts and eliminating the need for a third insert promoter. The advantages of this approach include placement of all vaccine antigens in one vector, and diminishing the dose of virus needed to attain sufficient immunity simultaneously against all of the included antigens.

Also as explained in U.S. Pat. No. 8,580,276, prior to conducting experiments with rMVA in clinical samples, the capacity for stimulation of both CD4+ and CD8+ T cells was assessed using the commercially available pp65 and IE1 library and a newly designed IE2 peptide library. Relationships among the T cell populations were similar to prior results: pp65 promotes a substantial CD4 and CD8 response in over 70% of participants, while IE1 and IE2 are recognized less frequently and mainly in the CD8+ T cell compartment. MVA expressing the IEfusion antigen with or without the pp65 antigen was evaluated in PBMC from healthy volunteers to establish their recognition properties using a fully human system. The results showed that the memory T cell expansion stimulated by the rMVA for both the IEfusion and pp65 antigens, followed the proportions found ex vivo for the same volunteers using the peptide library approach. While there was substantial amplification of the relevant T cell populations, the stimulation did not skew the population towards a particular subset or antigen specificity. The data also confirms that the IEfusion protein is processed and presented appropriately to stimulate existing T cell populations in a manner that maintains the phenotypic distribution as expected in the ex vivo analysis. The most rigorous evaluation of the processing of the rMVA for T cell response is using PBMC from transplant patients. PBMC from HCT recipients in all three risk categories were evaluated and an equivalently strong recognition of both rMVAs was found. In some cases, it was even more vigorous than in the PBMC of healthy adults. No interference with the recognition of the IE antigen by the co-expressed pp65 antigen was found from the same rMVA, which further confirms that the recognition of both antigens can take place at the same time and derived from the same vector.

Any of the vaccine compositions disclosed in U.S. Pat. Nos. 7,163,685, 8,580,276 and 9,675,689 as well as in US published application US20170246292 A1 may be used for the methods and compositions provided herein and are hereby incorporated by reference in their entirety and for all purposes.

In one embodiment, the nucleic acid sequence encoding vaccinia mH5 promoter has a sequence containing nucleotides 3075-3168 of SEQ ID NO:97 or 3022-3133 of SEQ ID NO:98.

Pharmaceutical Compositions

Pharmaceutical compositions include compositions wherein the active ingredient (e.g. compositions described herein, including embodiments or examples) is contained in a therapeutically effective amount, i.e., in an amount effective to achieve its intended purpose. The actual amount effective for a particular application will depend, inter alia, on the condition being treated. In an aspect, the pharmaceutical composition includes a population of T cells, wherein the T cells includes (e.g. expresses) the recombinant CAR protein and the T cell receptor specific for a viral antigen as described herein, optionally in combination with a pharmaceutically acceptable excipient. When administered in methods to treat a disease, the compostions including a population of T cells described herein will be provided in an effective to achieve the desired result, e.g., modulating the activity of a target molecule, and/or reducing, eliminating, or slowing the progression of disease symptoms. Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer and severity of such symptoms), kind of concurrent treatment, complications from the disease being treated or other health-related problems. Other therapeutic regimens or agents can be used in conjunction with the methods and compounds of the invention. Adjustment and manipulation of established dosages (e.g., frequency and duration) are well within the ability of those skilled in the art.

For any composition (e.g., recombinant protein, nucleic acid) provided herein, the therapeutically effective amount can be initially determined from cell culture assays. Target concentrations will be those concentrations of active compound(s) that are capable of achieving the methods described herein, as measured using the methods described herein or known in the art. As is well known in the art, effective amounts for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred "Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The pharmaceutical preparation is optionally in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The unit dosage form can be of a frozen dispersion.

Methods of Treatment

In another aspect, a method of treating cancer is provided. The method includes administering to a subject in need thereof an effective amount of the mammalian cell (e.g. T cells) provided herein including embodiments thereof, wherein the antibody region is an anti-cancer antibody region.

In another aspect, a method of treating cancer is provided. The method includes administering to a subject in need thereof an effective amount of the T-lymphocyte provided herein including embodiments thereof, wherein the antibody region is an anti-cancer antibody region. In embodiments, the T-lymphocyte is an autologous T-lymphocyte. In embodiments, the T-lymphocyte is a heterologous T-lymphocyte. In embodiments, the cancer is a solid tumor cancer or hematologic malignancy. In embodiments, the cancer is ovarian cancer, renal cell carcinoma, a B-cell malignancy, leukemia, lymphoma, breast cancer, colorectal cancer, prostate cancer, neuroblastoma, melanoma, medulloblastoma, lung cancer, osteosarcoma, glioblastoma or glioma. In embodiments, the leukemia is acute lymphoid leukemia. In embodiments, the leukemia is chronic lymphocytic leukemia. In embodiments, the leukemia is acute myeloid leukemia. In embodiments, the leukemia is chronic myeloid leukemia.

In another aspect, a method of reprogramming a T lymphocyte is provided. The method includes contacting a T lymphocyte with the expression vector provided herein including embodiments thereof.

In another aspect, a method of detecting a cancer is provided. The method includes (i) administering to a cancer patient an effective amount of a T lymphocyte including the recombinant CAR protein provided herein including embodiments thereof, the T cell receptor specific for a viral antigen provided herein including embodiments thereof and optionally a compound including a peptidyl moiety capable of binding to the peptide binding site, wherein the compound further optionally includes a detectable label, and wherein the antibody region is an anti-cancer antibody region. The method may include (ii) allowing the compound to bind to the peptide binding site thereby forming a recombinant protein-compound complex. The method may include (iii) detecting the recombinant protein-compound complex within the cancer patient thereby detecting the cancer.

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance. For example, certain methods herein treat cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma). For example certain methods herein treat cancer by decreasing or reducing or preventing the occurrence, growth, metastasis, or progression of cancer; or treat cancer by decreasing a symptom of cancer. Symptoms of cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma) would be known or may be determined by a person of ordinary skill in the art.

As used herein the terms "treatment," "treat," or "treating" refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

An "effective amount" is an amount sufficient to accomplish a stated purpose (e.g. achieve the effect for which it is administered, treat a disease, reduce enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom (s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme or protein relative to the absence of the antagonist. A "function disrupting amount," as used herein, refers to the amount of antagonist required to disrupt the function of an enzyme or protein relative to the absence of the antagonist. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In embodiments, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer.

The compositions described herein can be used in combination with one another, with other active agents known to be useful in treating a cancer such as anti-cancer agents.

Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, Inanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like. In embodiments, the compositions herein may be used in combination with adjunctive agents that may not be effective alone, but may contribute to the efficacy of the active agent in treating cancer.

In embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In embodiments, co-administration can be accomplished by co-formulation, i.e., preparing a single pharmaceutical composition including both active agents. In embodiments, the active agents can be formulated separately. In embodiments, the active and/or adjunctive agents may be linked or conjugated to one another.

EXAMPLES

Applicants have discovered a unique binding site for a cyclic peptide (the peptide or peptidyl moiety provided herein also referred to herein as a "meditope") within the central cavity of the Fab arm of the therapeutic mAb, cetuximab (1). Applicants demonstrated that this site is unique to cetuximab and absent in human mAbs. Applicants have also shown, biochemically and in cell culture and in animal xenograft studies, that occupancy of this site does not affect antigen binding. Moreover, Applicants demonstrated that this site can be grafted onto human mAbs ("meditope-enabling"), indicating that this peptide binding site may for example be used as a beacon for targeting imaging agents or as a "hitch" to tether new functionality to mAbs. Through extensive engineering, Applicants have improved the affinity of the meditope-Fab interaction by over 40,000-fold with an estimated half-life that exceeds six days at room temperature. Applicants further demonstrated that the fusion of the meditope to protein L, a Fab-binding protein, significantly improved the affinity and estimated the half-life of this complex to exceed 80 days. Finally, Applicants verified through SPR studies that conjugation of fluorescent markers, DOTA, GFP and other protein domains to the high affinity meditope and to the meditope-protein L (MPL) fusion do not affect the affinity of the MPL-Fab nor the Fab-antigen interactions. Collectively, these data show that functionality can be "snapped" on to any given meditope-enabled mAb.

CAR T cell therapy, which has produced durable responses especially in B cell malignancies(2-6), involves the reprogramming of patient T cells with an artificial receptor consisting of an extracellular antigen targeting moiety, a transmembrane domain and intracellular signaling modules, including CD3ζ and costimulatory domains of CD28 and/or CD137 (4-1BB), to activate the T cell and elicit an immune response. The antigen-targeting domain of the CAR generally is a tumor antigen recognizing single chain F variable antibody region (scFv). There is a need in the art for the ability to: 1) characterize the density of the CARs on the transformed cells, 2) to track administered CAR T cells at any point during the therapy and correlate this distribution to therapeutic outcomes, 3) to rapidly functionalize CAR T cells, and 4) to selectively eliminate CAR T cells if necessary. In embodiments, the constructs provided herein are capable of meeting these needs.

In embodiments, the constructs provided herein are useful in the following areas: (i) application of super resolution microscopy to characterize CAR expression through direct observation of the receptor distribution on the T cells. Applicants have fused a photo-activatable GFP (paGFP) to a high affinity meditope, and demonstrated that meditope-enabled mAbs bound to cell-derived receptors can be "counted" and their cluster size can be quantified. Such information can be correlated with therapeutic efficacy and used in the clinic for "quality control." (ii) Imaging of meditope-enabled CAR T cells with a DOTA-conjugated, high affinity meditope in situ. Applicants have demonstrated that high affinity, conjugated meditopes do not affect antigen binding. Thus, meCAR T cells can be pre-labeled with $^{64}$Cu-DOTA-conjugated, high affinity meditopes and their migration can be traced. Alternatively, meCAR T cells can be administered, allowed to localize and proliferate, and then subsequently imaged. Pre-targeted, mAb-based imaging methods as proposed have been demonstrated to produce high quality PET images using engineered antibodies (9-11). (iii) Novel orthogonal functionality that can be rapidly added to the meCAR T cell. Specifically, meditopes may be conjugated to biologics that recognize a second tumor-associated ligand, potent cytotoxins, immune modulators including cytokines, and tumor-activated prodrugs. These meditopes may be directly attached to the meCAR T cells before administration or subsequently added after the meCAR T cells are established.

Example 1

Enrichment of CMV-Specific T Cells from PBMC of Healthy Donors after Stimulation with cGMP Grade CMVpp65 Protein CMV-specific T cells were prepared from PBMC of healthy donors by stimulating the PBMC with cGMP grade CMVpp65 protein. Briefly, PBMCs were isolated by density gradient centrifugation over Ficoll-Paque (Pharmacia Biotech, Piscataway, NJ) from peripheral blood of consented healthy, HLA-A2 CMV-immune donors under a City of Hope Internal Review Board-approved protocol. PBMC were frozen for later use. After overnight rest in RPMI medium containing 5% Human AB serum (Gemini Bio Products) without cytokine, the PBMC were stimulated with current good manufacturing practice (cGMP) grade CMVpp65 protein (Miltenyi Biotec, Germany) at 10 ul/10× $10^6$ cells for 16 hours in RPMI 1640 (Irvine Scientific, Santa Ana, CA) supplemented with 2 mM L-glutamine (Irvine Scientific), 25 mM N-2-hydroxyethylpiperazine-N-2-ethanesulfonic acid (HEPES, Irvine Scientific), 100 U/mL penicillin, 0.1 mg/mL streptomycin (Irvine Scientific) in the presence of 5 U/ml IL-2 and 10% human AB serum. CMV-specific T cells were selected using the IFNγ capture (Miltenyi Biotec, Germany) technique according to the manufacturer's instructions.

To demonstrate the consistency of this clinically feasible process, the selection was repeated five times using PBMC from three different donors. IFNγ-positive T cells were consistently enriched from a baseline mean of 3.8% (range 1.8-5.6) to a post-capture mean of 71.8% (range 61-81) and contained polyclonal CD8$^+$ (34%) and CD4$^+$ T cells (37%) after selection (FIG. 14A and FIG. 14C). Moreover, the selected CMV-specific T cells included both CD4 and CD8 subsets and represented the entire spectrum of CMV-specificity, showing responsiveness to CMVpp65 pepmix stimulation with broad recognition.

Example 2

Genetic Modification of Enriched CMV-Specific T Cells to Express CD19 CAR and In Vitro Expansion of the CMV/CAR T Cells.

In the clinically adaptable procedure, IFNγ-captured CMV-specific T cells were transduced 2 days after the selection, without OKT3 activation, using the second generation CD19RCD28EGFRt lentiviral construct containing the IgG4 Fc hinge region mutations (L235E; N297Q) that improve potency due to distortion of the FcR binding domain. Starting seven days post lenti-transduction, the cells were stimulated on a weekly basis with 8000 cGy-irradiated, CD19-expressing NIH3T3 cells at a 1:10 ratio (T cells: CD19NIH 3T3). The percentage of CAR cells detected by cetuximab increased from 8% post transduction to 46% after 2 rounds of stimulation with a 120-150-fold total cell increase (FIG. 14B and FIG. 14D). Further details regarding the lentiviral construct, the CD19-expressing NIH3T3 cells and other materials and techniques used in the studies described herein are presented below.

Example 3

CMV/CAR T Cells Exhibited Specific Effector Function after Stimulation Through Pre-Defined Viral TCR and CD19CAR.

Recapitulating our previous studies (23), the ex vivo expanded CMV-specific T cells possessed an effector phenotype and no longer expressed the central memory markers of the originally selected cells, such as CD62L, CD28, and IL-7Ra (FIG. 15A and FIG. 15D). However, levels of CD27 remained high, suggesting a greater proliferative potential that has been associated with greater clinical efficacy (24). To investigate CMV/CAR T cell effector function via signaling by both the endogenous CMV-specific TCR and the introduced CD19CAR, we evaluated response to engineered pp65-expressing U251T cells from HLA-A2 donors, and also allogeneic CD19 LCLs, based on cytotoxicity, cytokine production and proliferation profiles. As expected, the expanded CMV/CAR T cells specifically lysed CD19 LCLs with the same maximum killing levels as the OKT3-expressing LCL used as positive controls. Likewise, specific killing was also observed when pp65U251T cells were used as targets as compared to parental U251T cells (FIG. 15B). Accordingly, after overnight stimulation, elevated IFNγ secretion was observed after either CD19 or pp65 antigen stimulation as compared to antigen-negative stimulators such as KG1a and U251T parental cells (FIG. 15C).

Antibodies and Flow Cytometry: Fluorochrome-conjugated isotype controls, anti-CD3, anti-CD4, anti-CD8, anti-CD28, anti-CD45, anti-CD27, anti-CD62L, anti-CD127, anti-IFN-γ, and streptavidin were obtained from BD Biosciences. Biotinylated cetuximab was generated from cetuximab purchased from the City of Hope pharmacy. The IFN-γ Secretion Assay—Cell Enrichment and Detection Kit and CMVpp65 protein were purchased from Miltenyi Biotec (Miltenyi Biotec, Germany). Phycoerythrin (PE)-conjugated CMV pp65 (NLVPMVATV)-HLA-A2*0201 iTag MHC tetramer, PE-conjugated multi-allele negative tetramer was obtained from Beckman Coulter (Fullerton, CA). Carboxyfluorescein diacetate succinimidyl ester (CFSE) was purchased from Invitrogen (Carlsbad, CA). All monoclonal antibodies, tetramers and CFSE were used according to the manufacturer's instructions. Flow cytometry data acquisition was performed on a MACSQuant (Miltenyi Biotec, Germany) or FACScalibur (BD Biosciences), and the percentage of cells in a region of analysis was calculated using FCS Express V3 (De Novo Software).

Cell lines: EBV-transformed lymphoblastoid cell lines (LCLs) were made from peripheral blood mononuclear cells (PBMC) as previously described (16). To generate LCL-OKT3, allogeneic LCLs were resuspended in nucleofection solution using the Amaxa Nucleofector kit T, OKT3-2A-Hygromycin_pEK plasmid was added to 5 µg/107 cells, the cells were electroporated using the Amaxa Nucleofector I, and the resulting cells were grown in RPMI 1640 with 10% FCS containing 0.4 mg/ml hygromycin. To generate firefly luciferase+GFP+LCLs (fflucGFPLCLs), LCLs were transduced with lentiviral vector encoding eGFP-ffluc. Initial transduction efficiency was 48.5%, so the GFP+ cells were sorted by FACS for >98% purity. To generate CD19 NIH3T3 cells, parental NIH3T3 cells (ATCC) were transduced with a retrovirus encoding CD80, CD54 and CD58 (17). The established cell line was further engineered to express CD19GFP by lentiviral transduction. GFP+ cells were purified by FACS sorting and expanded for the use of stimulation of CMV/CAR T cells. To generate pp65 stimulator cells, U251T cells derived from human glioblastoma cells from an HLA A2 donor (ATCC) were transduced with a lentiviral vector encoding full length pp65 fused to green fluorescent protein (GFP). pp65U251T cells were purified by GFP expression using flow cytometry. Banks of all cell lines were authenticated for the desired antigen/marker expression by flow cytometry prior to cryopreservation, and thawed cells were cultured for less than 6 months prior to use in assays.

Peptides: The pp65 peptide NLVPMVATV (HLA-A 0201 CMVpp65) at >90% purity was synthesized using automated solid phase peptide synthesis in (Department of Experimental Therapeutics, Beckman Research Institute of City of Hope). MP1 GIGFVFTL peptide (HLA-A 0201 influenza) was synthesized at the City of Hope DNA/RNA Peptide Synthesis Facility, (Duarte, CA). pepMix HCMVA (pp65) (pp65pepmix) was purchased from JPT peptide Technologies (GmbH, Berlin Germany). All peptides were used according to the manufacturer's instructions.

Lentivirus vector construction: The lentivirus CAR construct was modified from the previously described CD19-specific scFvFc:ζ chimeric immunoreceptor(18), to create a third-generation vector. The CD19CAR containing a CD28ζ co-stimulatory domain carries mutations at two sites (L235E; N297Q) within the CH2 region on the IgG4-Fc spacers to ensure enhanced potency and persistence after adoptive transfer. The lentiviral vector also expressed a truncated human epidermal growth factor receptor (huEGFRt), which includes a cetuximab (Erbitux™) binding domain but excludes the EGF-ligand binding and cytoplasmic signaling domains. A T2A ribosome skip sequence links the codon-optimized CD19R:CD28:ζ sequence to the huEGFRt sequence, resulting in coordinate expression of both CD19R:CD28:ζ and EGFRt from a single transcript (CD19CARCD28EGFRt) (19). The CD19RCD28EGFRt DNA sequence (optimized by GeneArt) was then cloned into a self-inactivating (SIN) lentiviral vector pHIV7 in which the CMV promoter was replaced by the EF-1α promoter.

Enrichment of CMV-specific T cells after CMVpp65 protein stimulation: PBMCs were isolated by density gradient centrifugation over Ficoll-Paque (Pharmacia Biotech, Piscataway, NJ) from peripheral blood of consented healthy, HLA-A2 CMV-immune donors under a City of Hope Internal Review Board-approved protocol. PBMC were frozen for later use. After overnight rest in RPMI medium containing 5% Human AB serum (Gemini Bio Products) without cytokine, the PBMC were stimulated with current good manufacturing practice (cGMP) grade CMVpp65 protein (Miltenyi Biotec, Germany) at 10 µl/10×10$^6$ cells for 16 hours in RPMI 1640 (Irvine Scientific, Santa Ana, CA) supplemented with 2 mM L-glutamine (Irvine Scientific), 25 mM N-2-hydroxyethylpiperazine-N'-2-ethanesulfonic acid (HEPES, Irvine Scientific), 100 U/mL penicillin, 0.1 mg/mL streptomycin (Irvine Scientific) in the presence of 5 U/ml IL-2 and 10% human AB serum. CMV-specific T cells were selected using the IFNγ capture (Miltenyi Biotec, Germany) technique according to the manufacturer's instructions.

Derivation and expansion of CMV/CAR T cells: The selected CMV-specific T cells were transduced on day 2 post IFNγ capture with lentiviral vector expressing CD19CARCD28EGFRt at MOI 3. Seven to ten days after lenti-transduction, the CMV/CAR T cells were expanded by stimulation through CAR-mediated activation signals using 8000 cGy-irradiated CD19-expressing NIH 3T3 cells at a 10:1 ratio (T cells:CD19 NIH3T3) once a week as described (17) in the presence of IL-2 50U/ml and IL-15 1 ng/ml. After 2 rounds of expansion, the growth and functionality of the CMV/CAR T cells was evaluated in vitro and in vivo.

Intracellular cytokine staining: CMV/CAR T cells ($10^5$) were activated overnight with 105 LCL-OKT3, LCL, or KG1a cells in 96-well tissue culture plates, and with 105 U251T and engineered pp65-expressing U251T cells (pp65U251T) in 24-well tissue culture plates in the presence of Brefeldin A (BD Biosciences). The cell mixture was then stained using anti-CD8, cetuximab and streptavidin, and pp65Tetramer to analyze surface co-expression of CD8, CAR and CMV-specific TCR, respectively. Cells were then fixed and permeabilized using the BD Cytofix/Cytoperm kit (BD Biosciences). After fixation, the T cells were stained with an anti-IFNγ.

CFSE Proliferation assays: CMV/CAR T cells were labeled with 0.5 µM CFSE and co-cultured with stimulator cells LCL-OKT3, LCLs, and pp65 U251T for 8 days.

Co-cultures with U251T and KG1a cells were used as negative controls. Proliferation of CD3− and CAR-positive populations was determined using multicolor flow cytometry.

Cytokine production assays: T cells ($10^5$) were co-cultured overnight in 96-well tissue culture plates with 105 LCL-OKT3, LCL, or KG1a cells and in 24-well tissue culture plates with 105 U251T and engineered pp65-expressing U251T cells. Supernatants were then analyzed by cytometric bead array using the Bio-Plex Human Cytokine 17-Plex Panel (Bio-Rad Laboratories) according to the manufacturer's instructions.

Cytotoxicity assays: 4-hour chromium-release assays (CRA) were performed as previously described (20) using effector cells that had been harvested directly after 2 rounds of CD19 Ag stimulations.

Example 4

Generation, Characterization and Identification of Meditope-Enabled CAR Constructs for Immunotherapy.

Different combinations of meditope-enabled Fab- and mAb-based CAR (meCAR) constructs that target HER2 positive tumors are generated, packaged each into a lentivirus, and transduced T-cells to generate meditope-enabled HER2+-CAR (meHER2+-CAR) T cells. The expression levels of each meCAR are characterized as well as its affinity for soluble extracellular HER2 with and without a DOTA-conjugated meditope. Finally, the tumor cell killing ability of each construct is quantified in the presence and absence of a DOTA-conjugated meditope in vitro.

CARs are a tool in the reprogramming of the immune system to recognize and destroy cancer cells. CARs are generally composed of an antigen recognition domain (e.g., an scFv), a spacer (e.g., the Fc domain of an IgG or hinge domain of CD8), a transmembrane region and intracellular costimulatory and activation domains (e.g., CD28 and/or CD137 and CD3 ζ chain). In embodiments, an antigen recognition domain composed of a meditope-enabled Fab or mAb provides a unique peptide binding site to rapidly and specifically add new functionality through the peptide without recourse to extensive re-engineering of the CAR itself. As noted, these functionalities may include the ability to image, target additional tumor-associated receptors, modulate immune function and selectively kill the CAR T cell. Provided herein are several expression plasmids for trastuzumab, an anti-HER2 mAb that is in the clinic for HER2 positive tumors and which Applicants have meditope-enabled (1). The order of light and heavy chain expression is altered and the efficacy of different internal ribosome entry sites versus the self-cleaving 2A peptide sequence (15) are tested. The binding of soluble HER2 is quantified as well as meditope for each construct using a variety of binding assays and super resolution microscopy. The in vitro functionality of the different CAR constructs is characterized by evaluating in vitro HER2-dependent T cell killing, degranulation, cytokine production and proliferation. The effect of meditope occupancy of the meCAR T cells is characterized using these same assays. A canonical HER2-specific CAR based on the scFv of trastuzumab are generated and characterized, which may serve as a reference point for both expression and functional assays.

A number of tumors aberrantly express HER2 including breast cancer, sarcomas, and lung cancer. Thus, there have been efforts in developing effective therapeutics, trastuzumab being one. However, 70% of HER2+ cancer patients do not respond to these systemic therapies and in fact may rapidly develop resistance to these agents (16). As such, vaccines to HER2 as well as HER2+ CAR T cells have been developed to go beyond the inhibition of HER2 signaling pathways and elicit a powerful immune response. Given the potency of CAR T cells and the possibility of adverse side effects (17), it is useful to monitor, modulate and potentially destroy HER2+ CAR T cells. Enabling CAR T cell with a meditope binding site addresses these problems.

Figure 1A:
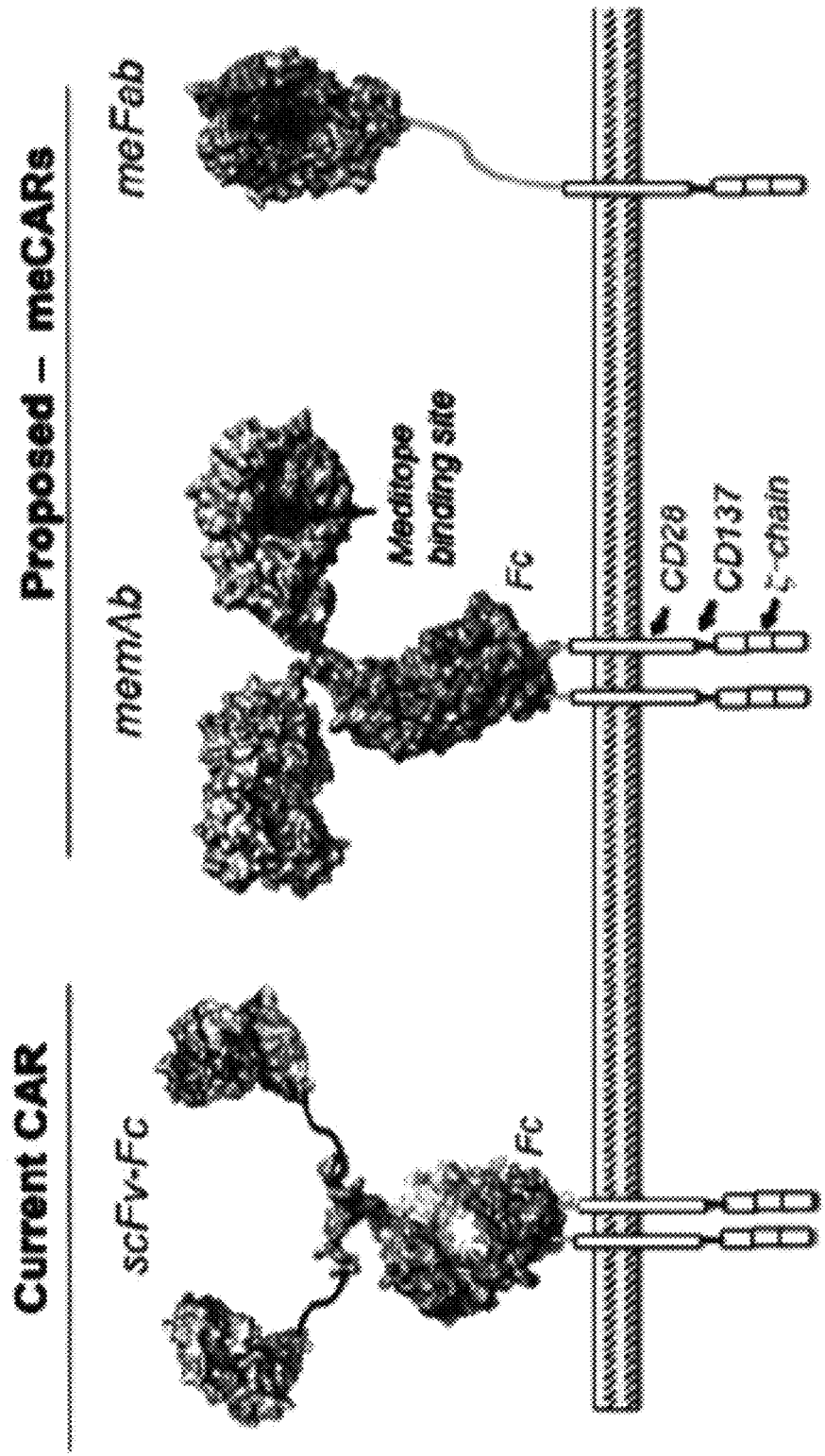
FIGS. 1A-1B.
Figure 1B:
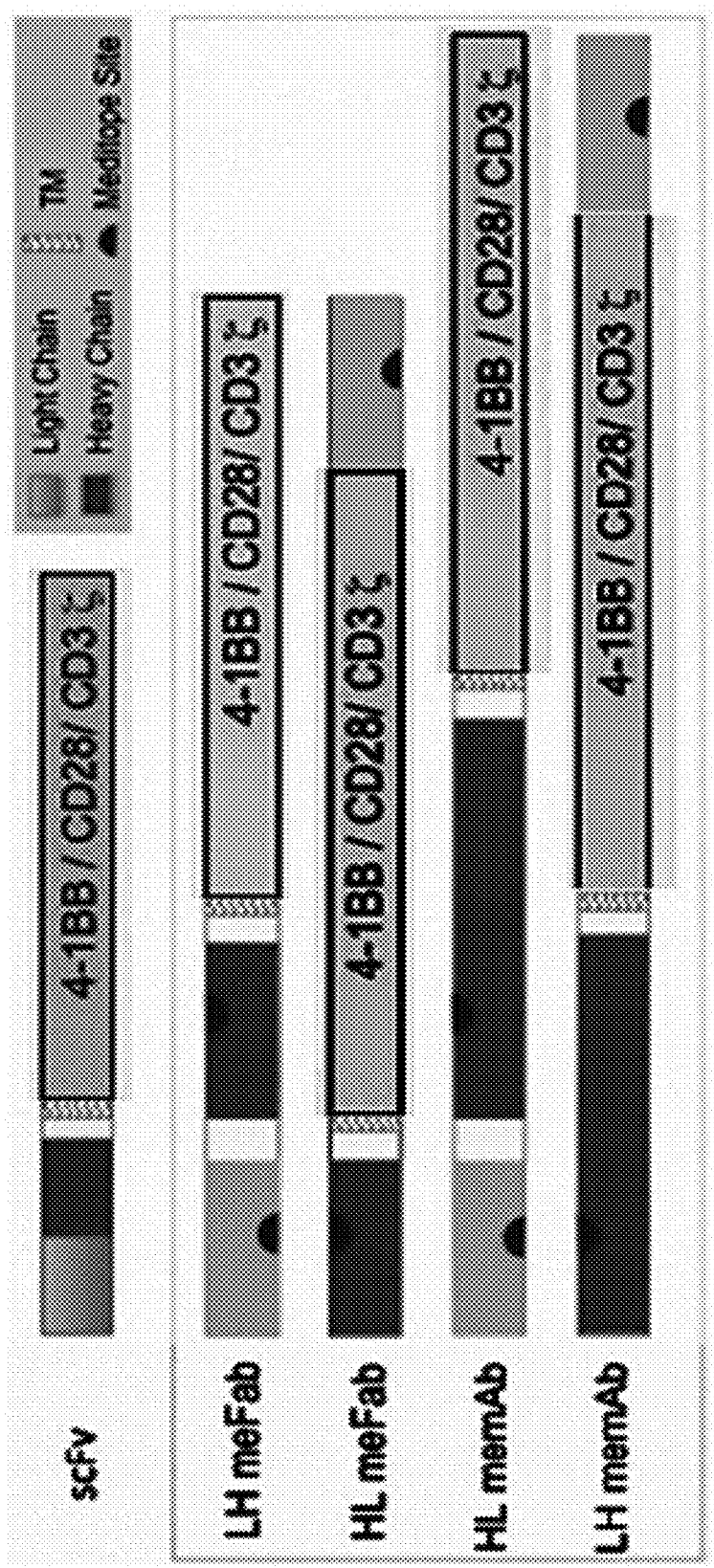
Figure 4A:
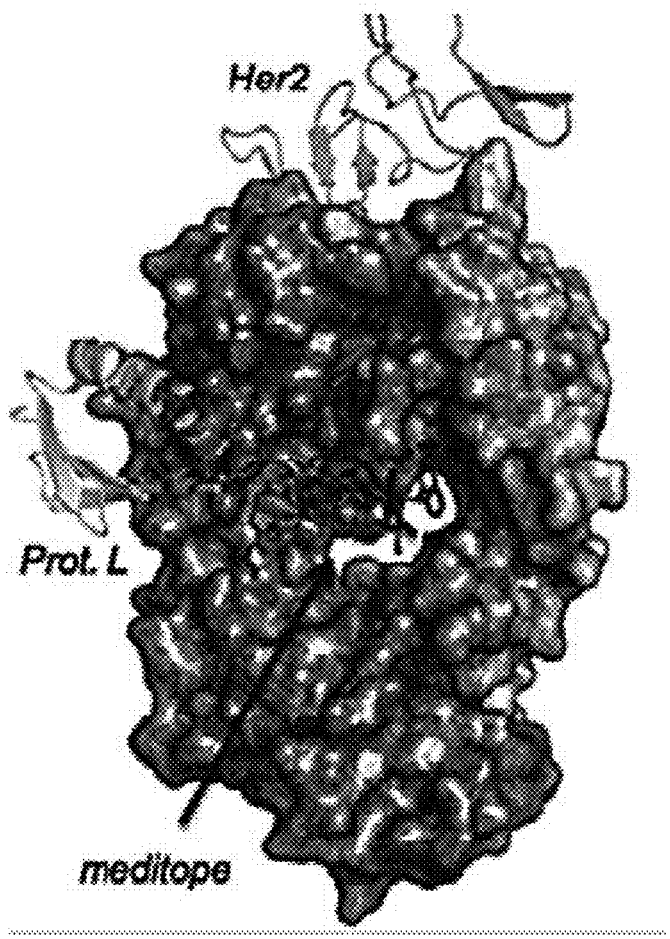
FIGS. 4A-4D. Meditope Studies.
Figure 4B:
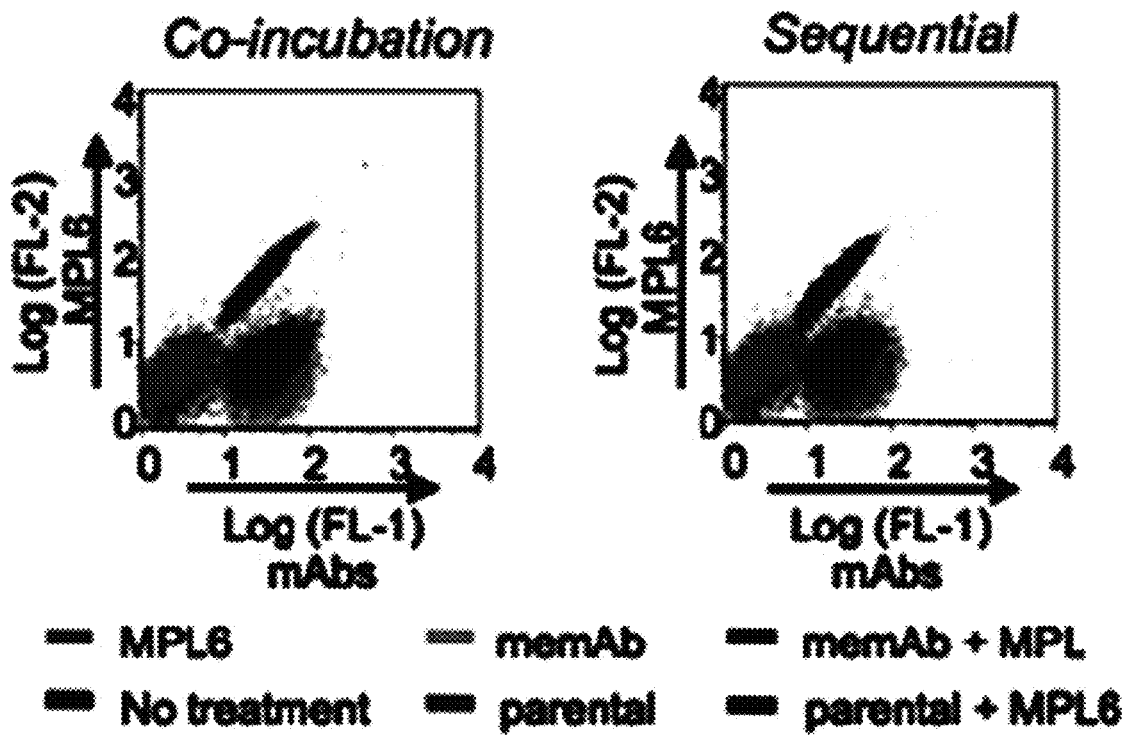
Figure 4C:
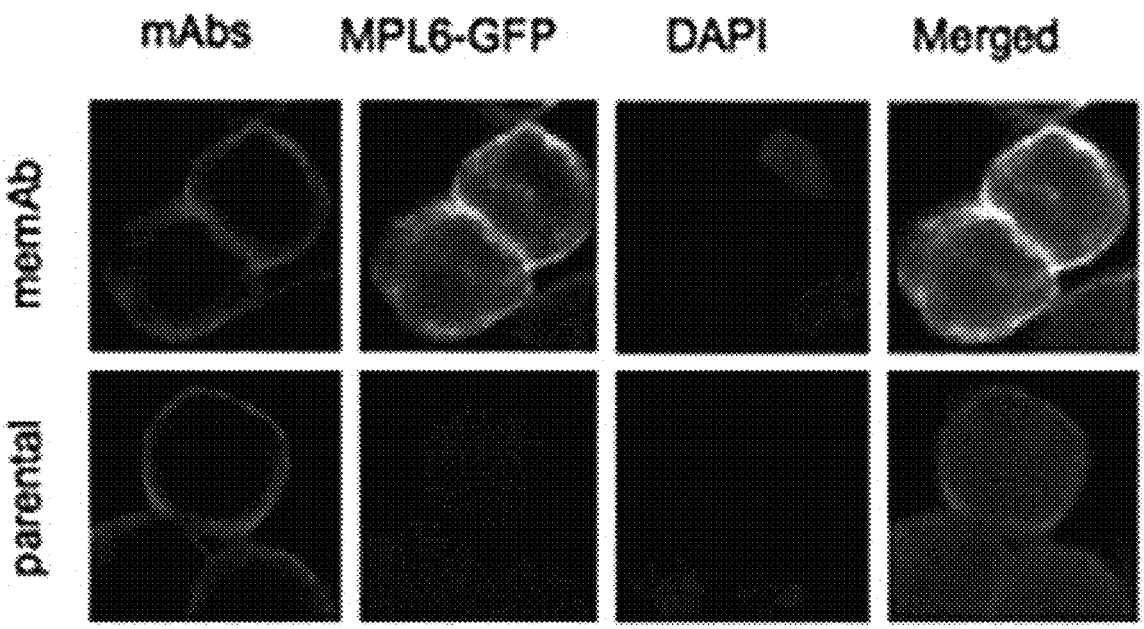
Figure 4D:
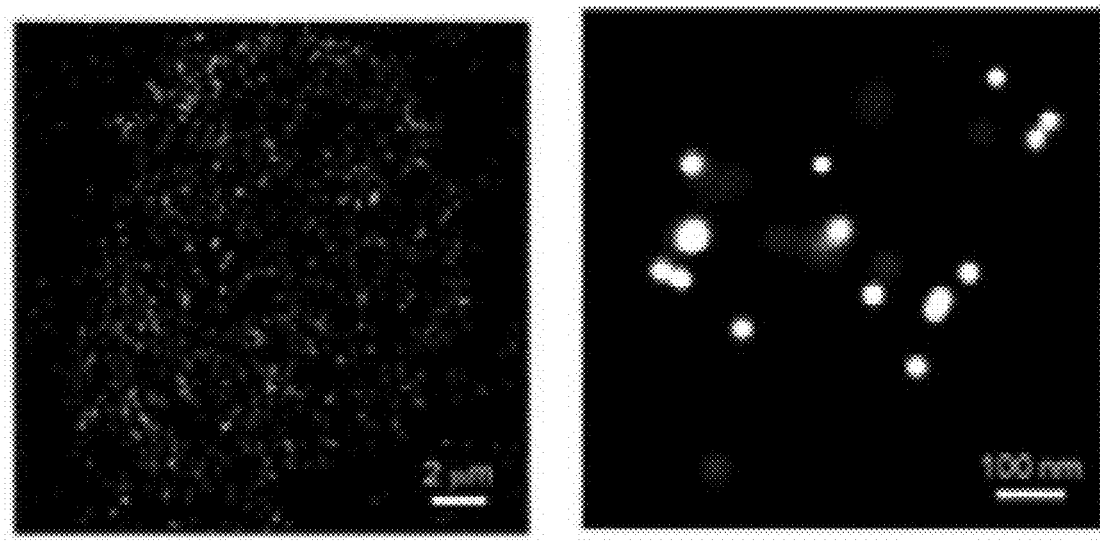

Meditope Interaction and Optimization. Described herein is a unique peptide binding site within the Fab arm of cetuximab including unique amino acid residues lining the site not found in human antibodies. This site may be grafted onto human mAbs including trastuzumab, a humanized anti-CEA, and other mAbs. Peptide binding does not affect the ability of the meditope-enabled antibodies to bind to their antigens. Due to the position of the binding site being in the central cavity of the Fab, the peptide may be referred to as a "meditope" ("medius" and "topo") (FIG. 1A and FIG. 4A). Meditope-enabled antibodies "memAbs" refer to meditope-enabled Fabs as meFabs (1).

Multiple of meditope variants have been produced, their affinity measure and crystallographic data accumulated for each. In these studies critical residues were identified, non-natural amino acids as well as D-amino acids were introduced, and different cyclization strategies to significantly improve the binding affinity were used Further, point mutations were introduced in the Fab at the meditope-binding interface (version 2) and observed a 100 fold increase in the binding affinity. Through these modifications, the affinity of meditopes increase from 1.2 μM to 860 pM at 37° ° C. (1000-fold increase). In addition, the termini of the meditope and protein L are, in embodiments, in close proximity when bound to the trastuzumab meFab and demonstrated favorable avidity through the fusion of meditope to protein L through a short linker (MPL). The affinity of the MPL construct for the original trastuzumab meFab as measured by Kinexa experiments is $K_D$=14 pM, or 87,000-fold over the affinity of the individual components at 25° ° C. (data not shown). Assuming that each modification acts independently, a 258 million-fold increase in affinity for the combination of a synthetic MPL and the memAb. Fusion of GFP to the MPL construct does not affect memAb binding and the GFP-MPL binding to memAb does not affect the association or dissociation kinetics or the affinity of HER2 binding (as shown in Avery et al. (37)).

Alexa Fluor 647-labeled MPL was either co-administered with Alexa Fluor 488-labeled memAb to HER2 overexpressing SKBR3 cells or after the cells were treated with the memAb and extensively washed. In both cases, the labeled MPL colocalized with the memAb and antigen (data not shown). In addition, it was demonstrated by fluorescence microscopy that the fusion of the bulky GFP to the MPL does not affect cell binding (data not shown). Lastly, a photoactivatable GFP was fused to the MPL construct and super-resolution microscopy was used to quantify HER2 receptors on BT474 cells (data not shown).

Figure 2A:
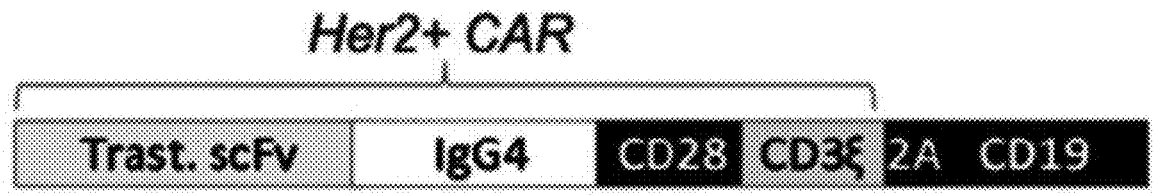
FIGS. 2A-2B: HER2-specific CAR.
Figure 2B:
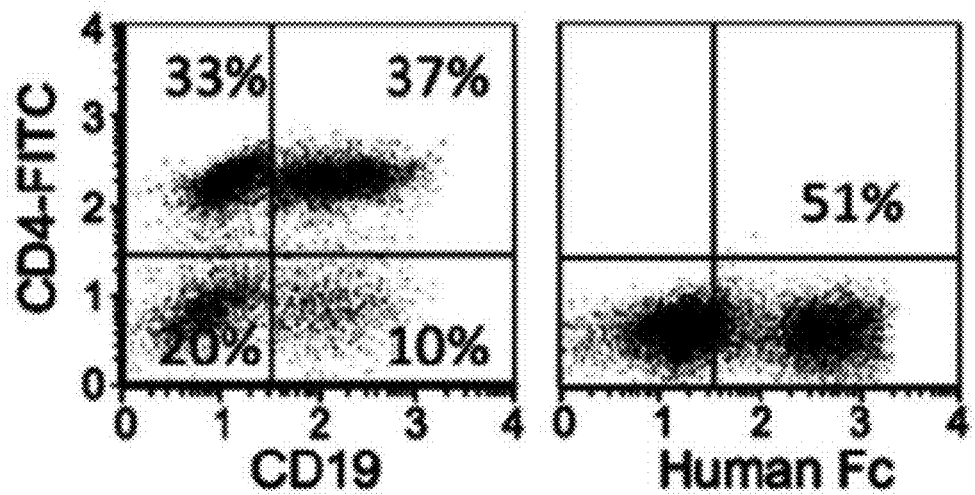

HER2-specific scFv-derived CAR T cells target and kill HER2-positive tumors. A second-generation HER2-specific CAR was generated composed of an scFv based on the trastuzumab antibody and intracellular signaling domains of CD28 and CD3ζ. A self-inactivating (SIN) lentiviral vector cassette was constructed encoding this HER2-specific scFv CAR (HER2-28ζ), followed by a 2A ribosomal skip sequence and a truncated CD19 (CD19t), an inert cell surface marker devoid of intracellular signaling that allows for specific detection of transduced T cells (FIG. 2A). The truncated CD19 (CD19t) as provided herein is also referred to as "marker peptide". The terms "marker peptide" or "tCD19" may be used interchangeably throughout. A human central memory T cells (Tcm) was constructed to express the HER2-28ζ CAR and CD19t polypeptides via lentiviral transduction, and expanded ex vivo using CD3/CD28 Dynabeads® stimulation and growth in X-Vivo media supplemented with IL-2 and IL-15 as per cGMP-compatible manufacturing platform (18).

Using mouse and non-human primate models relevant for human translation, it has been observed that T cells derived from CD62L⁺ Tcm persist in the blood after adoptive transfer, migrate to memory T cell niches in the lymph nodes and bone marrow, re-acquire phenotypic properties of memory T cells, and respond to antigen challenge in vivo (21, 22, 24, 25). Tcm or CD62L+ memory/naïve T cells may be engineered to express meditope-enabled HER2-CARs, taking advantage of the intrinsic long-term persistence of memory T cells, and the cGMP-compatible manufacturing platform which has been used to produce clinical products for two phase I clinical trials (BB-INDs 14645 and 15490) (18).

Figure 3A:
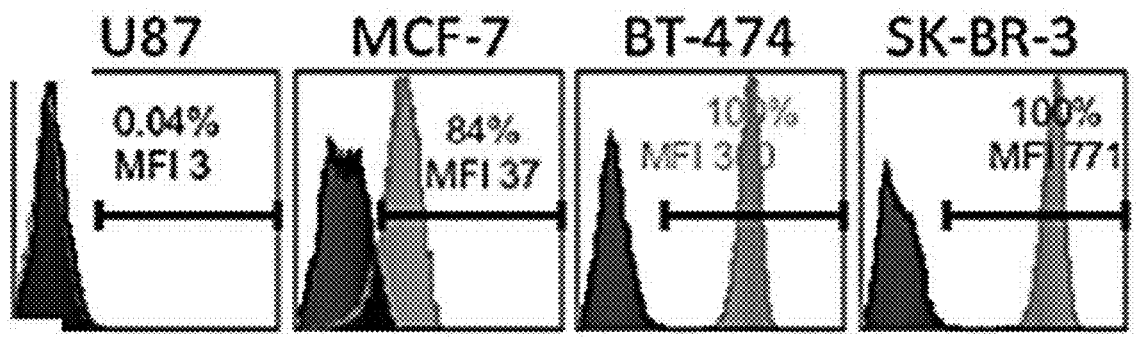
FIGS. 3A-3B. HER2-28ζ Tcm kill both high and low expressing HER2 targets.
Figure 3B:
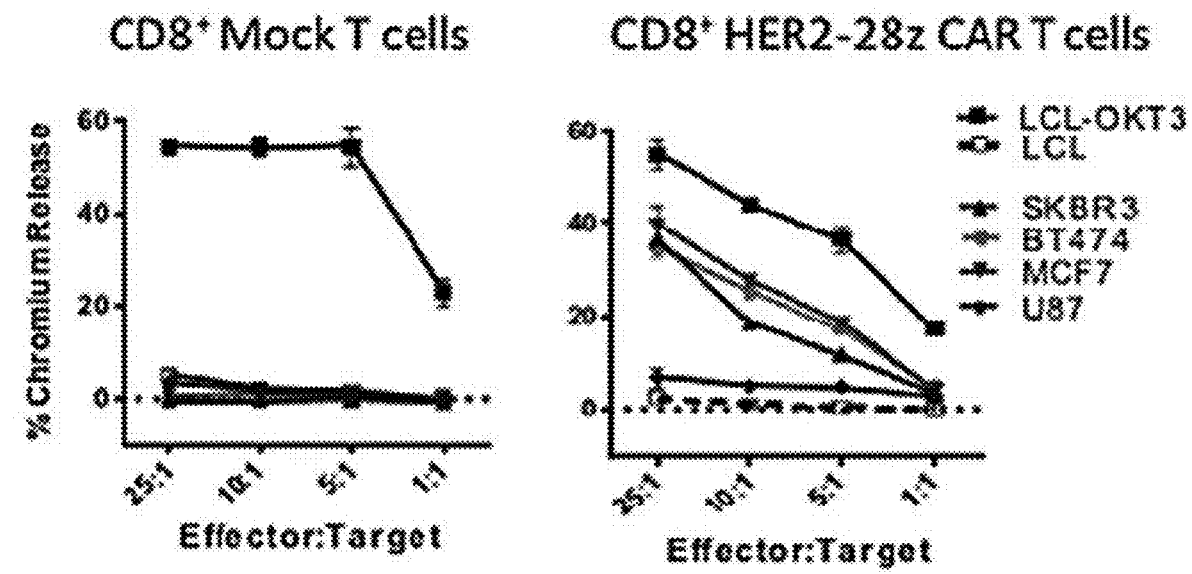

HER2-28ζ Tcm exhibit potent HER2-specific cytolytic activity in vitro against a panel of target cell lines that display both low (MCF7) and high (BT-474 and SK-BR-3) HER2 expression levels (FIGS. 3A-3B). Additionally, intracranial injection of HER2-28ζ Tcm can mediate regression of established brain tumors derived from the BT-474 HER2+ breast tumor cell line, and result in long term survival for 100% of the mice (data not shown).

The synthetic meditope-enabled trastuzumab heavy and the light chains may be sublconed into a lentiviral expression vector (FIG. 1A). Since each chain must be produced individually, an IRES motif will be incorporated between the light and heavy chain or use of a ribosomal skip sequence such as the T2A or the 2A sequence [15]. Further, a monomeric CAR using a meditope-enabled Fab may be created. Thus, the monomeric meditope-enabled Fab may be crosslinked with a bivalent meditope, allowing to regulation of the activity of the CAR T cell. The transmembrane domain is replaced with monomeric L-selectin (26) and a simple poly glycine-serine linker is used.

Meditope-enabled CAR T cells. Primary human T cells, for example CD62L+ Tcm cells, will be isolated from the peripheral blood of at least three healthy donors, engineered by lentiviral transduction to express HER2-CARs, and evaluated in vitro for specificity and functional activity. Following expansion of meditope-enabled HER2+ CAR Tcm with OKT3/CD28 Dynabead® and cytokine (IL-2 and IL-15) stimulation, the expression level of each construct will be characterized by FACS using anti-CD19 as a marker of cell transduction and anti-Fc for CAR expression, an Alexa fluor 488-labeled, extracellular Her2-Fc construct for antigen binding, and an Alexa fluor 647-conjugated meditope for functional meditope-CAR docking. Positive CAR T cells will be enriched, if necessary, by anti-CD19 magnetic cell selection or FACS. The ability of each construct, meditope-enabled Fab and meditope enabled mAb, to target and lyse HER2-positive (low and high HER2-expressing tumor lines; FIGS. 3A-3B) and HER2-negative breast cancer cell lines will be examined using standard chromium-release assays, and long-term co-culture assays (24-96 hrs) in the presence and absence of a DOTA-conjugated, high affinity meditope. To examine the effector function of different HER2-CAR T cells, HER2-dependent cytokine production will be measured, including secretion of IFNγ and TNFα following co-culture with tumor cells, again in the presence and absence of a DOTA-conjugated, high affinity meditope. Additionally, markers of activation and cytolytic activity will be included, namely CD69, Granzyme-B, and CD107a, as well as markers of cellular exhaustion, including PD-1. Furthermore, the antigen-dependent proliferative capacity of the different meditope-enabled HER2-CAR T cells in the presence and absence of DOTA-conjugated meditope will be measured by flow cytometry dye dilution analysis using CSFE. In each case, the results will be compared to the scFv CAR T cell. Methodologies for performing these in vitro functional assays are readily established in our group (6, 27).

Super resolution microscopy and autocorrelation analysis (28) will be used to investigate the distribution of receptors for each meditope-enabled CAR T cell. This approach will allow to quantitatively determine the size, occupancy, and density of proteins in the clusters. As demonstrated herein, an ultra-high affinity paGFP-MPL construct was produced and super resolution microscopy was utilized to detect single molecules with 15 nm resolution. In addition, a fluorescently labeled, high affinity 15-mer meditope was produced, which is less sterically constrained than the paGFP-MPL for super-resolution imaging. Using these reagents, ~12 individual cells expressing the meditope-enabled Fab or mAb will be analyzed and the efficacy of the meCAR T cell will be correlated with receptor distribution.

Example 5

Efficacy and in vivo imaging of meditope-enabled CAR in animal models. The efficacy of meditope-enabled CAR T cells on tumor growth inhibition will be evaluated and PET will be used to image meHER2+-CAR T cells pre-treated with $^{64}$Cu-labeled, DOTA-conjugated meditopes in NSG mice. NSG mice will be treated with the meHER2-CAR T cells and $^{64}$Cu labeled, DOTA-conjugated meditope will be administered at defined time points to assess meditope uptake by the meHER2-CAR T cells in situ.

Figure 5:
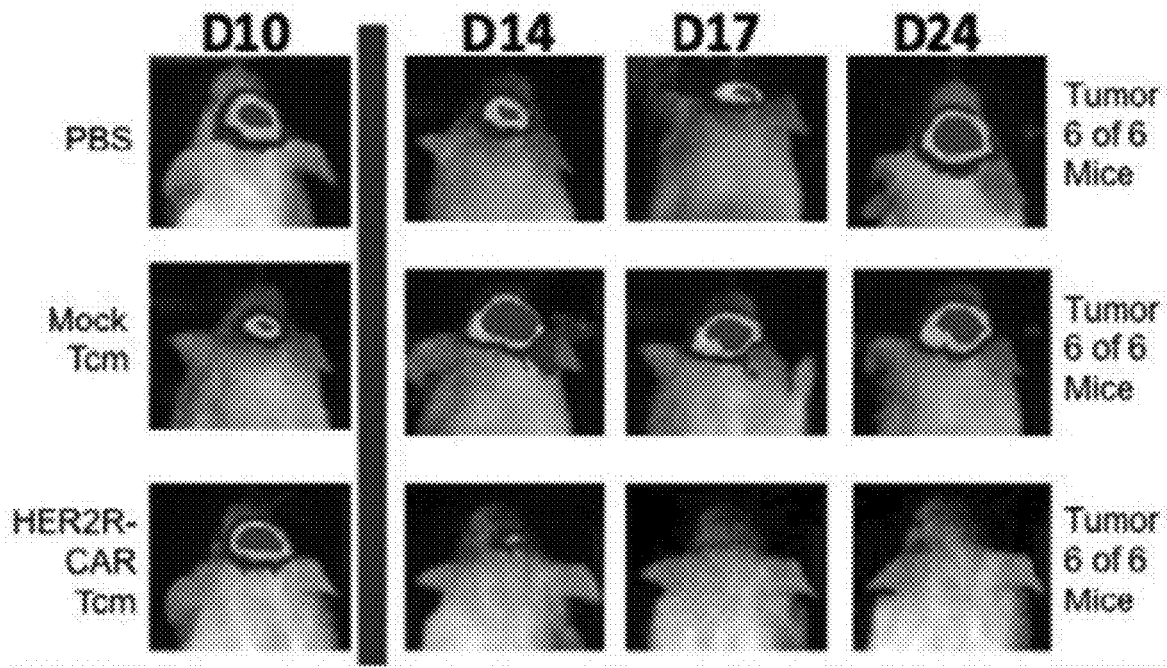
FIG. 5. HER2-scFv-CAR Tcm anti-tumor activity against intracranial engrafted breast tumors. Representative therapeutic responses to i.e. engrafted BT474 EGFP-ffLuc+ tumors ($1 \times 10^5$ cells) following intratumoral i.e. injection of HER2R-CAR T cells in NSG mice. On day 11, mice received either $1 \times 10^6$ HER2-CAR Tcm, mock Tcm or PBS.
Figure 6:
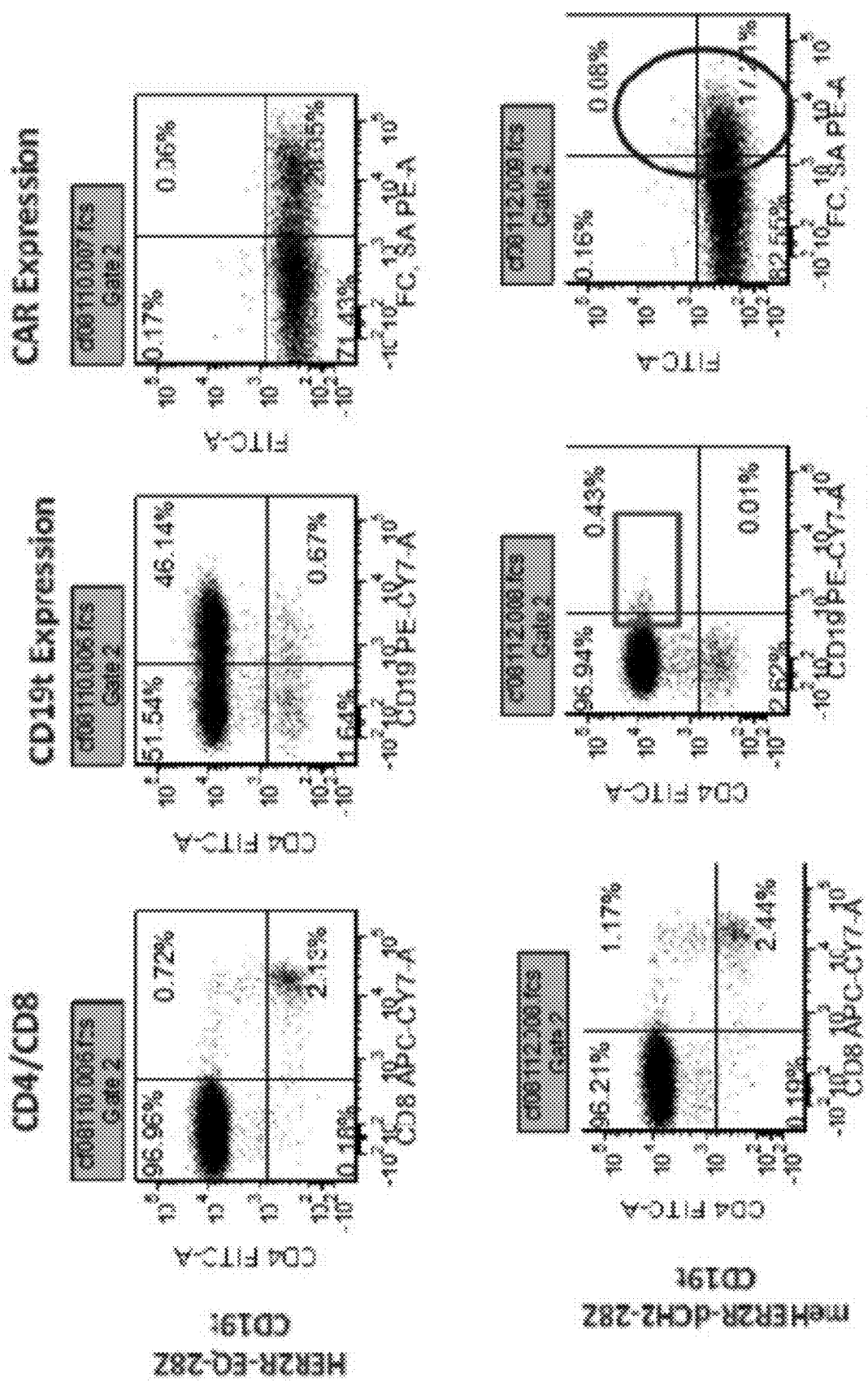
FIG. 6. meHER2R-CAR T cells. Primary human T cells were lentivirally transduced to express either the HER2-scFv-CAR (HER2R-EQ-28Z) or the meditope enabled HER2-CAR (meHER2R-dCH2-28Z). Cell surface expression of the meHER2-dCH2-28Z is confirmed by flow cytometry using anti-Fc antibody.
Figure 7:
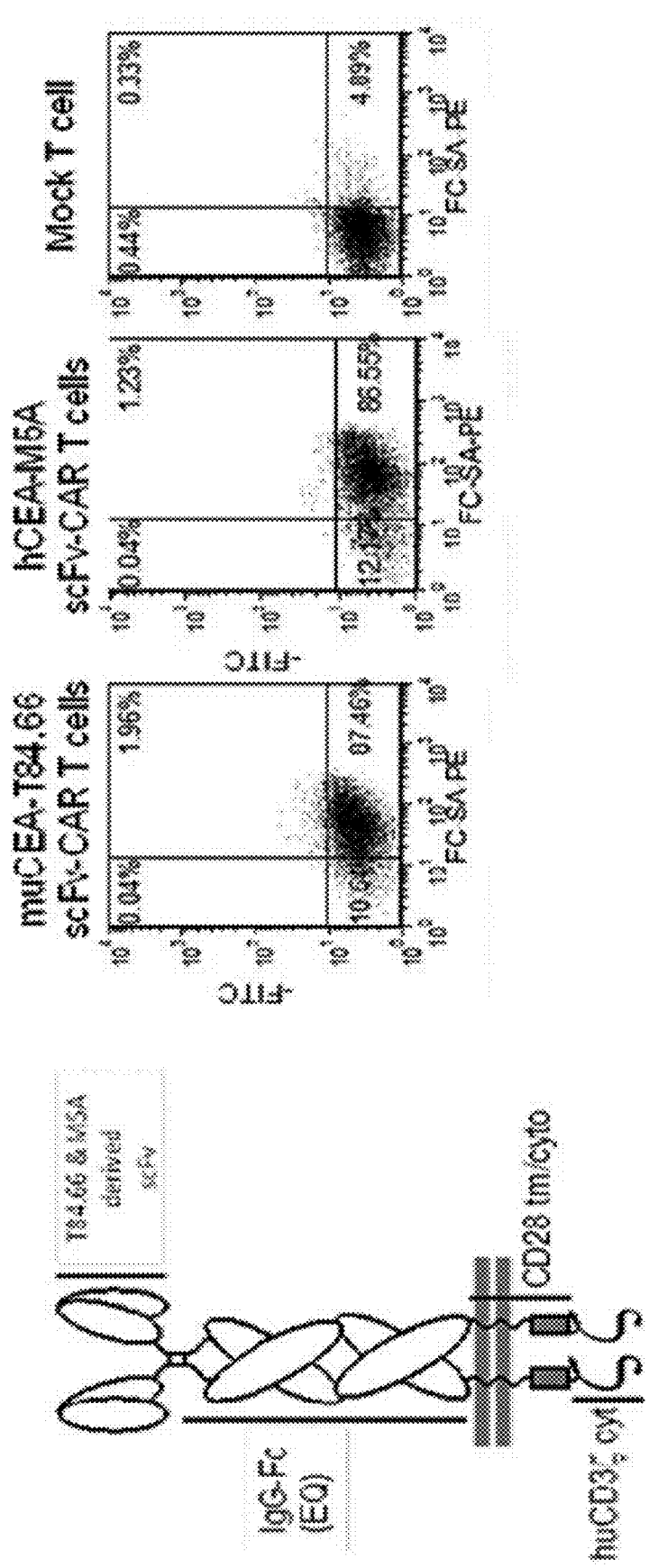
FIG. 7. Expression of murine T84.66 and humanized M5A derived scFv-CEA-specific CARs in Primary Human T cells. Both muT84.66 and M5A derived CEA-scFv-CARs are stably expressed by engineered cells.
Figure 8A:
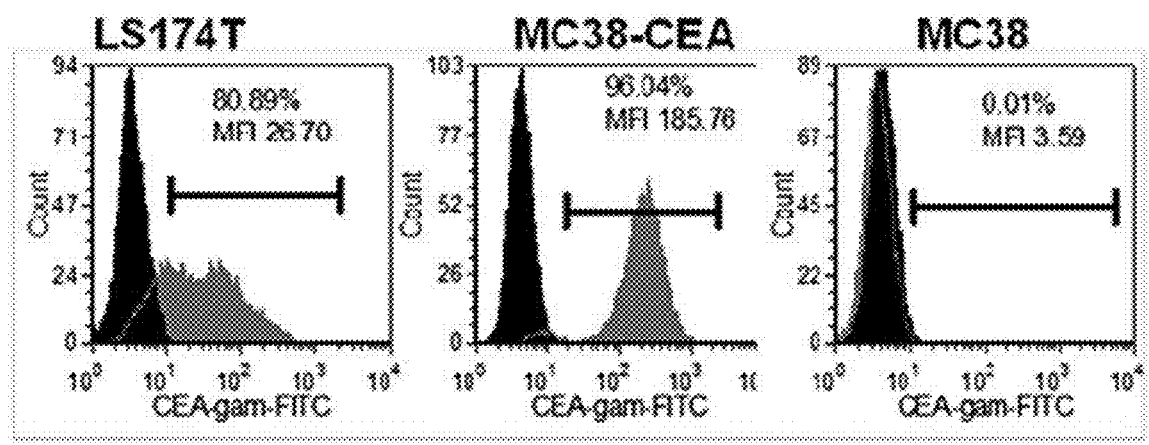
FIGS. 8A-8B. Comparing murine T84.66 versus humanized M5A scFv-CEA-specific CAR T cells for killing of CEA+ targets.
Figure 8B:
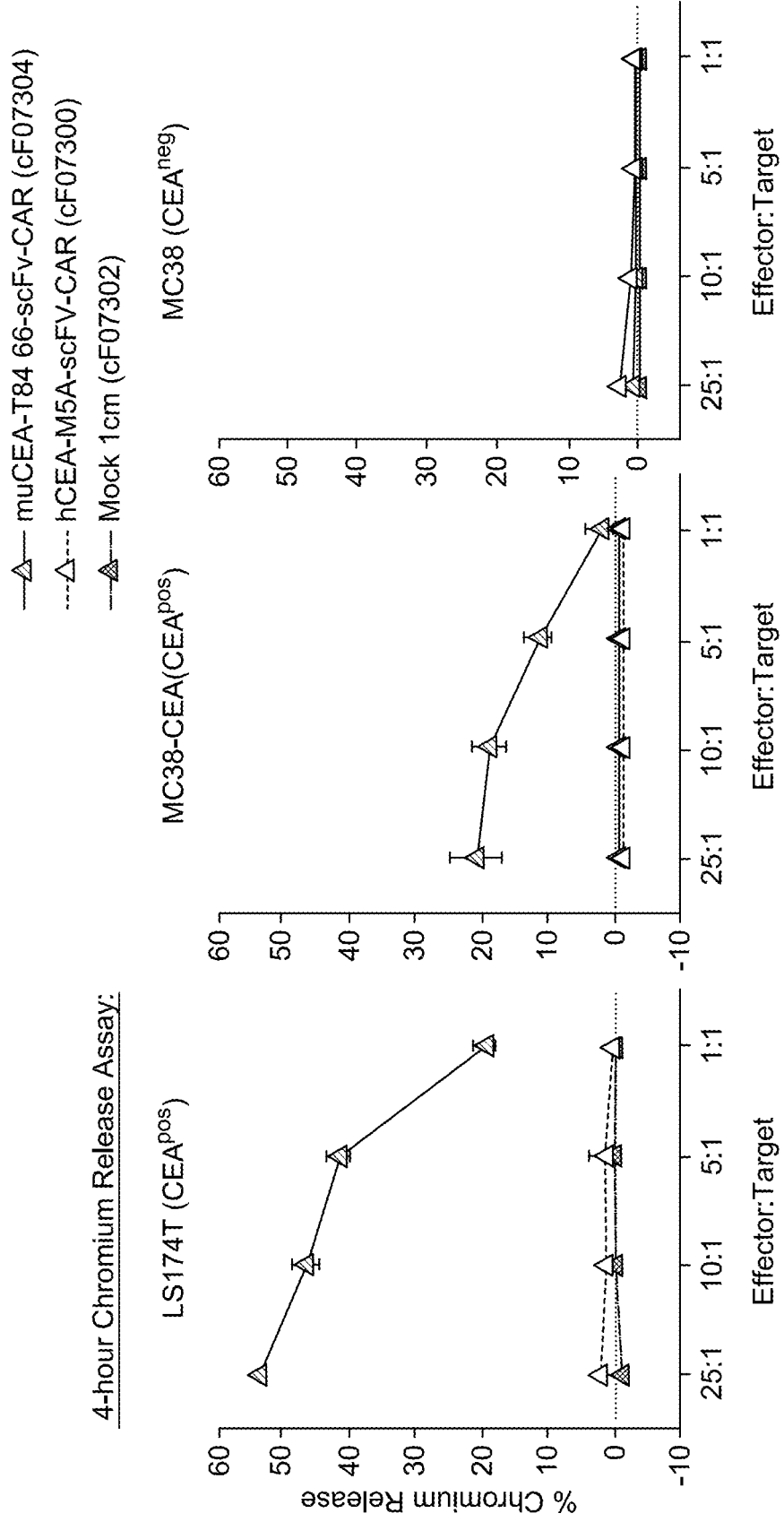
Figure 9:
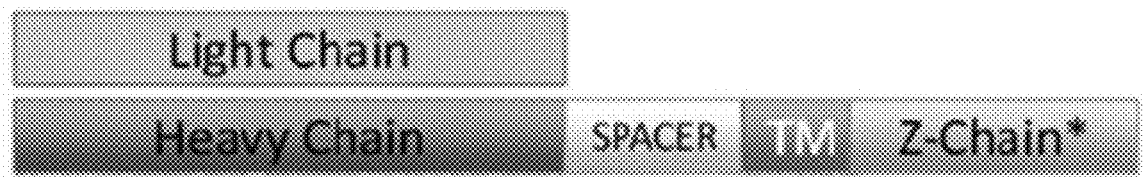
FIG. 9. Illustration of exemplary Fab and linker configuration.
Figure 10:
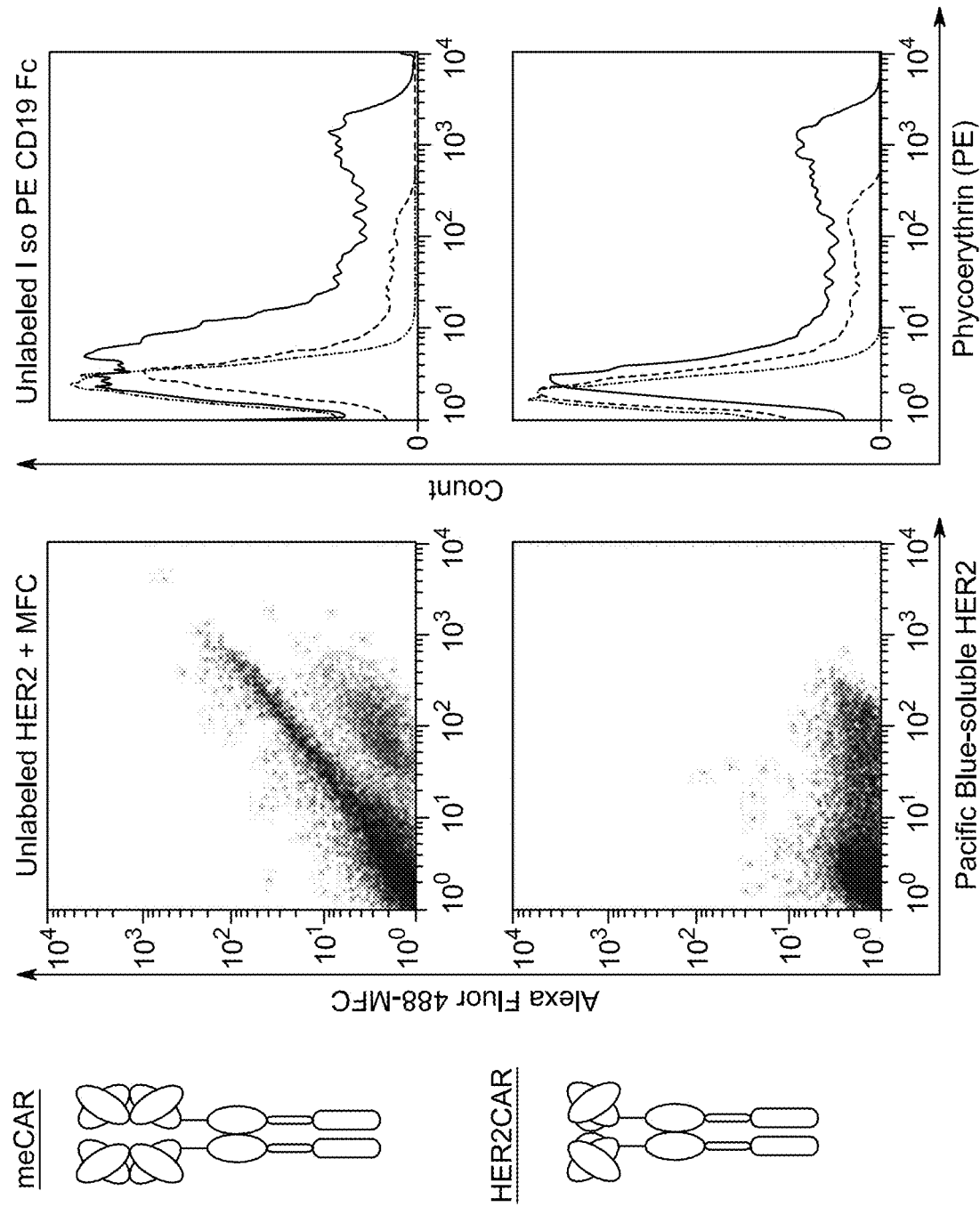
FIG. 10. CHO—S cells were transfected with either memAb trastuzumab Fab CAR (meCAR) or trastuzumab scFv-CAR (HER2CAR) plasmid for two days. The meCAR and HER2CAR construct differ only in the HER2-targeting component, each linked to CH3, CD28 transmembrane domain and CD3 zeta. A truncated CD19 can also be expressed from the plasmids and serves as a transfection control. The transfected CHO—S cells were filtered with 40 μm filter to remove debris and were washed once with 0.3%

Pre-targeted imaging separates the slow accumulation of mAbs at the tumor and slow clearance of mAbs from the blood from the relatively short half-life of useful PET metals through a two-step process. First, the patient is administered a conjugated mAb (streptavidin or with a unique binding domain) and then a homing ligand carrying $^{64}$Cu. The homing ligand rapidly binds to the tumor associated, modified mAb or is rapidly excreted. Since the $^{64}$Cu undergoes less half-lives, the signal is higher. Also, since the tracer is rapidly cleared, the background is reduced. Pre-clinical images using this approach have produced significantly better images than direct conjugation methods (10). Imaging CAR T cell location, expansion and longevity in patients will be tremendously useful in the development and clinical evaluation of this therapy. In vivo CAR T cell mouse models for the treatment of solid tumors, including brain tumors (FIG. 5), are well established in our lab (27, 34).

A dual orthotropic and metastatic tumor xenograft model will be employed using female NOD-scid IL2Rγnull (NSG) mice and the HER2-amplified breast cancer line BT474 that has been engineered to express both firefly luciferase (ffLuc) for non-invasive Xenogen imaging and a fluorescent reporter EGFP (27). EGFP-ffLuc+ BT474 tumor cells will be implanted concurrently into the mammary fat pad (1×10⁶ in a 50 μL mixture of PBS and Matrigel) to model primary disease, and intracranially (1×10⁵ in 2 μL PBS) to model metastatic disease. Once tumors are established (typically 7-14 days), a single dose of 5×10⁶ each HER2-meCAR Tcm or un-engineered Tcm (mock) or PBS will be infused intravenously. It has been shown that i.v. administered CAR T cell do traffic to the brain and mediate tumor regression (35, 36). Tumor growth/regression will be non-invasively quantified by Xenogen® IVIS optical imaging and caliper measurement, and survival analyzed by Kaplan-Meier. For these studies, T cell infiltration and persistence in tumors will be evaluated by immunohistochemistry using an Alexa Fluor-labeled meditope and CD3 markers, and Tcm persistence will be quantified by flow cytometry using Alexa Fluor-labeled meditopes, CD45, CD4/CD8, and CD62L markers in tumors and lymphoid tissue. Proliferation/apoptosis in tumors (Ki67, TUNEL), CAR T-cell activation and cytolytic function (CD69, Granzyme B, IFNγ) in tumors and in lymphoid tissues will be measured by flow cytometry. In vivo efficacy of meCAR T cells will be compared to previously characterized HER2-28ζ scFv CAR T cells. These studies will establish the capacity of meCAR T cells to mediate HER2+ tumor regression, and reveal potential differences in anti-tumor activity and T cell persistence between the meFab or memAb CAR T cells.

The high-affinity meditope with a C-terminal DOTA will be directly synthesized. The DOTA-meditope will be charged with $^{64}$Cu, purified by gel chromatography and mixed with the meCAR T cells. The cells will be administered to animals bearing EGFP-ffLuc+ BT474 tumors. MicroPET imaging will be conducted immediately following the injection and at defined time points thereafter. At day 1 and day 2, animals will be sacrificed and the bio distribution of the meditope and meCAR T cells will be determined for meCAR T cells at primary and metastatic disease sites. Next, pre-targeted imaging methods will be applied. The meCAR T cells will be administered in the same orthotopic and metastatic xenograft model. $^{64}$CU-DOTA meditope will be administered at 1 h post meCAR T cell administration and imaged at defined points thereafter (1, 2, 3 and 6 hours). The same imaging schedule will be conducted 1 day, 3 days and 10 days post meCAR T cell administration. Again, animals will be sacrificed and the bio distribution(s) will be determined through radiography.

Example 6

Genetic Modification of Enriched CMV-Specific T Cells to Express Second-Generation HER2-Specific CAR and In Vitro Expansion of the CMV/Meditope-Enabled CAR T Cells.

IFNγ-captured CMV-specific T cells will be transduced 2 days after the selection, without OKT3 activation, using the lentiviral construct encoding the meditope (me)-enabled trastuzumab Fab-CAR cassette (meHER2), with the T2A ribosomal skip sequence separating the antibody light chain (meLc) and the heavy chain fused to the IgG4-CH3-Fc linker, CD28 transmembrane domain (Tm) and the CD28 and CD3ζ cytoplasmic signaling domains (Hc28ζ). Expression is driven by the EF1α promoter and tested in two orientations: Lc-Hc28ζ and Hc28ζ-Lc. (FIG. 11A). Amino acid sequences of exemplary meHER2-CARs are set forth in SEQ ID NO: 17 and SEQ ID NO:28. Starting seven days post lentiviral transduction, the cells will be stimulated on a weekly basis with 8000 cGy-irradiated, HER2-expressing feeder cells (e.g., HER2+ breast cancer lines) at a 1:10 ratio (T cells:feeder cells). The percentage of CAR+ cells will be determined by detection using trastuzumab or protein L staining, which binds the Fab light chain, confirms cell surface expression of both CAR orientations. Meditope-AF647 staining will confirm the functional formation of the CAR meditope pocket.

To investigate CMV/meCAR T cell effector function via signaling by both the endogenous CMV-specific TCR and the introduced meHER2-CAR, we will evaluate response to engineered pp65-expressing U251T cells from HLA-A2 donors, and also allogeneic HER2+ cells, based on cytotoxicity, cytokine production and proliferation profiles.

Further, the ability of CMV/meCAR T cells, to target and lyse HER2-positive (low and high HER2-expressing tumor lines) and HER2-negative breast cancer cell lines will be examined using standard chromium-release assays, and long-term co-culture assays (24-96 hrs) in the presence and absence of a DOTA-conjugated, high affinity meditope. To examine the effector function of different CMV/HER2-CAR T cells, HER2-dependent cytokine production will be measured, including secretion of IFNγ and TNFα following co-culture with tumor cells, again in the presence and absence of a DOTA-conjugated, high affinity meditope. Additionally, markers of activation and cytolytic activity will be included, namely CD69, Granzyme-B, and CD107a, as well as markers of cellular exhaustion, including PD-1. Furthermore, the antigen-dependent proliferative capacity of the different CMV/meditope-enabled HER2-CAR T cells in the presence and absence of DOTA-conjugated meditope will be measured by flow cytometry dye dilution analysis using CSFE. In each case, the results will be compared to the scFv CAR T cell. Methodologies for performing these in vitro functional assays are readily established in our group (6, 27).

Efficacy and In Vivo Imaging of Meditope-Enabled CAR in Animal Models.

The efficacy of CMV/meditope-enabled CAR T cells on tumor growth inhibition will be evaluated and PET will be used to image CMV/meHER2+-CAR T cells pre-treated with $^{64}$Cu-labeled, DOTA-conjugated meditopes in NSG mice. NSG mice will be treated with the CMV/meHER2-CAR T cells and $^{64}$Cu labeled, DOTA-conjugated meditope will be administered at defined time points to assess meditope uptake by the CMV/meHER2-CAR T cells in situ. A single dose of 5×10$^6$ each CMV/HER2-meCAR Tcm or un-engineered Tcm (mock) or PBS will be infused intravenously. The high-affinity meditope with a C-terminal DOTA will be directly synthesized. The DOTA-meditope will be charged with 64Cu, purified by gel chromatography and mixed with the CMV/meCAR T cells. The cells will be administered to animals bearing EGFP-ffLuc+ BT474 tumors. MicroPET imaging will be conducted immediately following the injection and at defined time points thereafter. At day 1 and day 2, animals will be sacrificed and the bio distribution of the meditope and CMV/meCAR T cells will be determined for CMV/meCAR T cells at primary and metastatic disease sites. Next, pre-targeted imaging methods will be applied. The CMV/meCAR T cells will be administered in the same orthotopic and metastatic xenograft model. 64CU-DOTA meditope will be administered at 1 h post CMV/meCAR T cell administration and imaged at defined points thereafter (1, 2, 3 and 6 hours). The same imaging schedule will be conducted 1 day, 3 days and 10 days post CMV/meCAR T cell administration. Again, animals will be sacrificed and the bio distribution(s) will be determined through radiography.

Derivation and expansion of CMV/meCAR T cells: The selected CMV-specific T cells were transduced on day 2 post IFNγ capture with lentiviral vector expressing meditope (me)-enabled trastuzumab Fab-CAR cassette (meHER2), with the T2A ribosomal skip sequence separating the antibody light chain (meLc) and the heavy chain fused to the IgG4-CH3-Fc linker, CD28 transmembrane domain (Tm)

and the CD28 and CD3ζ cytoplasmic signaling domains (Hc28ζ). at MOI 3. Seven to ten days after lenti-transduction, the CMV/meCAR T cells were expanded by stimulation through CAR-mediated activation signals using 8000 cGy-irradiated HER2-expressing feeder cells (e.g., HER2⁺ breast cancer lines) at a 1:10 ratio (T cells:feeder cells) once a week as described (17) in the presence of IL-2 50U/ml and IL-15 1 ng/ml. After 2 rounds of expansion, the growth and functionality of the CMV/meCAR T cells was evaluated in vitro and in vivo.

CFSE Proliferation assays: CMV/meCAR T cells were labeled with 0.5 μM CFSE and co-cultured with stimulator cells LCL-OKT3, HER2⁺ cells, and pp65 U251T for 8 days. Co-cultures with U251T and KG1a cells were used as negative controls. Proliferation of CD3− and CAR-positive populations was determined using multicolor flow cytometry.

Cytokine production assays: T cells ($10^5$) were co-cultured overnight in 96-well tissue culture plates with 105 LCL-OKT3, HER2+ cells, or KG1a cells and in 24-well tissue culture plates with 105 U251T and engineered pp65-expressing U251T cells. Supernatants were then analyzed by cytometric bead array using the Bio-Plex Human Cytokine 17-Plex Panel (Bio-Rad Laboratories) according to the manufacturer's instructions.

Cytotoxicity assays: 4-hour chromium-release assays (CRA) were performed as previously described (20) using effector cells that had been harvested directly after 2 rounds of HER2⁺ Ag stimulations.

Tables

TABLE 1

Examples of transmembrane domains.

| Protein | NCBI Accession No. | Length | Transmembrane Domain Sequence |
|---|---|---|---|
| CD3z | GI:623041 | 21 aa | LCYLLDGILFIYGVILTALFL (SEQ ID NO: 1) |
| CD28 | GI:340545506 | 27 aa | FWVLVVVGGVLACYSLLVTVAFIIFWV (SEQ ID NO: 2) |
| CD4 | GI:179143 | 22 aa | MALIVLGGVAGLLLFIGLGIFF (SEQ ID NO: 3) |
| CD8 | GI:225007534 | 21 aa | IYIWAPLAGTCGVLLLSLVIT (SEQ ID NO: 4) |
| CD8 | GI:225007534 | 23 aa | IYIWAPLAGTCGVLLLSLVITLY (SEQ ID NO: 5) |
| CD8 | GI:225007534 | 24 aa | IYIWAPLAGTCGVLLLSLVITLYC (SEQ ID NO: 6) |
| 41BB | GI:315259099 | 27 aa | IISFFLALTSTALLFLLFF LTLRFSVV (SEQ ID NO: 7) |
| OX40 | GI:315360637 | 21 aa | VAAILGLGLVLGLLGPLAILL (SEQ ID NO: 8) |
| ICOS | GI:251823951 | 21 aa | FWLPIGCAAFVVVCILGCILI (SEQ ID NO: 9) |
| CD62L | GI:262206314 | 23 aa | PLFIPVAVMVTAFSGLAFIIWLA (SEQ ID NO: 10) |

TABLE 2

Examples of signaling domains

| Protein | NCBI Accession No. | Length | Endo Signaling |
|---|---|---|---|
| CD3ζ | GI:623041 | 113 aa | SEQ ID NO: 11: RVKFSRSADAPAYQQGQNQLYNELNLGRREEYD VLDKRRGRDPEMGGKPQRRKNPQEGLY |
| CD28 | GI:340545506 | 42 aa | SEQ ID NO: 12: RSKRSRLLHSDYMNMTPRRPGPTRKHYQPYAPPR DFAAYRS |
| CD28gg* | GI:340545506 | 42 aa | SEQ ID NO: 13: RSKRSRGGHSDYMNMTPRRPGPTRKHYQPYAPPR DFAAYRS (ref) |
| 41BB | GI:315259099 | 42 aa | SEQ ID NO: 14: KRGRKKLLYIFKQPFMRPVQTTQEEDGCSCRFPEE EEGGCEL |
| OX40 | GI:315360637 | 42 aa | SEQ ID NO: 15: ALYLLRRDQRLPPDAHKPPGGGSFRTPIQEEQADA HSTLAKI |

TABLE 2-continued

Examples of signaling domains

| Protein | NCBI Accession No. | Length | Endo Signaling |
|---|---|---|---|
| ICOS | GI:251823951 | 38 aa | SEQ ID NO: 16: CWLTKKKYSSSVHDPNGEYMFMRAVNTAKKSRLTDVTL |

TABLE 3

Examples of transmembrane domains.

| Name | Accession | Length | Sequence |
|---|---|---|---|
| CD3z | J04132.1 | 21 aa | LCYLLDGILFIYGVILTALFL (SEQ ID NO: 111) |
| CD28 | NM_006139 | 27 aa | FWVLVVVGGVLACYSLLVTVAFIIFWV (SEQ ID NO: 112) |
| CD28(M) | NM_006139 | 28 aa | MFWVLVVVGGVLACYSLLVTVAFIIFWV (SEQ ID NO: 113) |
| CD4 | M35160 | 22 aa | MALIVLGGVAGLLLFIGLGIFF (SEQ ID NO: 114) |
| CD8tm | NM_001768 | 21 aa | IYIWAPLAGTCGVLLLSLVIT (SEQ ID NO: 115) |
| CD8tm2 | NM_001768 | 23 aa | IYIWAPLAGTCGVLLLSLVITLY (SEQ ID NO: 116) |
| CD8tm3 | NM_001768 | 24 aa | IYIWAPLAGTCGVLLLSLVITLYC (SEQ ID NO: 117) |
| 41BB | NM_001561 | 27 aa | IISFFLALTSTALLFLLFF LTLRFSVV (SEQ ID NO: 118) |

TABLE 4

Examples of spacer regions.

| Name | Length | Sequence |
|---|---|---|
| a3 | 3 aa | AAA |
| linker | 10 aa | GGGSSGGGSG (SEQ ID NO: 100) |
| IgG4 hinge (S→P) (S228P) | 12 aa | ESKYGPPCPPCP (SEQ ID NO: 101) |
| IgG4 hinge | 12 aa | ESKYGPPCPSCP (SEQ ID NO: 102) |
| IgG4 hinge (S228P) + linker | 22 aa | ESKYGPPCPPCPGGGSSGGGSG (SEQ ID NO: 103) |
| CD28 hinge | 39 aa | IEVMYPPPYLDNEKSNGTIIHVKGKHLCPSPLFPGPSKP (SEQ ID NO: 104) |
| CD8 hinge-48 aa | 48 aa | AKPTTTPAPRPPTPAPTIASQPLSLRPEACRPAAGGAVHTRGLDFACD (SEQ ID NO: 105) |
| CD8 hinge-45 aa | 45 aa | TTTPAPRPPTPAPTIASQPLSLRPEACRPAAGGAVHTRGLDFACD (SEQ ID NO: 106) |

TABLE 4-continued

Examples of spacer regions.

| Name | Length | Sequence |
| --- | --- | --- |
| IgG4(HL-CH3) (includes S228P in hinge) | 129 aa | ESKYGPPCPPCPGGGSSGGGSGGQP REPQVYTLPPSQEEMTKNQVSLTCL VKGFYPSDIAVEWESNGQPENNYKT TPPVLDSDGSFFLYSRLTVDKSRWQ EGNVFSCSVMHEALHNHYTQKSLSL SLGK (SEQ ID NO: 107) |
| IgG4 (L235E, N297Q) | 229 aa | ESKYGPPCPSCPAPEFEGGPSVFLFPP KPKDTLMISRTPEVTCVVVDVSQED PEVQFNWYVDGVEVHQAKTKPREE QFQSTYRVVSVLTVLHQDWLNGKE YKCKVSNKGLPSSIEKTISKAKGQPR EPQVYTLPPSQEEMTKNQVSLTCLV KGFYPSDIAVEWESNGQPENNYKTT PPVLDSDGSFFLYSRLTVDKSRWQE GNVFSCSVMHEALHNHYTQKSLSLS LGK (SEQ ID NO: 108) |
| IgG4 (S228P, L235E, N297Q) | 229 aa | ESKYGPPCPPCPAPEFEGGPSVFLFPP KPKDTLMISRTPEVTCVVVDVSQED PEVQFNWYVDGVEVHQAKTKPREE QFQSTYRVVSVLTVLHQDWLNGKE YKCKVSNKGLPSSIEKTISKAKGQPR EPQVYTLPPSQEEMTKNQVSLTCLV KGFYPSDIAVEWESNGQPENNYKTT PPVLDSDGSFFLYSRLTVDKSRWQE GNVFSCSVMHEALHNHYTQKSLSLS LGK (SEQ ID NO: 109) |
| IgG4(CH3) | 107 aa | GQPREPQVYTLPPSQEEMTKNQVSL TCLVKGFYPSDIAVEWESNGQPENN YKTTPPVLDSDGSFFLYSRLTVDKSR WQEGNVFSCSVMHEALHNHYTQKS LSLSLGK (SEQ ID NO: 110) |

TABLE 5

CD3ζ Domain and Examples of Costimulatory Domains.

| Name | Accession | Length | Sequence |
| --- | --- | --- | --- |
| CD3ζ | J04132.1 | 113 aa | RVKFSRSADAPAYQQGQNQLYNELNL GRREEYDVLDKRRGRDPEMGGKPRRK NPQEGLYNELQKDKMAEAYSEIGMKG ERRRGKGHDGLYQGLSTATKDTYDAL HMQALPPR (SEQ ID NO: 119) |
| CD28 | NM_006139 | 42 aa | RSKRSRLLHSDYMNMTPRRPGPTRKHYQ PYAPPRDFAAYRS (SEQ ID NO: 120) |
| CD28gg* | NM_006139 | 42 aa | RSKRSRGGHSDYMNMTPRRPGPTRKHY QPYAPPRDFAAYRS (SEQ ID NO: 121) |
| 41BB | NM_001561 | 42 aa | KRGRKKLLYIFKQPFMRPVQTTQEEDGC SCRFPEEEEGGCEL (SEQ ID NO: 122) |
| OX40 | | 42 aa | ALYLLRRDQRLPPDAHKPPGGGSFRTPIQ EEQADAHSTLAKI (SEQ ID NO: 123) |

REFERENCES

1. Donaldson J M, Zer C, Avery K N, Bzymek K P, Horne D A, Williams J C. Identification and grafting of a unique peptide-binding site in the Fab framework of monoclonal antibodies. Proc Natl Acad Sci USA. 2013; 110(43): 17456-61. Epub 2013 Oct. 9. doi: 10.1073/pnas. 1307309110. PubMed PMID: 24101516 PMCID: PMC3808661.

2. Kochenderfer J N, Dudley M E, Feldman S A, Wilson W H, Spaner D E, Maric I, Stetler-Stevenson M, Phan G Q, Hughes M S, Sherry R M, Yang J C, Kammula U S, Devillier L, Carpenter R, Nathan D A, Morgan R A, Laurencot C, Rosenberg S A. B-cell depletion and remissions of malignancy along with cytokine-associated toxicity in a clinical trial of anti-CD19 chimeric-antigen-receptor-transduced T cells. Blood. 2012; 119(12):2709-

3. Davila M L, Riviere I, Wang X, Bartido S, Park J, Curran K, Chung S S, Stefanski J, Borquez-Ojeda O, Olszewska M, Qu J, Wasielewska T, He Q, Fink M, Shinglot H, Youssif M, Satter M, Wang Y, Hosey J, Quintanilla H, Halton E, Bernal Y, Bouhassira D C, Arcila M E, Gonen M, Roboz G J, Maslak P, Douer D, Frattini M G, Giralt S, Sadelain M, Brentjens R. Efficacy and toxicity management of 19-28z CAR T cell therapy in B cell acute lymphoblastic leukemia. Science translational medicine. 2014; 6(224):224ra25. Epub 2014 Jan. 21. doi: 10.1126/scitranslmed.3008226. PubMed PMID: 24553386.
4. Grupp S A, Kalos M, Barrett D, Aplenc R, Porter D L, Rheingold S R, Teachey D T, Chew A, Hauck B, Wright J F, Milone M C, Levine B L, June C H. Chimeric antigen receptor-modified T cells for acute lymphoid leukemia. N Engl J Med. 2013; 368(16):1509-18. Epub 2013 Mar. 27. doi: 10.1056/NEJMoa1215134. PubMed PMID: 23527958.
5. Kalos M, June C H. Adoptive T cell transfer for cancer immunotherapy in the era of synthetic biology. Immunity. 2013; 39(1):49-60. Epub 2013 Jul. 31. doi: 10.1016/j.immuni.2013.07.002. PubMed PMID: 23890063 PMCID: PMC3809038.
6. Mardiros A, Dos Santos C, McDonald T, Brown C E, Wang X, Budde L E, Hoffman L, Aguilar B, Chang W C, Bretzlaff W, Chang B, Jonnalagadda M, Starr R, Ostberg J R, Jensen M C, Bhatia R, Forman S J. T cells expressing CD123-specific chimeric antigen receptors exhibit specific cytolytic effector functions and antitumor effects against human acute myeloid leukemia. Blood. 2013; 122(18):3138-48. Epub 2013 Sep. 14. doi: 10.1182/blood-2012-12-474056. PubMed PMID: 24030378 PMCID: PMC3814731.
7. Turtle C J, Hudecek M, Jensen M C, Riddell S R. Engineered T cells for anti-cancer therapy. Curr Opin Immunol. 2012; 24(5):633-9. Epub 2012 Jul. 24. doi: 10.1016/j.coi.2012.06.004. PubMed PMID: 22818942 PMCID: PMC3622551.
8. NCI. CAR T-Cell Therapy: Engineering Patients' Immune Cells to Treat Their Cancers 2013. Available from: http://www.cancer.gov/cancertopics/research-updates/2013/CAR-T-Cells.
9. Sharkey R M, Chang C H, Rossi E A, McBride W J, Goldenberg D M. Pretargeting: taking an alternate route for localizing radionuclides. Tumour Biol. 2012; 33(3): 591-600. Epub 2012 Mar. 8. doi: 10.1007/s13277-012-0367-6. PubMed PMID: 22396041.
10. Goldenberg D M, Chang C H, Rossi E A, J W, McBride, Sharkey R M. Pretargeted molecular imaging and radioimmunotherapy. Theranostics. 2012; 2(5):523-40. Epub 2012 Jun. 28. doi: 10.7150/thno.3582. PubMed PMID: 22737190 PMCID: PMC3364558.
11. Rossi E A, Goldenberg D M, Cardillo T M, McBride W J, Sharkey R M, Chang C H. Stably tethered multifunctional structures of defined composition made by the dock and lock method for use in cancer targeting. Proc Natl Acad Sci USA. 2006; 103(18):6841-6. Epub 2006 Apr. 26. doi: 10.1073/pnas.0600982103. PubMed PMID: 16636283 PMCID: PMC1447525.
12. McConnell A D, Spasojevich V, Macomber J L, Krapf I P, Chen A, Sheffer J C, Berkebile A, Horlick R A, Neben S, King D J, Bowers P M. An integrated approach to extreme thermostabilization and affinity maturation of an antibody. Protein Eng Des Sel. 2013; 26(2): 151-64. Epub 2012 Nov. 23. doi: 10.1093/protein/gzs090. PubMed PMID: 23173178.
13. Honegger A. Engineering antibodies for stability and efficient folding. Handbook of experimental pharmacology. 2008(181):47-68. Epub 2007 Dec. 12. doi: 10.1007/978-3-540-73259-4_3. PubMed PMID: 18071941.
14. Donaldson J M, Kari C, Fragoso R C, Rodeck U, Williams J C. Design and development of masked therapeutic antibodies to limit off-target effects: Application to anti-EGFR antibodies. Cancer Biol Ther. 2009; 8(22). PubMed PMID: 19783899.
15. Szymczak A L, Workman C J, Wang Y, Vignali K M, Dilioglou S, Vanin E F, Vignali D A. Correction of multi-gene deficiency in vivo using a single 'self-cleaving' 2A peptide-based retroviral vector. Nat Biotechnol. 2004; 22(5):589-94. Epub 2004 Apr. 6. doi: 10.1038/nbt957. PubMed PMID: 15064769.
16. Kute T, Lack C M, Willingham M, Bishwokama B, Williams H, Barrett K, Mitchell T, Vaughn J P. Development of Herceptin resistance in breast cancer cells. Cytometry Part A: the journal of the International Society for Analytical Cytology. 2004; 57(2): 86-93. Epub 2004 Jan. 30. doi: 10.1002/cyto.a. 10095. PubMed PMID: 14750129.
17. Morgan R A, Yang J C, Kitano M, Dudley M E, Laurencot C M, Rosenberg S A. Case report of a serious adverse event following the administration of T cells transduced with a chimeric antigen receptor recognizing ERBB2. Molecular therapy: the journal of the American Society of Gene Therapy. 2010; 18(4):843-51. Epub 2010 Feb. 25. doi: 10.1038/mt.2010.24. PubMed PMID: 20179677 PMCID: PMC2862534.
18. Wang X, Naranjo A, Brown C E, Bautista C, Wong C W, Chang W C, Aguilar B, Ostberg J R, Riddell S R, Forman S J, Jensen M C. Phenotypic and functional attributes of lentivirus-modified CD19-specific human CD8+ central memory T cells manufactured at clinical scale. J Immunother. 2012; 35(9):689-701. Epub 2012 Oct. 24. doi: 10.1097/CJI.0b013e318270dec7. PubMed PMID: 23090078 PMCID: PMC3525345.
19. Rosenberg S A, Yang J C, Sherry R M, Kammula U S, Hughes M S, Phan G Q, Citrin D E, Restifo N P, Robbins P F, Wunderlich J R, Morton K E, Laurencot C M, Steinberg S M, White D E, Dudley M E. Durable complete responses in heavily pretreated patients with metastatic melanoma using T-cell transfer immunotherapy. Clin Cancer Res. 2011; 17(13):4550-7. PubMed PMID: 21498393.
20. Kalos M, Levine B L, Porter D L, Katz S, Grupp S A, Bagg A, June C H. T cells with chimeric antigen receptors have potent antitumor effects and can establish memory in patients with advanced leukemia. Sci Transl Med. 2011; 3(95):95ra73. Epub 2011 Aug. 13. doi: 3/95/95ra73 [pii]
21. Wang X, Berger C, Wong C W, Forman S J, Riddell S R, Jensen M C. Engraftment of human central memory-derived effector CD8+ T cells in immunodeficient mice. Blood. 2011; 117(6): 1888-98. Epub 2010 Dec. 3. doi: blood-2010-10-310599 [pii]
22. Berger C, Jensen M C, Lansdorp P M, Gough M, Elliott C, Riddell S R. Adoptive transfer of effector CD8 T cells derived from central memory cells establishes persistent T cell memory in primates. J Clin Invest. 2008; 118(1):294-305. PubMed PMID: 18060041.
23. Klebanoff C A, Gattinoni L, Restifo N P. Sorting through subsets: which T-cell populations mediate highly effective adoptive immunotherapy J Immunother. 2012; 35(9):651-

24. Gattinoni L, Klebanoff C A, Palmer D C, Wrzesinski C, Kerstann K, Yu Z, Finkelstein S E, Theoret M R, Rosenberg S A, Restifo N P. Acquisition of full effector function in vitro paradoxically impairs the in vivo antitumor efficacy of adoptively transferred CD8+ T cells. J Clin Invest. 2005; 115(6): 1616-26. doi: 10.1172/JCI24480. PubMed PMID: 15931392 PMCID: PMC1137001.
25. Kaech S M, Wherry E J. Heterogeneity and cell-fate decisions in effector and memory CD8+ T cell differentiation during viral infection. Immunity. 2007; 27(3):393-405. doi: 10.1016/j.immuni.2007.08.007. PubMed PMID: 17892848 PMCID: PMC3431921.
26. Srinivasan S, Deng W, Li R. L-selectin transmembrane and cytoplasmic domains are monomeric in membranes. Biochim Biophys Acta. 2011; 1808(6): 1709-15. Epub 2011 Feb. 15. doi: 10.1016/j.bbamem.2011.02.006. PubMed PMID: 21316337 PMCID: PMC3078985.
27. Brown C E, Starr R, Aguilar B, Shami A F, Martinez C, D'Apuzzo M, Barish M E, Forman S J, Jensen M C. Stem-like tumor-initiating cells isolated from IL 13Ralpha2 expressing gliomas are targeted and killed by IL 13-zetakine-redirected T Cells. Clin Cancer Res. 2012; 18(8):2199-209. Epub 2012 Mar. 13. doi: 10.1158/1078-0432.CCR-11-1669. PubMed PMID: 22407828 PMCID: PMC3578382.
28. Sengupta P, Jovanovic-Talisman T, Skoko D, Renz M, Veatch S L, Lippincott-Schwartz J. Probing protein heterogeneity in the plasma membrane using PALM and pair correlation analysis. Nat Methods. 2011; 8(11):969-75. Epub 2011 Sep. 20. doi: 10.1038/nmeth.1704. PubMed PMID: 21926998 PMCID: PMC3400087.
29. Hudecek M, Lupo-Stanghellini M T, Kosasih P L, Sommermeyer D, Jensen M C, Rader C, Riddell S R. Receptor affinity and extracellular domain modifications affect tumor recognition by ROR1-specific chimeric antigen receptor T cells. Clin Cancer Res. 2013; 19(12):3153-64. Epub 2013 Apr. 27. doi: 10.1158/1078-0432.CCR-13-0330. PubMed PMID: 23620405 PMCID: PMC3804130.
30. Wilkie S, Picco G, Foster J, Davies D M, Julien S, Cooper L, Arif S, Mather S J, Taylor-Papadimitriou J, Burchell J M, Maher J. Retargeting of human T cells to tumor-associated MUC1: the evolution of a chimeric antigen receptor. J Immunol. 2008; 180(7):4901-9. Epub 2008 Mar. 21. PubMed PMID: 18354214.
31. Guest R D, Hawkins R E, Kirillova N, Cheadle E J, Arnold J, O'Neill A, Irlam J, Chester K A, Kemshead J T, Shaw D M, Embleton M J, Stern P L, Gilham D E. The role of extracellular spacer regions in the optimal design of chimeric immune receptors: evaluation of four different scFvs and antigens. J Immunother. 2005; 28(3):203-11. Epub 2005 Apr. 20. PubMed PMID: 15838376.
32. Schlatter S, Stansfield S H, Dinnis D M, Racher A J, Birch J R, James D C. On the optimal ratio of heavy to light chain genes for efficient recombinant antibody production by CHO cells. Biotechnology progress. 2005; 21(1): 122-33. Epub 2005 May 21. doi: 10.1021/bp049780w. PubMed PMID: 15903249.
33. Akamatsu Y, Pakabunto K, Xu Z, Zhang Y, Tsurushita N. Whole IgG surface display on mammalian cells: Application to isolation of neutralizing chicken monoclonal anti-IL-12 antibodies. J Immunol Methods. 2007; 327(1-2):40-52. Epub 2007 Aug. 28. doi: 10.1016/j.jim.2007.07.007. PubMed PMID: 17719061.
34. Brown C E, Starr R, Martinez C, Aguilar B, D'Apuzzo M, Todorov I, Shih C C, Badie B, Hudecek M, Riddell S R, Jensen M C. Recognition and killing of brain tumor stem-like initiating cells by CD8+ cytolytic T cells. Cancer Res. 2009; 69(23):8886-93. Epub 2009 Nov. 12. doi: 10.1158/0008-5472.CAN-09-2687. PubMed PMID: 19903840 PMCID: PMC2789196.
35. Brown C E, Vishwanath R P, Aguilar B, Starr R, Najbauer J, Aboody K S, Jensen M C. Tumor-derived chemokine MCP-1/CCL2 is sufficient for mediating tumor tropism of adoptively transferred T cells. J Immunol. 2007; 179(5):3332-41. Epub 2007 Aug. 22. PubMed PMID: 17709550.
36. Miao H, Choi B D, Suryadevara C M, Sanchez-Perez L, Yang S, De Leon G, Sayour E J, Mclendon R, Herndon J E, 2nd, Healy P, Archer G E, Bigner D D, Johnson L A, Sampson J H. EGFRvIII-Specific Chimeric Antigen Receptor T Cells Migrate to and Kill Tumor Deposits Infiltrating the Brain Parenchyma in an Invasive Xenograft Model of Glioblastoma. PLOS One. 2014; 9(4): e94281. Epub 2014 Apr. 12. doi: 10.1371/journal.pone.0094281. PubMed PMID: 24722266 PMCID: PMC3983153.
37. Avery et al. 2015 (Scientific Reports 5:7817) Kendra N. Avery, Cindy Zer, Krzysztof P. Bzymek & John C. Williams. Development of a High Affinity, Non-covalent Biologic to Add Functionality to Fabs. Scientific Reports 5, Article Number: 7817 doi: 10.1038/srep07817. Published 15 January, 2015.

P1 Embodiments

P1 Embodiment 1. An isolated nucleic acid encoding a protein comprising: (i) an antibody region comprising a central cavity formed by a heavy chain variable (VH) region, a light chain variable (VL) region, a heavy chain constant region (CH) and a light chain constant region (CL), wherein said central cavity forms a peptide binding site comprising framework region amino acid residues; and (ii) a transmembrane domain.

P1 Embodiment 2. The isolated nucleic acid of P1 Embodiment 1, wherein said antibody region is an antibody fragment.

P1 Embodiment 3. The isolated nucleic acid of P1 Embodiment 1 or 2, wherein said antibody region comprises an Fc domain.

P1 Embodiment 4. The isolated nucleic acid of one of P1 Embodiments 1 to 3, wherein said antibody region is a humanized antibody region.

P1 Embodiment 5. The isolated nucleic acid of one of P1 Embodiment 1 to 4, further comprising an intracellular T-cell signaling sequence encoding an intracellular T-cell signaling domain.

P1 Embodiment 6. The isolated nucleic acid of P1 Embodiment 5, wherein said intracellular T-cell signaling domain is a CD3ζ intracellular T-cell signaling domain.

P1 Embodiment 7. The isolated nucleic acid of one of P1 Embodiments 1-6 further comprising an intracellular co-stimulatory signaling sequence encoding an intracellular co-stimulatory signaling domain.

P1 Embodiment 8. The isolated nucleic acid of P1 Embodiment 7, wherein said intracellular co-stimulatory signaling domain is a CD28 intracellular co-stimulatory signaling domain, a 4-1BB intracellular co-stimulatory signaling domain, a ICOS intracellular co-stimulatory signaling domain, or an OX-40 intracellular co-stimulatory signaling domain.

P1 Embodiment 9. The isolated nucleic acid of one of P1 Embodiments 1-8 further comprising a spacer sequence encoding a spacer region.

P1 Embodiment 10. The isolated nucleic acid of P1 Embodiment 9, wherein said spacer region is between said transmembrane domain and said antibody region.

P1 Embodiment 11. The isolated nucleic acid of one of P1 Embodiments 1-10 further comprising a linker sequence encoding a linker domain.

P1 Embodiment 12. The isolated nucleic acid of P1 Embodiment 11, wherein said linker domain is between said transmembrane domain and said intracellular T-cell signaling domain.

P1 Embodiment 13. The isolated nucleic acid of P1 Embodiment 11, wherein said linker domain is between said intracellular T-cell signaling domain and said intracellular co-stimulatory signaling domain.

P1 Embodiment 14. The isolated nucleic acid of P1 Embodiment 11, wherein said linker domain comprises the sequence GGCGG or GGG.

P1 Embodiment 15. The isolated nucleic acid of one of P1 Embodiments 1 to 14 comprising: (i) a heavy chain sequence encoding a heavy chain domain of said protein, said heavy chain domain comprising a variable heavy chain domain and said transmembrane domain; and (ii) a light chain sequence encoding a light chain domain of said protein, said light chain domain comprising a variable light chain domain, wherein said variable heavy chain domain and said variable light chain domain together form at least a portion of said antibody region.

P1 Embodiment 16. The isolated nucleic acid of P1 Embodiment 15 comprising a self- P1 Embodiment 17. The isolated nucleic acid of P1 Embodiment 16, wherein said self-cleaving peptidyl linker sequence is a T2A sequence or a 2A sequence.

P1 Embodiment 18. The isolated nucleic acid of one of P1 Embodiments 15 to 17, wherein said light chain sequence is 3' to said heavy chain sequence.

P1 Embodiment 19. The isolated nucleic acid of one of P1 Embodiments 1 to 18, wherein said antibody region is a cetuximab meditope enabled domain, trastuzumab meditope enabled domain, pertuzumab meditope enabled domain, M5A meditope enabled domain or rituximab meditope enabled domain.

P1 Embodiment 20. An isolated nucleic acid encoding a protein comprising a first portion comprising an antibody heavy chain variable domain and a second portion comprising an antibody light chain variable domain and an antibody light chain constant domain, wherein the first portion further comprises a transmembrane domain.

P1 Embodiment 21. The isolated nucleic acid of P1 Embodiment 20, wherein said first portion further comprises an intracellular T-cell signaling domain.

P1 Embodiment 22. The isolated nucleic acid of P1 Embodiment 20, wherein said intracellular T-cell signaling domain is a CD3ζ intracellular T-cell signaling domain.

P1 Embodiment 23. The isolated nucleic acid of one of P1 Embodiments 20-22, wherein said first portion further comprises an intracellular co-stimulatory signaling domain.

P1 Embodiment 24. The isolated nucleic acid of P1 Embodiment 23, wherein said intracellular co-stimulatory signaling domain is a CD28 intracellular co-stimulatory signaling domain, a 4-1BB intracellular co-stimulatory signaling domain, a ICOS intracellular co-stimulatory signaling domain, or an OX-40 intracellular co-stimulatory signaling domain.

P1 Embodiment 25. The isolated nucleic acid of one of P1 Embodiments 20-24 wherein said first portion further comprises a linker domain.

P1 Embodiment 26. The isolated nucleic acid of P1 Embodiment 25, wherein said linker domain is between said transmembrane domain and said intracellular T-cell signaling domain.

P1 Embodiment 27. The isolated nucleic acid of P1 Embodiment 25, wherein said linker domain is between said intracellular T-cell signaling domain and said intracellular co-stimulatory signaling domain.

P1 Embodiment 28. The isolated nucleic acid of P1 Embodiment 25, wherein said linker domain comprises the sequence GGCGG or GGG.

P1 Embodiment 29. The isolated nucleic acid of P1 Embodiment 20, wherein said first portion further comprises a CD3ζ intracellular T-cell signaling domain and an intracellular co-stimulatory signaling domain.

P1 Embodiment 30. The isolated nucleic acid molecule of P1 Embodiment 23, wherein the first portion comprises from the amino terminus to the carboxy terminus: the heavy chain variable domain, a heavy chain constant domain, the transmembrane domain, the CD3ζ intracellular T-cell signaling domain and an intracellular co-stimulatory signaling domain.

P1 Embodiment 31. The isolated nucleic acid molecule of one of P1 Embodiments 20-30 further comprising a spacer region positioned between the heavy chain variable domain and the transmembrane domain.

P1 Embodiment 32. The isolated nucleic acid of P1 Embodiment 31, wherein said spacer region further comprises a hinge region.

P1 Embodiment 33. The isolated nucleic acid of P1 Embodiment 20, wherein the antibody heavy chain variable domain and the antibody light chain variable domain are humanized.

P1 Embodiment 34. The isolated nucleic acid of P1 Embodiment 20, wherein said first portion comprises a heavy chain constant domain.

P1 Embodiment 35. The isolated nucleic acid of P1 Embodiment 20 comprising a self-cleaving peptidyl sequence between said first portion and said second portion.

P1 Embodiment 36. The isolated nucleic acid of P1 Embodiment 35, wherein said self-cleaving peptidyl encoding sequence is a T2A encoding sequence or a 2A encoding sequence.

P1 Embodiment 37. The isolated nucleic acid of one of P1 Embodiment 20, wherein the nucleic acid sequence encoding the second portion is 3' to the nucleic acid sequence encoding the first portion.

P1 Embodiment 38. The isolated nucleic acid of one of P1 Embodiment 1 to 37, wherein said protein is an anti-CD19 protein, anti-CD20 protein, anti-CD22 protein, anti-CD30 protein, anti-CD33 protein, anti-CD44v6/7/8 protein, anti-CD123 protein, anti-CEA protein, anti-EGP-2 protein, anti-EGP-40 protein, anti-erb-B2 protein, anti-erb-B2,3,4 protein, anti-FBP protein, anti-fetal acetylcholine receptor protein, anti-GD2 protein, anti-GD3 protein, anti-Her2/neu protein, anti-IL-13R-a2 protein, anti-KDR protein, anti k-light chain protein, anti-LeY protein, anti-L1 cell adhesion molecule protein, anti-MAGE-A1 protein, anti-mesothelin protein, anti-murine CMV infected cell protein, anti-MUC2 protein, anti-NKGD2 protein, anti, oncofetal antigen protein, anti-PCSA protein, anti-PSMA protein, anti-TAA (targeted by mAb IfE) protein, anti-EGFR protein, anti-TAG-72 protein or anti-VEGF-72 protein.

P1 Embodiment 39. The isolated nucleic acid of one of P1 Embodiments 1 to 38, further comprising a suicide gene sequence.

P1 Embodiment 40. An expression vector comprising the nucleic acid of one of P1 Embodiments 1 to 39.

P1 Embodiment 41. The expression vector of P1 Embodiment 40, wherein said expression vector is a viral vector.

P1 Embodiment 42. The expression vector of P1 Embodiment 41, wherein said virus is a lentivirus or onco-retrovirus.

P1 Embodiment 43. A T lymphocyte comprising the expression vector of one of P1 Embodiments 40 to 42.

P1 Embodiment 44. A T lymphocyte of P1 Embodiment 43, comprising a first polypeptide and a second polypeptide, the first polypeptide comprising a heavy chain variable domain, a heavy chain constant domain, a transmembrane domain, a CD3ζ signaling domain and a co-stimulatory T-cell signaling domain, the second polypeptide comprising a light chain variable domain and an light chain constant domain.

P1 Embodiment 45. A recombinant protein comprising: (i) an antibody region comprising a central cavity formed by a heavy chain variable (VH) region and a light chain variable (VL) region, wherein said central cavity forms a peptide binding site comprising framework region amino acid residues; and (ii) a transmembrane domain.

P1 Embodiment 46. The recombinant protein of P1 Embodiment 45, wherein said antibody region further comprises a heavy chain constant region (CH) and a light chain constant region (CL).

P1 Embodiment 47. The recombinant protein of P1 Embodiment 45 or 46, wherein said antibody region comprises an Fc domain.

P1 Embodiment 48. The recombinant protein of one of P1 Embodiments 45 to 47, wherein said antibody region is a humanized antibody region.

P1 Embodiment 49. The recombinant protein of one of P1 Embodiments 45 to 48, wherein said antibody region does not comprise a scFv antibody region.

P1 Embodiment 50. The recombinant protein of one of P1 Embodiments 45 to 49, wherein said protein further comprises an intracellular T-cell signaling domain.

P1 Embodiment 51. The recombinant protein of P1 Embodiment 50, wherein said intracellular T-cell signaling domain is a CD3ζ intracellular T-cell signaling domain.

P1 Embodiment 52. The recombinant protein of one of P1 Embodiments 45 to 51, further comprising an intracellular co-stimulatory signaling domain.

P1 Embodiment 53. The recombinant protein of P1 Embodiment 52, wherein said intracellular co-stimulatory signaling domain is a CD28 intracellular co-stimulatory signaling domain, a 4-1BB intracellular co-stimulatory signaling domain, a ICOS intracellular co-stimulatory signaling domain, or an OX-40 intracellular co-stimulatory signaling domain.

P1 Embodiment 54. The recombinant protein of one of P1 Embodiments 45 to 53, further comprising a spacer region.

P1 Embodiment 55. The recombinant protein of P1 Embodiment 54, wherein said spacer region is between said transmembrane domain and said antibody region.

P1 Embodiment 56. The recombinant protein of P1 Embodiment one of P1 Embodiments 45-55, further comprising a linker domain.

P1 Embodiment 57. The recombinant protein of P1 Embodiment 56, wherein said linker domain is between said transmembrane domain and said intracellular T-cell signaling domain.

P1 Embodiment 58. The recombinant protein of P1 Embodiment 56, wherein said linker domain is between said intracellular T-cell signaling domain and said intracellular co-stimulatory signaling domain.

P1 Embodiment 59. The recombinant protein of P1 Embodiment 57 or 58, wherein said linker domain comprises the sequence GGCGG or GGG.

P1 Embodiment 60. The recombinant protein of one of P1 Embodiments 45 to 59, wherein said antibody region is a cetuximab meditope enabled domain, trastuzumab meditope enabled domain, pertuzumab meditope enabled domain, M5A meditope enabled domain or rituximab meditope enabled domain.

P1 Embodiment 61. The recombinant protein of one of P1 Embodiments 45 to 60, wherein a compound comprising an peptidyl moiety is bound to said peptide binding site.

P1 Embodiment 62. The recombinant protein of P1 Embodiment 61, wherein said compound is a multivalent meditope.

P1 Embodiment 63. A recombinant protein comprising a first portion comprising an antibody heavy chain variable domain and a second portion comprising an antibody light chain variable domain and an antibody light chain constant domain, wherein the first portion further comprises a transmembrane domain, and wherein said antibody heavy chain variable domain, said antibody light chain variable domain and said antibody light chain constant domain together form an antibody region.

P1 Embodiment 64. A T lymphocyte comprising the recombinant protein of one of P1 Embodiments 45 to 63, wherein said transmembrane domain is within the cell membrane of said T lymphocyte.

P1 Embodiment 65. A method of treating cancer, said method comprising administering to a subject in need thereof an effective amount of the T-lymphocyte of P1 Embodiment 64, wherein said antibody region is an anti-cancer antibody region.

P1 Embodiment 66. The method of P1 Embodiment 65, wherein said T-lymphocyte is an autologous T-lymphocyte.

P1 Embodiment 67. The method of P1 Embodiment 65, wherein said T-lymphocyte is a heterologous T-lymphocyte.

P1 Embodiment 68. The method of P1 Embodiment 65, wherein said cancer is a solid tumor cancer or hematologic malignancy.

P1 Embodiment 69. The method of one of P1 Embodiments 65 to 68, wherein said cancer is ovarian cancer, renal cell carcinoma, a B-cell malignancy, leukemia, lymphoma, breast cancer, colorectal cancer, prostate cancer, neuroblastoma, melanoma, medulloblastoma, lung cancer, osteosarcoma, glioblastoma or glioma.

P1 Embodiment 70. A method of reprogramming a T lymphocyte, said method comprising contacting a T lymphocyte with the expression vector of one of P1 Embodiments 40 to 42.

P1 Embodiment 71. A method of detecting a cancer, said method comprising: (i) administering to a cancer patient an effective amount of a T lymphocyte comprising the recombinant protein of one of P1 Embodiments 45 to 63 and a compound comprising a peptidyl moiety capable of binding to said peptide binding site, wherein said compound further comprises a detectable label, and wherein said antibody region is an anti-cancer antibody region; (ii) allowing said compound to bind to said peptide binding site thereby forming a recombinant protein-compound complex; and (iii) detecting said recombinant protein-compound complex within said cancer patient thereby detecting said cancer.

P1 Embodiment 72. A T lymphocyte comprising the isolated nucleic acid of P1 Embodiment 1.

P2 Embodiments

P2 Embodiment 1. A method for treating a patient comprising:
(i) providing a composition comprising a population of T cells expressing a T cell receptor specific for a cytomegalovirus (CMV) antigen and a recombinant CAR protein,
wherein said recombinant CAR protein comprises:
(A) an antibody region comprising a central cavity formed by a heavy chain variable (VH) region, a light chain variable (VL) region, a heavy chain constant region (CH) and a light chain constant region (CL), wherein said central cavity forms a peptide binding site comprising framework region amino acid residues; and
(B) a transmembrane domain;
(ii) administering the composition to the patient; and
(iii) administering to the patient a viral vector encoding:
(i) CMV pp65 and (ii) a fusion protein comprising exon 4 of CMV protein IE1 (e4) and exon 5 of CMV protein IE2 (e5) either prior to or subsequent to administering the composition comprising a population of T cells to the patient.

P2 Embodiment 2. The method of P2 Embodiment 1, wherein said antibody region is an antibody fragment.

P2 Embodiment 3. The method of P2 Embodiment 1, wherein said antibody region comprises an Fc domain.

P2 Embodiment 4. The method of P2 Embodiment 1, wherein said antibody region is a humanized antibody region.

P2 Embodiment 5. The method of P2 Embodiment 1, wherein said recombinant CAR protein further comprises an intracellular T-cell signaling domain.

P2 Embodiment 6. The method of P2 Embodiment 5, wherein said intracellular T-cell signaling domain is a CD3ζ intracellular T-cell signaling domain.

P2 Embodiment 7. The method of P2 Embodiment 1, wherein said recombinant CAR protein further comprises an intracellular co-stimulatory signaling domain.

P2 Embodiment 8. The method of P2 Embodiment 7, wherein said intracellular co-stimulatory signaling domain is a CD28 intracellular co-stimulatory signaling domain, a 4-1BB intracellular co-stimulatory signaling domain, a ICOS intracellular co-stimulatory signaling domain, or an OX-40 intracellular co-stimulatory signaling domain.

P2 Embodiment 9. The method of P2 Embodiment 1, wherein said recombinant CAR protein further comprises a spacer region.

P2 Embodiment 10. The method of P2 Embodiment 9, wherein said spacer region is between said transmembrane domain and said antibody region.

P2 Embodiment 11. The method of P2 Embodiment 1, wherein said recombinant CAR protein further comprises a linker domain.

P2 Embodiment 12. The method of P2 Embodiment 11, wherein said linker domain is between said transmembrane domain and said intracellular T-cell signaling domain.

P2 Embodiment 13. The method of P2 Embodiment 11, wherein said linker domain is between said intracellular T-cell signaling domain and said intracellular co-stimulatory signaling domain.

P2 Embodiment 14. The method of P2 Embodiment 11, wherein said linker domain comprises the sequence GGCGG or GGG.

P2 Embodiment 15. The method of P2 Embodiment 1, wherein said recombinant CAR protein is an anti-CD19 protein, anti-CD20 protein, anti-CD22 protein, anti-CD30 protein, anti-CD33 protein, anti-CD44v6/7/8 protein, anti-CD123 protein, anti-CEA protein, anti-EGP-2 protein, anti-EGP-40 protein, anti-erb-B2 protein, anti-erb-B2,3,4 protein, anti-FBP protein, anti-fetal acetylcholine receptor protein, anti-GD2 protein, anti-GD3 protein, anti-Her2/neu protein, anti-IL-13R-a2 protein, anti-KDR protein, anti k-light chain protein, anti-LeY protein, anti-L1 cell adhesion molecule protein, anti-MAGE-A1 protein, anti-mesothelin protein, anti-murine CMV infected cell protein, anti-MUC2 protein, anti-NKGD2 protein, anti, oncofetal antigen protein, anti-PCSA protein, anti-PSMA protein, anti-TAA (targeted by mAb IfE) protein, anti-EGFR protein, anti-TAG-72 protein or anti-VEGF-72 protein.

P2 Embodiment 16. The method of any one of P2 Embodiments 1-15, wherein the step of administering a viral vector to the patient comprises administering recombinant MVA virus.

P2 Embodiment 17. The method of any one of P2 Embodiments 1-16, wherein expression of (i) CMV pp65 and (ii) the fusion protein comprising exon 4 of CMV protein IE1 (e4) and exon 5 of CMV protein IE2 (e5) is under the control of mH5 promoter.

P2 Embodiment 18. The method of P2 Embodiment 1, wherein the step of providing a population of T cells expressing a T cell receptor specific for a CMV antigen and a recombinant CAR protein comprises: (a) providing PBMC or a T cell subpopulation from a CMV-seropositive human donor; (b) exposing the PBMC or the T cell subpopulation to at least one CMV antigen; (c) treating the exposed cells to produce a population of cells enriched for stimulated cells specific for CMV; (d) transducing at least a portion of the enriched population of cells with a vector expressing a recombinant CAR protein.

P2 Embodiment 19. The method of P2 Embodiment 18, wherein the step of treating the exposed cells to produce a population of cells enriched for stimulated cells specific for CMV comprises treating the stimulated cells to produce a population of cells enriched for cells expressing an activation marker.

P2 Embodiment 20. The method of P2 Embodiment 1, wherein the step of providing a population of T cell expressing a T cell receptor specific for a CMV antigen and a recombinant CAR protein comprises: (a) administering a viral vector encoding: (i) CMV pp65 and (ii) a fusion protein comprising exon 4 of CMV protein IE1 (e4) and exon 5 of CMV protein IE2 (e5) to a human donor to convert a CMV-seronegative human donor to one containing T cells responsive to CMV antigens pp65, IE1 and IE2; (b) obtaining PBMC from the CMV-seropositive human donor; (c) exposing the PBMC to at least one CMV antigen; (d) treating the exposed cells to produce a population of cells enriched for stimulated cells specific for CMV; and (e) transducing at least a portion of the enriched population of cells with a vector expressing a recombinant CAR protein, thereby providing a population of T cell expressing a recombinant CAR protein and a T cell receptor specific for a CMV antigen.

P2 Embodiment 21. The method of P2 Embodiment 1, wherein the step of providing a population of T cell expressing a T cell receptor specific for a CMV antigen and a recombinant CAR protein comprises: (a) administering a viral vector encoding: (i) CMV pp65 and (ii) a fusion protein comprising exon 4 of CMV protein IE1 (e4) and exon 5 of CMV protein IE2 (e5) to a CMV-seropositive human donor;

(b) obtaining PBMC from the CMV-seropositive human donor; (b) exposing the PBMC to at least one CMV antigen; (c) treating the exposed cells to produce a population of cells enriched for stimulated cells specific for CMV; (d) transducing at least a portion of the enriched population of cells with a vector expressing a recombinant CAR protein, thereby providing a population of T cell expressing a recombinant CAR protein and a T cell receptor specific for a CMV antigen.

P2 Embodiment 22. A method for preparing T cells expressing a recombinant CAR protein and a T cell receptor specific for a CMV antigen, the method comprising: (a) administering a viral vector encoding: (i) CMV pp65 and (ii) a fusion protein comprising exon 4 of CMV protein IE1 (e4) and exon 5 of CMV protein IE2 (e5) to a human donor to convert a CMV-seronegative human donor to one containing T cells responsive to CMV antigens pp65, IE1 and IE2; (b) obtaining PBMC from the CMV-seropositive human donor; (b) exposing the PBMC to at least one CMV antigen; (c) treating the exposed cells to produce a population of cells enriched for stimulated cells specific for CMV; (d) transducing at least a portion of the enriched population of cells with a vector expressing a recombinant CAR protein, thereby providing a population of T cell expressing a recombinant CAR protein and a T cell receptor specific for a CMV antigen.

P2 Embodiment 23. A method for preparing T cells expressing a recombinant CAR protein and a T cell receptor specific for a CMV antigen, the method comprising: a) administering a viral vector encoding: (i) CMV pp65 and (ii) a fusion protein comprising exon 4 of CMV protein IE1 (e4) and exon 5 of CMV protein IE2 (e5) to a CMV-seropositive human donor; (b) obtaining PBMC from the CMV-seropositive human donor; (b) exposing the PBMC to at least one CMV antigen; (c) treating the exposed cells to produce a population of cells enriched for stimulated cells specific for CMV; (d) transducing at least a portion of the enriched population of cells with a vector expressing a recombinant CAR protein, thereby providing a population of T cell expressing a recombinant CAR protein and a T cell receptor specific for a CMV antigen.

P2 Embodiment 24. A method for treating a patient comprising:
(a) providing a composition comprising a population of T cells expressing both a T cell receptor specific for a viral antigen and a recombinant CAR protein, wherein said recombinant CAR protein comprises:
(A) an antibody region comprising a central cavity formed by a heavy chain variable (VH) region, a light chain variable (VL) region, a heavy chain constant region (CH) and a light chain constant region (CL), wherein said central cavity forms a peptide binding site comprising framework region amino acid residues; and
(B) a transmembrane domain;
(b) administering the composition to the patient; and
(c) administering to the patient said viral antigen either prior to or subsequent to administering the composition comprising a population of T cells to the patient.

P2 Embodiment 25. The method of P2 Embodiment 24, wherein said viral antigen is an endogenous viral antigen.

P2 Embodiment 26. A cell comprising a T cell receptor specific for a cytomegalovirus (CMV) antigen and a recombinant CAR protein, wherein said recombinant CAR protein comprises:
(A) an antibody region comprising a central cavity formed by a heavy chain variable (VH) region, a light chain variable (VL) region, a heavy chain constant region (CH) and a light chain constant region (CL), wherein said central cavity forms a peptide binding site comprising framework region amino acid residues; and
(B) a transmembrane domain.

P2 Embodiment 27. A cell comprising a T cell receptor specific for a viral antigen and a recombinant CAR protein, wherein said recombinant CAR protein comprises:
(A) an antibody region comprising a central cavity formed by a heavy chain variable (VH) region, a light chain variable (VL) region, a heavy chain constant region (CH) and a light chain constant region (CL), wherein said central cavity forms a peptide binding site comprising framework region amino acid residues; and
(B) a transmembrane domain.

Further Embodiments

Embodiment 1. A method for treating a disease in a subject in need thereof, said method comprising:
(i) administering to a subject a therapeutically effective amount of a composition comprising a population of human T cells expressing a T cell receptor specific for a cytomegalovirus (CMV) antigen and a recombinant chimeric antigen receptor (CAR) protein, wherein said recombinant CAR protein comprises:
(A) an antibody region comprising a central cavity formed by a heavy chain variable (VH) region, a light chain variable (VL) region, a heavy chain constant region (CH) and a light chain constant region (CL), wherein said central cavity forms a peptide binding site comprising framework region amino acid residues; and
(B) a transmembrane domain; and
(ii) administering to said subject a therapeutically effective amount of a viral vector, wherein said viral vector encodes (a) a CMV pp65 protein and (b) a fusion protein comprising exon 4 of CMV protein IE1 (e4) and exon 5 of CMV protein IE2 (e5); and
wherein said viral vector is administered either prior to or subsequent to administering said composition comprising a population of human T cells to said subject, thereby treating said subject.

Embodiment 2. The method of Embodiment 1, wherein said antibody region is an antibody fragment.

Embodiment 3. The method of Embodiment 1, wherein said antibody region comprises an Fc domain.

Embodiment 4. The method of Embodiment 1, wherein said antibody region is a humanized antibody region.

Embodiment 5. The method of Embodiment 1, wherein said recombinant CAR protein further comprises an intracellular T-cell signaling domain.

Embodiment 6. The method of Embodiment 5, wherein said intracellular T-cell signaling domain is a CD3ζ intracellular T-cell signaling domain.

Embodiment 7. The method of Embodiment 1, wherein said recombinant CAR protein further comprises an intracellular co-stimulatory signaling domain.

Embodiment 8. The method of Embodiment 7, wherein said intracellular co-stimulatory signaling domain is a CD28 intracellular co-stimulatory signaling domain, a 4-1BB intracellular co-stimulatory signaling domain, a ICOS intracellular co-stimulatory signaling domain, or an OX-40 intracellular co-stimulatory signaling domain.

Embodiment 9. The method of Embodiment 1, wherein said recombinant CAR protein further comprises a spacer region.

Embodiment 10. The method of Embodiment 9, wherein said spacer region is between said transmembrane domain and said antibody region.

Embodiment 11. The method of Embodiment 1, wherein said recombinant CAR protein further comprises a linker domain.

Embodiment 12. The method of Embodiment 11, wherein said linker domain is between said transmembrane domain and said intracellular T-cell signaling domain.

Embodiment 13. The method of Embodiment 11, wherein said linker domain is between said intracellular T-cell signaling domain and said intracellular co-stimulatory signaling domain.

Embodiment 14. The method of Embodiment 11, wherein said linker domain comprises the sequence GGCGG or GGG.

Embodiment 15. The method of Embodiment 1, wherein said recombinant CAR protein is an anti-CD19 protein, anti-CD20 protein, anti-CD22 protein, anti-CD30 protein, anti-CD33 protein, anti-CD44v6/7/8 protein, anti-CD123 protein, anti-CEA protein, anti-EGP-2 protein, anti-EGP-40 protein, anti-erb-B2 protein, anti-erb-B2,3,4 protein, anti-FBP protein, anti-fetal acetylcholine receptor protein, anti-GD2 protein, anti-GD3 protein, anti-Her2/neu protein, anti-IL-13R-a2 protein, anti-KDR protein, anti k-light chain protein, anti-LeY protein, anti-L1 cell adhesion molecule protein, anti-MAGE-A1 protein, anti-mesothelin protein, anti-murine CMV infected cell protein, anti-MUC2 protein, anti-NKGD2 protein, anti, oncofetal antigen protein, anti-PCSA protein, anti-PSMA protein, anti-TAA (targeted by mAb IfE) protein, anti-EGFR protein, anti-TAG-72 protein or anti-VEGF-72 protein.

Embodiment 16. The method of any one of Embodiments 1-15, wherein said step of administering a therapeutically effective amount of a viral vector to said subject comprises administering recombinant MVA virus.

Embodiment 17. The method of any one of Embodiments 1-16, wherein expression of (a) a CMV pp65 protein and (b) said fusion protein comprising exon 4 of CMV protein IE1 (e4) and exon 5 of CMV protein IE2 (e5) is under the control of mH5 promoter.

Embodiment 18. The method of any one of Embodiments 1-17, wherein said subject is immunocompromised.

Embodiment 19. The method of any one of Embodiments 1-18, wherein said subject receives immunosuppressive therapy.

Embodiment 20. The method of any one of Embodiments 1-17, wherein said subject is immunocompetent.

Embodiment 21. The method of any one of Embodiments 1-20, wherein said subject is CMV-seronegative prior to treatment.

Embodiment 22. The method of any one of Embodiments 1-21, wherein said subject received hematopoietic stem cells (HSCs) from a CMV-seropositive or a CMV-seronegative donor prior to administering said a therapeutically effective amount of said composition comprising a population of human T cells expressing a T cell receptor specific for a CMV antigen and a recombinant CAR protein.

Embodiment 23. The method of Embodiment 22, wherein said viral vector is administered to said hematopoietic stem cell donor prior to harvesting said stem cells.

Embodiment 24. The method of any one of Embodiments 1-23, wherein said recombinant CAR protein is capable of binding CD19.

Embodiment 25. The method of any one of Embodiments 1-23, wherein said recombinant CAR protein is capable of binding HER2.

Embodiment 26. The method of any one of Embodiments 22-25, wherein said HSCs are autologous HSCs.

Embodiment 27. The method of any one of Embodiments 22-25, wherein said HSCs are allogenic HSCs.

Embodiment 28. The method of any one of Embodiments 1-27, wherein said subject is suffering from cancer.

Embodiment 29. The method of any one of Embodiments 1-28, wherein said subject is suffering from non-Hodgkin's Lymphoma.

Embodiment 30. The method of any one of Embodiments 1-28, wherein said subject is suffering from a solid tumor cancer or a hematologic malignancy Embodiment 31. The method of any one of Embodiments 1-28, wherein said subject is suffering from ovarian cancer, renal cell carcinoma, a B-cell malignancy, leukemia, lymphoma, breast cancer, colorectal cancer, prostate cancer, neuroblastoma, melanoma, medulloblastoma, lung cancer, osteosarcoma, glioblastoma or glioma.

Embodiment 32. The method of any one of Embodiments 1-31, wherein administration of said viral vector occurs at least 5 days after treatment with said composition comprising a population of human T cells.

Embodiment 33. The method of any one of Embodiments 1-31, wherein said viral vector is administered to said subject prior to and subsequent to said administration of said composition comprising a population of human T cells.

Embodiment 34. The method of any one of Embodiments 1-31, wherein said viral vector is administered to said subject only prior to said administration of said composition comprising a population of human T cells.

Embodiment 35. The method of any one of Embodiments 1-31, wherein said viral vector is administered to said subject only subsequent to said administration of said composition comprising a population of human T cells.

Embodiment 36. The method of any one of Embodiments 1-35, wherein said viral vector is administered to said subject or said hematopoietic stem cell transplant donor at least twice subsequent to said administration of said composition comprising a population of human T cells.

Embodiment 37. The method of any one of Embodiments 1-36, wherein said viral vector is administered to said subject at least four times.

Embodiment 38. The method of Embodiment 1, wherein said population of human T cells expressing a T cell receptor specific for a CMV antigen and a recombinant CAR protein is formed by: (1) isolating PBMCs or a T cell subpopulation from a CMV-seropositive human donor; (2) contacting said PBMCs or said T cell subpopulation with at least one CMV antigen; (3) allowing said contacted cells to produce a population of cells enriched for stimulated cells specific for CMV; (4) transducing at least a portion of said enriched population of cells with a vector expressing a recombinant CAR protein, thereby forming a population of human T cells expressing a T cell receptor specific for a CMV antigen and a recombinant CAR protein.

Embodiment 39. The method of Embodiment 38, wherein said step of allowing said contacted cells to produce a population of cells enriched for stimulated cells specific for CMV comprises allowing said stimulated cells to produce a population of cells enriched for cells expressing an activation marker.

Embodiment 40. The method of Embodiment 1, wherein said population of human T cells expressing a T cell receptor specific for a CMV antigen and a recombinant CAR protein is formed by: (1) administering a viral vector encoding: (a) a CMV pp65 protein and (b) a fusion protein comprising exon 4 of CMV protein IE1 (e4) and exon 5 of CMV protein IE2 (e5) to a human donor to convert a CMV-seronegative human donor to a CMV-seropositive human donor containing T cells responsive to CMV antigens pp65, IE1 and IE2; (2) obtaining PBMCs from said CMV-seropositive human donor; (3) contacting said PBMCs with at least one CMV antigen; (4) allowing said contacted cells to produce a population of cells enriched for stimulated cells specific for CMV; (5) transducing at least a portion of said enriched population of cells with a vector expressing a recombinant CAR protein, thereby forming a population of T cell expressing a T cell receptor specific for a CMV antigen and a recombinant CAR protein.

Embodiment 41. The method of Embodiment 1, wherein said population of human T cells expressing a T cell receptor specific for a CMV antigen and a recombinant CAR protein is formed by: (1) administering a viral vector encoding: (a) a CMV pp65 protein and (b) a fusion protein comprising exon 4 of CMV protein IE1 (e4) and exon 5 of CMV protein IE2 (e5) to a CMV-seropositive human donor; (2) allowing PBMCs from said CMV-seropositive human donor; (3) contacting said PBMCs with at least one CMV antigen; (4) allowing said contacted cells to produce a population of cells enriched for stimulated cells specific for CMV; (5) transducing at least a portion of said enriched population of cells with a vector expressing a recombinant CAR protein, thereby providing a population of human T cells expressing a T cell receptor specific for a CMV antigen and a recombinant CAR protein.

Embodiment 42. A method for forming a population of human T cells expressing a recombinant CAR protein and a T cell receptor specific for a CMV antigen, said method comprising: (1) administering a viral vector encoding: (a) a CMV pp65 protein and (b) a fusion protein comprising exon 4 of CMV protein IE1 (e4) and exon 5 of CMV protein IE2 (e5) to a CMV-seronegative human donor; (2) obtaining PBMCs from said human donor; (3) contacting said PBMCs with at least one CMV antigen; (3) allowing said contacted cells to produce a population of cells enriched for stimulated cells specific for CMV; (4) transducing at least a portion of said enriched population of cells with a vector expressing a recombinant CAR protein, thereby forming a population of human T cells expressing a T cell receptor specific for a CMV antigen and a recombinant CAR protein.

Embodiment 43. A method for forming a population of human T cells expressing a recombinant CAR protein and a T cell receptor specific for a CMV antigen, said method comprising: (1) administering a viral vector encoding: (a) a CMV pp65 protein and (b) a fusion protein comprising exon 4 of CMV protein IE1 (e4) and exon 5 of CMV protein IE2 (e5) to a CMV-seropositive human donor; (2) obtaining PBMCs from said CMV-seropositive human donor; (3) contacting said PBMCs with at least one CMV antigen; (4) allowing said contacted cells to produce a population of cells enriched for stimulated cells specific for CMV; (5) transducing at least a portion of said enriched population of cells with a vector expressing a recombinant CAR protein, thereby forming a population of human T cells expressing a T cell receptor specific for a CMV antigen and a recombinant CAR protein.

Embodiment 44. The method of one of Embodiments 38-43, further comprising expanding said population of human T cells expressing a recombinant CAR protein and a T cell receptor specific for a CMV antigen.

Embodiment 45. The method of Embodiment 39, wherein said activation marker is IFN-γ, CD137 or CD107.

Embodiment 46. The method of one of Embodiments 38-43, wherein said CMV antigen is a pp65 protein or an antigenic portion thereof.

Embodiment 47. The method of one of Embodiments 38-43, wherein said CMV antigen comprises two or more different antigenic pp65 proteins.

Embodiment 48. The method of one of Embodiments 38-43, wherein said enriched population of cells is at least 40% IFN-γ positive, at least 20% CD8 positive, and at least 20% CD4 positive.

Embodiment 49. The method of one of Embodiments 38-43, wherein said enriched population of cells is cultured for fewer than 10 days prior to said step of transducing said enriched population of cells with a vector encoding a recombinant CAR protein.

Embodiment 50. The method of one of Embodiments 38-43, further comprising expanding said CMV specific T cells expressing a recombinant CAR protein by exposing said T cells to an antigen that binds to said recombinant CAR protein.

Embodiment 51. The method of one of Embodiments 38-43, wherein said step of expanding said CMV-specific T cells expressing a recombinant CAR protein comprises exposing said cells to T cells expressing said antigen that binds said recombinant CAR protein.

Embodiment 52. The method of one of Embodiments 38-43, wherein said expansion takes place in the presence of at least one exogenously added interleukin.

Embodiment 53. The method of Embodiment 1, wherein said population of human T cells is autologous to said subject.

Embodiment 54. The method of Embodiment 1, wherein said population of human T cells is allogeneic to said subject.

Embodiment 55. The method of Embodiment 1, wherein said method reduces the risk of CMV infection.

Embodiment 56. The method of Embodiment 1, wherein said method reduces CMV viremia and/or disease.

Embodiment 57. The method of Embodiment 1, wherein said subject was CMV-immune prior to treatment and said method reduces the risk of CMV infection.

Embodiment 58. The method of Embodiment 1, wherein said subject was not CMV-immune prior to treatment and said method reduces CMV viremia or disease.

Embodiment 59. A method for treating a disease in a subject in need thereof comprising:
 (i) administering to a subject a therapeutically effective amount of a composition comprising a population of human T cells expressing a T cell receptor specific for a viral antigen and a recombinant chimeric antigen receptor (CAR) protein, wherein said recombinant CAR protein comprises:
 (A) an antibody region comprising a central cavity formed by a heavy chain variable (VH) region, a light chain variable (VL) region, a heavy chain constant region (CH) and a light chain constant region (CL), wherein said central cavity forms a peptide binding site comprising framework region amino acid residues; and
 (B) a transmembrane domain; and
 (ii) administering to said subject said viral antigen either prior to or subsequent to administering said composition comprising a population of human T cells to said subject.

Embodiment 60. The method of Embodiment 59, wherein said viral antigen is an endogenous viral antigen.

Embodiment 61. A cell comprising a T cell receptor specific for a cytomegalovirus (CMV) antigen and a recombinant CAR protein, wherein said recombinant CAR protein comprises:
(A) an antibody region comprising a central cavity formed by a heavy chain variable (VH) region, a light chain variable (VL) region, a heavy chain constant region (CH) and a light chain constant region (CL), wherein said central cavity forms a peptide binding site comprising framework region amino acid residues; and
(B) a transmembrane domain.

Embodiment 62. A cell comprising a T cell receptor specific for a viral antigen and a recombinant CAR protein, wherein said recombinant CAR protein comprises:
(A) an antibody region comprising a central cavity formed by a heavy chain variable (VH) region, a light chain variable (VL) region, a heavy chain constant region (CH) and a light chain constant region (CL), wherein said central cavity forms a peptide binding site comprising framework region amino acid residues; and
(B) a transmembrane domain.

What is claimed is:

1. A cell comprising a T cell receptor specific for a cytomegalovirus (CMV) antigen and a recombinant CAR protein,
  wherein said recombinant CAR protein comprises:
  (A) an antibody region comprising a central cavity formed by a heavy chain variable (VH) region, a light chain variable (VL) region, a heavy chain constant region (CH) and a light chain constant region (CL), wherein said central cavity forms a peptide binding site comprising framework region amino acid residues; and
  (B) a transmembrane domain.

2. The cell of claim 1, wherein said CMV antigen is a pp65 protein or an antigenic portion thereof.

3. The cell of claim 1, wherein said CMV antigen comprises two or more different antigenic pp65 proteins.

4. The cell of claim 1, wherein said recombinant CAR protein further comprises an intracellular T-cell signaling domain.

5. The cell of claim 1, wherein said recombinant CAR protein further comprises an intracellular co-stimulatory signaling domain.

6. The cell of claim 1, wherein said recombinant CAR protein is an anti-CD19 protein, anti-CD20 protein, anti-CD22 protein, anti-CD30 protein, anti-CD33 protein, anti-CD44v6/7/8 protein, anti-CD123 protein, anti-CEA protein, anti-EGP-2 protein, anti-EGP-40 protein, anti-erb-B2 protein, anti-erb-B2,3,4 protein, anti-FBP protein, anti-fetal acetylcholine receptor protein, anti-GD2 protein, anti-GD3 protein, anti-Her2/neu protein, anti-IL-13R-a2 protein, anti-KDR protein, anti k-light chain protein, anti-LeY protein, anti-L1 cell adhesion molecule protein, anti-MAGE-A1 protein, anti-mesothelin protein, anti-murine CMV infected cell protein, anti-MUC2 protein, anti-NKGD2 protein, anti, oncofetal antigen protein, anti-PCSA protein, anti-PSMA protein, anti-TAA protein, anti-EGFR protein, antiTAG-72 protein or anti-VEGF-72 protein.

* * * * *

```
                        SEQUENCE LISTING

Sequence total quantity: 147
SEQ ID NO: 1            moltype = AA  length = 21
FEATURE                 Location/Qualifiers
REGION                  1..21
                        note = Artificial polypeptide
source                  1..21
                        mol_type = protein
                        organism = synthetic construct
SEQUENCE: 1
LCYLLDGILF IYGVILTALF L                                             21

SEQ ID NO: 2            moltype = AA  length = 27
FEATURE                 Location/Qualifiers
REGION                  1..27
                        note = Artificial polypeptide
source                  1..27
                        mol_type = protein
                        organism = synthetic construct
SEQUENCE: 2
FWVLVVVGGV LACYSLLVTV AFIIFWV                                       27

SEQ ID NO: 3            moltype = AA  length = 22
FEATURE                 Location/Qualifiers
REGION                  1..22
                        note = Artificial polypeptide
source                  1..22
                        mol_type = protein
                        organism = synthetic construct
SEQUENCE: 3
MALIVLGGVA GLLLFIGLGI FF                                            22

SEQ ID NO: 4            moltype = AA  length = 21
FEATURE                 Location/Qualifiers
REGION                  1..21
                        note = Artificial polypeptide
source                  1..21
                        mol_type = protein
                        organism = synthetic construct
SEQUENCE: 4
IYIWAPLAGT CGVLLLSLVI T                                             21

SEQ ID NO: 5            moltype = AA  length = 23
FEATURE                 Location/Qualifiers
REGION                  1..23
                        note = Artificial polypeptide
source                  1..23
                        mol_type = protein
                        organism = synthetic construct
SEQUENCE: 5
IYIWAPLAGT CGVLLLSLVI TLY                                           23

SEQ ID NO: 6            moltype = AA  length = 24
FEATURE                 Location/Qualifiers
REGION                  1..24
                        note = Artificial polypeptide
source                  1..24
                        mol_type = protein
                        organism = synthetic construct
SEQUENCE: 6
IYIWAPLAGT CGVLLLSLVI TLYC                                          24
```

-continued

```
SEQ ID NO: 7              moltype = AA   length = 27
FEATURE                   Location/Qualifiers
REGION                    1..27
                          note = Artificial polypeptide
source                    1..27
                          mol_type = protein
                          organism = synthetic construct
SEQUENCE: 7
IISFFLALTS TALLFLLFFL TLRFSVV                                         27

SEQ ID NO: 8              moltype = AA   length = 21
FEATURE                   Location/Qualifiers
REGION                    1..21
                          note = Artificial polypeptide
source                    1..21
                          mol_type = protein
                          organism = synthetic construct
SEQUENCE: 8
VAAILGLGLV LGLLGPLAIL L                                               21

SEQ ID NO: 9              moltype = AA   length = 21
FEATURE                   Location/Qualifiers
REGION                    1..21
                          note = Artificial polypeptide
source                    1..21
                          mol_type = protein
                          organism = synthetic construct
SEQUENCE: 9
FWLPIGCAAF VVVCILGCIL I                                               21

SEQ ID NO: 10             moltype = AA   length = 23
FEATURE                   Location/Qualifiers
REGION                    1..23
                          note = Artificial polypeptide
source                    1..23
                          mol_type = protein
                          organism = synthetic construct
SEQUENCE: 10
PLFIPVAVMV TAFSGLAFII WLA                                             23

SEQ ID NO: 11             moltype = AA   length = 60
FEATURE                   Location/Qualifiers
REGION                    1..60
                          note = Artificial polypeptide
source                    1..60
                          mol_type = protein
                          organism = synthetic construct
SEQUENCE: 11
RVKFSRSADA PAYQQGQNQL YNELNLGRRE EYDVLDKRRG RDPEMGGKPQ RRKNPQEGLY     60

SEQ ID NO: 12             moltype = AA   length = 41
FEATURE                   Location/Qualifiers
REGION                    1..41
                          note = Artificial polypeptide
source                    1..41
                          mol_type = protein
                          organism = synthetic construct
SEQUENCE: 12
RSKRSRLLHS DYMNMTPRRP GPTRKHYQPY APPRDFAAYR S                         41

SEQ ID NO: 13             moltype = AA   length = 41
FEATURE                   Location/Qualifiers
REGION                    1..41
                          note = Artificial polypeptide
source                    1..41
                          mol_type = protein
                          organism = synthetic construct
SEQUENCE: 13
RSKRSRGGHS DYMNMTPRRP GPTRKHYQPY APPRDFAAYR S                         41

SEQ ID NO: 14             moltype = AA   length = 42
FEATURE                   Location/Qualifiers
REGION                    1..42
                          note = Artificial polypeptide
source                    1..42
                          mol_type = protein
                          organism = synthetic construct
SEQUENCE: 14
KRGRKKLLYI FKQPFMRPVQ TTQEEDGCSC RFPEEEEGGC EL                        42
```

```
SEQ ID NO: 15              moltype = AA  length = 42
FEATURE                    Location/Qualifiers
REGION                     1..42
                           note = Artificial polypeptide
source                     1..42
                           mol_type = protein
                           organism = synthetic construct
SEQUENCE: 15
ALYLLRRDQR LPPDAHKPPG GGSFRTPIQE EQADAHSTLA KI                          42

SEQ ID NO: 16              moltype = AA  length = 38
FEATURE                    Location/Qualifiers
REGION                     1..38
                           note = Artificial polypeptide
source                     1..38
                           mol_type = protein
                           organism = synthetic construct
SEQUENCE: 16
CWLTKKKYSS SVHDPNGEYM FMRAVNTAKK SRLTDVTL                               38

SEQ ID NO: 17              moltype = AA  length = 818
FEATURE                    Location/Qualifiers
REGION                     1..818
                           note = Artificial polypeptide
source                     1..818
                           mol_type = protein
                           organism = synthetic construct
SEQUENCE: 17
MLLLVTSLLL CELPHPAFLL IPEVQLVESG GGLVQPGGSL RLSCAASGFN IKDTYIHWVR        60
QSPGKGLEWV ARIYPTNGYT RYADSVKGRF TISADTSKNT AYLQMNSLRA EDTAIYYCSR       120
WGGDGFYAMD YWGQGTLVTV SSASTKGPSV FPLAPSSKST SGGTAALGCL VKDYFPEPVT       180
VSWNSGALTS GVHTFPAVLQ SSGLYSLSSV VTVPSSSLGT QTYICNVNHK PSNTKVDKKV       240
EPKSCESKYG PPCPPCPGGG SSGGGSGGQP REPQVYTLPP SQEEMTKNQV SLTCLVKGFY       300
PSDIAVEWES NGQPENNYKT TPPVLDSDGS FFLYSRLTVD KSRWQEGNVF SCSVMHEALH       360
NHYTQKSLSL SLGKMFWVLV VVGGVLACYS LLVTVAFIIF WVRSKRSGG HSDYMNMTPR        420
RPGPTRKHYQ PYAPPRDFAA YRSGGGRVKF SRSADAPAYQ QGQNQLYNEL NLGRREEYDV       480
LDKRRGRDPE MGGKPRRKNP QEGLYNELQK DKMAEAYSEI GMKGERRRGK GHDGLYQGLS       540
TATKDTYDAL HMQALPPRLE GGGEGRGSLL TCGDVEENPG PRMLLLVTSL LLCELPHPAF       600
LLIPDIQMTQ SPILLSASVG DRVTITCRAS QDVNTAVAWY QQRTNGSPRL LIYSASFLYS       660
GVPSRFSGSR SGTDFTLTIS SLQPEDEADY YCQQHYTTPP TFGAGTKVEI KRTVAAPSVF       720
IFPPSDEQLK SGTASVVCLL NNFYPREAKV QWKVDNALQS GNSQESVTEQ DSKDSTYSLS       780
STLTLSKADY EKHKVYACEV THQGLSSPVT KSFNRGEC                              818

SEQ ID NO: 18              moltype = AA  length = 22
FEATURE                    Location/Qualifiers
REGION                     1..22
                           note = Artificial polypeptide
source                     1..22
                           mol_type = protein
                           organism = synthetic construct
SEQUENCE: 18
MLLLVTSLLL CELPHPAFLL IP                                                22

SEQ ID NO: 19              moltype = AA  length = 223
FEATURE                    Location/Qualifiers
REGION                     1..223
                           note = Artificial polypeptide
source                     1..223
                           mol_type = protein
                           organism = synthetic construct
SEQUENCE: 19
EVQLVESGGG LVQPGGSLRL SCAASGFNIK DTYIHWVRQS PGKGLEWVAR IYPTNGYTRY        60
ADSVKGRFTI SADTSKNTAY LQMNSLRAED TAIYYCSRWG GDGFYAMDYW GQGTLVTVSS       120
ASTKGPSVFP LAPSSKSTSG GTAALGCLVK DYFPEPVTVS WNSGALTSGV HTFPAVLQSS       180
GLYSLSSVVT VPSSSLGTQT YICNVNHKPS NTKVDKKVEP KSC                        223

SEQ ID NO: 20              moltype = AA  length = 12
FEATURE                    Location/Qualifiers
REGION                     1..12
                           note = Artificial polypeptide
source                     1..12
                           mol_type = protein
                           organism = synthetic construct
SEQUENCE: 20
ESKYGPPCPP CP                                                           12

SEQ ID NO: 21              moltype = AA  length = 117
FEATURE                    Location/Qualifiers
```

```
REGION                    1..117
                          note = Artificial polypeptide
source                    1..117
                          mol_type = protein
                          organism = synthetic construct
SEQUENCE: 21
GGGSSGGGSG GQPREPQVYT LPPSQEEMTK NQVSLTCLVK GFYPSDIAVE WESNGQPENN    60
YKTTPPVLDS DGSFFLYSRL TVDKSRWQEG NVFSCSVMHE ALHNHYTQKS LSLSLGK      117

SEQ ID NO: 22             moltype = AA  length = 28
FEATURE                   Location/Qualifiers
REGION                    1..28
                          note = Artificial polypeptide
source                    1..28
                          mol_type = protein
                          organism = synthetic construct
SEQUENCE: 22
MFWVLVVVGG VLACYSLLVT VAFIIFWV                                       28

SEQ ID NO: 23             moltype = AA  length = 41
FEATURE                   Location/Qualifiers
REGION                    1..41
                          note = Artificial polypeptide
source                    1..41
                          mol_type = protein
                          organism = synthetic construct
SEQUENCE: 23
RSKRSRGGHS DYMNMTPRRP GPTRKHYQPY APPRDFAAYR S                        41

SEQ ID NO: 24             moltype =     length =
SEQUENCE: 24
000

SEQ ID NO: 25             moltype = AA  length = 112
FEATURE                   Location/Qualifiers
REGION                    1..112
                          note = Artificial polypeptide
source                    1..112
                          mol_type = protein
                          organism = synthetic construct
SEQUENCE: 25
RVKFSRSADA PAYQQGQNQL YNELNLGRRE EYDVLDKRRG RDPEMGGKPR RKNPQEGLYN    60
ELQKDKMAEA YSEIGMKGER RRGKGHDGLY QGLSTATKDT YDALHMQALP PR           112

SEQ ID NO: 26             moltype = AA  length = 24
FEATURE                   Location/Qualifiers
REGION                    1..24
                          note = Artificial polypeptide
source                    1..24
                          mol_type = protein
                          organism = synthetic construct
SEQUENCE: 26
LEGGGEGRGS LLTCGDVEEN PGPR                                           24

SEQ ID NO: 27             moltype = AA  length = 214
FEATURE                   Location/Qualifiers
REGION                    1..214
                          note = Artificial polypeptide
source                    1..214
                          mol_type = protein
                          organism = synthetic construct
SEQUENCE: 27
DIQMTQSPIL LSASVGDRVT ITCRASQDVN TAVAWYQQRT NGSPRLLIYS ASFLYSGVPS    60
RFSGSRSGTD FTLTISSLQP EDEADYYCQQ HYTTPPTFGA GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 28             moltype = AA  length = 1162
FEATURE                   Location/Qualifiers
REGION                    1..1162
                          note = Artificial polypeptide
source                    1..1162
                          mol_type = protein
                          organism = synthetic construct
SEQUENCE: 28
MLLLVTSLLL CELPHPAFLL IPEVQLVESG GGLVQPGGSL RLSCAASGFN IKDTYIHWVR    60
QSPGKGLEWV ARIYPTNGYT RYADSVKGRF TISADTSKNT AYLQMNSLRA EDTAIYYCSR   120
WGGDGFYAMD YWGQGTLVTV SSASTKGPSV FPLAPSSKST SGGTAALGCL VKDYFPEPVT   180
VSWNSGALTS GVHTFPAVLQ SSGLYSLSSV VTVPSSSLGT QTYICNVNHK PSNTKVDKKV   240
```

```
EPKSCESKYG PPCPPCPGGG SSGGGSGGQP REPQVYTLPP SQEEMTKNQV SLTCLVKGFY    300
PSDIAVEWES NGQPENNYKT TPPVLDSDGS FFLYSRLTVD KSRWQEGNVF SCSVMHEALH    360
NHYTQKSLSL SLGKMFWVLV VVGGVLACYS LLVTVAFIIF WVRSKRSRGG HSDYMNMTPR    420
RPGPTRKHYQ PYAPPRDFAA YRSGGGRVKF SRSADAPAYQ QGQNQLYNEL NLGRREEYDV    480
LDKRRGRDPE MGGKPRRKNP QEGLYNELQK DKMAEAYSEI GMKGERRRGK GHDGLYQGLS    540
TATKDTYDAL HMQALPPRLE GGGEGRGSLL TCGDVEENPG PRMPPPRLLF FLLFLTPMEV    600
RPEEPLVVKV EEGDNAVLQC LKGTSDGPTQ QLTWSRESPL KPFLKLSLGL PGLGIHMRPL    660
AIWLFIFNVS QQMGGFYLCQ PGPPSEKAWQ PGWTVNVEGS GELFRWNVSD LGGLGCGLKN    720
RSSEGPSSPS GKLMSPKLYV WAKDRPEIWE GEPPCVPPRD SLNQSLSQDL TMAPGSTLWL    780
SCGVPPDSVS RGPLSWTHVH PKGPKSLLSL ELKDDRPARD MWVMETGLLL PRATAQDAGK    840
YYCHRGNLTM SFHLEITARP VLWHWLLRTG GWKVSAVTLA YLIFCLCSLV GILHLQRALV    900
LRRKRGGSTS EGRGSLLTCG DVEENPGPME TDTLLLWVLL LWVPGSTGDI QMTQSPILLS    960
ASVGDRVTIT CRASQDVNTA VAWYQQRTNG SPRLLIYSAS FLYSGVPSRF SGSRSGTDFT   1020
LTISSLQPED EADYYCQQHY TTPPTFGAGT KVEIKRTVAA PSVFIFPPSD EQLKSGTASV   1080
VCLLNNFYPR EAKVQWKVDN ALQSGNSQES VTEQDSKDST YSLSSTLTLS KADYEKHKVY   1140
ACEVTHQGLS SPVTKSFNRG EC                                           1162

SEQ ID NO: 29           moltype = AA  length = 323
FEATURE                 Location/Qualifiers
REGION                  1..323
                        note = Artificial polypeptide
source                  1..323
                        mol_type = protein
                        organism = synthetic construct
SEQUENCE: 29
MPPPRLLFFL LFLTPMEVRP EEPLVVKVEE GDNAVLQCLK GTSDGPTQQL TWSRESPLKP     60
FLKLSLGLPG LGIHMRPLAI WLFIFNVSQQ MGGFYLCQPG PPSEKAWQPG WTVNVEGSGE    120
LFRWNVSDLG GLGCGLKNRS SEGPSSPSGK LMSPKLYVWA KDRPEIWEGE PPCVPPRDSL    180
NQSLSQDLTM APGSTLWLSC GVPPDSVSRG PLSWTHVHPK GPKSLLSLEL KDDRPARDMW    240
VMETGLLLPR ATAQDAGKYY CHRGNLTMSF HLEITARPVL WHWLLRTGGW KVSAVTLAYL    300
IFCLCSLVGI LHLQRALVLR RKR                                           323

SEQ ID NO: 30           moltype = AA  length = 23
FEATURE                 Location/Qualifiers
REGION                  1..23
                        note = Artificial polypeptide
source                  1..23
                        mol_type = protein
                        organism = synthetic construct
SEQUENCE: 30
GGSTSEGRGS LLTCGDVEEN PGP                                            23

SEQ ID NO: 31           moltype = AA  length = 214
FEATURE                 Location/Qualifiers
REGION                  1..214
                        note = Artificial polypeptide
source                  1..214
                        mol_type = protein
                        organism = synthetic construct
SEQUENCE: 31
DIQMTQSPIL LSASVGDRVT ITCKASQNID KYLNWYQQRT NGSPRLLIYN TNNLQTGVPS     60
RFSGSGSGTD FTFTISSLQP EDIADYYCLQ HISRPRTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 32           moltype = AA  length = 220
FEATURE                 Location/Qualifiers
REGION                  1..220
                        note = Artificial polypeptide
source                  1..220
                        mol_type = protein
                        organism = synthetic construct
SEQUENCE: 32
QVQLQESGGG LVRPSQTLSL TCTVSGFTFT DFYMNWVRQS PGRGLEWIGF IRDKAKGYTT     60
EYNPSVKGRV TMLVDTSKNQ FSLRLSSVTA ADTAIYYCAR EGHTAAPFDY WGQGSLVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKKVE                          220

SEQ ID NO: 33           moltype = AA  length = 214
FEATURE                 Location/Qualifiers
REGION                  1..214
                        note = Artificial polypeptide
source                  1..214
                        mol_type = protein
                        organism = synthetic construct
SEQUENCE: 33
DIQMTQSPIL LSASVGDRVT ITCKASQNID KYLNWYQQRT NGSPRLLIYN TNNLQTGVPS     60
RFSGSGSGTD FTFTISSLQP EDEADYYCLQ HISRPRTFGQ GTKVEIKRTV AAPSVFIFPP    120
SDEQLKSGTA SVVCLLNNFY PREAKVQWKV DNALQSGNSQ ESVTEQDSKD STYSLSSTLT    180
```

```
LSKADYEKHK VYACEVTHQG LSSPVTKSFN RGEC                              214

SEQ ID NO: 34              moltype = AA   length = 220
FEATURE                    Location/Qualifiers
REGION                     1..220
                           note = Artificial polypeptide
source                     1..220
                           mol_type = protein
                           organism = synthetic construct
SEQUENCE: 34
QVQLQESGGG LVRPSQTLSL TCTVSGFTFT DFYMNWVRQS PGRGLEWIGF IRDKAKGYTT   60
EYNPSVKGRV TMLVDTSKNQ FSLRLSSVTA ADTAIYYCAR EGHTAAPFDY WGQGSLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE                         220

SEQ ID NO: 35              moltype = AA   length = 214
FEATURE                    Location/Qualifiers
REGION                     1..214
                           note = Artificial polypeptide
source                     1..214
                           mol_type = protein
                           organism = synthetic construct
SEQUENCE: 35
DIQMTQSPIL LSASVGDRVT ITCRASRDIK SYLNWYQQRT NGSPRLLIYY ATSLAEGVPS   60
RFSGSGSGTD YTLTISSLQP EDIADYYCLQ HGESPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 36              moltype = AA   length = 225
FEATURE                    Location/Qualifiers
REGION                     1..225
                           note = Artificial polypeptide
source                     1..225
                           mol_type = protein
                           organism = synthetic construct
SEQUENCE: 36
EVQLVESGGG LVQPGGSLRL SCAASGFNIK EYYMHWVRQS PGKGLEWVGL IDPEQGNTIY   60
DPKFQDRATI SADNSKNTAY LQMNSLRAED TAIYYCARDT AAYFDYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHT                   225

SEQ ID NO: 37              moltype = AA   length = 214
FEATURE                    Location/Qualifiers
REGION                     1..214
                           note = Artificial polypeptide
source                     1..214
                           mol_type = protein
                           organism = synthetic construct
SEQUENCE: 37
DIQMTQSPIL LSASVGDRVT ITCRASRDIK SYLNWYQQRT NGSPRLLIYY ATSLAEGVPS   60
RFSGSGSGTD YTLTISSLQP EDEADYYCLQ HGESPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 38              moltype = AA   length = 225
FEATURE                    Location/Qualifiers
REGION                     1..225
                           note = Artificial polypeptide
source                     1..225
                           mol_type = protein
                           organism = synthetic construct
SEQUENCE: 38
EVQLVESGGG LVQPGGSLRL SCAASGFNIK EYYMHWVRQS PGKGLEWVGL IDPEQGNTIY   60
DPKFQDRATI SADNSKNTAY LQMNSLRAED TAIYYCARDT AAYFDYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHT                   225

SEQ ID NO: 39              moltype = AA   length = 213
FEATURE                    Location/Qualifiers
REGION                     1..213
                           note = Artificial polypeptide
source                     1..213
                           mol_type = protein
                           organism = synthetic construct
SEQUENCE: 39
EIVLTQSPII MSASPGEKVT MTCSASSSVS YMHWYQQRTN GSPRRWIYDT SKLASGVPAR   60
FSGSGSGTSY SLTISSMEAE DIADYFCHQW RSNPYTFGGG TKLEIKRADA APTVSIFPPS   120
SEQLTSGGAS VVCFLNNFYP KEINVKWKID GSERQNGVLN SWTDQDSKDS TYSMSSTLTL   180
TKDEYERHNS YTCEATHKTS TSPIVKSFNR NEC                                213
```

```
SEQ ID NO: 40              moltype = AA  length = 215
FEATURE                    Location/Qualifiers
REGION                     1..215
                           note = Artificial polypeptide
source                     1..215
                           mol_type = protein
                           organism = synthetic construct
SEQUENCE: 40
EVQLQQSGGE LVKPGSSVKI SCKASRNTFT DYNLDWVKQS HGKTLEWIGN VYPNNGVTGY   60
NQKFRGKATL TVDKSSSTAY MELHSLTSED SAIYYCALYY YDVSYWGQGT LVTVSSAKTT  120
PPSVYPLAPG SAAQTSMVTL GCLVKGYFPE PVTVTWNSGS LSSGVHTFPA VLQSDLYTLS  180
SSVTVPSSTW PSQSVTCNVA HPASSTKVDK KITPR                             215

SEQ ID NO: 41              moltype = AA  length = 213
FEATURE                    Location/Qualifiers
REGION                     1..213
                           note = Artificial polypeptide
source                     1..213
                           mol_type = protein
                           organism = synthetic construct
SEQUENCE: 41
EIVLTQSPII MSASPGEKVT MTCSASSSVS YMHWYQQRTN GSPRRWIYDT SKLASGVPAR   60
FSGSGSGTSY SLTISSMEAE DEADYFCHQW RSNPYTFGGG TKLEIKRADA APTVSIFPPS  120
SEQLTSGGAS VVCFLNNFYP KEINVKWKID GSERQNGVLN SWTDQDSKDS TYSMSSTLTL  180
TKDEYERHNS YTCEATHKTS TSPIVKSFNR NEC                               213

SEQ ID NO: 42              moltype = AA  length = 215
FEATURE                    Location/Qualifiers
REGION                     1..215
                           note = Artificial polypeptide
source                     1..215
                           mol_type = protein
                           organism = synthetic construct
SEQUENCE: 42
EVQLQQSGGE LVKPGSSVKI SCKASRNTFT DYNLDWVKQS HGKTLEWIGN VYPNNGVTGY   60
NQKFRGKATL TVDKSSSTAY MELHSLTSED SAIYYCALYY YDVSYWGQGT LVTVSSAKTT  120
PPSVYPLAPG SAAQTSMVTL GCLVKGYFPE PVTVTWNSGS LSSGVHTFPA VLQSDLYTLS  180
SSVTVPSSTW PSQSVTCNVA HPASSTKVDK KITPR                             215

SEQ ID NO: 43              moltype = AA  length = 213
FEATURE                    Location/Qualifiers
REGION                     1..213
                           note = Artificial polypeptide
source                     1..213
                           mol_type = protein
                           organism = synthetic construct
SEQUENCE: 43
DIQMTQSPIL LSASVGDRVT ITCSASSSIS YMHWYQQRTN GSPRLLIYTT SNLASGVPAR   60
FSGSGSGTEF TLTISSLQPD DIADYYCHQR STYPLTFGQG TKVEVKRTVA APSVFIFPPS  120
DEQLKSGTAS VVCLLNNFYP REAKVQWKVD NALQSGNSSE SVTEQDSKDS TYSLSSTLTL  180
SKADYEKHKV YACEVTHQGL SSPVTKSFNR GEC                               213

SEQ ID NO: 44              moltype = AA  length = 216
FEATURE                    Location/Qualifiers
REGION                     1..216
                           note = Artificial polypeptide
source                     1..216
                           mol_type = protein
                           organism = synthetic construct
SEQUENCE: 44
QVQLVQSGGE VKKPGSSVKV SCKASGYTFT SYRMHWVRQS PGQGLEWIGY INPSTGYTEY   60
NQKFKDKATI TADESTNTAY MELSSLRSED TAIYYCARGG GVPDYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEP                            216

SEQ ID NO: 45              moltype = AA  length = 213
FEATURE                    Location/Qualifiers
REGION                     1..213
                           note = Artificial polypeptide
source                     1..213
                           mol_type = protein
                           organism = synthetic construct
SEQUENCE: 45
DIQMTQSPIL LSASVGDRVT ITCSASSSIS YMHWYQQRTN GSPRLLIYTT SNLASGVPAR   60
FSGSGSGTEF TLTISSLQPD DEADYYCHQR STYPLTFGQG TKVEVKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213
```

```
SEQ ID NO: 46              moltype = AA  length = 216
FEATURE                    Location/Qualifiers
REGION                     1..216
                           note = Artificial polypeptide
source                     1..216
                           mol_type = protein
                           organism = synthetic construct
SEQUENCE: 46
QVQLVQSGGE VKKPGSSVKV SCKASGYTFT SYRMHWVRQS PGQGLEWIGY INPSTGYTEY    60
NQKFKDKATI TADESTNTAY MELSSLRSED TAIYYCARGG GVFDYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEP                             216

SEQ ID NO: 47              moltype = AA  length = 213
FEATURE                    Location/Qualifiers
REGION                     1..213
                           note = Artificial polypeptide
source                     1..213
                           mol_type = protein
                           organism = synthetic construct
SEQUENCE: 47
DIELTQSPII MSASPGEKVT MTCSASSSVS YMHWYQQRTN GSPRRWIYDT SKLASGVPGR    60
FSGSGSGNSY SLTISSVEAE DIADYYCQQW SKHPLTFGSG TKVEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 48              moltype = AA  length = 231
FEATURE                    Location/Qualifiers
REGION                     1..231
                           note = Artificial polypeptide
source                     1..231
                           mol_type = protein
                           organism = synthetic construct
SEQUENCE: 48
EVQLQQSGGE LEKPGASVKI SCKASGYSFT GYTMNWVKQS HGKSLEWIGL ITPYNGASSY    60
NQKFRGKATL TVDKSSSTAY MDLLSLTSED SAIYFCARGG YDGRGFDYWG SGTPVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP C            231

SEQ ID NO: 49              moltype = AA  length = 213
FEATURE                    Location/Qualifiers
REGION                     1..213
                           note = Artificial polypeptide
source                     1..213
                           mol_type = protein
                           organism = synthetic construct
SEQUENCE: 49
DIELTQSPII MSASPGEKVT MTCSASSSVS YMHWYQQRTN GSPRRWIYDT SKLASGVPGR    60
FSGSGSGNSY SLTISSVEAE DEADYYCQQW SKHPLTFGSG TKVEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 50              moltype = AA  length = 231
FEATURE                    Location/Qualifiers
REGION                     1..231
                           note = Artificial polypeptide
source                     1..231
                           mol_type = protein
                           organism = synthetic construct
SEQUENCE: 50
EVQLQQSGGE LEKPGASVKI SCKASGYSFT GYTMNWVKQS HGKSLEWIGL ITPYNGASSY    60
NQKFRGKATL TVDKSSSTAY MDLLSLTSED SAIYFCARGG YDGRGFDYWG SGTPVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP C            231

SEQ ID NO: 51              moltype = AA  length = 214
FEATURE                    Location/Qualifiers
REGION                     1..214
                           note = Artificial polypeptide
source                     1..214
                           mol_type = protein
                           organism = synthetic construct
SEQUENCE: 51
EIVLTQSPIL LSLSPGERAT LSCRASQSVS SYLAWYQQRT NGSPRLLIYD ASNRATGIPA    60
RFSGSGSGTD FTLTISSLEP EDIADYYCQQ RSNWPITFGQ GTRLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 52              moltype = AA  length = 222
```

```
FEATURE                 Location/Qualifiers
REGION                  1..222
                        note = Artificial polypeptide
source                  1..222
                        mol_type = protein
                        organism = synthetic construct
SEQUENCE: 52
EVQLVESGGG LVQPGRSLRL SCAASGFTFN DYAMHWVRQS PGKGLEWVST ISWNSGSIGY    60
ADSVKGRFTI SRDNAKKSLY LQMNSLRAED TAIYYCAKDI QYGNYYYGMD VWGQGTTVTV   120
SSASTKGPSV FPLAPGSSKS TSGTAALGCL VKDYFPEPVT VSWNSGALTS GVHTFPAVLQ   180
SSGLYSLSSV VTVPSSSLGT QTYICNVNHK PSNTKVDKKV EP                     222

SEQ ID NO: 53           moltype = AA  length = 214
FEATURE                 Location/Qualifiers
REGION                  1..214
                        note = Artificial polypeptide
source                  1..214
                        mol_type = protein
                        organism = synthetic construct
SEQUENCE: 53
EIVLTQSPIL LSLSPGERAT LSCRASQSVS SYLAWYQQRT NGSPRLLIYD ASNRATGIPA    60
RFSGSGSGTD FTLTISSLEP EDIADYYCQQ RSNWPITFGQ GTRLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 54           moltype = AA  length = 222
FEATURE                 Location/Qualifiers
REGION                  1..222
                        note = Artificial polypeptide
source                  1..222
                        mol_type = protein
                        organism = synthetic construct
SEQUENCE: 54
EVQLVESGGG LVQPGRSLRL SCAASGFTFN DYAMHWVRQS PGKGLEWVST ISWNSGSIGY    60
ADSVKGRFTI SRDNAKKSLY LQMNSLRAED TAIYYCAKDI QYGNYYYGMD VWGQGTTVTV   120
SSASTKGPSV FPLAPGSSKS TSGTAALGCL VKDYFPEPVT VSWNSGALTS GVHTFPAVLQ   180
SSGLYSLSSV VTVPSSSLGT QTYICNVNHK PSNTKVDKKV EP                     222

SEQ ID NO: 55           moltype = AA  length = 214
FEATURE                 Location/Qualifiers
REGION                  1..214
                        note = Artificial polypeptide
source                  1..214
                        mol_type = protein
                        organism = synthetic construct
SEQUENCE: 55
DIQMTQSPIL LSASVGDRVT ITCRASQDVS TAVAWYQQRT NGSPRLLIYS ASFLYSGVPS    60
RFSGSGSGTD FTLTISSLQP EDIADYYCQQ FYTTPSTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 56           moltype = AA  length = 227
FEATURE                 Location/Qualifiers
REGION                  1..227
                        note = Artificial polypeptide
source                  1..227
                        mol_type = protein
                        organism = synthetic construct
SEQUENCE: 56
EVQLVESGGG LVQPGGSLRL SCAASGFTFS SYWIHWVRQS PGKGLEWVAR INPPNRSNQY    60
ADSVKGRFTI SADTSKNTAY LQMNSLRAED TAIYYCARGS GFRWVMDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHT                227

SEQ ID NO: 57           moltype = AA  length = 214
FEATURE                 Location/Qualifiers
REGION                  1..214
                        note = Artificial polypeptide
source                  1..214
                        mol_type = protein
                        organism = synthetic construct
SEQUENCE: 57
DIQMTQSPIL LSASVGDRVT ITCRASQDVS TAVAWYQQRT NGSPRLLIYS ASFLYSGVPS    60
RFSGSGSGTD FTLTISSLQP EDEADYYCQQ FYTTPSTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 58           moltype = AA  length = 227
FEATURE                 Location/Qualifiers
```

```
REGION                  1..227
                        note = Artificial polypeptide
source                  1..227
                        mol_type = protein
                        organism = synthetic construct
SEQUENCE: 58
EVQLVESGGG LVQPGGSLRL SCAASGFTFS SYWIHWVRQS PGKGLEWVAR INPPNRSNQY   60
ADSVKGRFTI SADTSKNTAY LQMNSLRAED TAIYYCARGS GFRWVMDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHT               227

SEQ ID NO: 59           moltype = AA  length = 220
FEATURE                 Location/Qualifiers
REGION                  1..220
                        note = Artificial polypeptide
source                  1..220
                        mol_type = protein
                        organism = synthetic construct
SEQUENCE: 59
DIVMTQSPIL LAVSLGERAT INCKSSQSVL NSGNQKNYLT WYQQRTNGSP RLLIYWASTR   60
ESGVPDRFSG SGSGTDFTLT ISSLQAEDIA DYYCQSDYSY PYTFGQGTKL EIKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                       220

SEQ ID NO: 60           moltype = AA  length = 227
FEATURE                 Location/Qualifiers
REGION                  1..227
                        note = Artificial polypeptide
source                  1..227
                        mol_type = protein
                        organism = synthetic construct
SEQUENCE: 60
QVQLVQSGGG VKKPGASVKV SCKASGYTFR SSYISWVRQS PGQGLEWMGW IYAGTGSPSY   60
NQKLQGRVTM TTDTSTSTAY MELRSLRSDD TAIYYCARHR DYYSNSLTYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTH               227

SEQ ID NO: 61           moltype = AA  length = 220
FEATURE                 Location/Qualifiers
REGION                  1..220
                        note = Artificial polypeptide
source                  1..220
                        mol_type = protein
                        organism = synthetic construct
SEQUENCE: 61
DIVMTQSPIL LAVSLGERAT INCKSSQSVL NSGNQKNYLT WYQQRTNGSP RLLIYWASTR   60
ESGVPDRFSG SGSGTDFTLT ISSLQAEDEA DYYCQSDYSY PYTFGQGTKL EIKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                       220

SEQ ID NO: 62           moltype = AA  length = 227
FEATURE                 Location/Qualifiers
REGION                  1..227
                        note = Artificial polypeptide
source                  1..227
                        mol_type = protein
                        organism = synthetic construct
SEQUENCE: 62
QVQLVQSGGG VKKPGASVKV SCKASGYTFR SSYISWVRQS PGQGLEWMGW IYAGTGSPSY   60
NQKLQGRVTM TTDTSTSTAY MELRSLRSDD TAIYYCARHR DYYSNSLTYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTH               227

SEQ ID NO: 63           moltype = AA  length = 213
FEATURE                 Location/Qualifiers
REGION                  1..213
                        note = Artificial polypeptide
source                  1..213
                        mol_type = protein
                        organism = synthetic construct
SEQUENCE: 63
QIVLSQSPII LSASPGEKVT MTCRASSSVS YIHWFQQRTN GSPRPWIYAT SNLASGVPVR   60
FSGSGSGTSY SLTISRVEAE DIADYYCQQW TSNPPTFGGG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                              213

SEQ ID NO: 64           moltype = AA  length = 224
FEATURE                 Location/Qualifiers
REGION                  1..224
```

```
                        note = Artificial polypeptide
source                  1..224
                        mol_type = protein
                        organism = synthetic construct
SEQUENCE: 64
QVQLQQPGGG LVKPGASVKM SCKASGYTFT SYNMHWVKQT PGRGLEWIGA IYPGNGDTSY     60
NQKFKGKATL TADKSSSTAY MQLSSLTSED SAIYYCARST YYGGDWYFNV WGAGTTVTVS    120
AASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKKVE PKSC                     224

SEQ ID NO: 65           moltype = AA  length = 213
FEATURE                 Location/Qualifiers
REGION                  1..213
                        note = Artificial polypeptide
source                  1..213
                        mol_type = protein
                        organism = synthetic construct
SEQUENCE: 65
QIVLSQSPII LSASPGEKVT MTCRASSSVS YIHWFQQRTN GSPRPWIYAT SNLASGVPVR     60
FSGSGSGTSY SLTISRVEAE DEADYYCQQW TSNPPTFGGG TKLEIKRTVA APSVFIFPPS    120
DEQLKSGTAS VVCLLNNFYP REAKVQWKVD NALQSGNSQE SVTEQDSKDS TYSLSSTLTL    180
SKADYEKHKV YACEVTHQGL SSPVTKSFNR GEC                                 213

SEQ ID NO: 66           moltype = AA  length = 224
FEATURE                 Location/Qualifiers
REGION                  1..224
                        note = Artificial polypeptide
source                  1..224
                        mol_type = protein
                        organism = synthetic construct
SEQUENCE: 66
QVQLQQPGGG LVKPGASVKM SCKASGYTFT SYNMHWVKQT PGRGLEWIGA IYPGNGDTSY     60
NQKFKGKATL TADKSSSTAY MQLSSLTSED SAIYYCARST YYGGDWYFNV WGAGTTVTVS    120
AASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKKVE PKSC                     224

SEQ ID NO: 67           moltype = AA  length = 214
FEATURE                 Location/Qualifiers
REGION                  1..214
                        note = Artificial polypeptide
source                  1..214
                        mol_type = protein
                        organism = synthetic construct
SEQUENCE: 67
YIQMTQSPIL LSVSVGETVT ITCRASENIY SFLAWYQQRT NGSPRLLVYA ATNLADGVPS     60
RFSGSGSGTQ FSLKINSLQS EDIADYYCQH FWGTPFTFGS GTKLEIKRSD AAPTVSIFPP    120
SAAQLSSGGG SVVCFLNNFY PKDINVKWKI DGAERGNGVL NSWTSQDSAD STYSMSSTLT    180
SGGDEYERHN SYTCEATHKT STSPIVKSFN RGEC                                214

SEQ ID NO: 68           moltype = AA  length = 216
FEATURE                 Location/Qualifiers
REGION                  1..216
                        note = Artificial polypeptide
source                  1..216
                        mol_type = protein
                        organism = synthetic construct
SEQUENCE: 68
EVQLVESGGG LVQPKGSLKI SCAASGFTFN IYAMNWVRQS PGKGLEWVAR IRSQSNNYTT     60
YYADSVKDRF TISRDDSQSM LYLQMNNLKT EDTAIYYCVR QMGDYWGQGT TLTVSSAVKT    120
PPSVYPLAPG GGAISNSMVT LGCLVNGYFP EPVTVTWNAG SLGSGVHTFP AVLQSDLYTL    180
SSSVTVPVST WPSEAVTCNV AHPASATSVD KAISPV                              216

SEQ ID NO: 69           moltype = AA  length = 214
FEATURE                 Location/Qualifiers
REGION                  1..214
                        note = Artificial polypeptide
source                  1..214
                        mol_type = protein
                        organism = synthetic construct
SEQUENCE: 69
YIQMTQSPIL LSVSVGETVT ITCRASENIY SFLAWYQQRT NGSPRLLVYA ATNLADGVPS     60
RFSGSGSGTQ FSLKINSLQS EDIADYYCQH FWGTPFTFGS GTKLEIKRSD AAPTVSIFPP    120
SAAQLSSGGG SVVCFLNNFY PKDINVKWKI DGAERGNGVL NSWTSQDSAD STYSMSSTLT    180
SGGDEYERHN SYTCEATHKT STSPIVKSFN RGEC                                214

SEQ ID NO: 70           moltype = AA  length = 216
FEATURE                 Location/Qualifiers
REGION                  1..216
                        note = Artificial polypeptide
```

```
                        -continued
source                  1..216
                        mol_type = protein
                        organism = synthetic construct
SEQUENCE: 70
EVQLVESGGG LVQPKGSLKI SCAASGFTFN IYAMNWVRQS PGKGLEWVAR IRSQSNNYTT    60
YYADSVKDRF TISRDDSQSM LYLQMNNLKT EDTAIYYCVR QMGDYWGQGT TLTVSSAVKT   120
PPSVYPLAPG GGAISNSMVT LGCLVNGYFP EPVTVTWNAG SLGSGVHTFP AVLQSDLYTL   180
SSSVTVPVST WPSEAVTCNV AHPASATSVD KAISPV                             216

SEQ ID NO: 71           moltype = AA  length = 219
FEATURE                 Location/Qualifiers
REGION                  1..219
                        note = Artificial polypeptide
source                  1..219
                        mol_type = protein
                        organism = synthetic construct
SEQUENCE: 71
DVVMTQTPLL LSVTIGQPAS ISCKSSQSLL DSDGKTYLNW LLQRTNGSPR RLIYLVSKLD    60
SGVPDRFTGS GSGTDFTLKI SRVEAEDIAD YYCWQGTHFP LTFGAGTKLE LKRADAAPTV   120
SIFPPSSEQL TSGGASVVCF LNNFYPKDIN VKWKIDGSER QNGVLNSWTD QDSKDSTYSM   180
SSTLTLTKDE YERHNSYTCE ATHKTSTSPI VKSFNRNEC                          219

SEQ ID NO: 72           moltype = AA  length = 228
FEATURE                 Location/Qualifiers
REGION                  1..228
                        note = Artificial polypeptide
source                  1..228
                        mol_type = protein
                        organism = synthetic construct
SEQUENCE: 72
EVQLQQSGGG LVKTGASVKI SCKASGYSFT SYYMHWVKQS HGKSLEWIGE INPYNGGASY    60
NQKIKGRATF TVDTSSRTAY MQFNSLTSED SAIYYCARSI YGHSVLDYWG QGTSVSVSSA   120
KTTPPSVYPL APGSAAQTNS MVTLGCLVKG YFPEPVTVTW NSGSLSSGVH TFPAVLQSDL   180
YTLSSSVTVP SSTWPSQTVT CNVAHPASST KVDKKIVPRD CGCKPCIC                228

SEQ ID NO: 73           moltype = AA  length = 219
FEATURE                 Location/Qualifiers
REGION                  1..219
                        note = Artificial polypeptide
source                  1..219
                        mol_type = protein
                        organism = synthetic construct
SEQUENCE: 73
DVVMTQTPLL LSVTIGQPAS ISCKSSQSLL DSDGKTYLNW LLQRTNGSPR RLIYLVSKLD    60
SGVPDRFTGS GSGTDFTLKI SRVEAEDEAD YYCWQGTHFP LTFGAGTKLE LKRADAAPTV   120
SIFPPSSEQL TSGGASVVCF LNNFYPKDIN VKWKIDGSER QNGVLNSWTD QDSKDSTYSM   180
SSTLTLTKDE YERHNSYTCE ATHKTSTSPI VKSFNRNEC                          219

SEQ ID NO: 74           moltype = AA  length = 228
FEATURE                 Location/Qualifiers
REGION                  1..228
                        note = Artificial polypeptide
source                  1..228
                        mol_type = protein
                        organism = synthetic construct
SEQUENCE: 74
EVQLQQSGGG LVKTGASVKI SCKASGYSFT SYYMHWVKQS HGKSLEWIGE INPYNGGASY    60
NQKIKGRATF TVDTSSRTAY MQFNSLTSED SAIYYCARSI YGHSVLDYWG QGTSVSVSSA   120
KTTPPSVYPL APGSAAQTNS MVTLGCLVKG YFPEPVTVTW NSGSLSSGVH TFPAVLQSDL   180
YTLSSSVTVP SSTWPSQTVT CNVAHPASST KVDKKIVPRD CGCKPCIC                228

SEQ ID NO: 75           moltype = AA  length = 215
FEATURE                 Location/Qualifiers
REGION                  1..215
                        note = Artificial polypeptide
source                  1..215
                        mol_type = protein
                        organism = synthetic construct
SEQUENCE: 75
IVLTQSPILL SVSPGERATL SCRASQVISH NLAWYQQRTN GSPRLLIYGA STRASGIPAR    60
FSGSGSGTDY TLTITSLQPE DIADYYCQHY SNWPPRLTFG GGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 76           moltype = AA  length = 228
FEATURE                 Location/Qualifiers
REGION                  1..228
                        note = Artificial polypeptide
source                  1..228
```

```
                              mol_type = protein
                              organism = synthetic construct
SEQUENCE: 76
EVQLQQSGGG LVKTGASVKI SCKASGYSFT SYYMHWVKQS HGKSLEWIGE INPYNGGASY      60
NQKIKGRATF TVDTSSRTAY MQFNSLTSED SAIYYCARSI YGHSVLDYWG QGTSVSVSSA     120
KTTPPSVYPL APGSAAQTNS MVTLGCLVKG YFPEPVTVTW NSGSLSSGVH TFPAVLQSDL     180
YTLSSSVTVP SSTWPSQTVT CNVAHPASST KVDKKIVPRD CGCKPCIC                  228

SEQ ID NO: 77                 moltype = AA  length = 215
FEATURE                       Location/Qualifiers
REGION                        1..215
                              note = Artificial polypeptide
source                        1..215
                              mol_type = protein
                              organism = synthetic construct
SEQUENCE: 77
IVLTQSPILL SVSPGERATL SCRASQVISH NLAWYQQRTN GSPRLLIYGA STRASGIPAR      60
FSGSGSGTDY TLTITSLQPE DEADYYCQHY SNWPPRLTFG GGTKVEIKRT VAAPSVFIFP     120
PSDEQLKSGT ASVVCLLNNF YPREAKVQWK VDNALQSGNS QESVTEQDSK DSTYSLSSTL     180
TLSKADYEKH KVYACEVTHQ GLSSPVTKSF NRGEC                                215

SEQ ID NO: 78                 moltype = AA  length = 228
FEATURE                       Location/Qualifiers
REGION                        1..228
                              note = Artificial polypeptide
source                        1..228
                              mol_type = protein
                              organism = synthetic construct
SEQUENCE: 78
EVQLQQSGGG LVKTGASVKI SCKASGYSFT SYYMHWVKQS HGKSLEWIGE INPYNGGASY      60
NQKIKGRATF TVDTSSRTAY MQFNSLTSED SAIYYCARSI YGHSVLDYWG QGTSVSVSSA     120
KTTPPSVYPL APGSAAQTNS MVTLGCLVKG YFPEPVTVTW NSGSLSSGVH TFPAVLQSDL     180
YTLSSSVTVP SSTWPSQTVT CNVAHPASST KVDKKIVPRD CGCKPCIC                  228

SEQ ID NO: 79                 moltype = AA  length = 214
FEATURE                       Location/Qualifiers
REGION                        1..214
                              note = Artificial polypeptide
source                        1..214
                              mol_type = protein
                              organism = synthetic construct
SEQUENCE: 79
DIVMTQSHIL MSTSVGDRVS ITCKASQDVS TAVAWYQQRT NGSPRLLISW ASTRHTGVPD      60
RFTGSGSGTD YTLTISSVQA EDIADYYCQQ HYTTPLTFGA GTKLELKRAD AAPTVSIFPP     120
SSEQLTSGGA SVVCFLNNFY PKDINVKWKI DGSERQNGVL NSWTDQDSKD STYSMSSTLT     180
LTKDEYERHN SYTCEATHKT STSPIVKSFN RGEC                                 214

SEQ ID NO: 80                 moltype = AA  length = 219
FEATURE                       Location/Qualifiers
REGION                        1..219
                              note = Artificial polypeptide
source                        1..219
                              mol_type = protein
                              organism = synthetic construct
SEQUENCE: 80
QVQLQQSGGG LMKPGASVQI SCKATGYTFS DYWIEWVKQS PGHGLEWIGD ILCGTGRTRY      60
NEKLKAMATF TADTSSNTAF MQLSSLTSED SAIYYCARSA SYGDYADYWG HGTTLTVSSA     120
KTTPPSVYPL APGCGDTTGS SVTLGCLVKG YFPESVTVTW NSGSLSSSVH TFPALLQSGL     180
YTMSSSVTVP SSTWPSQTVT CSVAHPASST TVDKKLEPS                            219

SEQ ID NO: 81                 moltype = AA  length = 214
FEATURE                       Location/Qualifiers
REGION                        1..214
                              note = Artificial polypeptide
source                        1..214
                              mol_type = protein
                              organism = synthetic construct
SEQUENCE: 81
DIVMTQSHIL MSTSVGDRVS ITCKASQDVS TAVAWYQQRT NGSPRLLISW ASTRHTGVPD      60
RFTGSGSGTD YTLTISSVQA EDEADYYCQQ HYTTPLTFGA GTKLELKRAD AAPTVSIFPP     120
SSEQLTSGGA SVVCFLNNFY PKDINVKWKI DGSERQNGVL NSWTDQDSKD STYSMSSTLT     180
LTKDEYERHN SYTCEATHKT STSPIVKSFN RGEC                                 214

SEQ ID NO: 82                 moltype = AA  length = 219
FEATURE                       Location/Qualifiers
REGION                        1..219
                              note = Artificial polypeptide
source                        1..219
                              mol_type = protein
```

```
                        organism = synthetic construct
SEQUENCE: 82
QVQLQQSGGG LMKPGASVQI SCKATGYTFS DYWIEWVKQS PGHGLEWIGD ILCGTGRTRY    60
NEKLKAMATF TADTSSNTAF MQLSSLTSED SAIYYCARSA SYGDYADYWG HGTTLTVSSA   120
KTTPPSVYPL APGCGDTTGS SVTLGCLVKG YFPESVTVTW NSGSLSSSVH TFPALLQSGL   180
YTMSSSVTVP SSTWPSQTVT CSVAHPASST TVDKKLEPS                         219

SEQ ID NO: 83           moltype = AA  length = 23
FEATURE                 Location/Qualifiers
REGION                  1..23
                        note = Artificial polypeptide
source                  1..23
                        mol_type = protein
                        organism = synthetic construct
SEQUENCE: 83
PVKQLLNFDL LKLAGDVESN PGP                                           23

SEQ ID NO: 84           moltype = AA  length = 20
FEATURE                 Location/Qualifiers
REGION                  1..20
                        note = Artificial polypeptide
source                  1..20
                        mol_type = protein
                        organism = synthetic construct
SEQUENCE: 84
QCTNYALLKL AGDVESNPGP                                               20

SEQ ID NO: 85           moltype = AA  length = 19
FEATURE                 Location/Qualifiers
REGION                  1..19
                        note = Artificial polypeptide
source                  1..19
                        mol_type = protein
                        organism = synthetic construct
SEQUENCE: 85
ATNFSLLKQA GDVEENPGP                                                19

SEQ ID NO: 86           moltype = AA  length = 18
FEATURE                 Location/Qualifiers
REGION                  1..18
                        note = Artificial polypeptide
source                  1..18
                        mol_type = protein
                        organism = synthetic construct
SEQUENCE: 86
EGRGSLLTCG DVESNPGP                                                 18

SEQ ID NO: 87           moltype = AA  length = 219
FEATURE                 Location/Qualifiers
REGION                  1..219
                        note = Artificial polypeptide
source                  1..219
                        mol_type = protein
                        organism = synthetic construct
SEQUENCE: 87
EVQLVESGGG LVQPGGSLRL SCAASGVSLP DYGVSWVRQS PGKGLEWVAV IWGSETTYYA    60
DSVKGRFTIS ADTSKNTYLQ MNSLRAEDTA IYYCSRHYYY GGSYAMDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEP                         219

SEQ ID NO: 88           moltype = AA  length = 214
FEATURE                 Location/Qualifiers
REGION                  1..214
                        note = Artificial polypeptide
source                  1..214
                        mol_type = protein
                        organism = synthetic construct
SEQUENCE: 88
DIQMTQSPIL LSASVGDRVT ITCRASQDIS KYLNWYQQRT NGSPRLLIYH TSRLHSGVPS    60
RFSGSRSGTD FTLTISSLQP EDIADYYCQQ GNTLPYTFGA GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 89           moltype = AA  length = 219
FEATURE                 Location/Qualifiers
REGION                  1..219
                        note = Artificial polypeptide
source                  1..219
                        mol_type = protein
```

```
                        organism = synthetic construct
SEQUENCE: 89
EVQLVESGGG LVQPGGSLRL SCAASGVSLP DYGVSWVRQS PGKGLEWVAV IWGSETTYYA    60
DSVKGRFTIS ADTSKNTYLQ MNSLRAEDTA IYYCSRHYYY GGSYAMDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEP                         219

SEQ ID NO: 90           moltype = AA   length = 214
FEATURE                 Location/Qualifiers
REGION                  1..214
                        note = Artificial polypeptide
source                  1..214
                        mol_type = protein
                        organism = synthetic construct
SEQUENCE: 90
DIQMTQSPIL LSASVGDRVT ITCRASQDIS KYLNWYQQRT NGSPRLLIYH TSRLHSGVPS    60
RFSGSRSGTD FTLTISSLQP EDEADYYCQQ GNTLPYTFGA GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 91           moltype = AA   length = 215
FEATURE                 Location/Qualifiers
REGION                  1..215
                        note = Artificial polypeptide
source                  1..215
                        mol_type = protein
                        organism = synthetic construct
SEQUENCE: 91
EVQLVESGGG LVQPGGSLRL SCAASGYTFT DHAIHWVRQS PGKGLEWVAY FSPGNDDFKY    60
ADSVKGRFTI SADTSKNTAY LQMNSLRAED TAIYYCSRSL NMAYWGQGTL VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEP                             215

SEQ ID NO: 92           moltype = AA   length = 220
FEATURE                 Location/Qualifiers
REGION                  1..220
                        note = Artificial polypeptide
source                  1..220
                        mol_type = protein
                        organism = synthetic construct
SEQUENCE: 92
DIQMTQSPIL LSASVGDRVT ITCKSSQSLL YSGNQKNYLA WYQQRTNGSP RLLIYWASAR    60
ESGVPSRFSG SRSGTDFTLT ISSLQPEDEA DYYCQQYYSY PLTFGAGTKV EIKRTVAAPS   120
VFIFPPSDEQ LKSGTASVVC LLNNFYPREA KVQWKVDNAL QSGNSQESVT EQDKDSTYS   180
LSSTLTLSKA DYEKHKVYAC EVTHQGLSSP VTKSFNRGEC                        220

SEQ ID NO: 93           moltype = AA   length = 222
FEATURE                 Location/Qualifiers
REGION                  1..222
                        note = Artificial polypeptide
source                  1..222
                        mol_type = protein
                        organism = synthetic construct
SEQUENCE: 93
EVQLVESGGG LVQPGGSLRL SCAASGFTFE AYAMHWVRQS PGKGLEWVAS INWNSGRIAY    60
ADSVKGRFTI SADTSKNTAY LQMNSLRAED TAIYYCSRDI RRFSTGAEFE YWGQGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EP                     222

SEQ ID NO: 94           moltype = AA   length = 218
FEATURE                 Location/Qualifiers
REGION                  1..218
                        note = Synthetic polypeptide
source                  1..218
                        mol_type = protein
                        organism = synthetic construct
SEQUENCE: 94
DIQMTQSPIL LSASVGDRVT ITCSGSSSNI GSNFVYWYQQ RTNGSPRLLI YRNNQRPSGV    60
PSRFSGSRSG TDFTLTISSL QPEDEADYYC AAWDDSLGHY VFGAGTKVEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                          218

SEQ ID NO: 95           moltype = AA   length = 223
FEATURE                 Location/Qualifiers
REGION                  1..223
                        note = Artificial polypeptide
source                  1..223
                        mol_type = protein
                        organism = synthetic construct
```

```
SEQUENCE: 95
EVQLVESGGG LVQPGGSLRL SCAASGFDLG FYFYACWVRQ SPGKGLEWVA CIYTAGSGST    60
YYADSVKGRF TISADTSKNT AYLQMNSLRA EDTAIYYCSR STANTRSTYL NLWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEP                    223

SEQ ID NO: 96          moltype = AA  length = 215
FEATURE                Location/Qualifiers
REGION                 1..215
                       note = Artificial polypeptide
source                 1..215
                       mol_type = protein
                       organism = synthetic construct
SEQUENCE: 96
DIQMTQSPIL LSASVGDRVT ITCQASQRIS SYLSWYQQRT NGSPRLLIYG ASTLASGVPS    60
RFSGSRSGTD FTLTISSLQP EDEADYYCQS YFDSNWHAFG AGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 97          moltype = DNA  length = 9388
FEATURE                Location/Qualifiers
misc_feature           1..9388
                       note = Synthetic polynucleotide
source                 1..9388
                       mol_type = other DNA
                       organism = synthetic construct
SEQUENCE: 97
cctcctgaaa aactggaatt taatacacca tttgtgttca tcatcagaca tgatattact    60
ggatttatat tgtttatggg taaggtagaa tctccttaat atgggtacgg tgtaaggaat   120
cattatttta tttatattga tgggtacgtg aaatctgaat tttcttaata aatattattt   180
ttattaaatg tgtatatgtt gttttgcgat agccatgtat ctactaatca gatctattag   240
agatattatt aattctggtg caatatgaca aaaattatac actaattagc gtctcgtttc   300
agacatggat ctgtcacgaa ttaatacttg aaagtctaag cagctgaaaa gctttctctc   360
tagcaaagat gcatttaagg cggatgtcca tggacatagt gccttgtatt atgcaatagc   420
tgataataac gtgcgtctag tatgtacgtt gttgaacgct ggagcattga aaaatcttct   480
agagaatgaa tttccattac atcaggcagc cacattggaa gataccaaaa tagtaaagat   540
tttggctatt cagtggactg gatgattcga ggtaccgact attgttctat attatatatg   600
gttgttgatg gatctgtgat gcatgcaata gctgataata gaacttacgc aaatattagc   660
aaaaatatat tagacaatac tacaattaac gatgagtgta gatgctgtta ttttgaacca   720
cagattagga ttcttgatag agatgagatg ctcaatggat catcgtgtga tatgaacaga   780
cattgtatta tgatgaattt acctgatgta ggcgaatttg gatctagtat gttggggaaa   840
tatgaacctg acatgattaa gattgctctt tcggtggctg gtaccaggc  gcgcatttca    900
ttttgtttt  tttctatgcta taaatggtac gtcctgtaga aaccccaacc cgtgaaatca   960
aaaaactcga cggcctgtgg gcattcagtc tggatcgcga aaactgtgga attgatcagc  1020
gttggtggga aagcgcgtta caagaaagcc gggcaattgc tgtgccaggc agttttaacg  1080
atcagttcgc cgatgcagat attcgtaatt atgcgggcaa cgtctggtat cagcgcgaag  1140
tctttatacc gaaaggttgg gcaggccagc gtatcgtcgc gcgtttcgat gcggtcactc  1200
attacggcaa agtgtgggtc aataatcagg aagtgatgga gcatcagggc ggctatacgc  1260
catttgaagc cgatgtcacg ccgtatgtta ttgccgggaa aagtgtacgt atcaccgttt  1320
gtgtgaacaa cgaactgaac tggcagacta tcccgccggg aatggtgatt accgacgaaa  1380
acggcaagaa aaagcagtct tacttccatg atttctttaa ctatgccgga atccatcgca  1440
gcgtaatgct ctacaccacg ccgaacacct gggtggacga tatcaccgtg gtgacgcatg  1500
tcgcgcaaga ctgtaaccac gcgtctgttg actggcaggt ggtggccaat ggtgatgtca  1560
gcgttgaact gcgtgatgcg gatcaacagg tggttgcaac tggacaaggc actagcggga  1620
ctttgcaagt ggtgaatccg cacctctggc aaccgggtga aggttatctc tatgaactgc  1680
gcgtcacagc caaaagccag acagagtgtg atatctaccc gcttcgcgtc ggcatccggt  1740
cagtggcagt gaagggcgaa cagttcctga ttaaccacaa accgttctac tttactggct  1800
ttggtcgtca tgaagatgcg gacttgcgtg gcaaaggatt cgataacgtg ctgatggtgc  1860
acgaccacgc attaatggac tggattgggg ccaactccta cctacctcg cattaccctt  1920
acgctgaaga gatgctcgac tgggcagatg aacatggcat cgtggtgatt gatgaaactg  1980
ctgctgtcgg ctttaacctc tctttaggca ttggtttcga agcgggcaac aagccgaaag  2040
aactgtacag cgaagaggca gtcaacgggg aaactcagca agcgcactta caggcgatta  2100
aagagctgat agcgcgtgac aaaaaccacc caagcgtggt gatgtggagt attgccaacg  2160
aaccggatac ccgtccgcaa ggtgcacggg aatatttcgc gccactggcg gaagcaacgc  2220
gtaaactcga cccgacgcgt ccgatcacct gcgtcaatgt aatgttctgc gacgctcaca  2280
ccgataccat cagcgatctc tttgatgtgc tgtgcctgaa ccgttattac ggatggtatg  2340
tccaaagcgg cgatttggaa acggcagaga aggtactgga aaagaacttc tggcctggc   2400
aggagaaact gcatcagccg attatcatca ccgaatacgg cgtggatacg ttagcgggc   2460
tgcactcaat gtacaccgac atgtggagtg aagagtatca gtgtgcatgg ctggatatgt  2520
atcaccgcgt ctttgatcgc gtcagcgccc tcgtcggtga acaggtatgg aatttcgccg  2580
attttgcgac ctcgcaaggc atattgcgcg ttggcggtaa caagaaaggg atcttcactc  2640
gcgaccgcaa accgaagtcg gcggcttttc tgctgcaaaa acgctggact ggcatgaact  2700
tcggtgaaaa accgcagcag ggaggcaaac aatgagagct cggttgttga tggatctgtg  2760
atgcatgga  tgataa tagaacttac gcaaatatta gcaaaaatat tagacaat       2820
actacaatta cgatgagtg tagatgctgt tattttgaac cacagattag gattcttgat   2880
agagatgaga tgctcaatgg atcatcgtgt gatatgaaca gacattgtat tatgatgaat  2940
ttacctgatg taggcgaatt tggatctagt atgttgggga aatatgaacc tgacatgatt  3000
aagattgctc tttcggtggc tggcggcccg ctcgagaaaa attgaaaata aatacaaagg  3060
ttcttgaggg ttgtgttaaa ttgaaagcga gaaataatca taaataagcc accacgtttt  3120
```

```
aaacgccacc acaatggtca aacagattaa ggttcgagtg gacatggtgc ggcatagaat   3180
caaggagcac atgctgaaaa aatatacccc gacggaagag aaattcactg gcgcctttaa   3240
tatgatggga ggatgtttgc agaatgcctt agatatctta gataaggttc atgagccttt   3300
cgaggagatg aagtgtattg ggctaactat gcagagcatg tatgagaact acattgtacc   3360
tgaggataag cgggagatgt ggatggcttg tattaaggag ctgcatgatg tgagcaaggg   3420
cgccgctaac aagttggggg gtgcactgca ggctaaggcc cgtgctaaaa aggatgaact   3480
taggagaaaa atgatgtata tgtgctacag gaatatagag ttctttacca agaactcagc   3540
cttccctaag accaccaatg gctgcagtca ggccatggcg gcactgcaga acttgcctca   3600
gtgctcccct gatgagaata tggcttatgc ccagaaaata tttaagattt tggatgagga   3660
gagagacaag gtgctcacgc acattgatca catatttatg gatatcctca ctacatgtgg   3720
ggaaacaatg tgtaatgagt acaaggtcac tagtgacgct tgtatgatga ccatgtacgg   3780
gggcatctct ctcttaagtg agttctgtcg ggtgctgtgc tgctatgtct tagaggagac   3840
tagtgtgatg ctggccaagc ggcctctgat aaccaagcct gaggttatca gtgtaatgaa   3900
gcgccgcatt gaggagatct gcatgaaggt ctttgcccag tacattctgg gggccgatcc   3960
tctgagagtc tgctctccta gtgtggatga cctacgggcc atcgccgagg agtcagatga   4020
ggaagaggct attgtagcct acactttggc caccgctggt gtcagctcct ctgattctct   4080
ggtgtcaccc ccagagtccc ctgtacccgc gactatccct ctgtcctcag taattgtggc   4140
tgagaacagt gatcaggaag aaagtgagca gagtgatgag gaagaggagg agggtgctca   4200
ggaggagcgg gaggacactg tgtctgtcaa gtctgagcca gtgtctgaga tagaggaagt   4260
tgccccagag gaagaggagg atggtgctga ggaacccacc gcctctggag gcaagagcac   4320
ccaccctatg gtgactagaa gcaaggctga ccagggtgac atcctcgccc aggctgtcaa   4380
tcatgccggt atcgattcca gtagcaccgg ccccacgctg acaacccact cttgcagcgt   4440
tagcagcgcc cctcttaaca agccgacccc caccagcgtc gcggttacta acactcctct   4500
ccccggggca tccgctactc ccgagctcag cccgcgtaag aaaccgcgca aaaccacgcg   4560
tcctttcaag gtgattatta aaccgcccgt gcctcccgcg cctatcatgc tgcccctcat   4620
caaacaggaa gacatccaag ccgagccgca ctttaccatc cagtaccgca acaagattat   4680
cgataccgcc ggctgtatcg tgatctctga tagcgaggaa gaacagggtg aagaagtcga   4740
aacccgcggt gctaccgcgt cttcccttc caccggcagc ggcacgccgc gagtgacctc   4800
tcccacgcac ccgctctccc agatgaacca ccctcctctt cccgatccct gggccggcc   4860
cgatgaagat agttcctctt cgtcttcctc ctcctgcagt tcggcttcgg actcggagag   4920
tgagtccgag gagatgaaat ccagcagtgg cggaggagca tccgtgacct cgagccacca   4980
tgggcgcggc ggtttggtg gcgcggcctc ctcctctctg ctgagctgcg gccatcagag   5040
cagcggcggg gcgagcaccg accccgcaa gaagaagagc aaacgcatct ccgagttgga   5100
caacgagaag gtgcgcaata tcatgaaaga taagcacacc cccttctgca cacccaacgt   5160
gcagactcgg cggggtcgcg tcaagattga cgaggtgagc cgcatgttcc gcaacaccaa   5220
tcgctctctt gagtacaaga acctgccctt cacgattccc agtatgcacc aggtgttaga   5280
tgaggccatc aaagcctgca aaaccatgca ggtgaacaac aagggcatcc agattatcta   5340
cacccgcaat catgaggtga agagtgaggt ggatgcggtg cggtgtcgcc tgggcaccat   5400
gtgcaacctg gccctctcca ctcccttcct catggagcac accatgcccg tgacacatcc   5460
acccgaagtg gcgcagcgca cagccgatgc ttgtaacgaa ggcgtcaagg ccgcgtggag   5520
cctcaaagaa ttgcacaccc accaattatg ccccgttcc tccgattacc gcaacatgat   5580
catccacgct gccacccccg tggacctgtt gggcgctctc aacctgtgcc tgcccctgat   5640
gcaaaagttt cccaaacagg tcatggtgcg catcttctcc accaaccagg gtgggttcat   5700
gctgcctatc tacgagacgg ccgcgaaggc ctacgccgtg gggcagtttg agcagcccac   5760
cgagaccct cccgaagacc tggacaccct gagcctggcc atcgaggcag ccatccagga   5820
cctgaggaac aagtctcagt aaaataaagg cgcgccataa aaatttttat actagtgtac   5880
cgcggtcgaa tcgatttaat taacgatgct agcattgtgc aggtggtgg ccgcgccgcc   5940
agtgtgatgg atatctgcag aattcggctt gggggctgc aggtggatgc gatcatgacg   6000
tcctctgcaa tggataacaa tgaacctaaa gtactagaaa tggtatatga tgctacaatt   6060
ttacccgaag gtagtagcat ggattgtata aacagacaca tcaatatgtg tatacaacgc   6120
acctatagtt ctagtataat tgccatattg gatagattcc taatgatgaa caaggatgaa   6180
ctaaataata cacagtgtca tataattaaa gaatttatga catacgaaca aatggcgatt   6240
gaccattatg gagaatatgt aaacgctatt ctatatcaaa ttcgtaaaag acctaatcaa   6300
catcacacca ttaatctgtt taaaaaaata aaaagaaccc ggtatgacac ttttaaagtg   6360
gatccgtag aattcgtaaa aaaagttatc ggatttgtat ctatcttgaa caaatataa   6420
ccggttttata gttacgtcct gtacgagaac gtcctgtacg atgagttcaa atgtttcatt   6480
gactacgtgg aaactaagta tttctaaaat taatgatgca ttaattttttg tattgattct   6540
caatcctaaa aactaaaata tgaataagta ttaaacatag cggtgtacta attgatttaa   6600
cataaaaaat agttgttaac taatcatgag gactctactt attagatata ttctttggag   6660
aaatgacaac gatcaaaccg ggcatgcaag cttgtctccc tatagtgagt cgtattagag   6720
cttggcgtaa tcatggtcat agctgtttcc tgtgtgaaat tgttatccgc tcacaattcc   6780
acacaacata cgagccggaa gcataaagtg taaagcctgg ggtgcctaat gagtgagcta   6840
actcacatta attgcgttgc gctcactgcc cgctttcgag tcgggaaacc tgtcgtgcca   6900
gctgcattaa tgaatcggcc aacgcgcggg gagaggcggt ttgcgtattg ggcgctcttc   6960
cgcttcctcg ctcactgact cgctgcgctc ggtcgttcgg ctgcggcgag cggtatcagc   7020
tcactcaaag gcggtaatac ggttatccac agaatcaggg gataacgcag gaaagaacat   7080
gtgagcaaaa ggccagcaaa aggccaggaa ccgtaaaaag gccgcgttgc tggcgttttt   7140
ccataggctc cgcccccctg acgagcatca caaaaatcga cgctcaagtc agaggtggcg   7200
aaacccgaca ggactataaa gataccaggc gtttccccct ggaagctccc tcgtgcgctc   7260
tcctgttccg accctgccgc ttaccggata cctgtccgcc tttctccctt cgggaagcgt   7320
ggcgctttct catagctcac gctgtaggta tctcagttcg gtgtaggtcg ttcgctccaa   7380
gctgggctgt gtgcacgaac ccccgttca gcccgaccgc tgcgccttat ccggtaacta   7440
tcgtcttgag tccaacccgg taagacacga cttatcgcca ctggcagcag ccactggtaa   7500
caggattagc agagcgaggt atgtaggcgg tgctacagag ttcttgaagt ggtggcctaa   7560
ctacggctac actagaagga cagtatttgg tatctgcgct ctgctgaagc cagttacctt   7620
cggaaaaaga gttggtagct cttgatccgg caaacaaacc accgctggta gcggtggttt   7680
ttttgtttgc aagcagcaga ttacgcgcag aaaaaaagga tctcaagaag atcctttgat   7740
cttttctacg gggtctgacg ctcagtggaa cgaaaactca cgttaaggga ttttggtcat   7800
gagattatca aaaaggatct tcacctagat ccttttaaat taaaaatgaa gttttaaatc   7860
```

```
aatctaaagt atatatgagt aaacttggtc tgacagttac caatgcttaa tcagtgaggc  7920
acctatctca gcgatctgtc tatttcgttc atccatagtt gcctgactcc ccgtcgtgta  7980
gataactacg atacgggagg gcttaccatc tggcccagt gctgcaatga taccgcgaga  8040
cccacgctca ccgggctccag atttatcagc aataaaccag ccagccggaa gggccgagcg  8100
cagaagtggt cctgcaactt tatccgcctc catccagtct attaattgtt gccgggaagc  8160
tagagtaagt agttcgccag ttaatagttt gcgcaacgtt gttggcattg ctacaggcat  8220
cgtggtgtca cgctcgtcgt ttggtatggc ttcattcagc tccggttccc aacgatcaag  8280
gcgagttaca tgatccccca tgttgtgcaa aaaagcggtt agctccttcg gtcctccgat  8340
cgttgtcaga agtaagttgg ccgcagtgtt atcactcatg gttatggcag cactgcataa  8400
ttctcttact gtcatgccat ccgtaagatg cttttctgtg actggtgagt actcaaccaa  8460
gtcattctga gaatagtgta tgcggcgacc gagttgctct gcccggcgt caatacggga  8520
taataccgcg ccacatagca gaactttaaa agtgctcatc attggaaaac gttcttcggg  8580
gcgaaaactc tcaaggatct taccgctgtt gagatccagt tcgatgtaac ccactcgtgc  8640
acccaactga tcttcagcat cttttacttt caccagcgtt tctgggtgag caaaaacagg  8700
aaggcaaaat gccgcaaaaa agggaataag ggcgacacgg aaatgttgaa tactcatact  8760
cttcctttt caatattatt gaagcattta tcagggttat tgtctcatga gcggatacat  8820
atttgaatgt atttagaaaa ataaacaaat aggggttccg cgcacatttc cccgaaaagt  8880
gccacctgac gtctaagaaa ccattattat catgacatta acctataaaa ataggcgtat  8940
cacgaggccc tttcgtctcg cgcgtttcgg tgatgacgagt gaaaacctct gacacatgca  9000
gctcccggag acggtcacag cttgtctgta agcggatgcc gggagcagac aagcccgtca  9060
gggcgcgtca gcgggtgttg gcgggtgtcg ggctggctt aactatgcgg catcagagca  9120
gattgtactg agagtgcacc atatgcggtg tgaaataccg cacagatgcg taaggagaaa  9180
ataccgcatc aggcgccatt cgccattcag gctgcgcaac tgttgggaag ggcgatcggt  9240
gcgggcctct tcgctattac gccagctggc gaaaggggga tgtgctgcaa ggcgattaag  9300
ttgggtaacg ccagggtttt cccagtcacg acgttgtaaa acgacggcca gtgaattgga  9360
tttaggtgac actatagaat acgaattc                                      9388

SEQ ID NO: 98          moltype = DNA   length = 8152
FEATURE                Location/Qualifiers
misc_feature           1..8152
                       note = Synthetic polynucleotide
source                 1..8152
                       mol_type = other DNA
                       organism = synthetic construct
SEQUENCE: 98
gaattcgttg gtggtcgcca tggatggtgt tattgtatac tgtctaaacg cgttagtaaa   60
acatggcgag gaaataaatc atataaaaaa tgatttcatg attaaccat gttgtgaaaa   120
agtcaagaac gttcacattg gcggacaatc taaaaacaat acagtgattg cagatttgcc   180
atatatggat aatgcggtat ccgatgtatg caattcactg tataaaaaga atgtatcaag   240
aatatccaga tttgctaatt tgataaagat agatgacgat gacaagactc ctactggtat   300
atataattat tttaaaccta agatgccat tcctgttatt atatccatag aaaggatag   360
agatgtttgt gaactattaa tctcatctga taaagcgtgt gcgtgtatag agttaaattc   420
atataaagta gccattcttc ccatggatgt ttccttttt accaaaggaa atgcatcatt   480
gattattctc ctgtttgatt tctctatcga tgcggcacct ctcttaagaa gtgtaaccga   540
taataatgtt attatatcta gacaccagcg tctacatgac gagcttccga gttccaattg   600
gttcaagttt tacataagta taaagtccga ctattgttct atattatata tggttgttga   660
tggatctgtg atgcatgcaa tagctgataa tagaacttac gcaaatatta gcaaaaatat   720
attagacaat actacaatta acgatgagtg tagatgctgt tatttttgaac cacagattag   780
gattcttgat agagatgaga tgctcaatgg atcatcgtgt gatatgaaca gacattgtat   840
tatgatgaat ttacctgatg taggcgaatt tggatcctagt atgttgggga aatatgaacc   900
tgacatgatt aagattgctc tttcggtggc tgggtaccag gcgcgcattt cattttgttt   960
ttttctatgc tataaatggt acgtcctgta gaaaccccaa cccgtgaaat caaaaaactc  1020
gacggcctgt gggcattcag tctggatcgc gaaaactgtg gaattgatca gcgttggtgg  1080
gaaagcgcgt tacaagaaag ccgggcaatt gctgtgccag gcagttttaa cgatcagttc  1140
gccgatgcag atattcgtaa ttatgcgggc aacgtctgta atcagcgcga agtctttata  1200
ccgaaaggtt gggcaggcca gcgtatcgtg ctgcgtttcg atgcggtcac tcattacgg   1260
aaagtgtggg tcaataatca ggaagtgatg gagcatcagg cggctatac gccatttgaa  1320
gccgatgtca cgccgtatgt tattgccggg aaaagtgtac gtatcaccgt ttgtgtgaac  1380
aacgaactga actggcagac tatcccgccg gaatggtga ttaccgacga aaacggcaag  1440
aaaaagcagt cttacttcca tgatttcttt aactatgccg gaatccatcg cagcgtaatg  1500
ctctacacca cgccgaacac ctgggtggac gatatcaccg tggtgacgca tgtcgcgcaa  1560
gactgtaacc acgcgtctgt tgactggcag gtggtggcca atggtgatgt cagcgttgaa  1620
ctgcgtgatg cggatcaaca ggtggttgca actggacaag gcactagcgg gactttgcaa  1680
gtggtgaatc cgcacctctg gcaacccggt gaaggttatc tctatgaact gtgcgtcaca  1740
gccaaaagcc agacagagtg tgatatctac ccgcttcgcg tcggcatccg gtcagtggca  1800
gtgaagggcg aacagttcct gattaaccac aaaccgttct actttactgg ctttggtcgt  1860
catgaagatg cggacttgcg tggcaaagga ttcgataacg tgctgatggt gcacgaccac  1920
gcattaatgg actggattgg ggccaactcc taccgtacct cgcattaccc ttacgctgaa  1980
gagatgctcg actgggcaga tgaacatggc atcgtggtga ttgatgaaac tgctgctgtc  2040
ggctttaacc tctctttagg cattggtttc gaagcgggca acaagccgaa agaactgtac  2100
agcgaagagg cagtcaacgg ggaaactcag caagcgcact acaggcgat taagagctg  2160
atagcgcgtg acaaaaacca cccagccgtg gtgatgtgga gtattgccaa cgaaccggat  2220
acccgtccgc aaggtgcacg gaatatttc gcgccactgg cggaagcaac gcgtaaactc  2280
gacccgacgc gtccgatcac ctgcgtcaat gtaatgttcg cagacgcacc caccgatacc  2340
atcagcgatc tctttgatgt gctgtgcctg aaccgttatt acggatggta tgtccaaagc  2400
ggcgatttgg aaacggcaga aggtactga gaaaagaac ttctgcctg caggagaaa   2460
ctgcatcagc cgattatcat caccgaatac ggcgtggata cgttagccgg gctgcactca  2520
atgtacaccg acatgtggag tgaagagtat cagtgtgcat gcctggatat gatcaccgc  2580
gtctttgatc gcgtcagcgc cgtcgtcggt gaacaggtat ggaatttcgc cgattttgcg  2640
```

```
acctcgcaag gcatattgcg cgttggcggt aacaagaaag ggatcttcac tcgcgaccgc 2700
aaaccgaagt cggcggcttt tctgctgcaa aaacgctgga ctggcatgaa cttcggtgaa 2760
aaaccgcagc agggaggcaa acaatgagag ctcggttgtt gatggatctg tgatgcatgc 2820
aatagctgat aatagaactt acgcaaatat tagcaaaaat atattagaca atactacaat 2880
taacgatgag tgtagatgct gttatttga accacagatt aggattcttg atagagatga 2940
gatgctcaat ggatcatcgt gtgatatgaa cagacattgt attatgatga atttacctga 3000
tgtaggcgaa tttggatcta gtatgttggg gaaatatgaa cctgacatga ttaagattgc 3060
tctttcggtg gctggcggcc cgctcgagaa aaattgaaaa taaatacaaa ggttcttgag 3120
ggttgtgtta aattgaaagc gagaaataat cataaataag ccaccaccgt ttaaacagtc 3180
gacggtatcg ataagcttga tatcgaattc ctgcagcccg tacgcgcagg cagcatggag 3240
tcgcgcggtc gccgttgtcc cgaaatgata tccgtactgg gtccatttc ggggcacgtg 3300
ctgaaagccg tgtttagtcg cggcgacacg ccggtgctgc cgcacgagac gcgactcctg 3360
cagacgggta tccacgtgcg cgtgagccag ccctcgctga tcctggtgtc gcagtacacg 3420
cccgactcga cgccatgcca ccgcggcgac aatcagctgc aggtgcagca cacgtacttt 3480
acgggcagcg aggtggagaa cgtgtcggtc aacgtgcaca accccacggg ccggagcatc 3540
tgccccagcc aagagcccat gtcgatctat gtgtacgcgc tgccgctcaa gatgctgaac 3600
atccccagca tcaacgtgca ccactacccg tcggcggccg agcgcaaaca ccgacacctg 3660
cccgtagctg acgctgtgat tcacgcgtcg ggcaagcaga tgtggcaggc gcgtctcacg 3720
gtctcgggac tggcctggac gcgtcagcag aaccagtgga aagagcccga cgtctactac 3780
acgtcagcgt tcgtgtttcc caccaaggac gtggcactgc ggcacgtggt gtgcgcgcac 3840
gagctggttt gctccatgga gaacacgcgc gcaaccaaga tgcaggtgat aggtgaccag 3900
tacgtcaagg tgtacctgga gtccttctgc gaggacgttgc cctccggcaa gctctttatg 3960
cacgtcacgc tgggctctga cgtggaagag gacctgacga tgacccgcaa cccgcaaccc 4020
ttcatgcgcc cccacgagcg caacggcttt acggtgttgt gtcccaaaaa tatgataatc 4080
aaaccgggca agatctcgca catcatgctg gatgtggctt ttacctcaca cgagcatttt 4140
gggctgctgt gtcccaagag catcccgggc ctgagcatct caggtaacct attgatgaac 4200
gggcagcaga tcttcctgga ggtgcaagcg atacgcgaga ccgtggaact cgtcagtac 4260
gatcccgtgg ctgcgctctt cttttttcgat atcgacttgc tgctgcagcg cgggcctcag 4320
tacagcgaac accccacctt caccagccag tatcgcatcc agggcaagct tgagtaccga 4380
cacacctgga accggcacga cgagggtgcc gcccagggcg acgacgatctg ctggaccagc 4440
ggatcggact ccgacgagga actcgtaacc accgagcgca agacgccccg cgttaccggc 4500
ggcggcgcca tggcgggcgc ctccacttcc gcgggccgca aacgcaaatc agcatcctcg 4560
gcgacggcgt gcacggcggg cgttatgaca cgcggccgcc ttaaggccga gtccaccgtc 4620
gcgcccgaag aggacaccga cgaggattcc gacaacgaaa tccacaatcc ggccgtgttc 4680
acctggccgc cctggcaggc cggcatcctg gcccgcaacc tggtgcccat ggtggctacg 4740
gttcagggtc agaatctgaa gtaccaggag ttccttctgg gacgccaacga catctaccgc 4800
atcttcgccg aattggaagg cgtatggcag cccgctgcgc aacccaaacg tcgccgccac 4860
cggcaagacg ccttgcccgg gccatgcatc gcctcgacgt ccaaaaagca ccgaggttga 4920
ttttatggc gcgccctgca gggaaagttt tataggtagt tgatagaaca aaatacataa 4980
ttttgtaaaa ataaatcact ttttatacta atatgacacg attaccaata cttttgttac 5040
taatatcatt agtatacgct acaccttttc ctcagacatc taaaaaaata ggtgatgatg 5100
caactttatc atgtaatcga aataatacaa atgactacgt tgttatgagt gcttggtata 5160
aggagcccaa ttccattatt cttttagctg ctaaaagcga cgtcttgtat tttgataatt 5220
ataccaagga taaatatct tacgactctc catacgatga tctagttaca actatccaca 5280
ttaaatcatt gactgctaga gatgccggta cttatgtatg tgcattcttt atgacatcgc 5340
ctacaaatga cactgataaa gtagattatg aagaatactc cacagagttg attgtaaata 5400
cagatagtga atcgactata gacataatac tatctggatc tacacattca ccagaaacta 5460
gttaagcttg tctccctata gtgagtcgta ttagagcttg gcgtaatcat ggtcatagct 5520
gtttcctgtg tgaaattgtt atccgctcac aattccacac aacatacgag ccggaagcat 5580
aaaagtgtaaa gcctggggtg cctaatgagt gagctaactc acattaattg cgttgcgctc 5640
actgcccgct ttcgagtcgg gaaacctgtc gtgccaactg cattaatgaa tcggccaacg 5700
cgcggggaga ggcggtttgc gtattgggcg ctcttccgct tcctcgctca ctgactcgct 5760
gcgctcggtc gttcggctgc ggcgagcggt atcagctcac tcaaaggcgg taatacggtt 5820
atccacagaa tcaggggata acgcaggaaa gaacatgtga gcaaaaggcc agcaaaaggc 5880
caggaaccgt aaaaaggccg cgttgctggc gtttttcgat aggctccgcc ccctgacga 5940
gcatcacaaa aatcgacgct caagtcagag gtggcgaaac ccgacaggac tataaagata 6000
ccaggcgttt ccccctggaa gctccctcgt gcgctctcct gttccgaccc tgccgcttac 6060
cggatacctg tccgccttc tcccttcggg aagcgtggcg ctttctcata gctcacgctg 6120
taggtatctc agttcggtgt aggtcgttcg ctccaagctg ggctgtgtgc acgaacccc 6180
cgttcagccc gaccgctgcg ccttatccgg taactatcgt cttgagtcca acccggtaag 6240
acacgactta tcgccactgg cagcagccac tggtaacagg attagcagag cgaggtatgt 6300
aggcggtgct acagagttct tgaagtggtg gcctaactac ggctacacta aaggacagt 6360
atttggtatc tgcgctctgc tgaagccagt taccttcgga aaaagagttg gtagctcttg 6420
atccggcaaa caaccaccg ctggtagcgg tggtttttt gtttgcaagc agcagattac 6480
gcgcagaaaa aaggatctc aagaagatcc tttgatcttt tctacggggt ctgacgctca 6540
gtggaacgaa aactcacgtt aagggatttt ggtcatgaga ttatcaaaaa ggatcttcac 6600
ctagatcctt ttaaattaaa aatgaagttt taaatcaatc taaagtatat atgagtaaac 6660
ttggtctgac agttaccaat gcttaatcag tgaggcacct atctcagcga tctgtctatt 6720
tcgttcatcc atagttgcct gactccccgt cgtgtagata actacgatac gggagggctt 6780
accatctggc cccagtgctg caatgatacc gcgagaccca cgctcaccgg ctccagattt 6840
atcagcaata accagccag ccggaagggc cgagcgcaga agtggtcctg caactttatc 6900
cgcctccatc cagtctatta attgttgccg ggaagctaga gtaagtagtt cgccagttaa 6960
tagtttgcgc aacgttgttg gcattgctac aggcatcgtg gtgtcacgct cgtcgtttgg 7020
tatggcttca ttcagctccg gttcccaacg atcaaggcga gttacatgat ccccatgtt 7080
gtgcaaaaaa gcggttagct ccttcggtcc tccgatcgtt gtcagaagta agttggccgc 7140
agtgttatca ctcatggtta tggcagcact gcataattct cttactgtca tgccatccgt 7200
aagatgcttt tctgtgactg gtgagtactc aaccaagtca ttctgagaat agtgtatgcg 7260
gcgaccgagt tgctcttgcc cggcgtcaat acgggataat accgcgccac atagcagaac 7320
tttaaaagtg ctcatcattg gaaaacgttc ttcggggcga aaactctcaa ggatcttacc 7380
```

```
gctgttgaga tccagttcga tgtaacccac tcgtgcaccc aactgatctt cagcatcttt  7440
tactttcacc agcgtttctg ggtgagcaaa acaggaagg  caaaatgccg caaaaaggg   7500
aataagggcg acacggaaat gttgaatact catactcttc cttttcaat  attattgaag  7560
catttatcag ggttattgtc tcatgagcgg atacatattt gaatgtattt agaaaaataa  7620
acaaatgggg gttccgcgca catttccccg aaaagtgcca cctgacgtct aagaaaccat  7680
tattatcatg acattaacct ataaaaatag gcgtatcacg aggcccttc  gtctcgcgcg  7740
tttcggtgat gacggtgaaa acctctgaca catgcagctc ccggagacgg tcacagcttg  7800
tctgtaagcg gatgccggga gcagacaagc ccgtcagggc gcgtcagcgg gtgttggcgg  7860
gtgtcggggc tggcttaact atgcggcatc agagcagatt gtactgagag tgcaccatat  7920
gcggtgtgaa ataccgcaca gatgcgtaag gagaaaatac cgcatcaggc gccattcgcc  7980
attcaggctg cgcaactgtt gggaagggcg atcggtgcgg gcctcttcgc tattacgcca  8040
gctggcgaaa gggggatgtg ctgcaagcg  attaagttgg gtaacgccag ggttttccca  8100
gtcacgacgt tgtaaaacga cggccagtga attggattta ggtgacacta ta          8152

SEQ ID NO: 99          moltype = DNA  length = 2709
FEATURE                Location/Qualifiers
misc_feature           1..2709
                       note = Synthetic polynucleotide
source                 1..2709
                       mol_type = other DNA
                       organism = synthetic construct
SEQUENCE: 99
atggtcaaac agattaaggt tcgagtggac atggtgcggc atagaatcaa ggagcacatg   60
ctgaaaaaat atcccagac  ggaagagaaa ttcactggcg cctttaatat gatgggagga  120
tgtttgcaga atgccttaga tatcttagat aaggttcatg agcctttcga ggagatgaag  180
tgtattgggc taactatgca gagcatgtat gagaactaca ttgtacctga ggataagcgg  240
gagatgtgga tggcttgtat taaggagctg catgatgtga gcaagggcgc cgctaacaag  300
ttgggggggtg cactgcaggc taaggcccgt gctaaaaagg atgaacttag gagaaagatg  360
atgtatatgt gctacaggaa tatagagttc tttaccaaga actcagcctt ccctaagacc  420
accaatggct gcagtcaggc catggcggca ctgcagaact tgcctcagtg ctcccctgat  480
gagattatgg cttatgccca gaaaatattt aagattttgg atgaggagag agacaaggtg  540
ctcacgcaca ttgatcacat atttatggat atcctcacta catgtgtgga aacaatgtgt  600
aatgagtaca aggtcactag tgacgcttgt atgatgacca tgtacggggg catctctctc  660
ttaagtgagt tctgtcgggt gctgtgctgc tatgtcttag aggagactag tgtgatgctg  720
gccaagcggc ctctgataac caagcctgag gttatcagtg taatgaagcg ccgcattgtg  780
gagatctgca tgaaggtctt tgcccagtac attctggggg ccgatcctct gagagtctgc  840
tctcctagtg tggatgacct acgggccatc gccgaggagt cagatgagga agaggctatt  900
gtagcctaca ctttggccac cgctggtgtc agctcctctg attctctggt gtcaccccca  960
gagtccctg  tacccgcgac tatccctctg tcctcagtga ttgtggctga gaacagtgat 1020
caggaagaaa gtgagcagag tgatgaggaa gaggaggagg gtgctcagga ggagcgggag 1080
gacactgtgt ctgtcaagtc tgagccagtg tctgagatag aggaagttgc cccagaggaa 1140
gaggaggatg gtgctgagga acccaccgcc tctggaggca agagcaccca ccctatggtg 1200
actagaagca aggctgacca gggtgacatc ctcgcccagg ctgtcaatca tgccggtcgg 1260
gattccagta gcaccggccc cacgctgaca acccactctt gcagcgttag cagcgcccct 1320
cttaacaagc cgacccccac cagcgtcgcg gttactaaca ctcctctccc cggggcatcc 1380
gctactcccg agctcagccc cgctaagaaa ccgcgcaaaa ccacgcgtcc tttcaaggtg 1440
attattaaac cgcccgtgcc tccgcgcgct atcatgctgc ccctcatcaa acaggaagac 1500
atcaagcccg agcccgactt taccatccag taccgcaaca gattatcga  taccgccggc 1560
tgtatcgtga tctctgatag cgaggaagaa cagggtgaaa aagtcgaaac ccgccggtgct 1620
accgcgtctt cccccttcca cggcagcggc acgccgcgca tgacctctcc cacgcacccg 1680
ctctccagga tgaaccaccc tcctcttccc gatcccttgg gccggcccga tgaagatagt 1740
tcctcttcgt cttcctcctc ctgcagttcg gcttcggact cggagagtga gtccgaggag 1800
atgaaatgca gcagtggcgg aggagcatcc gtgacctcga gccaccatgg gcgcggcggt 1860
tttggtggcg cggcctcctc ctctctgctg agctgcggcc atcagagcag cggcggggcg 1920
agcaccggac cccgcaagaa gaaggcaaaa cgcatctccg agttggacaa cgagaaggtg 1980
cgcaatatca tgaaagataa gaacacccc  ttctgcacac ccaacgtgca gactcggcgg 2040
ggtcgcgtca agattgacga ggtgagccgc atgttccgca acaccaatcg ctctcttgag 2100
tacaagaacc tgcccttcac gattcccagt atgcaccagg tgttagatga ggccatcaaa 2160
gcctgcaaaa ccatgcaggt gaacaacaag ggcatcctca ttatctacac ccgcaatcat 2220
gaggtgaaga gtgaggtgga tgcggtgcgg tgtcgcctgg gcaccatgtg caacctggcc 2280
ctctccactc ccttcctcat ggagcacacc atgcccgtga cacatccacc cgaagtggcg 2340
cagcgcacag ccgatgcttg taacgaaggc gtcaaggccg cgtggagcct caagaattg  2400
cacacccacc aattatgccc ccgttcctcc gattaccgca acatgatcat ccacgctgcc 2460
accccgtgg  acctgttggg cgctctcaac ctgtgcctga aaagtttccc aaacaggtca 2520
aaacaggtca tggtgcgcat cttctccacc aaccagggtg ggttcatgct gcctatctac 2580
gagacggccg cgaaggccta cgccgtgggg cagtttgagc agcccaccga gacccctccc 2640
gaagacctgg acaccctgag cctggccatc gaggcagcca tccaggacct gaggaacaag 2700
tctcagtaa                                                         2709

SEQ ID NO: 100         moltype = AA  length = 10
FEATURE                Location/Qualifiers
REGION                 1..10
                       note = Artificial polypeptide
source                 1..10
                       mol_type = protein
                       organism = synthetic construct
SEQUENCE: 100
GGGSSGGGSG                                                          10
```

```
SEQ ID NO: 101           moltype = AA  length = 12
FEATURE                  Location/Qualifiers
REGION                   1..12
                         note = Artificial polypeptide
source                   1..12
                         mol_type = protein
                         organism = synthetic construct
SEQUENCE: 101
ESKYGPPCPP CP                                                          12

SEQ ID NO: 102           moltype = AA  length = 12
FEATURE                  Location/Qualifiers
REGION                   1..12
                         note = Artificial polypeptide
source                   1..12
                         mol_type = protein
                         organism = synthetic construct
SEQUENCE: 102
ESKYGPPCPS CP                                                          12

SEQ ID NO: 103           moltype = AA  length = 22
FEATURE                  Location/Qualifiers
REGION                   1..22
                         note = Artificial polypeptide
source                   1..22
                         mol_type = protein
                         organism = synthetic construct
SEQUENCE: 103
ESKYGPPCPP CPGGGSSGGG SG                                               22

SEQ ID NO: 104           moltype = AA  length = 39
FEATURE                  Location/Qualifiers
REGION                   1..39
                         note = Artificial polypeptide
source                   1..39
                         mol_type = protein
                         organism = synthetic construct
SEQUENCE: 104
IEVMYPPPYL DNEKSNGTII HVKGKHLCPS PLFPGPSKP                             39

SEQ ID NO: 105           moltype = AA  length = 48
FEATURE                  Location/Qualifiers
REGION                   1..48
                         note = Artificial polypeptide
source                   1..48
                         mol_type = protein
                         organism = synthetic construct
SEQUENCE: 105
AKPTTTPAPR PPTPAPTIAS QPLSLRPEAC RPAAGGAVHT RGLDFACD                   48

SEQ ID NO: 106           moltype = AA  length = 45
FEATURE                  Location/Qualifiers
REGION                   1..45
                         note = Artificial polypeptide
source                   1..45
                         mol_type = protein
                         organism = synthetic construct
SEQUENCE: 106
TTTPAPRPPT PAPTIASQPL SLRPEACRPA AGGAVHTRGL DFACD                      45

SEQ ID NO: 107           moltype = AA  length = 129
FEATURE                  Location/Qualifiers
REGION                   1..129
                         note = Artificial polypeptide
source                   1..129
                         mol_type = protein
                         organism = synthetic construct
SEQUENCE: 107
ESKYGPPCPP CPGGGSSGGG SGGQPREPQV YTLPPSQEEM TKNQVSLTCL VKGFYPSDIA      60
VEWESNGQPE NNYKTTPPVL DSDGSFFLYS RLTVDKSRWQ EGNVFSCSVM HEALHNHYTQ     120
KSLSLSLGK                                                             129

SEQ ID NO: 108           moltype = AA  length = 229
FEATURE                  Location/Qualifiers
REGION                   1..229
                         note = Artificial polypeptide
source                   1..229
                         mol_type = protein
                         organism = synthetic construct
```

```
SEQUENCE: 108
ESKYGPPCPS CPAPEFEGGP SVFLFPPKPK DTLMISRTPE VTCVVVDVSQ EDPEVQFNWY    60
VDGVEVHQAK TKPREEQFQS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGK              229

SEQ ID NO: 109          moltype = AA   length = 229
FEATURE                 Location/Qualifiers
REGION                  1..229
                        note = Artificial polypeptide
source                  1..229
                        mol_type = protein
                        organism = synthetic construct
SEQUENCE: 109
ESKYGPPCPP CPAPEFEGGP SVFLFPPKPK DTLMISRTPE VTCVVVDVSQ EDPEVQFNWY    60
VDGVEVHQAK TKPREEQFQS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGK              229

SEQ ID NO: 110          moltype = AA   length = 107
FEATURE                 Location/Qualifiers
REGION                  1..107
                        note = Artificial polypeptide
source                  1..107
                        mol_type = protein
                        organism = synthetic construct
SEQUENCE: 110
GQPREPQVYT LPPSQEEMTK NQVSLTCLVK GFYPSDIAVE WESNGQPENN YKTTPPVLDS    60
DGSFFLYSRL TVDKSRWQEG NVFSCSVMHE ALHNHYTQKS LSLSLGK                107

SEQ ID NO: 111          moltype = AA   length = 21
FEATURE                 Location/Qualifiers
REGION                  1..21
                        note = Artificial polypeptide
source                  1..21
                        mol_type = protein
                        organism = synthetic construct
SEQUENCE: 111
LCYLLDGILF IYGVILTALF L                                             21

SEQ ID NO: 112          moltype = AA   length = 27
FEATURE                 Location/Qualifiers
REGION                  1..27
                        note = Artificial polypeptide
source                  1..27
                        mol_type = protein
                        organism = synthetic construct
SEQUENCE: 112
FWVLVVVGGV LACYSLLVTV AFIIFWV                                       27

SEQ ID NO: 113          moltype = AA   length = 28
FEATURE                 Location/Qualifiers
REGION                  1..28
                        note = Artificial polypeptide
source                  1..28
                        mol_type = protein
                        organism = synthetic construct
SEQUENCE: 113
MFWVLVVVGG VLACYSLLVT VAFIIFWV                                      28

SEQ ID NO: 114          moltype = AA   length = 22
FEATURE                 Location/Qualifiers
REGION                  1..22
                        note = Artificial polypeptide
source                  1..22
                        mol_type = protein
                        organism = synthetic construct
SEQUENCE: 114
MALIVLGGVA GLLLFIGLGI FF                                            22

SEQ ID NO: 115          moltype = AA   length = 21
FEATURE                 Location/Qualifiers
REGION                  1..21
                        note = Artificial polypeptide
source                  1..21
                        mol_type = protein
                        organism = synthetic construct
SEQUENCE: 115
IYIWAPLAGT CGVLLLSLVI T                                             21
```

```
SEQ ID NO: 116            moltype = AA   length = 23
FEATURE                   Location/Qualifiers
REGION                    1..23
                          note = Artificial polypeptide
source                    1..23
                          mol_type = protein
                          organism = synthetic construct
SEQUENCE: 116
IYIWAPLAGT CGVLLLSLVI TLY                                              23

SEQ ID NO: 117            moltype = AA   length = 24
FEATURE                   Location/Qualifiers
REGION                    1..24
                          note = Artificial polypeptide
source                    1..24
                          mol_type = protein
                          organism = synthetic construct
SEQUENCE: 117
IYIWAPLAGT CGVLLLSLVI TLYC                                             24

SEQ ID NO: 118            moltype = AA   length = 27
FEATURE                   Location/Qualifiers
REGION                    1..27
                          note = Artificial polypeptide
source                    1..27
                          mol_type = protein
                          organism = synthetic construct
SEQUENCE: 118
IISFFLALTS TALLFLLFFL TLRFSVV                                          27

SEQ ID NO: 119            moltype = AA   length = 112
FEATURE                   Location/Qualifiers
REGION                    1..112
                          note = Artificial polypeptide
source                    1..112
                          mol_type = protein
                          organism = synthetic construct
SEQUENCE: 119
RVKFSRSADA PAYQQGQNQL YNELNLGRRE EYDVLDKRRG RDPEMGGKPR RKNPQEGLYN       60
ELQKDKMAEA YSEIGMKGER RRGKGHDGLY QGLSTATKDT YDALHMQALP PR              112

SEQ ID NO: 120            moltype = AA   length = 41
FEATURE                   Location/Qualifiers
REGION                    1..41
                          note = Artificial polypeptide
source                    1..41
                          mol_type = protein
                          organism = synthetic construct
SEQUENCE: 120
RSKRSRLLHS DYMNMTPRRP GPTRKHYQPY APPRDFAAYR S                           41

SEQ ID NO: 121            moltype = AA   length = 41
FEATURE                   Location/Qualifiers
REGION                    1..41
                          note = Artificial polypeptide
source                    1..41
                          mol_type = protein
                          organism = synthetic construct
SEQUENCE: 121
RSKRSRGGHS DYMNMTPRRP GPTRKHYQPY APPRDFAAYR S                           41

SEQ ID NO: 122            moltype = AA   length = 42
FEATURE                   Location/Qualifiers
REGION                    1..42
                          note = Artificial polypeptide
source                    1..42
                          mol_type = protein
                          organism = synthetic construct
SEQUENCE: 122
KRGRKKLLYI FKQPFMRPVQ TTQEEDGCSC RFPEEEEGGC EL                          42

SEQ ID NO: 123            moltype = AA   length = 42
FEATURE                   Location/Qualifiers
REGION                    1..42
                          note = Artificial polypeptide
source                    1..42
                          mol_type = protein
                          organism = synthetic construct
```

```
SEQUENCE: 123
ALYLLRRDQR LPPDAHKPPG GGSFRTPIQE EQADAHSTLA KI                  42

SEQ ID NO: 124          moltype = AA  length = 24
FEATURE                 Location/Qualifiers
REGION                  1..24
                        note = Artificial polypeptide
source                  1..24
                        mol_type = protein
                        organism = synthetic construct
SEQUENCE: 124
LEGGGEGRGS LLTCGDVEEN PGPR                                      24

SEQ ID NO: 125          moltype = AA  length = 354
FEATURE                 Location/Qualifiers
REGION                  1..354
                        note = Artificial polypeptide
source                  1..354
                        mol_type = protein
                        organism = synthetic construct
SEQUENCE: 125
LVTSLLLCEL PHPAFLLIPR KVCNGIGIGE FKDSLSINAT NIKHFKNCTS ISGDLHILPV   60
AFRGDSFTHT PPLDPQELDI LKTVKEITGF LLIQAWPENR TDLHAFENLE IIRGRTKQHG  120
QFSLAVVSLN ITSLGLRSLK EISDGDVIIS GNKNLCYANT INWKKLFGTS GQKTKIISNR  180
GENSCKATGQ VCHALCSPEG CWGPEPRDCV SCRNVSRGRE CVDKCNLLEG EPREFVENSE  240
CIQCHPECLP QAMNITCTGR GPDNCIQCAH YIDGPHCVKT CPAGVMGENN TLVWKYADAG  300
HVCHLCHPNC TYGCTGPGLE GCPTNGPKIP SIATGMVGAL LLLLVVALGI GLFM        354

SEQ ID NO: 126          moltype = AA  length = 22
FEATURE                 Location/Qualifiers
REGION                  1..22
                        note = Synthetic Polypeptide
source                  1..22
                        mol_type = protein
                        organism = synthetic construct
SEQUENCE: 126
MLLLVTSLLL CELPHPAFLL IP                                        22

SEQ ID NO: 127          moltype = AA  length = 214
FEATURE                 Location/Qualifiers
REGION                  1..214
                        note = Synthetic polypeptide
source                  1..214
                        mol_type = protein
                        organism = synthetic construct
SEQUENCE: 127
DIQMTQSPIL LSASVGDRVT ITCRASQDVN TAVAWYQQRT NGSPRLLIYS ASFLYSGVPS   60
RFSGSRSGTD FTLTISSLQP EDEADYYCQQ YTTPPPTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 128          moltype = AA  length = 22
FEATURE                 Location/Qualifiers
REGION                  1..22
                        note = Synthetic polypeptide
source                  1..22
                        mol_type = protein
                        organism = synthetic construct
SEQUENCE: 128
LEGGGEGRGS LLTCGDVEEN PG                                        22

SEQ ID NO: 129          moltype = AA  length = 245
FEATURE                 Location/Qualifiers
REGION                  1..245
                        note = Synthetic polypeptide
source                  1..245
                        mol_type = protein
                        organism = synthetic construct
SEQUENCE: 129
MLLLVTSLLL CELPHPAFLL IPEVQLVESG GGLVQPGGSL RLSCAASGFN IKDTYIHWVR   60
QSPGKGLEWV ARIYPTNGYT RYADSVKGRF TISADTSKNT AYLQMNSLRA EDTAIYYCSR  120
WGGDGFYAMD YWGQGTLVTV SSASTKGPSV FPLAPSSKST SGGTAALGCL VKDYFPEPVT  180
VSWNSGALTS GVHTFPAVLQ SSGLYSLSSV VTVPSSSLGT QTYICNVNHK PSNTKVDKKV  240
EPKSC                                                             245

SEQ ID NO: 130          moltype = AA  length = 12
FEATURE                 Location/Qualifiers
REGION                  1..12
                        note = Synthetic polypeptide
```

```
source                       1..12
                             mol_type = protein
                             organism = synthetic construct
SEQUENCE: 130
ESKYGPPCPP CP                                                            12

SEQ ID NO: 131               moltype = AA  length = 10
FEATURE                      Location/Qualifiers
REGION                       1..10
                             note = Synthetic polypeptide
source                       1..10
                             mol_type = protein
                             organism = synthetic construct
SEQUENCE: 131
GGGSSGGGSG                                                               10

SEQ ID NO: 132               moltype = AA  length = 107
FEATURE                      Location/Qualifiers
REGION                       1..107
                             note = Synthetic polypeptide
source                       1..107
                             mol_type = protein
                             organism = synthetic construct
SEQUENCE: 132
GQPREPQVYT LPPSQEEMTK NQVSLTCLVK GFYPSDIAVE WESNGQPENN YKTTPPVLDS         60
DGSFFLYSRL TVDKSRWQEG NVFSCSVMHE ALHNHYTQKS LSLSLGK                      107

SEQ ID NO: 133               moltype = AA  length = 28
FEATURE                      Location/Qualifiers
REGION                       1..28
                             note = Synthetic polypeptide
source                       1..28
                             mol_type = protein
                             organism = synthetic construct
SEQUENCE: 133
MFWVLVVVGG VLACYSLLVT VAFIIFWV                                           28

SEQ ID NO: 134               moltype = AA  length = 41
FEATURE                      Location/Qualifiers
REGION                       1..41
                             note = Synthetic polypeptide
source                       1..41
                             mol_type = protein
                             organism = synthetic construct
SEQUENCE: 134
RSKRSRGGHS DYMNMTPRRP GPTRKHYQPY APPRDFAAYR S                            41

SEQ ID NO: 135               moltype =     length =
SEQUENCE: 135
000

SEQ ID NO: 136               moltype = AA  length = 112
FEATURE                      Location/Qualifiers
REGION                       1..112
                             note = Synthetic polypeptide
source                       1..112
                             mol_type = protein
                             organism = synthetic construct
SEQUENCE: 136
RVKFSRSADA PAYQQGQNQL YNELNLGRRE EYDVLDKRRG RDPEMGGKPR RKNPQEGLYN         60
ELQKDKMAEA YSEIGMKGER RRGKGHDGLY QGLSTATKDT YDALHMQALP PR                112

SEQ ID NO: 137               moltype = AA  length = 22
FEATURE                      Location/Qualifiers
REGION                       1..22
                             note = Synthetic polypeptide
source                       1..22
                             mol_type = protein
                             organism = synthetic construct
SEQUENCE: 137
MLLLVTSLLL CELPHPAFLL IP                                                 22

SEQ ID NO: 138               moltype = AA  length = 223
FEATURE                      Location/Qualifiers
REGION                       1..223
                             note = Synthetic polypeptide
source                       1..223
                             mol_type = protein
                             organism = synthetic construct
```

```
SEQUENCE: 138
EVQLVESGGG LVQPGGSLRL SCAASGFNIK DTYIHWVRQS PGKGLEWVAR IYPTNGYTRY    60
ADSVKGRFTI SADTSKNTAY LQMNSLRAED TAIYYCSRWG GDGFYAMDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSC                    223

SEQ ID NO: 139          moltype = AA  length = 12
FEATURE                 Location/Qualifiers
REGION                  1..12
                        note = Synthetic polypeptide
source                  1..12
                        mol_type = protein
                        organism = synthetic construct
SEQUENCE: 139
ESKYGPPCPP CP                                                       12

SEQ ID NO: 140          moltype = AA  length = 10
FEATURE                 Location/Qualifiers
REGION                  1..10
                        note = Synthetic polypeptide
source                  1..10
                        mol_type = protein
                        organism = synthetic construct
SEQUENCE: 140
GGGSGGGGSG                                                          10

SEQ ID NO: 141          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 141
GQPREPQVYT LPPSQEEMTK NQVSLTCLVK GFYPSDIAVE WESNGQPENN YKTTPPVLDS    60
DGSFFLYSRL TVDKSRWQEG NVFSCSVMHE ALHNHYTQKS LSLSLGK                107

SEQ ID NO: 142          moltype = AA  length = 28
FEATURE                 Location/Qualifiers
REGION                  1..28
                        note = Synthetic polypeptide
source                  1..28
                        mol_type = protein
                        organism = synthetic construct
SEQUENCE: 142
MFWVLVVVGG VLACYSLLVT VAFIIFWV                                      28

SEQ ID NO: 143          moltype = AA  length = 41
FEATURE                 Location/Qualifiers
REGION                  1..41
                        note = Synthetic polypeptide
source                  1..41
                        mol_type = protein
                        organism = synthetic construct
SEQUENCE: 143
RSKRSRGGHS DYMNMTPRRP GPTRKHYQPY APPRDFAAYR S                       41

SEQ ID NO: 144          moltype =     length =
SEQUENCE: 144
000

SEQ ID NO: 145          moltype = AA  length = 112
FEATURE                 Location/Qualifiers
REGION                  1..112
                        note = Synthetic polypeptide
source                  1..112
                        mol_type = protein
                        organism = synthetic construct
SEQUENCE: 145
RVKFSRSADA PAYQQGQNQL YNELNLGRRE EYDVLDKRRG RDPEMGGKPR RKNPQEGLYN    60
ELQKDKMAEA YSEIGMKGER RRGKGHDGLY QGLSTATKDT YDALHMQALP PR           112

SEQ ID NO: 146          moltype = AA  length = 24
FEATURE                 Location/Qualifiers
REGION                  1..24
                        note = Synthetic polypeptide
source                  1..24
                        mol_type = protein
                        organism = synthetic construct
```

```
SEQUENCE: 146
LEGGGEGRGS LLTCGDVEEN PGPR                                          24

SEQ ID NO: 147         moltype = AA  length = 236
FEATURE                Location/Qualifiers
REGION                 1..236
                       note = Synthetic polypeptide
source                 1..236
                       mol_type = protein
                       organism = synthetic construct
SEQUENCE: 147
MLLLVTSLLL CELPHPAFLL IPDIQMTQSP ILLSASVGDR VTITCRASQD VNTAVAWYQQ    60
RTNGSPRLLI YSASFLYSGV PSRFSGSRSG TDFTLTISSL QPEDEADYYC QQHYTTPPTF   120
GAGTKVEIKR TVAAPSVFIF PPSDEQLKSG TASVVCLLNN FYPREAKVQW KVDNALQSGN   180
SQESVTEQDS KDSTYSLSST LTLSKADYEK HKVYACEVTH QGLSSPVTKS FNRGEC       236
```